United States Patent
Chen et al.

(10) Patent No.: US 12,037,616 B2
(45) Date of Patent: Jul. 16, 2024

(54) METHODS AND COMPOSITIONS FOR TREATING ANGIOPOIETIN-LIKE 3 (ANGPTL3) RELATED CONDITIONS

(71) Applicant: CRISPR Therapeutics AG, Zug (CH)

(72) Inventors: Yi-Shan Chen, South Boston, MA (US); Sandeep Soni, South Boston, CA (US); Laura Serwer, South Boston, MA (US); Jonathan Terrett, South Boston, MA (US); John Kulman, South Boston, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 0 days.

(21) Appl. No.: 18/176,197

(22) Filed: Feb. 28, 2023

(65) Prior Publication Data

US 2023/0279376 A1    Sep. 7, 2023

Related U.S. Application Data

(60) Provisional application No. 63/380,557, filed on Oct. 21, 2022, provisional application No. 63/352,747, filed on Jun. 16, 2022, provisional application No. 63/332,234, filed on Apr. 18, 2022, provisional application No. 63/315,372, filed on Mar. 1, 2022.

(51) Int. Cl.
  *C12N 9/22* (2006.01)
  *A61P 3/00* (2006.01)
  *C12N 15/11* (2006.01)

(52) U.S. Cl.
  CPC .................. *C12N 9/22* (2013.01); *A61P 3/00* (2018.01); *C12N 15/11* (2013.01); *C12N 2310/20* (2017.05)

(58) Field of Classification Search
  None
  See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,173,414 A | 12/1992 | Lebkowski et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |

(Continued)

FOREIGN PATENT DOCUMENTS

| | | |
|---|---|---|
| EP | 2112235 A1 | 10/2009 |
| WO | WO1993/007883 | 4/1993 |

(Continued)

OTHER PUBLICATIONS

International Search Report and Written Opinion, dated Jun. 12, 2023 in International Application No. PCT/IB2023/051870.
Adam et al. "Angiopoietin-like protein 3 governs LDL-cholesterol levels through endothelial lipase-dependent VLDL clearance," Journal of Lipid Research 2020, 61(9), 1271-1286.
Adams et al., "Patisiran, an RNAi therapeutic, for hereditary transthyretin amyloidosis," New England Journal of Medicine 2018, 379(1), 11-21.
Aim-High Investigators, "Niacin in patients with low HDL cholesterol levels receiving intensive statin therapy," New England Journal of Medicine 2011, 365(24), 2255-2267.
Altschul et al., "Basic local alignment search tool," Journal of Molecular Biology 1990, 215(3), 403-410.

(Continued)

*Primary Examiner* — Nancy J Leith
(74) *Attorney, Agent, or Firm* — Sheppard, Mullin, Richter & Hampton LLP

(57) ABSTRACT

The present disclosure relates to methods, compositions and kits for treating conditions that are related with angiopoietin-like 3 (ANGPTL3) by gene editing.

20 Claims, 57 Drawing Sheets

Specification includes a Sequence Listing.

(56) References Cited

U.S. PATENT DOCUMENTS

| | | |
|---|---|---|
| 5,317,098 A | 5/1994 | Shizuya et al. |
| 5,321,131 A | 6/1994 | Agrawal et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Grawal et al. |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer, Jr. et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,658,776 A | 8/1997 | Flotte et al. |
| 5,663,312 A | 9/1997 | Chaturvedula |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,786,211 A | 7/1998 | Johnson |
| 5,830,653 A | 11/1998 | Froehler et al. |
| 5,871,982 A | 2/1999 | Wilson et al. |
| 6,005,096 A | 12/1999 | Matteucci et al. |
| 6,140,081 A | 10/2000 | Barbas |
| 6,156,303 A | 12/2000 | Russell et al. |
| 6,258,595 B1 | 7/2001 | Gao et al. |
| 6,287,860 B1 | 9/2001 | Monia et al. |
| 6,453,242 B1 | 9/2002 | Eisenberg et al. |
| 6,534,261 B1 | 3/2003 | Cox, III et al. |
| 7,427,396 B2 | 9/2008 | Arbetman et al. |
| 7,588,772 B2 | 9/2009 | Kay et al. |
| 7,888,121 B2 | 2/2011 | Urnov et al. |
| 7,972,854 B2 | 7/2011 | Miller et al. |
| 8,252,538 B2 | 8/2012 | Croce et al. |
| 8,389,210 B2 | 3/2013 | Croce et al. |
| 8,415,096 B2 | 4/2013 | Mohapatra et al. |
| 9,193,769 B2 | 11/2015 | Chiorini et al. |
| 9,238,800 B2 | 1/2016 | Bossis et al. |
| 2003/0158403 A1 | 8/2003 | Manoharan et al. |
| 2005/0059005 A1 | 3/2005 | Tuschl et al. |
| 2005/0261218 A1 | 11/2005 | Esau et al. |
| 2009/0092974 A1 | 4/2009 | Davison et al. |
| 2009/0131348 A1 | 5/2009 | Labourier et al. |
| 2009/0263803 A1 | 10/2009 | Beaudenon et al. |
| 2010/0286232 A1 | 11/2010 | Schmittgen et al. |
| 2010/0323357 A1 | 12/2010 | Nana-Sin Kam et al. |
| 2011/0145940 A1 | 6/2011 | Voytas et al. |
| 2011/0171646 A1 | 7/2011 | Schmittgen et al. |
| 2011/0281756 A1 | 11/2011 | Wu et al. |
| 2012/0053224 A1 | 3/2012 | Meister et al. |
| 2012/0214699 A1 | 8/2012 | Croce et al. |
| 2012/0264626 A1 | 10/2012 | Nana-Sin Kam et al. |
| 2012/0283310 A1 | 11/2012 | Croce et al. |
| 2012/0309645 A1 | 12/2012 | Keller et al. |
| 2012/0316081 A1 | 12/2012 | List et al. |
| 2012/0329672 A1 | 12/2012 | Croce et al. |
| 2013/0042333 A1 | 2/2013 | Judde et al. |
| 2013/0053263 A1 | 2/2013 | Keller et al. |
| 2013/0053264 A1 | 2/2013 | Keller et al. |
| 2013/0059015 A1 | 3/2013 | Lancaster et al. |
| 2014/0068797 A1 | 3/2014 | Doudna et al. |
| 2014/0179768 A1 | 6/2014 | Bettencourt et al. |
| 2015/0315594 A1 | 11/2015 | Prakash |
| 2016/0017005 A1 | 1/2016 | Asokan et al. |
| 2016/0153004 A1 | 6/2016 | Zhang et al. |
| 2016/0153005 A1 | 6/2016 | Zhang et al. |
| 2016/0175462 A1 | 6/2016 | Zhang et al. |
| 2021/0355463 A1 | 11/2021 | Cobaugh |
| 2023/0159926 A1* | 5/2023 | Chadwick ............ C12N 9/6454 514/44 R |

FOREIGN PATENT DOCUMENTS

| | | |
|---|---|---|
| WO | WO1995/013365 | 5/1995 |
| WO | WO1995/013392 | 5/1995 |
| WO | WO1996/017947 | 6/1996 |
| WO | WO1997/006243 | 2/1997 |
| WO | WO1997/008298 | 3/1997 |
| WO | WO1997/009441 | 3/1997 |
| WO | WO1997/021825 | 6/1997 |
| WO | WO1998/053058 | 11/1998 |
| WO | WO1998/053059 | 11/1998 |
| WO | WO1998/053060 | 11/1998 |
| WO | WO1999/011764 | 3/1999 |
| WO | WO2001/083692 | 11/2001 |
| WO | WO2002/016536 | 2/2002 |
| WO | WO2003/016496 | 2/2003 |
| WO | WO2007/081740 | 7/2007 |
| WO | WO2008/016473 | 2/2008 |
| WO | WO2008/054828 | 5/2008 |
| WO | WO2008/073915 | 6/2008 |
| WO | WO2008/154098 | 12/2008 |
| WO | WO2008/157688 | 12/2008 |
| WO | WO2009/070653 | 6/2009 |
| WO | WO2009/100430 | 8/2009 |

(56) References Cited

FOREIGN PATENT DOCUMENTS

| WO | WO2009/149253 | 12/2009 | | |
|---|---|---|---|---|
| WO | WO2010/018563 | 2/2010 | | |
| WO | WO2011/015347 | 2/2011 | | |
| WO | WO2011/076142 | 6/2011 | | |
| WO | WO2011/076143 | 6/2011 | | |
| WO | WO2011/095623 | 8/2011 | | |
| WO | WO2011/157294 | 12/2011 | | |
| WO | WO2012/151212 | 11/2012 | | |
| WO | WO2012/177784 | 12/2012 | | |
| WO | WO2013/011378 | 1/2013 | | |
| WO | WO2013/033640 | 3/2013 | | |
| WO | WO2013/052523 | 4/2013 | | |
| WO | WO2013/059475 | 4/2013 | | |
| WO | WO2013/066678 | 5/2013 | | |
| WO | WO2013/090648 | 6/2013 | | |
| WO | WO2013/151666 | 10/2013 | | |
| WO | WO2013/176772 | 11/2013 | | |
| WO | WO2014/204726 | 12/2014 | | |
| WO | WO2014/204728 | 12/2014 | | |
| WO | WO2014/204729 | 12/2014 | | |
| WO | WO2015/100394 | 7/2015 | | |
| WO | WO 2015/100394 A1 * | 7/2015 | ........... | C12N 15/113 |
| WO | WO2015/121501 | 8/2015 | | |
| WO | WO2015/168589 | 11/2015 | | |
| WO | WO2015/188933 | 12/2015 | | |
| WO | WO2016/193226 | 12/2016 | | |
| WO | WO2017/053297 | 3/2017 | | |
| WO | WO2017/066781 | 4/2017 | | |
| WO | WO2017/066782 | 4/2017 | | |
| WO | WO2017/066789 | 4/2017 | | |
| WO | WO2017/066791 | 4/2017 | | |
| WO | WO2017/066793 | 4/2017 | | |
| WO | WO2017/066797 | 4/2017 | | |
| WO | WO2017/077386 | 5/2017 | | |
| WO | WO2017/093804 | 6/2017 | | |
| WO | WO2017/109757 | 6/2017 | | |
| WO | WO2017/134529 | 8/2017 | | |
| WO | WO2017/141109 | 8/2017 | | |
| WO | WO2017/158422 | 9/2017 | | |
| WO | WO2018/002719 | 1/2018 | | |
| WO | WO2018/002730 | 1/2018 | | |
| WO | WO2018/020323 | 2/2018 | | |
| WO | WO2018/075827 | 4/2018 | | |
| WO | WO2018/154387 | 8/2018 | | |
| WO | WO2020/247604 | 12/2020 | | |
| WO | WO2021/207711 | 10/2021 | | |

OTHER PUBLICATIONS

An et al., "Recurrent atherosclerotic cardiovascular event rates differ among patients meeting the very high risk definition according to age, sex, race/ethnicity, and socioeconomic status," Journal of the American Heart Association 2020, 9(23), in 23 pages.
Anand et al., "Micro RNA-mediated regulation of the angiogenic switch," Curr. Opin. Hematol. 2011, 18, 171-176.
Angart et al., "Design of siRNA therapeutics from the molecular scale," Pharmaceuticals 2013, 6(4), 440-468.
Annoni et al., "In vivo delivery of a microRNA-regulated transgene induces antigen-specific regulatory T cells and promotes immunologic tolerance," Blood 2009, 114, 5152-5161.
Athyros et al., "Drugs that mimic the effect of gene mutations for the prevention or the treatment of atherosclerotic disease: from PCSK9 inhibition to ANGPTL3 inactivation," Current Pharmaceutical Design 2018, 24(31), 3638-3646.
Barquera et al., "Global overview of the epidemiology of atherosclerotic cardiovascular disease," Archives of Medical Research 2015, 46(5), 328-338.
Barrangou et al., "CRISPR provides acquired resistance against viruses in prokaryotes," Science 2007, 315(5819), 1709-1712.
Barrett et al., "Reliable generation of induced pluripotent stem cells from human lymphoblastoid cell lines," Stem Cells Translational Medicine 2014, 3(12), 1429-1434.

Barros & Gollob, "Safety profile of RNAi nanomedicines," Advanced Drug Delivery Reviews 2012, 64(15), 1730-1737.
Bartel, "MicroRNAs: Target recognition and regulatory functions," Cell 2009, 136, 215-233.
Barter et al., "Effects of torcetrapib in patients at high risk for coronary events," New England Journal of Medicine 2007, 357(21), 2109-2122.
Behlke, "Chemical modification of siRNAs for in vivo use," Oligonucleotides 2008, 18(4), 305-320.
Belfort & Bonocora, "Homing endonucleases: from genetic anomalies to programmable genomic clippers," Homing Endonucleases: Methods and Protocols. Methods in Molecular Biology 2014, 1123, 1-26.
Benn et al., "Mutations causative of familial hypercholesterolaemia: screening of 98 098 individuals from the Copenhagen General Population Study estimated a prevalence of 1 in 217," European Heart Journal 2016, 37(17), 1384-1394.
Bergmann, "Non-HDL cholesterol and evaluation of cardiovascular disease risk," The Journal of the International Federation of Clinical Chemistry and Laboratory Medicine 2010, 21(3), 64-67.
Bhatia et al., "Controlling cell interactions of micropatterning in co-cultures: hepatocytes and 3T3 fibroblasts," J. Biomedical Materials Research 1997, 34(2), 189-199.
Bhatia et al., "Effect of cell-cell interactions in preservation of cellular phenotype: cocultivation of hepatocytes and nonparenchymal cells," The FASEB Journal 1999, 13(14), 1883-1900.
Bhatt et al., "Cardiovascular risk reduction with icosapent ethyl for hypertriglyceridemia," New England Journal of Medicine 2019, 380(1), 11-22.
Boch et al., "Breaking the code of DNA binding specificity of TAL-type III effectors," Science 2009, 326(5959), 1509-1512.
Boissel & Scharenberg, "Assembly and characterization of megaTALs for hyperspecific genome engineering applications," Chromosomal Mutagenesis 2015, 171-196.
Boissel et al., "megaTALs: a rare-cleaving nuclease architecture for therapeutic genome engineering," Nucleic Acids Research 2014, 42(4), 2591-2601.
Bonauer et al., "Vascular micrornas," Current Drug Targets 2010, 11(8), 943-949.
Bortesi et al., "The CRISPR/Cas9 system for plant genome editing and beyond," Biotechnology Advances 2015, 33, 41-52.
Braasch & Corey, "Novel antisense and peptide nucleic acid strategies for controlling gene expression," Biochemistry 2002, 41(14), 4503-4510.
Brahm & Hegele, "Chylomicronaemia—current diagnosis and future therapies," Nature Reviews Endocrinology 2015, 11(6), 352-362.
Bramsen & Kjems, "Development of therapeutic-grade small interfering RNAs by chemical engineering," Frontiers in Genetics 2012, 3, in 22 pages.
Brett et al., "Evolving worldwide approaches to lipid management and implications for Australian general practice," Australian Journal of General Practice 2021, 50(5), 297-304.
Brinkman et al., "Easy quantitative assessment of genome editing by sequence trace decomposition," Nucleic Acids Research 2014, 42(22), in 8 pages.
Budniatzky & Gepstein, "Concise review: reprogramming strategies for cardiovascular regenerative medicine: from induced pluripotent stem cells to direct reprogramming," Stem Cells Translational Medicine 2014, 3(4), 448-457.
Burnett et al., "Current progress of siRNA/shRNA therapeutics in clinical trials," Biotechnology Journal 2011, 6(9), 1130-1146.
Calandra et al., "Familial combined hypolipidemia due to mutations in the ANGPTL3 gene," Clinical Lipidology 2013, 8(1), 81-95.
Calandra et al., "Impact of rare variants in autosomal dominant hypercholesterolemia causing genes," Current Opinion in Lipidology 2017, 28(3), 267-272.
Canver et al., "BCL11A enhancer dissection by Cas9-mediated in situ saturating mutagenesis," Nature 2015, 527(7577), 192-197.
Carr et al., "A new on-line dual enzymatic method for simultaneous quantification of cholesterol and triglycerides iEnzymatic determination of triglyceride, free cholesterol, and total cholesterol in tissue lipid extracts," Clinical Biochemistry 1993, 26(1), 39-42.

(56) References Cited

OTHER PUBLICATIONS

Carr et al., "Non-HDL-cholesterol and apolipoprotein B compared with LDL-cholesterol in atherosclerotic cardiovascular disease risk assessment," Pathology 2019, 51(2), 148-154.
Carter, "Adeno-associated virus vectors," Current Opinion in Biotechnology 1992, 3(5), 533-539.
Ceccaldi et al. "Homologous-recombination-deficient tumours are dependent on Pole-mediated repair," Nature 2015, 518(7538), 258-262.
Cekaite et al., "Gene expression analysis in blood cells in response to unmodified and 2'-modified siRNAs reveals TLR-dependent and independent effects," Journal of Molecular Biology 2007, 365(1), 90-108.
Cermak et al., "Efficient design and assembly of custom TALEN and other TAL effector-based constructs for DNA targeting," Nucleic Acids Research 2011, 39(12), in 11 pages.
Cermak et al., "Efficient design and assembly of custom TALENs using the Golden Gate platform," Chromosomal Mutagenesis 2015, 133-159.
Chen et al., "Global microRNA depletion suppresses tumor angiogenesis," Genes & Development 2014, 28(10), 1054-1067.
Chernolovskaya & Zenkova, "Chemical modification of siRNA," Current Opinion in Molecular Therapeutics 2010, 12(2), 158-167.
Cho & Greenberg, "Familiar ends with alternative endings," Nature 2015, 518(7538), 174-175.
Christopoulou et al., "Effects of angiopoietin-like 3 on triglyceride regulation, glucose homeostasis, and diabetes," Disease Markers 2019, in 9 pages.
Chylinski et al., "The tracrRNA and Cas9 families of type II CRISPR-Cas immunity systems," RNA Biology 2013, 10(5), 726-737.
Clark et al., "A stable cell line carrying adenovirus-inducible rep and cap genes allows for infectivity titration of adeno-associated virus vectors," Gene Therapy 1996, 3, (12), 1124-1132.
Coelho et al., "Safety and efficacy of RNAi therapy for transthyretin amyloidosis," New England Journal of Medicine 2013, 369(9), 819-829.
Conklin et al., "Identification of a mammalian angiopoietin-related protein expressed specifically in liver," Genomics 1999, 62(3), 477-482.
Contreras & Rao, "MicroRNAs in inflammation and immune responses," Leukemia 2012, 26(3), 404-413.
Cox et al., Therapeutic genome editing: prospects and challenges, Nature Medicine 2015, 21(2), 121-131.
Cristea et al., "In vivo cleavage of transgene donors promotes nuclease-mediated targeted integration," Biotechnology and Bioengineering 2013, 110(3), 871-880.
Crooke et al., "Pharmacokinetic properties of several novel oligonucleotide analogs in mice," Journal of Pharmacology and Experimental Therapeutics 1996, 277(2), 923-937.
D'Erasmo et al., "Spectrum of mutations and long-term clinical outcomes in genetic chylomicronemia syndromes," Arteriosclerosis, Thrombosis, and Vascular Biology 2019, 39(12), 2531-2541.
De Mesmaeker et al., "Antisense oligonucleotides," Accounts of Chemical Research 1995, 28(9), 366-374.
Deleavey et al., "Chemical modification of siRNA," Current Protocols in Nucleic Acid Chemistry 2009, 39(1), in 22 pages.
Deltcheva et al., "CRISPR RNA maturation by trans-encoded small RNA and host factor RNase III," Nature 2011, 471(7340), 602-607.
Deverman et al., "Cre-dependent selection yields AAV variants for widespread gene transfer to the adult brain," Nature Biotechnology 2016, 34(2), 204-209.
Dewey et al., "Genetic and pharmacologic inactivation of ANGPTL3 and cardiovascular disease," New England Journal of Medicine 2017, 377(3), 211-221.
Dreier et al., "Development of zinc finger domains for recognition of the 5'-CNN-3' family DNA sequences and their use in the construction of artificial transcription factors," Journal of Biological Chemistry 2005, 280(42), 35588-35597.
Dreier et al., "Development of zinc finger domains for recognition of the 5'-ANN-3' family of DNA sequences and their use in the construction of artificial transcription factors," Journal of Biological Chemistry 2001, 276(31), 29466-29478.
Dreier et al., "Insights into the molecular recognition of the 5'-GNN-3' family of DNA sequences by zinc finger domains," Journal of Molecular Biology 2000, 303(4), 489-502.
Duan et al., "Differentiation and characterization of metabolically functioning hepatocytes from human embryonic stem cells," Stem Cells 2010, 28(4), 674-686.
Elseweidy et al., "Azelastine a potent antihistamine agent, as hypolipidemic and modulator for aortic calcification in diabetic hyperlipidemic rats model," Archives of Physiology and Biochemistry 2022, 128(6), 1611-1618.
Elseweidy et al., "Losartan and azelastine either alone or in combination as modulators for endothelial dysfunction and platelets activation in diabetic hyperlipidemic rats," Journal of Pharmacy and Pharmacology 2020, 72(12), 1812-1821.
Englisch & Gauss, "Chemically modified oligonucleotides as probes and inhibitors," Angewandte Chemie International Edition in English 1991, 30(6), 613-629.
Fan et al., "Prevalence of US adults with triglycerides≥ 150 mg/dl: NHANES 2007-2014," Cardiology and Therapy 2020, 9, 207-213.
Farrell et al., "RefSeq Functional Elements as experimentally assayed nongenic reference standards and functional interactions in human and mouse," Genome Research 2022, 32(1), 175-188.
FDA, "Drug-induced liver injury: premarketing clinical evaluation," U.S. Department of Health and Human Services 2009, in 28 pages.
Ference et al., "Association of triglyceride-lowering LPL variants and LDL-C-lowering LDLR variants with risk of coronary heart disease," JAMA 2019, 321(4), 364-373.
Focosi et al., "Induced pluripotent stem cells in hematology: current and future applications," Blood Cancer Journal 2014, 4(5), in 8 pages.
Fonfara et al., "Phylogeny of Cas9 determines functional exchangeability of dual-RNA and Cas9 among orthologous type II CRISPR-Cas systems," Nucleic Acids Research 2014, 42(4), 2577-2590.
Fucini et al., "Adenosine modification may be preferred for reducing siRNA immune stimulation," Nucleic Acid Therapeutics 2012, 22(3), 205-210.
Fujimoto et al., "Angptl3-null mice show low plasma lipid concentrations by enhanced lipoprotein lipase activity," Experimental Animals 2006, 55(1), 27-34.
Gaglione & Messere, "Recent progress in chemically modified siRNAs," Mini Reviews in Medicinal Chemistry 2010, 10(7), 578-595.
Gebeyehu et al., "Novel biotinylated nucleotide-analogs for labeling and colorimetric detection of DNA," Nucleic Acids Research 1987, 15(11), 4513-4534.
Genbank, "*Homo sapiens* chromosome 1, GRCh38.p14 Primary Assembly," National Library of Medicine 2023, in 3 pages.
Genbank, "Q99ZW2.1," GenBank 2014 in 17 pages.
Gentner & Naldini, "Exploiting microRNA regulation for genetic engineering," Tissue Antigens 2012, 80(5), 393-403.
Gillmore et al., "CRISPR-Cas9 in vivo gene editing for transthyretin amyloidosis," New England Journal of Medicine 2021, 385(6), 493-502.
Goldberg & Chait, "A comprehensive update on the chylomicronemia syndrome," Frontiers in Endocrinology 2020, 11, in 13 pages.
Gong et al., "A Versatile Nonviral Delivery System for Multiplex Gene-Editing in the Liver," Advanced Materials 2020, 32(46), 2003537.
Graham et al., "Cardiovascular and metabolic effects of ANGPTL3 antisense oligonucleotides," New England Journal of Medicine 2017, 377, 222-232.
Grimm et al., "In vitro and in vivo gene therapy vector evolution via multispecies interbreeding and retargeting of adeno-associated viruses," Journal of Virology 2008, 82(12), 5887-5911.
Grimson et al., "MicroRNA targeting specificity in mammals: determinants beyond seed pairing," Molecular Cell 2007, 27(1), 91-105.

(56) References Cited

OTHER PUBLICATIONS

Grundy et al., "2018 AHA/ACC/AACVPR/AAPA/ABC/ACPM/ADA/AGS/APhA/ASPC/NLA/PCNA guideline on the management of blood cholesterol: a report of the American College of Cardiology/American Heart Association Task Force on Clinical Practice Guidelines," Circulation 2019, 139(25), e1082-e1143.
Gryn et al., "Novel therapeutics in hypertriglyceridemia," Curr. Opin. Lipidol., 2015, 26(6), 484-491.
Guilinger et al., "Fusion of catalytically inactive Cas9 to FokI nuclease improves the specificity of genome modification," Nature Biotechnology 2014, 32(6), 577-582.
Gusarova et al., "ANGPTL3 blockade with a human monoclonal antibody reduces plasma lipids in dyslipidemic mice and monkeys," Journal of Lipid Research 2015, 56(7), 1308-1317.
Haeussler et al., "Evaluation of off-target and on-target scoring algorithms and integration into the guide RNA selection tool CRISPOR," Genome Biology 2016, 17, in 12 pages.
Hafez & Hausner, "Homing endonucleases: DNA scissors on a mission," Genome 2012, 55(8), 553-569.
Hale et al., "RNA-guided RNA cleavage by a CRISPR RNA-Cas protein complex," Cell 2009, 139(5), 945-956.
Han et al., "Comparison of lipoprotein separation and lipid analysis methodologies for human and cynomolgus monkey plasma samples," Journal of Cardiovascular Translational Research 2012, 5, 75-83.
Heasman, "Morpholino oligos: making sense of antisense?," Developmental Biology 2002, 243(2), 209-214.
Hegele et al., "A polygenic basis for four classical Fredrickson hyperlipoproteinemia phenotypes that are characterized by hypertriglyceridemia," Human Molecular Genetics 2009, 18(21), 4189-4194.
Helgadottir et al., "Variants with large effects on blood lipids and the role of cholesterol and triglycerides in coronary disease," Nature Genetics 2016, 48(6), 634-639.
Hermonat & Muzyczka, "Use of adeno-associated virus as a mammalian DNA cloning vector: transduction of neomycin resistance into mammalian tissue culture cells," Proceedings of the National Academy of Sciences 1984, 81(20), 6466-6470.
Herranz & Cohen, "MicroRNAs and gene regulatory networks: managing the impact of noise in biological systems," Genes & Development 2010, 24(13), 1339-1344.
Herrera et al., "Isolation and characterization of a stem cell population from adult human liver," Stem Cells 2006, 24(12), 2840-2850.
Horvath et al., "Diversity, activity, and evolution of CRISPR loci in *Streptococcus thermophilus*," Journal of Bacteriology 2008, 190(4), 1401-1412.
HPS2-THRIVE Collaborative Group, "HPS2-THRIVE randomized placebo-controlled trial in 25 673 high-risk patients of ER niacin/laropiprant: trial design, pre-specified muscle and liver outcomes, and reasons for stopping study treatment," European Heart Journal 2013, 34(17), 1279-1291.
Hu et al., "Physiological roles of asialoglycoprotein receptors (ASGPRs) variants and recent advances in hepatic-targeted delivery of therapeutic molecules via ASGPRs," Protein and Peptide Letters 2014, 21(10), 1025-1030.
Huangfu et al., "Induction of pluripotent stem cells by defined factors is greatly improved by small-molecule compounds," Nature Biotechnology 2008, 26(7), 795-797.
International Preliminary Report on Patentability, dated Sep. 6, 2019 in International Application No. PCT/IB2018/000228.
International Search Report and Written Opinion, dated May 23, 2018 in International Application No. PCT/IB2018/000228.
Jin et al., "Hepatic proprotein convertases modulate HDL metabolism," Cell Metabolism 2007, 6(2), 129-136.
Jinek et al., "A programmable dual-RNA-guided DNA endonuclease in adaptive bacterial immunity," Science 2012, 337(6096), 816-821.
Judge & MacLachlan, "Overcoming the innate immune response to small interfering RNA," Human Gene Therapy 2008, 19(2), 111-124.
Judge et al., "Design of noninflammatory synthetic siRNA mediating potent gene silencing in vivo," Molecular Therapy 2006, 13(3), 494-505.
Kabanov et al., "A new class of antivirals: antisense oligonucleotides combined with a hydrophobic substituent effectively inhibit influenza virus reproduction and synthesis of virus-specific proteins in MDCK cells," FEBS letters 1990, 259(2), 327-330.
Kanasty et al., "Action and reaction: the biological response to siRNA and its delivery vehicles," Molecular Therapy 2012, 20(3), 513-524.
Karikó et al., "Suppression of RNA recognition by Toll-like receptors: the impact of nucleoside modification and the evolutionary origin of RNA," Immunity 2005, 23(2), 165-175.
Kasiewicz et al., "Lipid nanoparticles incorporating a GalNAc ligand enable in vivo liver ANGPTL3 editing in wild-type and somatic LDLR knockout non-human primates," bioRxiv 2021, in 7 pages.
Kathiresan et al., "Common variants at 30 loci contribute to polygenic dyslipidemia," Nature Genetics 2009, 41(1), 56-65.
Kathiresan et al., "Six new loci associated with blood low-density lipoprotein cholesterol, high-density lipoprotein cholesterol or triglycerides in humans," Nature Genetics 2008, 40(2), 189-197.
Keech & Sleight, "Lipid screening in aircrew: pros and cons," European Heart Journal 1992, 13(suppl_H), 50-53.
Kent et al., "Mechanism of microhomology-mediated end-joining promoted by human DNA polymerase θ," Nature Structural & Molecular Biology 2015, 22(3), 230-237.
Kersten, "ANGPTL3 as therapeutic target," Current Opinion in Lipidology 2021, 32(6), 335-341.
Kim et al., "Digenome-seq: genome-wide profiling of CRISPR-Cas9 off-target effects in human cells," Nature Methods 2015, 12(3), 237-243.
Kim et al., "Genome-wide target specificities of CRISPR-Cas9 nucleases revealed by multiplex Digenome-seq," Genome Research 2016, 26(3), 406-415.
Kim et al., "Identifying genome-wide off-target sites of CRISPR RNA—guided nucleases and deaminases with Digenome-seq," Nature Protocols 2021, 16(2), 1170-1192.
Kleinstiver et al., "The I-TevI nuclease and linker domains contribute to the specificity of monomeric TALENs," G3: Genes, Genomes, Genetics 2014, 4(6) 1155-1165.
Kole et al., "RNA therapeutics: beyond RNA interference and antisense oligonucleotides," Nature Reviews Drug Discovery 2012, 11(2), 125-140.
Kormann et al., "Expression of therapeutic proteins after delivery of chemically modified mRNA in mice," Nature biotechnology 2011, 29(2), 154-157.
Köster et al., "Transgenic angiopoietin-like (angptl) 4 overexpression and targeted disruption of angptl4 and angptl3: regulation of triglyceride metabolism," Endocrinology 2005, 146(11), 4943-4950.
Kroschwitz, "Concise Encyclopedia of Polymer Science and Engineering," Edited by Jacqueline I. Kroschwitz. Wiley 1990, 858-859.
Labrijn et al., "Therapeutic IgG4 antibodies engage in Fab-arm exchange with endogenous human IgG4 in vivo," Nature Biotechnology 2009, 27(8), 767-771.
Lacerra et al., "Restoration of hemoglobin A synthesis in erythroid cells from peripheral blood of thalassemic patients," Proceedings of the National Academy of Sciences 2000, 97(17), 9591-9596.
Landgraf et al., "A mammalian microRNA expression atlas based on small RNA library sequencing," Cell 2007, 129(7), 1401-1414.
Laufs et al., "Clinical review on triglycerides, " European Heart Journal 2020, 41(1): 99-109c.
Lebkowski et al., "Adeno-associated virus: a vector system for efficient introduction and integration of DNA into a variety of mammalian cell types," Molecular and Cellular Biology 1988, 8(10), 3988-3996.
Lee et al., "Identification of a new functional domain in angiopoietin-like 3 (ANGPTL3) and angiopoietin-like 4 (ANGPTL4) involved in binding and inhibition of lipoprotein lipase (LPL)," Journal of Biological Chemistry 2009, 284(20), 13735-13745.

(56) References Cited

OTHER PUBLICATIONS

LEES & Sloane Stanley, "A simple method for the isolation and purification of total lipides from animal tissues," Journal of Biological Chemistry 1956, 226, 497-509.
Letsinger et al., "Cholesteryl-conjugated oligonucleotides: synthesis, properties, and activity as inhibitors of replication of human immunodeficiency virus in cell culture," Proceedings of the National Academy of Sciences 1989, 86(17), 6553-6556.
Li et al., "Modularly assembled designer TAL effector nucleases for targeted gene knockout and gene replacement in eukaryotes," Nucleic Acids Research 2011, 39(14), 6315-6325.
Li, "Toward better understanding of artifacts in variant calling from high-coverage samples," Bioinformatics 2014, 30(20), 2843-2851.
Liu et al., "Angiopoietin-like protein 3 inhibits lipoprotein lipase activity through enhancing its cleavage by proprotein convertases," Journal of Biological Chemistry 2010, 285(36), 27561-27570.
Liu et al., "Validated zinc finger protein designs for all 16 GNN DNA triplet targets," Journal of Biological Chemistry 2002, 277(6), 3850-3856.
Ma et al., "Highly efficient differentiation of functional hepatocytes from human induced pluripotent stem cells," Stem Cells Translational Medicine 2013, 2(6), 409-419.
Ma et al., "Pol III promoters to express small RNAs: delineation of transcription initiation," Molecular Therapy-Nucleic Acids 2014, 3, in 11 pages.
Mach et al., "2019 ESC/EAS Guidelines for the management of dyslipidaemias: lipid modification to reduce cardiovascular risk: the Task Force for the management of dyslipidaemias of the European Society of Cardiology (ESC) and European Atherosclerosis Society (EAS)," European Heart Journal 2020, 41(1), 111-188.
Maherali & Hochedlinger, "Guidelines and techniques for the generation of induced pluripotent stem cells," Cell Stem Cell 2008, 3(6), 595-605.
Mak et al., "The crystal structure of TAL effector PthXo1 bound to its DNA target," Science 2012, 335(6069), 716-719.
Manoharan et al., "Chemical modifications to improve uptake and bioavailability of antisense oligonucleotides," Annals of the New York Academy of Sciences 1992, 660(1), 306-309.
Manoharan et al., "Cholic acid-oligonucleotide conjugates for antisense applications," Bioorganic & Medicinal Chemistry Letters 1994, 4(8), 1053-1060.
Manoharan et al., "Introduction of a lipophilic thioether tether in the minor groove of nucleic acids for antisense applications," Bioorganic & Medicinal Chemistry Letters 1993, 3(12), 2765-2770.
Manoharan et al., "Lipidic nucleic acids," Tetrahedron Letters 1995, 36(21), 3651-3654.
Manoharan et al., "Oligonucleotide conjugates: alteration of the pharmacokinetic properties of antisense agents," Nucleosides, Nucleotides & Nucleic Acids 1995, 14(3-5), 969-973.
Maresca et al., "Obligate ligation-gated recombination (ObLiGaRe): custom-designed nuclease-mediated targeted integration through nonhomologous end joining," Genome Research 2013, 23(3), 539-546.
Marson et al., "Wnt signaling promotes reprogramming of somatic cells to pluripotency," Cell Stem Cell 2008, 3(2), 132-135.
Martín-Campos et al., "Identification of a novel mutation in the ANGPTL3 gene in two families diagnosed of familial hypobetalipoproteinemia without APOB mutation," Clinica Chimica Acta 2012, 413(5-6), 552-555.
Martin, "Ein Neuer Zugang Zu 2'-O-Alkylribonucleosiden Und Eigenschaften Deren Oligonucleotide," Helvetica Chimica Acta 1995, 78(2), 486-504.
März et al., "Utilization of lipid-modifying therapy and low-density lipoprotein cholesterol goal attainment in patients at high and very-high cardiovascular risk: real-world evidence from Germany," Atherosclerosis 2018, 268, 99-107.
Mateos-Gomez et al., "Mammalian polymerase θ promotes alternative NHEJ and suppresses recombination," Nature 2015, 518(7538), 254-257.

McGowan et al., "Diagnosis and treatment of heterozygous familial hypercholesterolemia," Journal of the American Heart Association 2019, 8(24), e013225.
McLaughlin et al., "Adeno-associated virus general transduction vectors: analysis of proviral structures," Journal of Virology 1988, 62(6), 1963-1973.
Merkel et al., "Lipoprotein lipase: genetics, lipid uptake, and regulation," Journal of Lipid Research 2002, 43(12), 1997-2006.
Minicocci et al., "Clinical characteristics and plasma lipids in subjects with familial combined hypolipidemia: a pooled analysis," Journal of Lipid Research 2013, 54(12), 3481-3490.
Minicocci et al., "Mutations in the ANGPTL3 gene and familial combined hypolipidemia: a clinical and biochemical characterization," The Journal of Clinical Endocrinology & Metabolism 2012, 97(7), E1266-E1275.
Mishra et al., "Improved leishmanicidal effect of phosphorotioate antisense oligonucleotides by LDL-mediated delivery," Biochimica et Biophysica Acta (BBA)—Gene Structure and Expression 1995, 1264(2), 229-237.
Mojica et al., "Short motif sequences determine the targets of the prokaryotic CRISPR defence system," Microbiology 2009, 155(3), 733-740.
Moscou & Bogdanove, "A simple cipher governs DNA recognition by TAL effectors," Science 2009, 326(5959), 1501-1501.
Murphy et al., "Mice with megabase humanization of their immunoglobulin genes generate antibodies as efficiently as normal mice," Proceedings of the National Academy of Sciences 2014, 111(14), 5153-5158.
Musunuru et al., "Exome sequencing, ANGPTL3 mutations, and familial combined hypolipidemia," New England Journal of Medicine 2010, 363(23), 2220-2227.
Muzyczka, "Use of adeno-associated virus as a general transduction vector for mammalian cells," Viral Expression Vectors 1992, 97-129.
Myszka, "Improving biosensor analysis," Journal of Molecular Recognition 1999, 12(5), 279-284.
Nasevicius & Ekker, "Effective targeted gene 'knockdown' in zebrafish," Nature Genetics 2000, 26(2), 216-220.
Nielsen et al., "Sequence-selective recognition of DNA by strand displacement with a thymine-substituted polyamide," Science 1991, 254(5037), 1497-1500.
Notice of Allowance dated Feb. 21, 2023 in Japanese Patent Application No. 2019-545759, in 6 pages.
Noto et al., "Prevalence of ANGPTL3 and APOB gene mutations in subjects with combined hypolipidemia," Arteriosclerosis, Thrombosis, and Vascular Biology 2012, 32(3), 805-809.
NVDPA, "Guidelines for the Management of Absolute Cardiovascular Disease Risk," National Vascular Disease Prevention Alliance (Endorsed by The Royal Australian College of General Practitioners) 2012, in 124 pages.
Oberhauser & Wagner, "Effective incorporation of 2'-O-methyl-oligoribonuclectides into liposomes and enhanced cell association through modification with thiocholesterol," Nucleic Acids Research 1992, 20(3), 533-538.
Office Action dated Nov. 3, 2022 in Chinese Patent Application No. 201880026603.5, in 24 pages.
Office Action dated Apr. 19, 2023 in Chinese Application No. 201880026603.5.
Office Action dated Aug. 23, 2022 in Japanese Patent Application No. 2019-545759, in 9 pages.
Office Action dated Feb. 8, 2022 in Japanese Patent Application No. 2019-545759, in 8 pages.
Office Action dated Aug. 23, 2023 in U.S. Appl. No. 16/487,300.
Oh et al., "Management of hypertriglyceridemia: common questions and answers," American Family Physician 2020, 102(6), 347-354.
Ono et al., "Protein region important for regulation of lipid metabolism in angiopoietin-like 3 (ANGPTL3): ANGPTL3 is cleaved and activated in vivo," Journal of Biological Chemistry 2003, 278(43), 41804-41809.
Pacific Biosciences, "Template Preparation and Sequencing Guide," Pacific Biosciences 2014, in 52 pages.

(56) References Cited

OTHER PUBLICATIONS

Paul et al., "Increased viral titer through concentration of viral harvests from retroviral packaging lines," Human Gene Therapy 1993, 4(5), 609-615.

Pearson et al., "2021 Canadian Cardiovascular Society guidelines for the management of dyslipidemia for the prevention of cardiovascular disease in adults," Canadian Journal of Cardiology 2021, 37(8), 1129-1150.

Peer & Lieberman, "Special delivery: targeted therapy with small RNAs," Gene Therapy 2011, 18(12), 1127-1133.

Perrin et al., "An experimental rabies vaccine produced with a new BHK-21 suspension cell culture process: use of serum-free medium and perfusion-reactor system," Vaccine 1995, 13(13), 1244-1250.

Pisciotta et al., "Characterization of three kindreds with familial combined hypolipidemia caused by loss-of-function mutations of ANGPTL3," Circulation: Cardiovascular Genetics 2012, 5(1), 42-50.

Pittenger et al., "Multilineage potential of adult human mesenchymal stem cells," Science 1999, 284(5411), 143-147.

Posadas & Carthew, "MicroRNAs and their roles in developmental canalization," Current Opinion in Genetics & Development 2014, 27, 1-6.

Pulicherla et al., "Engineering liver-detargeted AAV9 vectors for cardiac and musculoskeletal gene transfer," Molecular Therapy 2011, 19(6), 1070-1078.

Qiu et al., "Lipid nanoparticle-mediated codelivery of Cas9 mRNA and single-guide RNA achieves liver-specific in vivo genome editing of Angptl3," Proceedings of the National Academy of Sciences 2021, 118(10), in 10 pages.

Raal et al., "Evinacumab for homozygous familial hypercholesterolemia," New England Journal of Medicine 2020, 383(8), 711-720.

Rallidis et al., "Very high-risk familial hypercholesterolaemia patients in real life: the remaining gap in achieving the current LDL-C targets despite the use of PCSK9 inhibitors," Atherosclerosis 2020, 309, 67-69.

Reeskamp et al., "ANGPTL3 inhibition with evinacumab results in faster clearance of IDL and LDL apoB in patients with homozygous familial hypercholesterolemia-brief report," Arteriosclerosis, Thrombosis, and Vascular Biology 2021, 41(5), 1753-1759.

Renaud et al., "Improved Genome Editing Efficiency and Flexibility Using Modified Oligonucleotides with TALEN and CRISPR-Cas9 Nucleases," Cell Reports 2016, 2263-2272.

Robciuc et al., "Angptl3 deficiency is associated with increased insulin sensitivity, lipoprotein lipase activity, and decreased serum free fatty acids," Arteriosclerosis, Thrombosis, and Vascular Biology 2013, 33(7), 1706-1713.

Romeo et al., "Rare loss-of-function mutations in ANGPTL family members contribute to plasma triglyceride levels in humans," The Journal of Clinical Investigation 2009, 119(1), 70-79.

Rosenson et al., "Cholesterol efflux and atheroprotection: advancing the concept of reverse cholesterol transport," Circulation 2012, 125(15), 1905-1919.

Rosenson et al., "Evinacumab in patients with refractory hypercholesterolemia," New England Journal of Medicine 2020, 383(24), 2307-2319.

Rygiel, "Hypertriglyceridemia-common causes, prevention and treatment strategies," Current Cardiology Reviews 2018, 14(1), 67-76.

Saj & Lai, "Control of microRNA biogenesis and transcription by cell signaling pathways," Current Opinion in Genetics & Development 2011, 21(4), 504-510.

Sajja et al., "Comparison of methods to estimate low-density lipoprotein cholesterol in patients with high triglyceride levels," JAMA Network Open 2021, 4(10), in 14 pages.

Samulski et al., "Helper-free stocks of recombinant adeno-associated viruses: normal integration does not require viral gene expression," Journal of Virology 1989, 63(9), 3822-3828.

Sapranauskas et al., "The *Streptococcus thermophilus* CRISPR/Cas system provides immunity in *Escherichia coli*," Nucleic Acids Research 2011, 39(21), 9275-9282.

Sarwar et al. "Triglycerides and the risk of coronary heart disease: 10 158 incident cases among 262 525 participants in 29 Western prospective studies," Circulation 2007, 115(4), 450-458.

Sato et al., "Different kinetics for the hepatic uptake of lipid nanoparticles between the apolipoprotein E/low density lipoprotein receptor and the N-acetyl-d-galactosamine/asialoglycoprotein receptor pathway," Journal of Controlled Release 2020, 322, 217-226.

Sawitza et al., "Bile acids induce hepatic differentiation of mesenchymal stem cells," Scientific Reports 2015, 5(1), in 15 pages.

Segal et al., "Toward controlling gene expression at will: selection and design of zinc finger domains recognizing each of the 5'-GNN-3' DNA target sequences," Proceedings of the National Academy of Sciences 1999, 96(6), 2758-2763.

Shah et al., "Protospacer recognition motifs: mixed identities and functional diversity," RNA Biology 2013, 10(5), 891-899.

Shea et al., "Synthesis, hybridization properties and antiviral activity of lipid-oligodeoxynucleotide conjugates," Nucleic Acids Research 1990, 18(13), 3777-3783.

Shi et al., "A combined chemical and genetic approach for the generation of induced pluripotent stem cells," Cell Stem Cell 2008, 2(6), 525-528.

Shimamura et al., "Angiopoietin-like protein3 regulates plasma HDL cholesterol through suppression of endothelial lipase," Arteriosclerosis, Thrombosis, and Vascular Biology 2007, 27(2), 366-372.

Shimizugawa et al., "ANGPTL3 decreases very low density lipoprotein triglyceride clearance by inhibition of lipoprotein lipase," Journal of Biological Chemistry 2002, 277(37), 33742-33748.

Sjouke et al., "Homozygous autosomal dominant hypercholesterolaemia in the Netherlands: prevalence, genotype-phenotype relationship, and clinical outcome," European Heart Journal 2015, 36(9), 560-565.

Sniderman et al., "Apolipoprotein B particles and cardiovascular disease: a narrative review," JAMA Cardiology 2019, 4(12), 1287-1295.

Sonnenburg et al., "GPIHBP1 stabilizes lipoprotein lipase and prevents its inhibition by angiopoietin-like 3 and angiopoietin-like 4," Journal of Lipid Research 2009, 50(12), 2421-2429.

Soutar & Naoumova, "Mechanisms of disease: genetic causes of familial hypercholesterolemia," Nature Clinical Practice Cardiovascular Medicine 2007, 4(4), 214-225.

Soutschek et al., "Therapeutic silencing of an endogenous gene by systemic administration of modified siRNAs," Nature 2004, 432(7014), 173-178.

Steentoft et al., "Precision genome editing: a small revolution for glycobiology," Glycobiology 2014, 24(8), 663-680.

Stem-Ginossar et al., "Host Immune System Gene Targeting by a Viral miRNA," Science 2007, 317(5836), 376-381.

Stitziel et al., "ANGPTL3 deficiency and protection against coronary artery disease," Journal of the American College of Cardiology 2017, 69(16), 2054-2063.

Sturm et al., "Clinical genetic testing for familial hypercholesterolemia: JACC scientific expert panel," Journal of the American College of Cardiology 2018, 72(6), 662-680.

Svinarchuk et al., "Inhibition of HIV proliferation in MT-4 cells by antisense oligonucleotide conjugated to lipophilic groups," Biochimie 1993, 75, 49-54.

Takahashi & Yamanaka, "Induction of pluripotent stem cells from mouse embryonic and adult fibroblast cultures by defined factors," Cell 2006, 126(4), 663-676.

Takahashi et al., "Induction of Pluripotent Stem Cells from Adult Human Fibroblasts by Defined Factors," Cell 2007, 131(5), 861-872.

Tarugi et al., "Angiopoietin-like protein 3 (ANGPTL3) deficiency and familial combined hypolipidemia," Journal of Biomedical Research 2019, 33(2), 73-81.

Teslovich et al., "Biological, clinical and population relevance of 95 loci for blood lipids," Nature 2010, 466(7307), 707-713.

Tratschin et al., "A human parvovirus, adeno-associated virus, as a eucaryotic vector: transient expression and encapsidation of the procaryotic gene for chloramphenicol acetyltransferase," Molecular and Cellular Biology 1984, 4(10), 2072-2081.

(56) References Cited

OTHER PUBLICATIONS

Tratschin et al., "Adeno-associated virus vector for high-frequency integration, expression, and rescue of genes in mammalian cells," Molecular and Cellular Biology 1985, 5(11), 3251-3260.
Tsai et al., "Dimeric CRISPR RNA-guided FokI nucleases for highly specific genome editing," Nature Biotechnology 2014, 32(6), 569-576.
U.S. National Library of Medicine, "Study to Evaluate Safety, Tolerability, Pharmacokinetics, and Pharmacodynamics of NTLA-2001 in Patients With Hereditary Transthyretin Amyloidosis With Polyneuropathy (ATTRv-PN) and Patients With Transthyretin Amyloidosis-Related Cardiomyopathy (ATTR-CM)," ClinicalTrials.gov 2023, in 17 pages. https://clinicaltrials.gov/study/NCT04601051?term=nct04601051&rank=1.
Usui et al., "A new on-line dual enzymatic method for simultaneous quantification of cholesterol and triglycerides in lipoproteins by HPLC," Journal of Lipid Research 2002, 43(5), 805-814.
Valenzuela et al., "High-throughput engineering of the mouse genome coupled with high-resolution expression analysis." Nature Biotechnology 2003, 21(6), 652-659.
Van Zwol et al., "The future of lipid-lowering therapy," Journal of Clinical Medicine 2019, 8(7), in 16 pages.
Verma & Eckstein, "Modified oligonucleotides: synthesis and strategy for users," Annual Review of Biochemistry 1998, 67(1), 99-134.
Vijayaraghavan, "Treatment of dyslipidemia in patients with type 2 diabetes," Lipids in Health and Disease 2010, 9(1), in 12 pages.
Virani et al., "2021 ACC expert consensus decision pathway on the management of ASCVD risk reduction in patients with persistent hypertriglyceridemia: a report of the American College of Cardiology Solution Set Oversight Committee," Journal of the American College of Cardiology 2021, 78(9), 960-993.
Virani et al., "Heart disease and stroke statistics-2021 update: a report from the American Heart Association," Circulation 2021, 143(8), e254-e743.
Voight et al., "Plasma HDL cholesterol and risk of myocardial infarction: a mendelian randomisation study," The Lancet 2012, 380(9841), 572-580.
Volkov et al., "Selective protection of nuclease-sensitive sites in siRNA prolongs silencing effect," Oligonucleotides 2009, 19(2), 191-202.
Wang & Eckel, "Lipoprotein lipase: from gene to obesity," American Journal of Physiology-Endocrinology and Metabolism 2009, 297(2), E271-E288.
Wang et al., "Cyclohexene nucleic acids (CeNA): serum stable oligonucleotides that activate RNase H and increase duplex stability with complementary RNA," Journal of the American Chemical Society 2000, 122(36), 8595-8602.
Wang et al., "Inactivation of ANGPTL3 reduces hepatic VLDL-triglyceride secretion," Journal of Lipid Research 2015, 56(7), 1296-1307.
Wang et al., "Mice lacking ANGPTL8 (Betatrophin) manifest disrupted triglyceride metabolism without impaired glucose homeostasis," Proceedings of the National Academy of Sciences 2013, 110(40), 16109-16114.
Wang et al., "Rapid and efficient assembly of transcription activator-like effector genes by USER cloning," Journal of Genetics and Genomics 2014, 41(6), 339-347.
Warren et al., "Highly efficient reprogramming to pluripotency and directed differentiation of human cells with synthetic modified mRNA," Cell Stem Cell 2010, 7(5), 618-630.
Watts et al., "Integrated guidance for enhancing the care of familial hypercholesterolaemia in Australia," Heart, Lung and Circulation 2021, 30(3), 324-349.
Watts et al., "RNA interference targeting hepatic angiopoietin-like protein 3 results in prolonged reductions in plasma triglycerides and LDL-C in human subjects," Circulation 2019, 140(25), E987-E988.
Watts et al., "Transcriptomic therapy for dyslipidemias utilizing nucleic acids targeted at ANGPTL3," Future Cardiology 2021, 18(2), 143-153.
Weber et al., "A modular cloning system for standardized assembly of multigene constructs," PloS One 2011, 6(2), in 11 pages.
Weber et al., "Methylation of human microRNA genes in normal and neoplastic cells," Cell Cycle 2007, 6(9), 1001-1005.
Whitehead et al., "Silencing or stimulation? siRNA delivery and the immune system," Annual Review of Chemical and Biomolecular Engineering 2011, 2, 77-96.
Willer et al., "Newly identified loci that influence lipid concentrations and risk of coronary artery disease," Nature Genetics 2008, 40(2), 161-169.
Winkler, "Oligonucleotide conjugates for therapeutic applications," Therapeutic Delivery 2013, 4(7), 791-809.
Wolfs et al., "MegaTevs: single-chain dual nucleases for efficient gene disruption," Nucleic Acids Research 2014, 42(13), 8816-8829.
Wood & Seitzer, "Development of NTLA-2001, a CRISPR/Cas9 genome editing therapeutic for the treatment of ATTR," Second European Congress for ATTR Amyloidosis, Berlin 2019.
Wright et al., "Pooled patient-level analysis of inclisiran trials in patients with familial hypercholesterolemia or atherosclerosis," Journal of the American College of Cardiology 2021, 77(9), 1182-1193.
Xu et al., "Role of angiopoietin-like 3 (ANGPTL3) in regulating plasma level of low-density lipoprotein cholesterol," Atherosclerosis 2018, 268, 196-206.
Yamarnoto, "Genome Editing," Cosmo Bio Company, the 2nd Edition 2015, Table of Contents and pp. 85-87.
Yang et al., "Lipid disorders in NAFLD and chronic kidney disease," Biomedicines 2021, 9(10), in 18 pages.
Zhao et al., "Sequence-specific inhibition of microRNA via CRISPR/CRISPRi system," Scientific Reports 2014, 4(1), in 5 pages.

\* cited by examiner

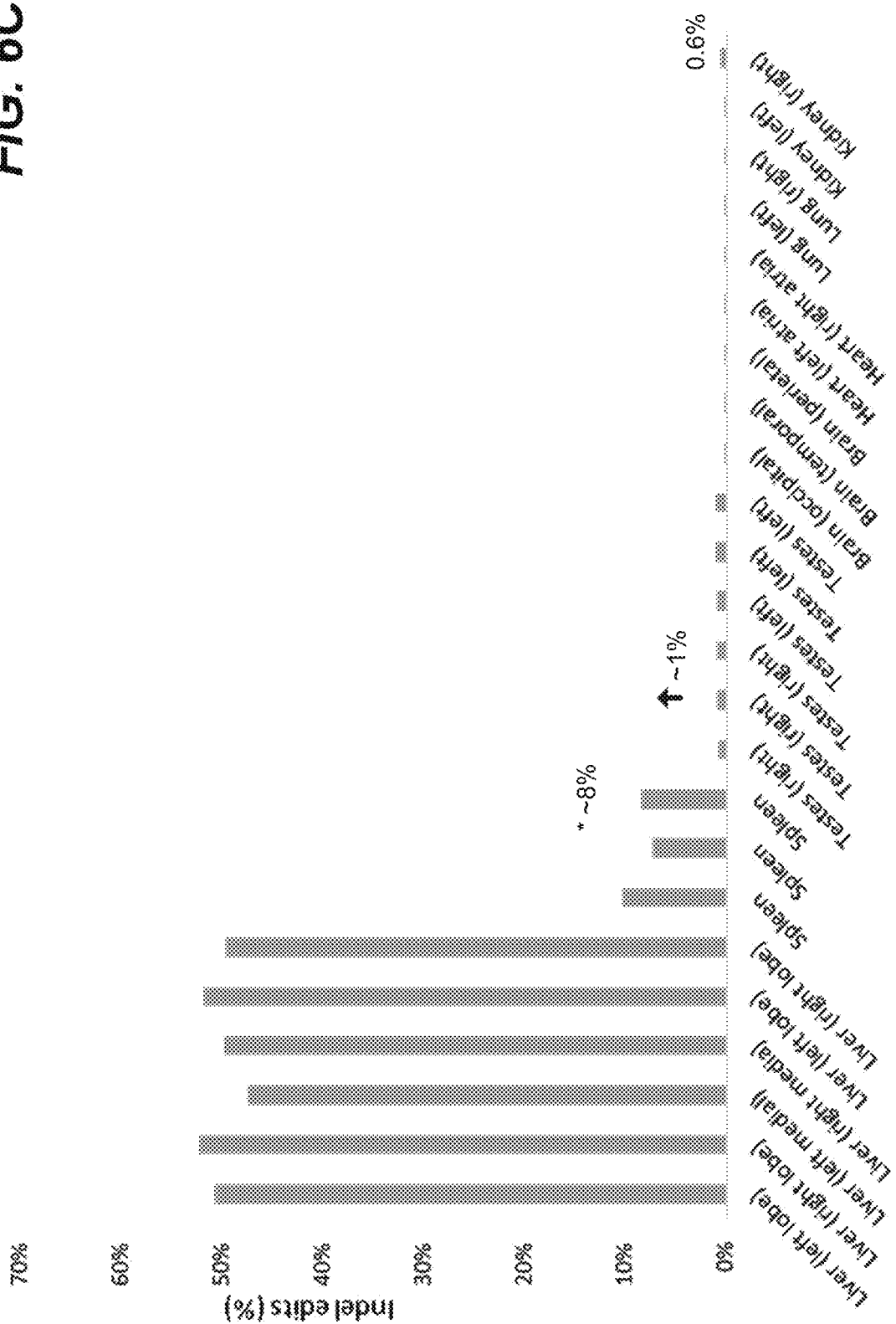

EC: effective concentration

PHH: primary human hepatocyte; EC: effective concentration

METHODS AND COMPOSITIONS FOR TREATING ANGIOPOIETIN-LIKE 3 (ANGPTL3) RELATED CONDITIONS

RELATED APPLICATIONS

The present application claims priority to U.S. Provisional Patent Application Ser. No. 63/315,372, filed Mar. 1, 2022, U.S. Provisional Patent Application Ser. No. 63/332,234, filed Apr. 18, 2022, U.S. Provisional Patent Application Ser. No. 63/352,747, filed Jun. 16, 2022, and U.S. Provisional Patent Application Ser. No. 63/380,557, filed Oct. 21, 2022. The entire contents of these applications are hereby expressly incorporated by reference in their entireties.

REFERENCE TO SEQUENCE LISTING

The present application is being filed along with a Sequence Listing in electronic format. The Sequence Listing is provided as a file entitled 80EM-341711-US_SeqListing, created Feb. 25, 2023, which is 383,556 bytes in size. The information in the electronic format of the Sequence Listing is incorporated herein by reference in its entirety.

BACKGROUND

Field

The present disclosure generally relates to the field of molecular biology and biotechnology, including gene editing.

Description of the Related Art

Angiopoietin-like 3 (ANGPTL3) is a member of the angiopoietin-like family of secreted factors that regulates lipid metabolism and that is predominantly expressed in the liver. ANGPTL3 dually inhibits the catalytic activities of lipoprotein lipase (LPL), which catalyzes the hydrolysis of triglycerides, and of endothelial lipase (EL), which hydrolyzes high density lipoprotein (HDL) phospholipids. ANGPTL3 is associated with various conditions, including lipid metabolism disorders (e.g., hyperlipidemia).

The targeting of DNA using the RNA-guided, DNA-targeting principle of CRISPR (Clustered Regularly Interspaced Short Palindromic Repeats)-Cas (CRISPR associated) systems has been widely used. CRISPR-Cas systems can be divided in two classes, with class 1 systems utilizing a complex of multiple Cas proteins (such as type I, III, and IV CRISPR-Cas systems) and class 2 systems utilizing a single Cas protein (such as type II, V, and VI CRISPR-Cas systems). Type II CRISPR-Cas-based systems have been used for genome editing, and require a Cas polypeptide or variant thereof guided by a customizable guide RNA (gRNA) for programmable DNA targeting.

There is a need for developing safe and effective therapy for treating ANGPTL3-related diseases and disorders.

SUMMARY

Disclosed herein include methods, compositions, and kits for treating ANGPTL3-related diseases or disorders. The method for treating an ANGPTL3-related disease or disorder, in some embodiments, comprises administering to a subject (e.g., primate subject) a plurality of nanoparticles complexed with (a) a guide RNA (gRNA) targeting ANGPTL3 gene or a nucleic acid encoding the gRNA, and (b) a nucleic acid encoding an RNA-guided endonuclease, thereby treating the ANGPTL3-related disease or disorder in the subject. In some embodiments, the subject is administered the plurality of nanoparticles two or more times. In some embodiments, each two of the two or more administrations is about 1 year, about 2 years, or about 5 years apart. In some embodiments, each two of the two or more administrations is about two weeks to about four weeks apart. In some embodiments, the plurality of nanoparticles is administered to the subject at a dose of about 0.01-5 mg/kg (determined by the total nucleic acids (e.g., the total of ANGPTL3 gRNA and Cas9 mRNA)) per administration, including 0.01 mg/kg, 0.05 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.5 mg/kg, 4 mg/kg, 4.5 mg/kg, or 5 mg/kg, or a number or a range between any two of these values. In some embodiments, the plurality of nanoparticles is administered to the subject at a dose of, or a dose about, 0.1 mg/kg, 0.3 mg/kg, 0.5 mg/kg, 0.6 mg/kg, 1 mg/kg, 1.5 mg/kg, 2 mg/kg or 3 mg/kg (determined by the total of ANGPTL3 gRNA and SpCas9 mRNA).

The ANGPTL3 expression (e.g., ANGPTL3 gene expression or ANGPTL3 protein expression) in the subject can be reduced, for example, by at least 20%, by at least 30%, by at least 40%, by at least 50%, by at least 60%, or by at least 70% after the administration. The concentration of ANGPTL3 protein in the subject (e.g., in the blood or plasma of the subject) can be reduced, for example, by at least 20%, by at least 30%, by at least 40%, by at least 50%, by at least 60%, or by at least 70% after the administration. The reduction can be relative to (a) the ANGPTL3 expression or the concentration of ANGPTL3 protein in the plasma of the subject prior to being administered the plurality of nanoparticles; (b) the ANGPTL3 expression or the concentration of ANGPTL3 protein in one or more untreated subjects; and/or (3) a reference level of ANGPTL3 expression or the concentration of ANGPTL3 protein of healthy subjects.

The level (e.g., plasma level) of one or more of the non-high-density lipoprotein (non-HDL) lipids of the subject can be reduced by at least 20%, by at least 30%, by at least 40%, by at least 50%, by at least 60%, or by at least 70% after the administration. The one or more of non-HDL lipids can be triglyceride, very low density lipoprotein (VLDL), low-density lipoprotein (LDL), or a combination thereof. In some embodiments, the reduction of the non-HDL level is relative to (a) the non-HDL level in the plasma of the subject prior to being administered the plurality of nanoparticles; (b) the non-HDL level in one or more untreated subjects; and/or (3) a reference non-HDL level in healthy subjects.

In some embodiments, the concentration of apolipoprotein B (ApoB) protein in the plasma of the subject is reduced by at least 20%, by at least 40%, or by at least 70% after the administration. In some embodiments, the reduction is relative to (a) the concentration of ApoB protein in the plasma of the subject prior to being administered the plurality of nanoparticles; (b) the concentration of ApoB protein in one or more untreated subjects; and/or (3) a reference level of the concentration of ApoB protein of healthy subjects.

In some embodiments, the reduction of the concentration of ANGPTL3 protein, the level of one or more of the non-high-density lipoprotein (non-HDL) lipids, and/or the concentration of ApoB protein is at least 20%, at least 40%, or at least 70% three weeks, four weeks, five weeks, one month, two months, three months, four months, five months, six months, seven months, eight months, nine months, ten months, eleven months, twelve months, or longer after the administration. In some embodiments, the reduction of the concentration of ANGPTL3 protein, the level of one or more of the non-high-density lipoprotein (non-HDL) lipids, and/or the concentration of ApoB protein by at least 20%, at least 30%, at least 40%, at least 50%, at least 60%, at least 70%, at least 80%, or a number or a range between any two of these values, is for three weeks, four weeks, five weeks, one month, two months, three months, four months, five months, six months, seven months, eight months, nine months, ten months, eleven months, twelve months, eighteen months, two years, three years, four years, five years, six years, seven years, eight years, nine years, ten years, 12 years, 15 years, 20 years, or longer after the administration.

In some embodiments, the subject in need has a triglyceride level of more than 150 mg/dl. In some embodiments, the subject in need has a triglyceride level of more than 300 mg/dL, a non-high-density lipoprotein (HDL) level of more than 160 mg/dL, a low-density lipoprotein cholesterol (LDL-C) level greater than 100 mg/dL, an ApoB level of more than 100 mg/dL, or a combination thereof. The method can comprise measuring the blood level of one or more of ANGPTL3, ApoB, triglyceride, very low density lipoprotein (VLDL), low-density lipoprotein (LDL), LDL-C, HDL, and non-HDL lipids in the subject prior to, during, and/or after the administration. The method can, for example, further comprises identifying a subject in need of the treatment.

In some embodiments, the ANGPTL3-related disease or disorder is a metabolic disease, a cardiovascular disease, a lipid metabolism disease, or a combination thereof. In some embodiments, one or more symptoms of the ANGPTL3-related disease or disorder in the subject is reduced or relieved. Non-limiting examples of ANGPTL3-related disease or disorder include obesity, diabetes, atherosclerosis, dyslipidemia, coronary heart disease, non-alcoholic fatty liver disease (NAFLD), hyperfattyacidemia, metabolic syndrome, and a combination thereof. Dyslipidemia can be hyperlipidemia, for example hypercholesterolemia, hypertriglyceridemia, or both. In some embodiments, ANGPTL3-related disease or disorder is familial hypercholesterolemia, familial combined hyperlipidemia, familial chylomicronemia syndrome, multifactorial chylomicronemia syndrome, elevated Lp(a), or a combination thereof. NAFLD can be hepatic steatosis or steatohepatitis. The diabetes can be type 2 diabetes or type 2 diabetes with dyslipidemia. In some embodiments, administering to the subject a plurality of the nanoparticles reduces dyslipidemias, cardiovascular risk, likelihood of mortality related to cardiovascular events, or a combination thereof.

In some embodiments, the nucleic acid encoding the RNA-guided endonuclease is an mRNA of the RNA-guided endonuclease. The RNA-guided endonuclease can be, for example, a Cas9 endonuclease. Non-limiting examples of Cas9 endonuclease include *S. pyogenes* Cas9, *S. aureus* Cas9, *N. meningitides* Cas9, *S. thermophilus* Cas9, *S. thermophilus* 3 Cas9, *T denticola* Cas9, and variants thereof.

The gRNA can be, for example, a single-guide RNA (sgRNA). In some embodiments, the gRNA targets exon 1 of ANGPTL3 gene. In some embodiments, the gRNA comprises a spacer sequence of any one of SEQ ID NOs: 3-9 or SEQ ID NOs: 20-26. In some embodiments, the gRNA or the nucleic acid encoding a gRNA, and the RNA-guided nuclease are encapsulated in the nanoparticles. The nanoparticles can be or comprise lipid nanoparticles. In some embodiments, the subject is a primate subject. In some embodiments, the subject is human.

The method, in some embodiments, further comprises determining (i) a level of one or more of alanine transaminase (ALT), aspartate transaminase (AST), gamma-glutamyl transferase (GGT), bilirubin, alkaline phosphatase (Alk Phos) and albumin; (ii) prothrombin time (PT), and/or (iii) partial thromboplastin time (PTT) in the subject. The determining can occur before the administration, after the administration, during the administration, or any combination thereof. In some embodiments, the determining comprises determining (i), (ii) and/or (iii) in the subject one time, two times, three times, four times, or more during a desirable duration of time. For example, the determining can comprise determining (i), (ii) and/or (iii) once or daily up to Day 7, Day 14, Day 21, Day 28, Day 35, Day 42, Day 49, Day 56, Day 63 after the administration. In some embodiments, the determining comprises determining (i), (ii) and/or (iii) in the subject daily, weekly, or monthly for at least 3 months, at least 6 months, or at least 12 months after the administration. In some embodiments, the plurality of nanoparticles is administered to the subject at a single dose of about 0.1 mg/kg, 0.3 mg/kg, 0.5 mg/kg, 0.6 mg/kg, 1 mg/kg, 1.5 mg/kg, 2.0 mg/kg, 2.5 mg/kg or, 3.0 mg/kg of nucleic acids (a) and (b).

Disclosed herein include methods for treating an ANGPTL3-related disease or disorder in a subject in need thereof, where the method comprises administering to the subject a plurality of nanoparticles complexed with (a) a gRNA that targets ANGPTL3 gene (ANGPTL3 gRNA) and (b) a Cas9 mRNA, at a single dose of about 0.1 mg/kg, 0.3 mg/kg, 0.5 mg/kg, 0.6 mg/kg, 1 mg/kg, 1.5 mg/kg, 2.0 mg/kg, 2.5 mg/kg or 3.0 mg/kg of nucleic acids (a) and (b), thereby treating the ANGPTL3-related disease or disorder in the subject.

The methods disclosed herein, in some embodiments, comprise a single administration of the plurality of nanoparticles to the subject. For example, in some embodiments, the plurality of nanoparticles is administered to the subject in the single administration at a dose of, or a dose of about, 0.5 mg/kg, 0.6 mg/kg, 1 mg/kg, 1.5 mg/kg, 2.0 mg/kg, 2.5 mg/kg, or 3.0 mg/kg of RNA content of (a) the guide RNA (gRNA) or the nucleic acid encoding a gRNA that targets ANGPTL3 gene, and (b) the nucleic acid encoding a RNA-guided endonuclease (e.g., Cas9). In some embodiments, the gRNA comprises a spacer sequence of SEQ ID NO: 3, SEQ ID NO: 20 or SEQ ID NO: 12. In some embodiments, the gRNA comprises the sequence of SEQ ID NO: 10 or SEQ ID NO: 13. In some embodiments, a single dose of the plurality of nanoparticles is complexed with (a) the ANGPTL3 gRNA at about 1.5 mg/mL, and (b) the Cas9 mRNA at about 0.5 mg/mL. In some embodiments, the single dose of the plurality of nanoparticles is about 58.2 mg/mL.

In some embodiments, the subject is administered an additional treatment. In some embodiments, the additional treatment comprises administration of a corticosteroid, an anti-H1 antihistamine, an anti-H2 antihistamine, or any combination thereof. In some embodiments, the additional treatment is administered to the subject 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, or more prior to, or after, the administration of the plurality of nanoparticles to the subject. In some embodiments, the additional treatment and the plurality of nanoparticles are administered simultaneously.

Also disclosed herein include compositions. In some embodiments, the composition comprises a plurality of nanoparticles complexed with (a) a guide RNA (gRNA) targeting ANGPTL3 gene (ANGPTL3 gRNA), and (b) an mRNA encoding Cas9 endonuclease, wherein the gRNA comprises a spacer sequence of SEQ ID NO: 3, SEQ ID NO: 20, or SEQ ID NO: 12. In some embodiments, the gRNA comprises the sequence of SEQ ID NO: 10 or SEQ ID NO: 13. In some embodiments, the Cas9 endonuclease is *S. pyogenes* Cas9 endonuclease. In some embodiments, the concentration of the plurality of nanoparticles is about 58.2 mg/mL, and is complexed with a total of about 2 mg/mL of nucleic acid of (a) the ANGPTL3 gRNA and (b) the Cas9 mRNA. In some embodiments, the concentration of the plurality of nanoparticles is about 58.2 mg/mL, and is complexed with (a) the ANGPTL3 gRNA at about 1.5 mg/mL, and (b) the Cas9 mRNA at about 0.5 mg/mL.

The Cas9 mRNA can, in some embodiments, comprise SEQ ID NO: 16. In some embodiments, two or more of the uracil residues of the Cas9 mRNA are N1-methylpseudouridines. In some embodiments, the Cas9 mRNA comprises the sequence of SEQ ID NO: 18. In some embodiments, the Cas9 mRNA comprises the sequence of SEQ ID NO: 19.

Disclosed herein include a method for treating an ANGPTL3-related disease or disorder in a subject in need thereof. The method, in some embodiments, comprises administering to the subject a plurality of nanoparticles complexed with (a) a guide RNA (gRNA) targeting ANGPTL3 gene (ANGPTL3 gRNA) or a nucleic acid encoding the gRNA, wherein the ANGPTL3 gRNA comprises a spacer sequence of SEQ ID NO: 20, and (b) a Cas9 mRNA comprising the sequence of SEQ ID NO: 16, thereby treating the ANGPTL3-related disease or disorder in the subject. Disclosed herein provides a composition for use in treating ANGPTL3-related disease or disorder. In some embodiments, the composition comprises a plurality of nanoparticles complexed with (a) a guide RNA (gRNA) targeting ANGPTL3 gene (ANGPTL3 gRNA) or a nucleic acid encoding the gRNA, wherein the ANGPTL3 gRNA comprises a spacer sequence of SEQ ID NO: 20, and (b) a Cas9 mRNA comprising the sequence of SEQ ID NO: 16. In some embodiments, the ANGPTL3 gRNA comprises the space sequence of SEQ ID NO: 12. In some embodiments, the ANGPTL3 gRNA is a single guide RNA (sgRNA) comprising the sequence of SEQ ID NO: 13. Two or more of the uracil residues of the Cas9 mRNA can be modified uracil residues, for example N1-methylpseudouridines. In some embodiments, the Cas9 mRNA comprises the sequence of SEQ ID NO: 18. The method, in some embodiments, comprises administering to the subject the plurality of nanoparticles at a single dose of about 0.1 mg/kg, 0.3 mg/kg, 0.6 mg/kg, or 1.0 mg/kg of total nucleic acids of (a) and (b). In some embodiments, the expression of ANGPTL3 in the subject is reduced by at least 20% after the administration, the concentration of ANGPTL3 protein in the plasma of the subject is reduced by at least 20% after the administration, or both. In some embodiments, the reduction is relative to (a) the ANGPTL3 expression or the concentration of ANGPTL3 protein in the plasma of the subject prior to being administered the plurality of nanoparticles; (b) the ANGPTL3 expression or the concentration of ANGPTL3 protein in one or more untreated subjects; and/or (3) a reference level of ANGPTL3 expression or the concentration of ANGPTL3 protein of healthy subjects. In some embodiments, the reduction in the concentration of ANGPTL3 protein in the plasma of the subject is at least 70% one month after the administration. In some embodiments, the plasma level of one or more of non-high-density lipoprotein (non-HDL) lipids of the subject is reduced by at least 20% after the administration. In some embodiments, the one or more of non-HDL lipids is triglyceride, very low density lipoprotein (VLDL), low-density lipoprotein (LDL), or a combination thereof. In some embodiments, the reduction of the non-HDL level is relative to (a) the non-HDL level in the plasma of the subject prior to being administered the plurality of nanoparticles; (b) the non-HDL level in one or more untreated subjects; and/or (3) a reference non-HDL level in healthy subjects. In some embodiments, the reduction in the plasma triglyceride level in the subject is at least 30% one month, two months, three months, six months, or longer, after the administration. In some embodiments, the concentration of apolipoprotein B (ApoB) protein in the plasma of the subject is reduced by at least 20% after the administration. In some embodiments, the reduction is relative to (a) the concentration of ApoB protein in the plasma of the subject prior to being administered the plurality of nanoparticles; (b) the concentration of ApoB protein in one or more untreated subjects; and/or (3) a reference level of the concentration of ApoB protein of healthy subjects. The reduction resulted by the methods or compositions described herein can be, for example, for at least four weeks, two months, six months, one year, two years, five years, ten years, or more. In some embodiments, the subject in need has a triglyceride level of more than 300 mg/dL, a non-high-density lipoprotein (HDL) level of more than 160 mg/dL, a low-density lipoprotein cholesterol (LDL-C) level greater than 100 mg/dL, an ApoB level of more than 100 mg/dL, or a combination thereof. The ANGPTL3-related disease or disorder can be, for example, a metabolic disease, a cardiovascular disease, a lipid metabolism disease, or a combination thereof. In some embodiments, the ANGPTL3-related disease or disorder is obesity, diabetes, atherosclerosis, dyslipidemia, coronary heart disease, non-alcoholic fatty liver disease (NAFLD), hyperfattyacidemia, metabolic syndrome, or a combination thereof. In some embodiments, the method comprises a single administration of the plurality of nanoparticles to the subject. In some embodiments, a single dose of the plurality of nanoparticles is complexed with (a) the ANGPTL3 gRNA and (b) the Cas9 mRNA at a concentration of 2.0 mg/mL total RNA. In some embodiments, the total RNA comprises (a) the ANGPTL3 gRNA at about 1.5 mg/mL and (b) the Cas9 mRNA at about 0.5 mg/mL. In some embodiments, the lipid nanoparticles comprise one or more neutral lipids, charged lipids, ionizable lipids, steroids, and polymers conjugated lipids. In some embodiments, the lipid nanoparticles comprise cholesterol, a polyethylene glycol (PEG) lipid, or both.

BRIEF DESCRIPTION OF THE DRAWINGS

FIG. 3A is a graph showing the plasma triglyceride level of the NHPs in Group 1 before and after treatment. FIG. 3B is a graph showing the percentage change of the plasma triglyceride level from the baseline of the NHPs in Group 1.

FIG. 4A is a graph showing the plasma triglyceride level of the NHPs in Group 3 before and after treatment. FIG. 4B is a graph showing the percentage change of the plasma triglyceride level from the baseline of the NHPs in Group 3.

FIG. 5A-FIG. 5B are two graphs showing the maximal percentage change of the plasma triglyceride level of the NHPs in Group 1 (FIG. 5A) and Group 3 (FIG. 5B). FIG. 5C-FIG. 5D are graphs showing the percentage change of the plasma triglyceride level from baseline at day 36 in Group 1 (FIG. 5C) and Group 3 (FIG. 5D).

FIG. 6A-FIG. 6D are graphs showing ANGPTL3 gene editing efficiency in different organ tissues.

FIG. 10D depicts the percentage of ANGPTL3 gene editing in different organ tissues of the NHPs treated with 0.5 mg/kg, 1.5 mg/kg, and 3.0 mg/kg CTX310 formulation after about 3 months following administration.

FIG. 12A is a graph showing the plasma ANGPTL3 protein level of the cynomolgus monkeys treated with three different doses of CTX310 formulation (0.5, 1.5 and 3.0 mg/kg) in comparison to a control group. FIG. 12B is a graph showing the percentage change of the plasma ANGPTL3 protein level with respect to a baseline of the cynomolgus monkeys treated with three different doses of CTX310 formulation (0.5, 1.5 and 3.0 mg/kg) in comparison to a control group. FIG. 12C is a graph showing the percentage change of the plasma ANGPTL3 protein from a baseline of the cynomolgus monkeys on Day 37 after the CTX310 treatments. FIG. 12D is a graph showing the percentage change of the serum ANGPTL3 protein after the CTX310 treatment. FIG. 12E is a graph showing the percentage change of the plasma ANGPTL3 protein about 3 months following CTX310 treatment.

FIG. 13A-FIG. 13C are graphs showing the percentage change of the plasma triglyceride level normalized to a baseline of the cynomolgus monkeys after the treatments with three different doses of CTX310 formulation: 0.5 mg/kg (FIG. 13A), 1.5 mg/kg (FIG. 13B) and 3.0 mg/kg (FIG. 13C). FIG. 13D is a graph showing the percentage change of the plasma triglyceride level from the baseline of the cynomolgus monkeys on Day 37 after the CTX310 treatments. FIG. 13E is a graph showing the percentage change of the serum triglyceride level from baseline one month after the CTX310 treatment. FIG. 13F-FIG. 13H depict changes in triglyceride levels as mg/dL with three different doses of CTX310 formulation: 0.5 mg/kg (FIG. 13F), 1.5 mg/kg (FIG. 13G) and 3.0 mg/kg (FIG. 13H). FIG. 13I is a graph showing the percentage change of the plasma triglyceride level from the baseline of the cynomolgus monkeys about 3 months after the CTX310 treatment.

FIG. 14A is a plot showing the correlation between triglyceride reduction and ANGPTL3 gene editing percentage in liver. FIG. 14B is a plot showing the correlation between ANGPTL3 protein reduction and ANGPTL3 gene editing percentage in liver.

FIG. 16E-FIG. 16H depict data from LDLR mutant mice one month after administration of RIV-000005. FIG. 16E depicts editing in liver, FIG. 16F shows a reduction in ANGPTL3 protein levels, and FIG. 16G shows plasma TG levels in both male and female groups after RIV-000005 treatment compared to untreated control mice. FIG. 16H depicts a moderate decrease in LDL was observed in female mice administered with RIV-000005 compared to the control female mice but a similar effect was not seen in the male mice dosed with RIV-000005.

DETAILED DESCRIPTION

Figure 1:
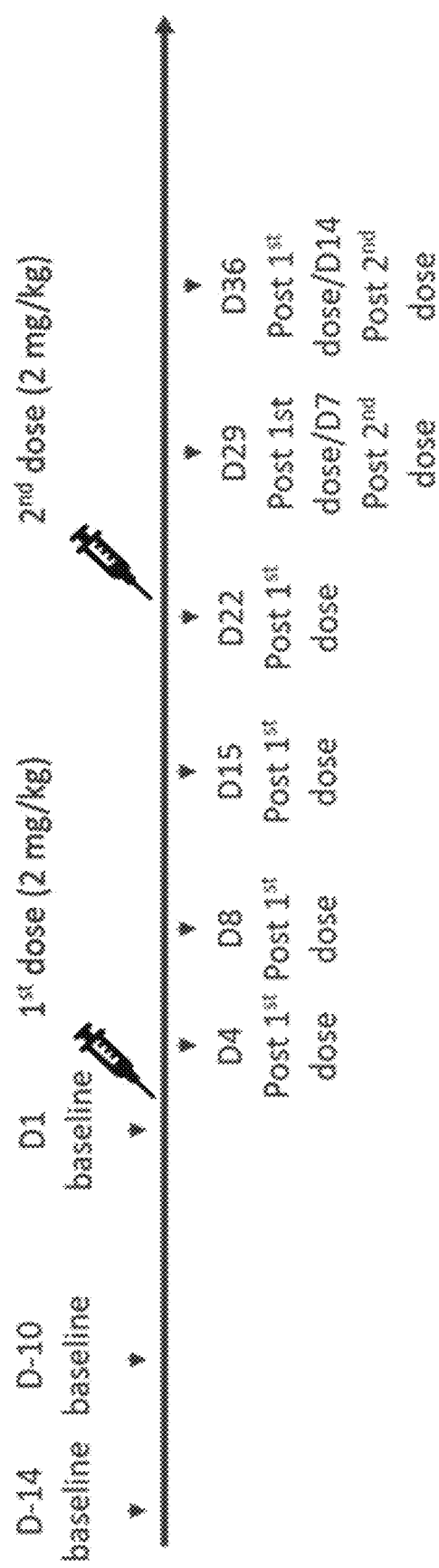
FIG. 1 depicts a non-limiting exemplary nonhuman primate (NHP) study design.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Angiopoietin-like 3 (ANGPTL3) protein is a secretory protein regulating plasma lipid levels via affecting lipoprotein lipase- and endothelial lipase-mediated hydrolysis of triglycerides and phospholipids. In human, ANGPTL3 is a determinant factor of high-density lipoprotein (HDL) cholesterol level as well as non-HDL levels such as low-density lipoprotein (LDL) cholesterol, triglycerides, and very low-density lipoprotein (VLDL) cholesterol. ANGPTL3 has been associated with diseases and disorders involving abnormal lipoprotein metabolism such as dyslipidemias, hypobetalipoproteinemia, hypercholesterolemia, hypertriglyceridemia, hyperlipidemia, and coronary heart disease. ANGPTL3 can be a potential therapeutic target for treatment of various ANGPTL3-associated diseases and disorders.

Disclosed herein include methods, compositions and kits for treating ANGPTL3-related disease or disorder in a subject (e.g., a primate). In some embodiments, the method comprises administering to a primate subject in need thereof a plurality of nanoparticles complexed with (a) a guide RNA (gRNA) or a nucleic acid encoding a gRNA that targets ANGPTL3 gene, and (b) a nucleic acid encoding a RNA-guided endonuclease, thereby treating the ANGPTL3-related disease or disorder in the primate subject.

Definition

As used herein, the term "about" means plus or minus 5% of the provided value.

As used herein, the term "RNA-guided endonuclease" refers to a polypeptide capable of binding an RNA (e.g., a gRNA) to form a complex targeted to a specific DNA sequence (e.g., in a target DNA). A non-limiting example of RNA-guided endonuclease is a Cas polypeptide (e.g., a Cas endonuclease, such as a Cas9 endonuclease). In some embodiments, the RNA-guided endonuclease as described herein is targeted to a specific DNA sequence in a target DNA by an RNA molecule to which it is bound. The RNA molecule can include a sequence that is complementary to and capable of hybridizing with a target sequence within the target DNA, thus allowing for targeting of the bound polypeptide to a specific location within the target DNA.

As used herein, the term "guide RNA" or "gRNA" refers to a site-specific targeting RNA that can bind an RNA-guided endonuclease to form a complex, and direct the activities of the bound RNA-guided endonuclease (such as a Cas endonuclease) to a specific target sequence within a target nucleic acid. The guide RNA can include one or more RNA molecules.

As used herein, a "secondary structure" of a nucleic acid molecule (e.g., an RNA fragment, or a gRNA) refers to the base pairing interactions within the nucleic acid molecule.

As used herein, the term "target DNA" refers to a DNA that includes a "target site" or "target sequence." The term "target sequence" is used herein to refer to a nucleic acid sequence present in a target DNA to which a DNA-targeting sequence or segment (also referred to herein as a "spacer") of a gRNA can hybridize, provided sufficient conditions for hybridization exist. For example, the target sequence 5'-GAGCATATC-3' within a target DNA is targeted by (or is capable of hybridizing with, or is complementary to) the RNA sequence 5'-GAUAUGCUC-3'. Hybridization between the DNA-targeting sequence or segment of a gRNA and the target sequence can, for example, be based on Watson-Crick base pairing rules, which enables programmability in the DNA-targeting sequence or segment. The DNA-targeting sequence or segment of a gRNA can be designed, for instance, to hybridize with any target sequence.

As used herein, the term "Cas endonuclease" or "Cas nuclease" refers to an RNA-guided DNA endonuclease associated with the CRISPR adaptive immunity system.

Unless otherwise indicated "nuclease" and "endonuclease" are used interchangeably herein to refer to an enzyme which possesses endonucleolytic catalytic activity for polynucleotide cleavage.

As used herein, the term "invariable region" of a gRNA refers to the nucleotide sequence of the gRNA that associates with the RNA-guided endonuclease. In some embodiments, the gRNA comprises a crRNA and a transactivating crRNA (tracrRNA), wherein the crRNA and tracrRNA hybridize to each other to form a duplex. In some embodiments, the crRNA comprises 5' to 3': a spacer sequence and minimum CRISPR repeat sequence (also referred to as a "crRNA repeat sequence" herein); and the tracrRNA comprises a minimum tracrRNA sequence complementary to the minimum CRISPR repeat sequence (also referred to as a "tracrRNA anti-repeat sequence" herein) and a 3' tracrRNA sequence. In some embodiments, the invariable region of the gRNA refers to the portion of the crRNA that is the minimum CRISPR repeat sequence and the tracrRNA.

As used herein, the term "donor template" refers to a nucleic acid strand containing exogenous genetic material which can be introduced into a genome (e.g., by a homology directed repair) to result in targeted integration of the exogenous genetic material. In some embodiments, a donor template can have no regions of homology to the targeted location in the DNA and can be integrated by NHEJ-dependent end joining following cleavage at the target site. A donor template can be DNA or RNA, single-stranded or double-stranded, and can be introduced into a cell in linear or circular form.

The terms "polynucleotide" and "nucleic acid" are used interchangeably herein and refer to a polymeric form of nucleotides of any length, either ribonucleotides or deoxyribonucleotides. A polynucleotide can be single-, double-, or multi-stranded DNA or RNA, genomic DNA, cDNA, DNA-RNA hybrids/triple helices, or a polymer including purine and pyrimidine bases or other natural, chemically or biochemically modified, non-natural, or derivatized nucleotide bases.

As used herein, the term "binding" refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it means that the molecule X binds to molecule Y in a non-covalent manner). Binding interactions can be characterized by a dissociation constant (Kd), for example a Kd of, or a Kd less than, $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-15}$ M, or a number or a range between any two of these values. Kd can be dependent on environmental conditions, e.g., pH and temperature. "Affinity" refers to the strength of binding, and increased binding affinity is correlated with a lower Kd.

As used herein, the term "hybridizing" or "hybridize" refers to the pairing of substantially complementary or complementary nucleic acid sequences within two different molecules. Pairing can be achieved by any process in which a nucleic acid sequence joins with a substantially or fully complementary sequence through base pairing to form a hybridization complex. "Hybridizing" or "hybridize" can comprise denaturing the molecules to disrupt the intramolecular structure(s) (e.g., secondary structure(s)) in the molecule. In some embodiments, denaturing the molecules comprises heating a solution comprising the molecules to a temperature sufficient to disrupt the intramolecular structures of the molecules. In some instances, denaturing the molecules comprises adjusting the pH of a solution comprising the molecules to a pH sufficient to disrupt the intramolecular structures of the molecules. For purposes of hybridization, two nucleic acid sequences or segments of sequences are "substantially complementary" if at least 80% of their individual bases are complementary to one another. In some embodiments, a splint oligonucleotide sequence is not more than about 50% identical to one of the two polynucleotides (e.g., RNA fragments) to which it is designed to be complementary. The complementary portion of each sequence can be referred to herein as a "segment", and the segments are substantially complementary if they have 80% or greater identity.

The terms "complementarity" and "complementary" mean that a nucleic acid can form hydrogen bond(s) with another nucleic acid based on traditional Watson-Crick base paring rule, that is, adenine (A) pairs with thymine (U) and guanine (G) pairs with cytosine (C). Complementarity can be perfect (e.g. complete complementarity) or imperfect (e.g. partial complementarity). Perfect or complete complementarity indicates that each and every nucleic acid base of one strand is capable of forming hydrogen bonds according to Watson-Crick canonical base pairing with a corresponding base in another, antiparallel nucleic acid sequence. Partial complementarity indicates that only a percentage of the contiguous residues of a nucleic acid sequence can form Watson-Crick base pairing with the same number of contiguous residues in another, antiparallel nucleic acid sequence. In some embodiments, the complementarity can be at least 70%, 80%, 90%, 100% or a number or a range between any two of these values. In some embodiments, the complementarity is perfect, i.e. 100%. For example, the complementary candidate sequence segment is perfectly complementary to the candidate sequence segment, whose sequence can be deducted from the candidate sequence segment using the Watson-Crick base pairing rules.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

As used herein, the terms "transfection" or "infection" refer to the introduction of a nucleic acid into a host cell, such as by contacting the cell with liposomes or nanoparticles (e.g., lipid nanoparticles) as described herein.

As used herein, "treatment" refers to a clinical intervention made in response to a disease, disorder or physiological condition manifested by a patient or to which a patient may be susceptible. The aim of treatment includes, but is not limited to, the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Subjects in need of treatment include those already affected by a disease or disorder or undesired physiological condition as well as those in which the disease or disorder or undesired physiological condition is to be prevented.

As used herein, the terms "effective amount" or "pharmaceutically effective amount" or "therapeutically effective amount" refer to an amount sufficient to effect beneficial or desirable biological and/or clinical results.

The term "pharmaceutically acceptable excipient" as used herein refers to any suitable substance that provides a pharmaceutically acceptable carrier, additive or diluent for administration of a compound(s) of interest to a subject.

Pharmaceutically acceptable excipient can encompass substances referred to as pharmaceutically acceptable diluents, pharmaceutically acceptable additives, and pharmaceutically acceptable carriers.

As used herein, a "subject" refers to an animal for whom a diagnosis, treatment, or therapy is desired. In some embodiments, the subject is a mammal. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a primate. In some embodiments, the mammal is a human. In some embodiments, the mammal is not a human. In some aspects, the subject has or is suspected of having an ANGPTL3-associated disease or disorder.

The term "plasma level" used herein in the context of a molecule refers to a concentration or an amount of the molecule, e.g., the number of moles or the weight of the molecule present in a given volume of plasma.

ANGPTL3 is a secretory protein regulating plasma lipid levels via affecting lipoprotein lipase- and endothelial lipase-mediated hydrolysis of triglycerides and phospholipids. ANGPTL3 has been associated with diseases and disorders involving abnormal lipoprotein metabolism such as dyslipidemias, hypobetalipoproteinemia, hyperlipidemia, hypertriglyceridemia, and familial hypercholesterolemia. There remains a need for a novel gene therapy that can stably reduce the levels of ANGPTL3 protein and lipids (e.g., cholesterol, HDLs, LDLs, triglycerides, and non-HDLs) in the blood over an extended period of time or permanently lowers the ANGPTL3 protein levels. The present disclosure provides a highly efficient gene editing method and related compositions and kits that directly target the ANGPTL3 gene or variants thereof and permanently reduce the expression, function, or activity of the ANGPTL3 gene. In some embodiments, the methods, compositions, and kits described herein can reduce the plasma ANGPTL3 protein levels by at least 70% or greater. In some embodiments, the lipids levels (e.g., triglycerides) following carrying out the method can be reduced to 40 mg/dL or lower. The gRNA sequences used herein can also significantly minimize the number and frequency of off-target effects, thus reducing the risk of genotoxicity. The methods, compositions, and kits described herein can be used to treat ANGPTL3-associated diseases or disorders in a subject.

Angiopoietin-Like Protein 3 (ANGPTL3)

Provided herein include vectors, compositions, methods, and kits for editing an ANGPTL3 gene or variants thereof in a cell genome to modulate (e.g., decrease) the expression, function, or activity of the ANGPTL3 gene in the cell. The vectors, compositions, methods and kits described herein can be particularly useful for treating ANGPTL3-associated diseases and conditions, such as dyslipidemia, hypobetalipoproteinemia, familial hypercholesterolemia, hypertriglyceridemia, familial combined hyperlipidemia, familial chylomicronemia syndrome, and multifactorial chylomicronemia syndrome, by permanently reducing the levels of ANGPTL3 protein, ApoB protein, and lipids such as total cholesterol, triglycerides, LDLs, HDLs, and/or other non-HDLs in the blood.

The ANGPTL3 gene encodes the ANGPTL3 protein, a member of a family of secreted proteins that function in angiogenesis. The ANGPTL3 protein, which is expressed predominantly in the liver, comprises a distinctive signal peptide sequence, an N-terminal helical domain (predicted to form dimeric or trimeric coiled-coil structures) and a C-terminal globular fibrinogen homology domain. The N-terminal coiled-coil region affects plasma triglyceride levels via reversibly inhibiting catalytic activity of lipoprotein lipase. The fibrinogen-like domain binds to integrin αvβ3 receptor and affects angiogenesis. A short linker region between the N- and C-terminal domains functions as a furin cleavage site. Upon secretion, ANGPTL3 targets the adipose tissue and muscles activating lipolysis in the former, increasing the release of fatty free acids and glycerol from adipocytes, and inhibiting lipoprotein lipase in the latter, increasing triglyceride rich lipoproteins.

ANGPTL3 acts as dual inhibitor of lipoprotein lipase (LPL) and endothelial lipase (EL) and has been considered a potent modulator of plasma triglyceride, low-density lipoprotein (LDL) cholesterol and high-density lipoprotein (HDL) cholesterol. From experimental evidence, it has been observed that individuals with loss-of-function mutations in the ANGPTL3 gene are affected by familial combined hypolipidemia and characterized by very low levels of apolipoprotein B, apolipoprotein A1 and their associated lipoproteins (e.g., very low-density lipoprotein, LDL and HDL) compared to individuals without the mutations. These subjects are protected from cardiovascular events, making ANGPTL3 an important pharmacological target for reducing cardiovascular risk.

The ANGPTL3 gene (also known as ANL3, ANG-5, FHBL2 and ANGPT5) has a cytogenetic location of 1p31.3 and the genomic coordinate is on Chromosome 1 on the forward strand at position 62,597,520-62,606,313. The nucleotide sequence of ANGPTL3 can be found at NCBI website with the NCBI reference sequence: NC_000001.11. USP1 is the gene upstream of ANGPTL3 on the forward strand and ATG4C is the gene downstream of ANGPTL3 on the forward strand. DOCK7 is the genes located on the reverse strand opposite of ANGPTL3. ANGPTL3 has a NCBI gene ID of 27329, Uniprot ID of Q9Y5C1 and Ensembl Gene ID of ENSG00000132855. ANGPTL3 has 2 SNPs, 9 introns and 12 exons. Additional information about the ANGPTL3 gene including the exons, the start/stop sites of the introns and exons as well as the information on the transcripts of the ANGPTL3 gene is described in details in WO2018154387, the content of which is incorporated by reference herein.

Gene Editing

Provided herein includes methods, compositions and kits for editing an ANGPTL3 gene, thereby reducing the expression level of ANGPTL3 protein (e.g., plasma concentrations of ANGPTL3 protein), the levels of ApoB protein (e.g., plasma concentrations of ApoB protein), and lipid levels (e.g., or triglycerides, LDLs, HDLs and non-HDLs etc.) in a subject. Gene editing (including genomic editing) is a type of genetic engineering in which nucleotide(s)/nucleic acid(s) is/are inserted, deleted, and/or substituted in a DNA sequence, such as in the genome of a targeted cell. Targeted gene editing enables insertion, deletion, and/or substitution at pre-selected sites in the genome of a targeted cell (e.g., in a targeted gene or targeted DNA sequence). When an sequence of an endogenous gene is edited, for example by deletion, insertion or substitution of nucleotide(s)/nucleic acid(s), the endogenous gene comprising the affected sequence can be knocked-out or knocked-down due to the sequence alteration. Therefore, targeted editing can be used to disrupt endogenous gene expression. "Targeted integration" refers to a process involving insertion of one or more exogenous sequences, with or without deletion of an endogenous sequence at the insertion site. Targeted integration can result from targeted gene editing when a donor template containing an exogenous sequence is present.

Targeted editing can be achieved either through a nuclease-independent approach, or through a nuclease-dependent approach. In the nuclease-independent targeted editing approach, homologous recombination is guided by homologous sequences flanking an exogenous polynucleotide to be introduced into an endogenous sequence through the enzymatic machinery of the host cell. The exogenous polynucleotide can introduce deletions, insertions or replacement of nucleotides in the endogenous sequence.

Alternatively, the nuclease-dependent approach can achieve targeted editing with higher frequency through the specific introduction of double strand breaks (DSBs) by specific rare-cutting nucleases (e.g., endonucleases). Such nuclease-dependent targeted editing also utilizes DNA repair mechanisms, for example, non-homologous end joining (NHEJ), which occurs in response to DSBs. DNA repair by NHEJ often leads to random insertions or deletions (indels) of a small number of endogenous nucleotides. In contrast to NHEJ mediated repair, repair can also occur by a homology directed repair (HDR). When a donor template containing exogenous genetic material flanked by a pair of homology arms is present, the exogenous genetic material can be introduced into the genome by HDR, which results in targeted integration of the exogenous genetic material.

Available endonucleases capable of introducing specific and targeted DSBs include, but are not limited to, zinc-finger nucleases (ZEN), transcription activator-like effector nucleases (TALEN), and RNA-guided CRISPR-Cas9 nuclease (CRISPR/Cas9; Clustered Regular Interspaced Short Palindromic Repeats Associated 9). Additionally, DICE (dual integrase cassette exchange) system utilizing phiC31 and Bxb1 integrases may also be used for targeted integration.

ZFNs are targeted nucleases comprising a nuclease fused to a zinc finger DNA binding domain (ZFBD), which is a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but not limited to, C2H2 zinc fingers, C3H zinc fingers, and C4 zinc fingers. A designed zinc finger domain is a domain not occurring in nature whose design/composition results principally from rational criteria, e.g., application of substitution rules and computerized algorithms for processing information in a database storing information of existing ZFP designs and binding data. See e.g., U.S. Pat. Nos. 6,140,081; 6,453,242; and 6,534,261; WO 98/53058; WO 98/53059; WO 98/53060; WO 02/016536 and WO 03/016496, the contents of which are incorporated by reference in their entireties. A selected zinc finger domain is a domain not found in nature whose production results primarily from an empirical process such as phage display, interaction trap or hybrid selection. ZFNs are described in greater detail in U.S. Pat. Nos. 7,888,121 and 7,972,854. The most recognized example of a ZFN is a fusion of the FokI nuclease with a zinc finger DNA binding domain.

A TALEN is a targeted nuclease comprising a nuclease fused to a TAL effector DNA binding domain. A "transcription activator-like effector DNA binding domain", "TAL effector DNA binding domain", or "TALE DNA binding domain" is a polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US2011/0145940. The most recognized example of a TALEN in the art is a fusion polypeptide of the FokI nuclease to a TAL effector DNA binding domain.

Additional examples of targeted nucleases suitable for use as provided herein include, but are not limited to, Bxb1, phiC31, R4, PhiBT1, and Wβ/SPBc/TP901-1, whether used individually or in combination. Other non-limiting examples of targeted nucleases include naturally-occurring and recombinant nucleases, e.g., CRISPR/Cas9, restriction endonucleases, meganucleases homing endonucleases, and the like.

CRISPR-Cas Gene Editing System and RNA-Guided Nuclease

In some embodiments, the vectors, compositions, methods, and kits described herein can be used in a gene editing system, such as in a CRISPR-Cas gene editing system, to genetically edit the ANGPTL3 gene. For example, the CRISPR-Cas9 system is a naturally-occurring defense mechanism in prokaryotes that has been repurposed as a RNA-guided DNA-targeting platform used for gene editing. It relies on the DNA nuclease Cas9, and two noncoding RNAs-crisprRNA (crRNA) and trans-activating RNA (tracrRNA) to target the cleavage of DNA. crRNA drives sequence recognition and specificity of the CRISPR-Cas9 complex through Watson-Crick base pairing typically with a 20 nucleotide (nt) sequence in the target DNA. The CRISPR-Cas9 complex only binds DNA sequences that contain a sequence match to the first 20 nt of the crRNA, single-guide RNA (sgRNA), if the target sequence is followed by a specific short DNA motif (with the sequence NGG) referred to as a protospacer adjacent motif (PAM). TracrRNA hybridizes with the 3' end of crRNA to form an RNA-duplex structure that is bound by the Cas9 endonuclease to form the catalytically active CRISPR-Cas9 complex, which can then cleave the target DNA. Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end). After binding of CRISPR-Cas9 complex to DNA at a specific target site and formation of the site-specific DSB, the next key step is repair of the DSB. Cells use two main DNA repair pathways to repair the DSB: non-homologous end-joining (NHEJ) and homology-directed repair (HDR). In some embodiments, CRISPR-Cas9 gene editing system comprises an RNA-guided nuclease and one or more guide RNAs targeting one or more target genes.

As described herein, the RNA-guided endonuclease can be naturally-occurring or non-naturally occurring. Non-limiting examples of RNA-guided endonucleases include a Cas1, Cas1B, Cas2, Cas3, Cas4, Cas5, Cash, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1 endonuclease, and functional derivatives thereof. In some instances, the RNA-guided endonuclease is a Cas9 endonuclease. The Cas9 endonuclease can be from, e.g., *Strepto-*

*coccus pyogenes* (SpyCas9), *Staphylococcus lugdunensis* (SluCas9), or *Staphylococcus aureus* (SaCas9). In some embodiments, the RNA-guided endonuclease is a variant of Cas9, including but not limited to, a small Cas9, a dead Cas9 (dCas9), and a Cas9 nickase. In some embodiments, a Cas nuclease can comprise a RuvC or RuvC-like nuclease domain (e.g., Cpf1) and/or a HNH or HNH-like nuclease domain (e.g., Cas9). In some embodiments, the Cas9 endonuclease is *S. pyogenes* Cas9, *S. aureus* Cas9, *N. meningitides* Cas9, *S. thermophilus* Cas9, *S. thermophilus* 3 Cas9, *T denticola* Cas9, or a variant thereof.

The RNA-guided endonuclease can be a small RNA-guided endonuclease. The small RNA-guided endonucleases can be engineered from portions of RNA-guided endonucleases derived from any of the RNA-guided endonucleases described herein and known in the art. The small RNA-guided endonucleases can be, e.g., small Cas endonucleases. In some cases, a small RNA-guided nuclease is shorter than about 1,100 amino acids in length.

The RNA-guided endonuclease can be a mutant RNA-guided endonuclease. For example, the RNA-guided endonuclease can be a mutant of a naturally occurring RNA-guided endonuclease. The mutant RNA-guided endonuclease can also be a mutant RNA-guided endonuclease with altered activity compared to a naturally occurring RNA-guided endonuclease, such as altered endonuclease activity (e.g., altered or abrogated DNA endonuclease activity without substantially diminished binding affinity to DNA). Such modification can allow for the sequence-specific DNA targeting of the mutant RNA-guided endonuclease for the purpose of transcriptional modulation (e.g., activation or repression); epigenetic modification or chromatin modification by methylation, demethylation, acetylation or deacetylation, or any other modifications of DNA binding and/or DNA-modifying proteins known in the art. In some embodiments, the mutant RNA-guided endonuclease has no DNA endonuclease activity.

The RNA-guided endonuclease can be a nickase that cleaves the complementary strand of the target DNA but has reduced ability to cleave the non-complementary strand of the target DNA, or that cleaves the non-complementary strand of the target DNA but has reduced ability to cleave the complementary strand of the target DNA. In some embodiments, the RNA-guided endonuclease has a reduced ability to cleave both the complementary and the non-complementary strands of the target DNA.

In some embodiments, a nucleic acid encoding an RNA-guided endonuclease is administered to the subject. In some embodiments, the nucleic acid can be generated by an in vitro transcription reaction. In some embodiments, generating in vitro transcribed RNA comprises incubating a linear DNA template with an RNA polymerase and a nucleotide mixture under conditions to allow (run-off) RNA in vitro transcription. The nucleotide mixture can be part of an in vitro transcription mix (IVT-mix). In some embodiments, the RNA polymerase is a T7 RNA polymerase.

The nucleotide mixture used in RNA in vitro transcription can additionally contain modified nucleotides as defined below. In some embodiments, the nucleotide mixture (e.g., the fraction of each nucleotide in the mixture) used for RNA in vitro transcription reactions can be optimized for the given RNA sequence (optimized NTP mix). Such methods are described, for example in WO2015/188933. RNA obtained by a process using an optimized NTP mix is, in some embodiments, characterized by reduced immune stimulatory properties.

In some embodiments, the nucleotide mixture is composed of (chemically) non-modified ribonucleoside triphosphates (NTPs) GTP, ATP, CTP and UTP. In some embodiments, the in vitro transcription can include the presence of at least one cap analog, e.g., a cap 1 trinucleotide cap analog, m7G(5') ppp(5') (2' OMeA)pG or m7G(5') ppp(5') (2' OMeG)pG, m7G(5')ppp(5')(2'OMeA)pG or m7(3'OMeG)(5')ppp (5')(2'OMeA)pG. In some embodiments, a 5'-cap structure is formed via enzymatic capping using capping enzymes (e.g. vaccinia virus capping enzymes and/or cap-dependent 2'-O-methyltransferases) to generate cap0 or cap1 or cap2 structures. The 5'-cap structure (cap0 or cap1) may also be added using immobilized capping enzymes and/or cap-dependent 2'-O-methyltransferases using methods and means disclosed in WO2016/193226. In some embodiments, a part or all of at least one (ribo)nucleoside triphosphate is replaced by a modified nucleoside triphosphate. In some embodiments, the modified nucleoside triphosphate comprises pseudouridine (ψ), N1-methylpseudouridine (m1 ψ), 5-methylcytosine, or 5-methoxyuridine. In some embodiments, uracil nucleotides in the nucleotide mixture are replaced (either partially or completely) by pseudouridine (ψ) and/or N1-methylpseudouridine (m1 ψ) to obtain a modified RNA. In some embodiments, the chemically modified nucleotide is pseudouridine (ψ). In some embodiments the chemically modified nucleotide is N1-methylpseudouridine (m1ψ). In some embodiments, the nucleotide mixture comprises at least one modified nucleotide and/or at least one nucleotide analogue or nucleotide derivative for incorporation into an RNA. For example, the modified nucleotide as defined herein can include nucleotide analogs/modifications, e.g., backbone modifications, sugar modifications or base modifications. A backbone modification can comprise a modification, in which phosphates of the backbone of the nucleotides are chemically modified. A sugar modification can comprise a chemical modification of the sugar of the nucleotides. Furthermore, a base modification can comprise a chemical modification of the base moiety of the nucleotides. In this context nucleotide analogs or modifications can comprise nucleotide analogs which are applicable for transcription and/or translation. In some embodiments the nucleotide mixture comprises least one modified nucleotide and/or at least one nucleotide analogues is selected from a backbone modified nucleotide, a sugar modified nucleotide and/or a base modified nucleotide, or any combination thereof.

The modified nucleosides and nucleotides, which may be included in the nucleotide mixture and incorporated into the RNA can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_{2O}$)nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, can be alkylamino, dialkylamino, heterocyclyl, arylamino, diarylamino, heteroarylamino, or diheteroaryl amino, ethylene diamine, polyamino) or aminoalkoxy. "Deoxy" modifications include hydrogen, amino (e.g., NH$_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O. The sugar group can also contain one or more carbons that possess the opposite stereochemical configuration than that of the corresponding carbon in ribose. Thus, a modified RNA molecule can include nucleotides containing, for instance, arabinose as the sugar.

The phosphate backbone can further be modified in the modified nucleosides and nucleotides, which can be included in the nucleotide mixture and incorporated into a modified in vitro transcribed RNA. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

A nucleotide as described herein can be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications includes an amino group, a thiol group, an alkyl group, or a halo group.

In some embodiments, the nucleotide analogues/modifications comprise 2-amino-6-chloropurineriboside-5'-triphosphate, 2-Aminopurine-rib oside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl-inosine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, 06-methylguanosine-5'-triphosphate, pseudouridine-5'-triphosphate, puromycin-5'-triphosphate, xanthosine-5'-triphosphate. Base-modified nucleotides can comprise 5-methylcytidine-5'-triphosphate, 7-deazaguanosine-5'-triphosphate, 5-bromocytidine-5'-triphosphate, and pseudouridine-5'-triphosphate, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methylcytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2, 6-diaminopurine, 7-deaza-8-aza-2, 6-diaminopurine, 1-methyl-adenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyl-adenosine, N6-threonylcarbamoyladenosine, 2-methylthio-N6-threonylcarbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethyl-guanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, 5'-O-(1-thiophosphate)-adenosine, 5'-O-(1-thiophosphate)-cytidine, 5'-O-(1-thiophosphate)-guanosine, 5'-O-(1-thiophosphate)-uridine, 5'-O-(1-thiophosphate)-pseudouridine, 6-aza-cytidine, 2-thio-cytidine, alpha-thio-cytidine, Pseudo-iso-cytidine, 5-aminoallyl-uridine, 5-iodo-uridine, N1-methyl-pseudouridine, 5,6-dihydrouridine, alpha-thio-uridine, 4-thio-uridine, 6-aza-uridine, 5-hydroxy-uridine, deoxy-thymidine, 5-methyl-uridine, Pyrrolo-cytidine, inosine, alpha-thio-guanosine, 6-methyl-guanosine, 5-methyl-cytdine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, alpha-thio-adenosine, 8-azido-adenosine, or 7-deaza-adenosine.

At least one modified nucleotide and/or the at least one nucleotide analog can comprise 1-methyladenosine, 2-methyladenosine, N6-methyladenosine, 2'-O-methyladenosine, 2-methylthio-N6-methyladenosine, N6-isopentenyladenosine, 2-methylthio-N6-isopentenyladenosine, N6-threonylcarbamoyladenosine, 2-methylthio-N6-threonylcarbamoyladenosine, N6-methyl-N6-threonylcarbamoyladenosine, N6-hydroxynorvalylcarbamoyladenosine, 2-methylthio-N6-hydroxynorvalylcarbamoyladenosine, inosine, 3-methylcytidine, 2-O-methylcytidine, 2-thiocytidine, N4-acetylcytidine, lysidine, 1-methylguanosine, 7-methylguanosine, 2'-O-methylguanosine, queuosine, epoxyqueuosine, 7-cyano-7-deazaguanosine, 7-aminomethyl-7-deazaguanosine, pseudouridine, dihydrouridine, 5-methyluridine, 2'-O-methyluridine, 2-thiouridine, 4-thiouridine, 5-methyl-2-thiouridine, 3-(3-amino-3-carb oxypropyl)uridine', 5-hydroxyuridine, 5-methoxyuridine, uridine 5-oxyacetic acid, uridine 5-oxyacetic acid methyl ester, 5-aminomethyl-2-thiouridine, 5-methylaminomethyluridine, 5-methyl aminomethyl-2-thiouridine, 5-methylaminomethyl-2-selenouridine, 5-carboxymethylaminomethyluridine, 5-carboxymethylaminomethyl-2'-O-methyluridine, 5-carboxymethylaminomethyl-2-thiouridine, 5-(isopentenylaminomethyl) uridine, 5-(isopentenylaminomethyl)-2-thiouridine, or 5-(isopentenylaminomethyl)-2'-O-methyluridine.

In some embodiments, chemical modifications comprise pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyluridine.

In some embodiments, 100% of the uracil in the coding sequence as defined herein can have a chemical modification. In some embodiments, a chemical modification is in the 5'-position of the uracil. In some embodiments, 100% of the uracil in the coding sequence (cds) of the RNA can have a chemical modification, e.g., a chemical modification that is in the 5'-position of the uracil. In other embodiments, at least 10%, 20%, 30%, 40%, 50%, 60%, 70%, 80%, or 90% of the uracil nucleotides in the cds have a chemical modification, e.g., a chemical modification that is in the 5-position of said uracil nucleotides. Such modifications may reduce the stimulation of the innate immune system (after in vivo administration of the RNA comprising such a modified nucleotide).

The terms "cds" or "coding sequence" or "coding region" as used herein will be recognized and understood by the person of ordinary skill in the art, and are e.g., can refer to a sequence of several nucleotide triplets, which may be translated into a peptide or protein. The cds of the RNA may comprise at least one modified nucleotide, wherein said at least one modified nucleotide may be selected from pseudouridine (ψ), N1-methylpseudouridine (m1ψ), 5-methylcytosine, and 5-methoxyuridine.

As used herein, the terms "modified nucleotides" or "chemically modified nucleotides" can refer to all potential natural and non-natural chemical modifications of the building blocks of an RNA, namely the ribonucleotides A, G, C, and U.

In various embodiments the nucleotide mixture in an in vitro transcription reaction comprises a cap analog. Accordingly, in some embodiments the cap analog is a cap0, cap1, cap2, a modified cap0 or a modified cap1 analog, or a cap1 analog as described below.

The term "cap analog" or "5'-cap structure" as used herein can refer to the 5' structure of the RNA, particularly a guanine nucleotide, positioned at the 5'-end of an RNA, e.g., an mRNA. In some embodiments, the 5'-cap structure is connected via a 5'-5'-triphosphate linkage to the RNA. In some embodiments, a "5'-cap structure" or a "cap analogue" is not considered to be a "modified nucleotide" or "chemically modified nucleotides". 5'-cap structures which may be suitable include cap0 (methylation of the first nucleobase, e.g., m7GpppN), cap1 (additional methylation of the ribose of the adjacent nucleotide of m7GpppN), cap2 (additional methylation of the ribose of the 2nd nucleotide downstream of the m7GpppN), cap3 (additional methylation of the ribose of the 3rd nucleotide downstream of the m7GpppN), cap4 (additional methylation of the ribose of the 4th nucleotide downstream of the m7GpppN), ARCA (anti-reverse cap analogue), modARCA (e.g. phosphothioate modARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

A 5'-cap (cap0 or cap1) structure can be formed in chemical RNA synthesis, using capping enzymes, or in RNA in vitro transcription (co-transcriptional capping) using cap analogs. The term "cap analog" as used herein can refer to a non-polymerizable di-nucleotide or tri-nucleotide that has cap functionality in that it facilitates translation or localization, and/or prevents degradation of the RNA when incorporated at the 5'-end of the RNA. Non-polymerizable means that the cap analogue will be incorporated only at the 5'-terminus because it does not have a 5' triphosphate and therefore cannot be extended in the 3'-direction by a template-dependent polymerase, (e.g., a DNA-dependent RNA polymerase). Examples of cap analogues include m7GppG, m7GpppA, m7GpppC; unmethylated cap analogues (e.g., GpppG); dimethylated cap analogue (e.g., m2,7GpppG), trimethylated cap analogue (e.g. m2,2,7GpppG), dimethylated symmetrical cap analogues (e.g. m7Gpppm7G), or anti reverse cap analogues (e.g., ARCA; m7,2'OmeGpppG, m7,2'dGpppG, m7,3'OmeGpppG, m7,3'dGpppG and their tetraphosphate derivatives). Further cap analogues have been described previously, e.g., WO2008/016473, WO2008/157688, WO2009/149253, WO2011/015347, and WO2013/059475. Further suitable cap analogues in that context are described in, e.g., WO2017/066793, WO2017/066781, WO2017/066791, WO2017/066789, WO2017/053297, WO2017/066782, WO2018/075827 and WO2017/066797 wherein the disclosures relating to cap analogues are incorporated herewith by reference.

In some embodiments, a cap1 structure is generated using tri-nucleotide cap analogue as disclosed in WO2017/053297, WO2017/066793, WO2017/066781, WO2017/066791, WO2017/066789, WO2017/066782, WO2018/075827 and WO2017/066797. For example, any cap analog derivable from the structure disclosed in claim 1-5 of WO2017/053297 may be suitably used to co-transcriptionally generate a cap1 structure. In some embodiments, any cap analog derivable from the structure described in WO2018/075827 can be suitably used to co-transcriptionally generate a cap1 structure. In some embodiments, the cap1 analog is a cap1 trinucleotide cap analog. In some embodiments, the cap1 structure of the in vitro transcribed RNA is formed using co-transcriptional capping using tri-nucleotide cap analog m7G(5')ppp(5')(2'OMeA)pG or m7G(5') ppp(5') (2' OMeG)pG. In some embodiments, the cap1 analog is m7G(5') ppp(5') (2' OMeA)pG.

In some embodiments, the RNA (e.g., mRNA) comprises a 5'-cap structure, e.g., a cap1 structure. In some embodiments, the 5' cap structure can improve stability and/or expression of the mRNA. A cap1 structure comprising mRNA (produced by, e.g., in vitro transcription) has several advantageous features including an increased translation efficiency and a reduced stimulation of the innate immune system. In some embodiments, the in vitro transcribed RNA comprises at least one coding sequence encoding at least one peptide or protein. In some embodiments, the protein is an RNA-guided endonuclease. In some embodiments, the RNA-guided endonuclease is Cas9 or a derivative thereof.

The present disclosure provides optimized mRNAs encoding an *S. pyogenes* Cas9 endonuclease ("SpCas9 mRNA"), and which optionally include chemically modified nucleotides, that provide effective genome editing of a target cell population when administered with one or more gRNAs. In some embodiments, the disclosure provides an mRNA comprising (i) a 5' untranslated region (UTR); (ii) an open reading frame (ORF) comprising a nucleotide sequence that encodes a site-directed endonuclease; and (iii) a 3' untranslated region (UTR). In some embodiments, the site-directed endonuclease is a Cas nuclease. In some embodiments, the Cas nuclease is a Cas9 polypeptide. In some embodiments, the Cas9 polypeptide is a *Streptococcus pyogenes*-derived Cas9 (SpCas9) polypeptide. In some embodiments, the ORF further comprises one or more nucleotide sequences encoding a nuclear localization signal, such as one described herein. In some embodiments, the ORF comprises a nucleotide sequence encoding a site-directed endonuclease, such as a SpCas9 polypeptide and at least one NLS that is a nucleoplasmin and/or SV40 NLS. In some embodiments, the ORF comprises a nucleotide sequence encoding an N-terminal and/or C-terminal NLS operably-linked to a site-directed endonuclease, such as a SpCas9 polypeptide. In some embodiments the ORF comprises a nucleotide sequence encoding an N-terminal SV40 NLS operably-linked to a site-directed endonuclease, such as a SpCas9 polypeptide, and a C-terminal nucleoplasmin NLS operably-linked to the site-directed endonuclease, such as the SpCas9 polypeptide.

In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 17. In some embodiments, the disclosure provides an mRNA comprising a nucleotide sequence that is 100% identical to the nucleotide sequence of SEQ ID NO: 17. In some embodiments, the mRNA comprises a codon-optimized sequence comprising a nucleotide sequence that is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 17.

In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 16. In some embodiments, the disclosure provides an mRNA comprising a nucleotide sequence that is 100% identical to the nucleotide sequence of SEQ ID NO: 16.

In some embodiments, the mRNA can comprise at least one chemically modified nucleoside and/or nucleotide. In some embodiments, the chemically modified nucleoside is selected from pseudouridine, N1-methylpseudouridine, and 5-methoxyuridine. In some embodiments, the chemically modified nucleoside is N1-methylpseudouridine (e.g., 1-methylpseudouridine). In some embodiments, at least about 80% or more (e.g., about 85%, 90%, 91%, 92%, 93%, 94%, 95%, 96%, 97%, 98%, 99%) of uridines in the mRNA are modified or replaced with N1-methylpseudouridine. In some embodiments, 100% of the uridines (e.g., uracils) in the mRNA are modified or replaced with N1-methylpseudouridine. In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 16, wherein 100% of the uridines or uracils of the mRNA are modified or replaced with N1-methylpseudouridine. In some embodiments, two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800 or more) of the uridine or uracil residues are N1-methylpseudouridine.

In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 18. In some embodiments, the disclosure provides an mRNA comprising a nucleotide sequence that has one, two, three, four, or five mismatches to the nucleotide sequence of SEQ ID NO: 18. In some embodiments, the disclosure provides an mRNA comprising a nucleotide sequence that is 100% identical to the nucleotide sequence of SEQ ID NO: 18.

In some embodiments, the disclosure provides an mRNA comprising a nucleotide sequence that is at least 85% or more (e.g., 86%, 87%, 88%, 89%, 90%, 91%, 92%, 93%, 94%, 95%, 96%, 97%, 98%, 99%, 100%) identical to the nucleotide sequence of SEQ ID NO: 19. In some embodiments, the disclosure provides an mRNA comprising a nucleotide sequence that has one, two, three, four, or five mismatches to the nucleotide sequence of SEQ ID NO: 19. In some embodiments, the disclosure provides an mRNA comprising a nucleotide sequence that is 100% identical to the nucleotide sequence of SEQ ID NO: 19.

In some embodiments, the disclosure provides an mRNA comprising a nucleotide sequence that is 100% identical to the nucleotide sequence of SEQ ID NO: 16, wherein 100% of the uridines (e.g., uracils) of the mRNA are modified or replaced with N1-methylpseudouridine. In some embodiments, the disclosure provides an mRNA comprising or consisting of the nucleotide sequence of SEQ ID NO: 18. In some embodiments, the disclosure provides an mRNA comprising or consisting of the nucleotide sequence of SEQ ID NO: 19. In some embodiments, a mRNA can further comprise a 5' cap, such as one described herein. In some embodiments, the 5' cap is a cap-0, a cap-1, or a cap-2 structure. SEQ ID NO: 17 is the sequence of an non-limiting exemplary parent Cas9 mRNA. SEQ ID NOs: 18 and 19 are codon-optimized sequence derived from the parent Cas9 mRNA, and some u are N1-methylpseudouridines in SEQ ID Nos: 18 and 19.

Guide RNAs (gRNAs)

In some embodiments, the CRISPR/Cas-mediated gene editing system used to genetically edit a ANGPTL3 gene comprises a genome-targeting nucleic acid (e.g., a guide RNA) that can direct the activities of an RNA-guided endonuclease to a specific target sequence within the ANGPTL3 gene. A guide RNA comprises at least a spacer sequence that hybridizes to a target nucleic acid sequence of interest, and a CRISPR repeat sequence. The gRNA can be a single-molecule guide RNA (sgRNA) or a double-molecule guide RNA. The RNA-guided endonuclease can be, for example a Cas endonuclease, including Cas9 endonuclease. The Cas9 endonuclease can be, for example, a SpyCas9, a SaCas9, or a SluCas9 endonuclease. In some embodiments, the RNA-endonuclease is a Cas9 variant. In some embodiments, the RNA-guided endonuclease is a small RNA-guided endonuclease. In some embodiments, the RNA-guided endonuclease is a small Cas endonuclease.

In some embodiments, the gRNA comprise 5' to 3': a crRNA and a tracrRNA, wherein the crRNA and tracrRNA hybridize to form a duplex. In some embodiments, the crRNA comprises a spacer sequence capable of targeting a target sequence in a target nucleic acid (e.g., genomic DNA molecule) and a crRNA repeat sequence. In some embodiments, the tracrRNA comprises a tracrRNA anti-repeat sequence and a 3' tracrRNA sequence. In some embodiments, the 3' end of the crRNA repeat sequence is linked to the 5' end of the tracrRNA anti-repeat sequence, e.g., by a tetraloop, wherein the crRNA repeat sequence and the tracrRNA anti-repeat sequence hybridize to form the sgRNA. In some embodiments, the sgRNA comprises 5' to 3': a spacer sequence, a crRNA repeat sequence, a tetraloop, a tracrRNA anti-repeat sequence, and a 3' tracrRNA sequence. In some embodiments, the sgRNA comprise a 5' spacer extension sequence. In some embodiments, the sgRNA comprise a 3' tracrRNA extension sequence. The 3' tracrRNA can comprise, or consist of, one or more stem loops, for example one, two, three, or more stem loops.

In some embodiments, the invariable sequence of the sgRNA comprises the nucleotide sequence of GUUUUA-GAGCUAGAAAUAGCAAGUUAAAAUAAGGCUAGU-CCGUUAUCAACUUGAAA AAGUGGCACCGAGUCG-GUGCUUUU (SEQ ID NO: 1), or a nucleotide sequence having up to 1, 2, 3, 4, 5, 6, 7, 8, 9, or 10 nucleotide deletions, insertions, or substitutions relative to SEQ ID NO: 1. In some embodiments, the sgRNA is for use with a SpyCas9 endonuclease.

The guide RNA disclosed herein can target any sequence of interest via the spacer sequence in the crRNA. A spacer sequence in a gRNA is a sequence (e.g., a 20 nucleotide sequence) that defines the target sequence (e.g., a DNA target sequences, such as a genomic target sequence) of a target gene of interest (e.g., ANGPTL3 gene). In some embodiments, the spacer sequence range from 15 to 30 nucleotides. For example, the spacer sequence can be, can be about, can be at least, or can be at most 10, 15, 16, 17, 18, 19, 29, 21, 22, 23, 24, 25, 26, 27, 28, 29, 30, 40, 50, or a number or a range between any of these values, of nucleotides in length. In some embodiments, a spacer sequence contains 20 nucleotides. In some embodiments, the gRNA is capable of hybridizing to the forward strand of the target dsDNA. In some embodiments, the gRNA is capable of hybridizing to the reverse strand of the target dsDNA.

The terms "target nucleic acid," "target site," and "target sequence" may be used interchangeably throughout and can refer to any nucleic acid sequence that may be targeted by a gRNA sequence described herein. In some embodiments, the "target sequence" is in a target gene that is adjacent to a PAM sequence and is the sequence to be modified by an RNA-guided nuclease (e.g., Cas9). The "target sequence" is on the so-called PAM-strand in a "target nucleic acid," which is a double-stranded molecule containing the PAM-strand and a complementary non-PAM strand. One of skill in the art recognizes that the gRNA spacer sequence hybridizes to the complementary sequence located in the non-PAM strand of the target nucleic acid of interest. Thus, the gRNA spacer sequence is the RNA equivalent of the target sequence. The spacer of a gRNA interacts with a target nucleic acid of interest in a sequence-specific manner via hybridization (i.e., base pairing). The nucleotide sequence of the spacer thus varies depending on the target sequence of the target nucleic acid of interest. In some embodiments, the target sequence of the ANGPTL3 gene is within exon 1, 2, 3, 4, 5, 6 or 7 of the ANGPTL3 gene. In some embodiments, the target sequence of the ANGPTL3 gene is within exon 1 of the ANGPTL3 gene. In some embodiments, the spacer of the gRNA binds complementarily to the target sequence located at chr1: 62597719-62597738 (-) (without PAM) or at chr1: 62597716-62597738 (-) (with PAM).

In a CRISPR/Cas system used herein, the spacer sequence is designed to hybridize to a region of the target nucleic acid that is located 5' of a PAM recognizable by a Cas9 enzyme used in the system. The spacer can perfectly match the target sequence or can have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence has 20 nucleotides in length. In some embodiments, the target nucleic acid has less than 20 nucleotides in length. In some embodiments, the target nucleic acid has more than 20 nucleotides in length. In some embodiments, the target nucleic acid has at least: 5, 10, 15, 16, 17, 18, 19, 20, 21, 22, 23, 24, 25, 30 or more nucleotides in length. In some embodiments, the target nucleic acid has at most: 5, 10, 15, 16, 17, 18, 19, 20, 21, 22, 23, 24, 25, 30 or more nucleotides in length. In some embodiments, the target nucleic acid sequence has 20 bases immediately 5' of the first nucleotide of the PAM. For example, in a sequence comprising 5'-NNNNNNNNNNNNNNNNNNNNGR-3', the target nucleic acid can be the sequence that corresponds to the Ns, wherein N can be any nucleotide, and the underlined NRG sequence (R is G or A) is the S. pyogenes PAM. In some embodiments, the PAM sequence used in the compositions and methods of the present disclosure as a sequence recognized by SpCas9 is NGG, wherein N can be A, T, C or G.

In some embodiments, the percent complementarity between the spacer sequence and the target nucleic acid is about, at least, at least about, at most or at most about 30%, 40%, 50%, 60%, 65%, 70%, 75%, 80%, 85%, 90%, 95%, 97%, 98%, 99%, or 100%. In some embodiments, the spacer sequence of the guide RNA and the target nucleic acid in the target gene is 100% complementary. In some embodiments, the percent complementarity between the spacer sequence and the target nucleic acid is 100% over the six contiguous 5'-most nucleotides of the target sequence of the complementary strand of the target nucleic acid. In some embodiments, the percent complementarity between the spacer sequence and the target nucleic acid is at least 60% over about 20 contiguous nucleotides. In other embodiments, the spacer sequence of the guide RNA and the target sequence in the target gene can contain up to 10 mismatches, e.g., up to 9, up to 8, up to 7, up to 6, up to 5, up to 4, up to 3, up to 2, or up to 1 mismatch.

In some embodiments, the gRNA comprises a spacer sequence selected from SEQ ID NOs: 3-9 and SEQ ID NOs: 20-26, listed in Table 1. In some embodiments, the gRNA comprises a spacer sequence capable of hybridizing to a sequence selected from SEQ ID NOs: 3-9 listed in Table 1 or a sequence that is complementary to a sequence selected from SEQ ID NOs: 3-9.

TABLE 1

EXEMPLARY SPACER SEQUENCES

| Guide RNA | Guide Spacer Sequence/ Target Site | *SEQ ID NO: | PAM |
|---|---|---|---|
| ANGPTL3 T10 | TAAGACCATGTCCCAACTGA | 3, 20 | AGG |
| ANGPTL3 T6 | GCCAATGGCCTCCTTCAGTT | 4, 21 | GGG |

TABLE 1-continued

EXEMPLARY SPACER SEQUENCES

| Guide RNA | Guide Spacer Sequence/ Target Site | *SEQ ID NO: | PAM |
|---|---|---|---|
| ANGPTL3 T1 | TATATTGGTCTTCCACGGTC | 5, 22 | TGG |
| ANGPTL3 T7 | CCAGAAAAGGTAAGGTTGGT | 6, 23 | AGG |
| ANGPTL3 T3 | GGTCTTCCACGGTCTGGAGA | 7, 24 | AGG |
| ANGPTL3 T9 | GGCCTCCTTCAGTTGGGACA | 8, 25 | TGG |
| A4 | TTACTAAAGGAACAACAAAA | 9, 26 | |

*SEQ ID NOs: 3-9 are DNA and SEQ ID NOs: 20-26 are RNA

In some embodiments, the gRNA comprises a spacer sequence from any one of SEQ ID NOs: 3-9 and SEQ ID NOs: 20-26 or variants thereof having about, at least, at least about 80%, 85%, 90%, 95%, 97%, 98%, 99%, or 100% homology to any spacer of SEQ ID NOs: 3-9 and SEQ ID NOs: 20-26. In some embodiments, the gRNA comprises a spacer sequence of any one of SEQ ID NOs: 3-9 and SEQ ID NOs: 20-26. In some embodiments, the gRNA is an sgRNA. In some embodiments, the gRNA comprises a spacer sequence from any one of SEQ ID NOs: 3-9 and SEQ ID NOs: 20-26 or a variant thereof having no more than 3 mismatches compared to any one of SEQ ID NOs: 3-9 and SEQ ID NOs: 20-26.

In some embodiments, two gRNAs comprising spacers complementary to a target sequence of the ANGPLT3 gene are provided to a cell. In some embodiments, the gRNAs are any two gRNAs comprising spacers selected from the group consisting of SEQ ID NOs:3-9 and SEQ ID NOs: 20-26 or variants thereof having at least 85% homology to the spacers of SEQ ID NOs: 3-9 and SEQ ID NOs: 20-26 or variants having no more than 3 mismatches compared to any one of SEQ ID NOs: 3-9 and SEQ ID NOs: 20-26.

In some embodiments, the gRNA comprises a spacer sequence of SEQ ID NO: 4 or SEQ ID NO: 21 or variants thereof having about, at least, at least about 80%, 85%, 90%, 95%, 97%, 98%, 99%, or 100% homology to the spacer of SEQ ID NO: 4 or SEQ ID NO: 21. In some embodiments, the gRNA comprises a spacer sequence of SEQ ID NO: 4 or SEQ ID NO: 21 or a variant thereof having no more than 3 mismatches compared to SEQ ID NO: 4 or SEQ ID NO: 21. In some embodiments, the gRNA comprises a spacer sequence of SEQ ID NO: 4 or SEQ ID NO: 21.

In some embodiments, the gRNA comprises a spacer sequence of SEQ ID NO: 3 or SEQ ID NO: 20 or variants thereof having about, at least, or at least about 80%, 85%, 90%, 95%, 97%, 98%, 99%, or 100% homology to the spacer of SEQ ID NO: 3 or SEQ ID NO: 20. In some embodiments, the gRNA comprises a spacer sequence of SEQ ID NO: 3 or SEQ ID NO: 20 or a variant thereof having no more than 3 mismatches compared to SEQ ID NO: 3 or SEQ ID NO: 20. In some embodiments, the gRNA comprises a spacer sequence of SEQ ID NO: 3 or SEQ ID NO: 20. In some embodiments, the gRNA is a sgRNA.

In some embodiments, the gRNAs comprise a first gRNA comprising a spacer sequence of SEQ ID NO: 3 or SEQ ID NO: 20 (or a variant having about, at least, or at least about 85% homology to SEQ ID NO: 3 or SEQ ID NO: 20) and a second gRNA comprising a spacer sequence of SEQ ID NO: 4 or SEQ ID NO: 21 (or a variant having about, at least, or at least about 85% homology to SEQ ID NO: 4 or SEQ ID NO: 21). The gRNAs can further comprise one or more gRNA having a spacer sequence of any one of SEQ ID NOs: 5-8 and SEQ ID NOs: 22-25 or variants having about, at least, or at least about 85% homology to any one of SEQ ID NOs: 5-8 and SEQ ID NOs: 22-25.

In some embodiments, the gRNA is a chemically modified gRNA. Various types of RNA modifications can be introduced to the gRNAs to enhance stability, reduce the likelihood or degree of innate immune response, and/or enhance other attributes as described in the art. The gRNAs described herein can comprise one or more modifications including internucleoside linkages, purine or pyrimidine bases, or sugar. In some embodiments, a modification is introduced at the terminal of a gRNA with chemical synthesis or with a polymerase enzyme. Examples of modified nucleic acids and their synthesis are disclosed in WO2013/052523. Synthesis of modified polynucleotides is also described in Verma and Eckstein, Annual Review of Biochemistry, vol. 76, 99-134 (1998).

In some embodiments, the chemically-modified gRNA comprises phosphorothioated 2'-O-methyl nucleotides at the 3' end and the 5' end of the gRNA. In some embodiments, the chemically-modified gRNA comprises phosphorothioated 2'-O-methyl nucleotides at the 3' end of the gRNA. In some embodiments, the chemically-modified gRNA comprises phosphorothioated 2'-O-methyl nucleotides at the 5'end of the gRNA. In some embodiments, the chemically-modified gRNA comprises three or four phosphorothioated 2'-O-methyl nucleotides at the 3' end and/or three or four at the 5' end of the gRNA. In some embodiments, any one of a gRNA comprising any of SEQ ID NOs: 3-9 and SEQ ID NOs: 20-26 can be chemically modified to have four phosphorothioated 2'-O-methyl nucleotides at the 3' end and/or three at the 5' end of the gRNA.

The number and position of the phosphorothioate linkages can vary. In some embodiments, the linkage can be between the first and second, the second and third, the third and fourth position, fourth and fifth, fifth and sixth, sixth and seventh, seventh and eighth, eighth and ninth, ninth or tenth, or further, position from the 5' end of the gRNA. In some embodiments, the linkage can be between the first and second, the second and third, the third and fourth position, fourth and fifth, fifth and sixth, sixth and seventh, seventh and eighth, eighth and ninth, ninth or tenth, or further, position from the 3' end of the gRNA.

In some embodiments, the nucleotide analogues/modifications can comprise 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl-inosine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, 06-methylguanosine-5'-triphosphate, pseudouridine-5'-triphosphate, puromycin-5'-triphosphate, or xanthosine-5'-triphosphate. Base-modified nucleotides can comprise 5-methylcytidine-5'-triphosphate, 7-deazaguanosine-5'-triphosphate, 5-bromocytidine-5'-triphosphate, and pseudouridine-5'-triphosphate, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carb oxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine, 5-azacytidine, pseudoisocytidine, 3-methyl-cytidine, N4-acetyl-cytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2, 6-diaminopurine, 7-deaza-8-aza-2, 6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonylcarbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, 5'-O-(1-thiophosphate)-adenosine, 5'-O-(1-thiophosphate)-cytidine, 5'-O-(1-thiophosphate)-guanosine, 5'-O-(1-thiophosphate)-uridine, 5'-O-(1-thiophosphate)-pseudouridine, 6-aza-cytidine, 2-thio-cytidine, alpha-thio-cytidine, Pseudo-iso-cytidine, 5-aminoallyl-uridine, 5-iodo-uridine, N1-methyl-pseudouridine, 5,6-dihydrouridine, alpha-thio-uridine, 4-thio-uridine, 6-aza-uridine, 5-hydroxy-uridine, deoxy-thymidine, 5-methyl-uridine, Pyrrolo-cytidine, inosine, alpha-thio-guanosine, 6-methyl-guanosine, 5-methyl-cytdine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, alpha-thio-adenosine, 8-azido-adenosine, or 7-deaza-adenosine.

At least one modified nucleotide and/or the at least one nucleotide analog can comprise 1-methyladenosine, 2-methyladenosine, N6-methyladenosine, 2'-O-methyladenosine, 2-methylthio-N6-methyladenosine, N6-isopentenyladenosine, 2-methylthio-N6-isopentenyladenosine, N6-threonylcarbamoyladenosine, 2-methylthio-N6-threonylcarbamoyladenosine, N6-methyl-N6-threonylcarbamoyladenosine, N6-hydroxynorvalylcarbamoyladenosine, 2-methylthio-N6-hydroxynorvalyl carbamoyladenosine, inosine, 3-methylcytidine, 2-O-methylcytidine, 2-thiocytidine, N4-acetylcytidine, lysidine, 1-methylguanosine, 7-methylguanosine, 2'-O-methylguanosine, queuosine, epoxyqueuosine, 7-cyano-7-deazaguanosine, 7-aminomethyl-7-deazaguanosine, pseudouridine, dihydrouridine, 5-methyluridine, 2'-O-methyluridine, 2-thiouridine, 4-thiouridine, 5-methyl-2-thiouridine, 3-(3-amino-3-carb oxypropyl)uridine', 5-hydroxyuridine, 5-methoxyuridine, uridine 5-oxyacetic acid, uridine 5-oxyacetic acid methyl ester, 5-aminomethyl-2-thiouridine, 5-methylaminomethyluridine, 5-methyl aminomethyl-2-thiouridine, 5-methylaminomethyl-2-selenouridine, 5-carboxymethylaminomethyluridine, 5-carboxymethylaminomethyl-2'-O-methyluridine, 5-carboxymethyl-aminomethyl-2-thiouridine, 5-(isopentenylaminomethyl) uridine, 5-(isopentenylaminomethyl)-2-thiouridine, or 5-(isopentenylaminomethyl)-2'-O-methyluridine.

In some embodiments, chemical modifications comprise pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine or 2'-O-methyluridine. In some embodiments, the modification comprises a 2'-O-methyluridine (2'OMe-rU), a 2-O-methylcytidine (2'OMe-rC), 2'-O-methyladenosine (2'OMe-rA), or 2'-O-methylguanosine (2'OMe-rG).

The gRNA can comprise any number of modified nucleic acids. In some embodiments, the percentage of nucleic acids in a gRNA molecule that are modified can be, can be at least, can be about, or can be at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% of the gRNA sequence.

For example, SEQ ID NO: 20 can be chemically modified as: "u*a*a*GAC CAU GUC CCA ACU GA" (SEQ ID NO: 12) (Ts are converted to Us), in which u=2'OMe-rU; a = 2'OMe-rA; *=Thiolated Phosphate.

In some embodiments, the gRNA comprises a sequence of SEQ ID NO: 10, and the RNA sequence can be modified as:
5'-u*a*a* GAC CAU GUC CCA ACU GAG UUU UAG Agc uag aaa uag cAA GUU AAA AUA AGG CUA GUC CGU UAU Caa cuu gaa aaa gug gca ccg agu cgg ugc u*u*u-3' (SEQ ID NO: 13) wherein, u=2'OMe-rU; a=2'OMe-rA; c=2'OMe-rC; g=2'OMe-rG; *=Thiolated Phosphate. The underlined sequence corresponds to the spacer.

In another example, a gRNA spacer sequence of SEQ ID NO: 9 can be chemically modified as: "u*u*a* CUA AAG GAA CAA CAA AA" (SEQ ID NO: 14) (Ts are converted to Us), in which u=2'OMe-rU; a=2'OMe-rA; *=Thiolated Phosphate.

In some embodiments, the gRNA comprises a sequence of SEQ ID NO: 11, and can be chemically modified as:

5'-u*u*a* CUA AAG GAA CAA CAA AAG UUU UAG Agc uag aaa uag cAA GUU AAA AUA AGG CUA GUC CGU UAU CAa cuu gaa aaa gug gca ccg agu cgg ugc u*u*u*u-3' (SEQ ID NO:15), wherein, u=2'OMe-rU; a=2'OMe-rA; c=2'OMe-rC; g=2'OMe-rG; *=Thiolated Phosphate. The underlined sequence corresponds to the spacer.

In some embodiments, more than one guide RNA can be used with a CRISPR/Cas nuclease system. Each guide RNA can contain a different targeting sequence, such that the CRISPR/Cas system cleaves more than one target nucleic acid. In some embodiments, one or more guide RNAs can have the same or differing properties such as activity or stability within the Cas9 RNP complex. Where more than one guide RNA is used, each guide RNA can be encoded on the same or on different vectors.

In some embodiments, the gRNAs described herein can be produced by in vitro transcription (IVT), synthetic and/or chemical synthesis methods, or a combination thereof. One or more of enzymatic IVT, solid-phase, liquid-phase, combined synthetic methods, small region synthesis, and ligation methods can be utilized. In some embodiments, the gRNAs are made using IVT enzymatic synthesis methods. Methods of making polynucleotides by IVT are known in the art and are described in WO2013/151666. Polynucleotides constructs and vectors can be used to in vitro transcribe a gRNA described herein.

Methods of Editing ANGPTL3

Provided herein includes a method of using genome editing to edit ANGPTL3 by functionally knocking out or reducing the expression of the ANGPTL3 gene in the genome of a cell. The method can be used to treat a subject, e.g., a patient with a ANGPTL3-associated diseases or condition.

Provided herein includes a method for treating an ANGPTL3-related disease or disorder in a subject (e.g., a primate subject) in need thereof. In some embodiments, the method comprises administering to the primate subject a plurality of nanoparticles complexed with (a) a guide RNA (gRNA) or a nucleic acid encoding a gRNA that targets ANGPTL3 gene, and (b) a nucleic acid encoding a RNA-guided endonuclease, thereby relieve the ANGPTL3-related disease or disorder in the primate subject. The subject can be administered with the plurality of nanoparticles two or more times, for example twice, for the treatment. Two administration of the nanoparticles to the subject can be separated by a suitable time period. In some embodiments, the suitable time period is, or is about, one week, two weeks, three weeks, four weeks, five weeks, six weeks, seven weeks, eight weeks, three months, four months, five months, six months, a year, two years, three years, or more. In some embodiments, two of the two or more administrations are about two weeks to about two months apart, for example about three weeks. In some embodiments, each two of the two or more administrations are about two weeks to about two months apart, for example about three weeks. The suitable time period between two administrations can be the same as or different from the suitable time period between another two administrations. In some embodiments, the plurality of nanoparticles is administered to the subject at a dose of about 0.01-5 mg/kg, for example 0.05-2 mg/kg, 0.5-3 mg/kg or 0.1-1 mg/kg, per administration. In some embodiments, the ANGPTL3 gRNA or the nucleic acid encoding the ANGPTL3 gRNA is administered to the subject at a dose of, or a dose of about, 0.01-5 mg/kg, for example 0.1-1 mg/kg gRNA per administration. In some embodiments, the nucleic acid encoding the RNA-guided endonuclease is administered to the subject at a dose of, or a dose of about, 0.1-5 mg/kg, for example 0.5-3 mg/kg or 0.3-2 mg/kg per administration. The dose can be the same or different for each of the administration to the subject.

In some embodiments, the gRNA targets within or near a coding sequence in the ANGPTL3 gene. In some embodiments, the gRNA targets a sequence within one of the 12 exons of the ANGPTL3 gene. In some embodiments, the gRNA targets a sequence within exon 1 of the ANGPTL3 gene. In some embodiments, the gRNA targets a sequence within exon 1 of the ANGPTL3 gene. The gRNA can comprise a spacer sequence complementary to a target sequence within exon 1 of the ANGPTL3 gene. In some embodiments, the spacer(s) are complementary to a sequence within or near (for example, within any of 1, 2, 3, 4, 5, 6, 7, 8, 9, 10, 15, 20, 25, 30, 35, 40, 45, 50, 55, 60, 65, 70, 75, 80, 85, 90, 95, 100 or more bases from) exon 1 of the ANGPTL3 gene. In some embodiments, the spacer of the gRNA binds complementarily to the target sequence located at chr1: 62597719-62597738 (-) (without PAM) or at chr1: 62597716-62597738 (-) (with PAM). The complementarity between the spacer of the gRNA and the target sequence in the ANGPTL3 gene can be perfect or imperfect. In some embodiments, the complementarity can be at least 70%, 80%, 90%, 100% or a number or a range between any two of these values. In some embodiments, the complementarity is perfect, i.e. 100%.

In some embodiments, the gRNA comprises a spacer sequence selected from SEQ ID NOs: 3-9 and SEQ ID NOs: 20-26 or variants thereof having about, at least, at least about 80%, 85%, 90%, 95%, 97%, 98%, 99%, or 100% homology to any spacer of SEQ ID NOs: 3-9 and SEQ ID NOs: 20-26. In some embodiments, the gRNA comprises a spacer sequence selected from SEQ ID NOs: 3-9 and SEQ ID NOs: 20-26 or a variant thereof having no more than 3 mismatches compared to any one of SEQ ID NOs: 3-9 and SEQ ID NOs: 20-26. In some embodiments, the gRNA comprises a spacer sequence selected from SEQ ID NOs: 3-9 and SEQ ID NOs: 20-26. In some embodiments, the gRNA comprises or consists of a spacer sequence of SEQ ID NO: 12.

In some embodiments, the gRNAs used in the methods herein can comprise two or more gRNAs, each comprising a spacer complementary to a target sequence of the ANGPLT3 gene (e.g., any one of SEQ ID NOs: 3-9 and SEQ ID NOs: 20-26 or variants thereof having at least 85% homology to any one of SEQ ID Nos: 3-9 and SEQ ID NOs: 20-26 or variants having no more than 3 mismatches compared to any one of SEQ ID NOs: 3-9 and SEQ ID NOs: 20-26).

In some embodiments, the guide sequence comprises a spacer sequence of SEQ ID NO: 4 or SEQ ID NO: 21 or variants thereof having about, at least, at least about 80%, 85%, 90%, 95%, 97%, 98%, 99%, or 100% homology to the spacer of SEQ ID NO: 4 or SEQ ID NO: 21. In some embodiments, the guide sequence comprises a spacer sequence of SEQ ID NO: 4 or SEQ ID NO: 21.

In some embodiments, the guide sequence comprises a spacer sequence of SEQ ID NO: 3, SEQ ID NO: 20, or variants thereof having about, at least, at least about 80%, 85%, 90%, 95%, 97%, 98%, 99%, or 100% homology to the spacer of SEQ ID NO: 3 or SEQ ID NO: 20. In some embodiments, the guide sequence comprises a spacer sequence of SEQ ID NO: 3 or SEQ ID NO: 20. In some embodiments, the guide sequence comprises or consists of a spacer sequence of SEQ ID NO: 12. In some embodiments, the guide sequence comprises a sequence of SEQ ID NO: 10 or variants thereof having about, at least, at least about 80%, 85%, 90%, 95%, 97%, 98%, 99%, or 100% homology to the sequence of SEQ ID NO: 10. In some embodiments, the guide sequence comprises a sequence of SEQ ID NO: 10. In some embodiments, the guide sequence comprises or consists of the sequence of SEQ ID NO: 13.

The gRNAs used herein can enhance on-target activity while significantly reducing potential off-target effects (i.e., cleaving genomic DNA at undesired locations other than ANGPTL3 gene). In some embodiments, the off-target binding is reduced by about, at least or at least about 80%, 85%, 90%, 95%, 98%, 99% or 100%.

In some embodiments, the DNA endonuclease is a Cas endonuclease described herein or known in the art. The Cas endonuclease can be naturally-occurring or non-naturally-occurring (e.g., recombinant or with mutations). In some embodiments, the DNA endonuclease is selected from the group consisting of a Cas1, Cas1B, Cas2, Cas3, Cas4, Cas5, Cash, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a functional derivative thereof. In some embodiments, the DNA endonuclease is a Cas9 endonuclease or a variant thereof. In some embodiments, the Cas9 endonuclease is from *Streptococcus pyogenes* (SpyCas9). In some embodiments, the Cas9 endonuclease is from *Staphylococcus lugdunensis* (SluCas9)

In some embodiments, the genetic modification of the ANGPTL3 gene results in a significantly reduced plasma ANGPTL3 protein, plasma ApoB protein, and/or lipid levels such as triglyceride level in the subject (e.g., mammal, NHP, a human subject). In some embodiments, the plasma ANGPTL3 protein level is reduced by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values. In some embodiments, the methods described herein can decrease the plasma ANGPTL3 protein level by about, at least or at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values.

In some embodiments, the genetic modification of the ANGPTL3 gene results in significantly reduced lipid levels (e.g., total cholesterols, triglycerides, HDLs, LDLs, and other non-HDL lipids) in the subject (e.g., mammal, NHP, a human subject). In some embodiments, the gene editing methods described herein can reduce the non-HDL lipid levels (e.g., LDLs, VLDLs, and/or triglycerides) by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values. In some embodiments, the plasma triglyceride level is reduced by about, at least or at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values.

In some embodiments, the genetic modification of the ANGPTL3 gene results in a significantly reduced plasma ApoB protein levels in the subject (e.g., mammal, NHP, a human subject). In some embodiments, the plasma ApoB protein level is reduced by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values. In some embodiments, the methods described herein can decrease the plasma ApoB protein level by about, at least or at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or a number or a range between any two of these values.

In some embodiments, the plasma ANGPTL3 protein, ApoB protein, and/or non-HDL lipid levels (e.g., triglycerides) in a genetically modified subject (e.g., mammal, NHP, a human subject) are about, less than or less than about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as compared to a corresponding unmodified mammal.

In some embodiments, the reduction of the concentration of ANGPTL3 protein, the level of one or more of the non-high-density lipoprotein (non-HDL) lipids, and/or the concentration of ApoB protein in the subject (e.g., mammal, NHP, a human subject) is at least 20%, at least 40%, or at least 70% three weeks, four weeks, five weeks, one month, two months, three months, four months, five months, six months, seven months, eight months, nine months, ten months, eleven months, twelve months, or longer after the administration. In some embodiments, the reduction of the concentration of ANGPTL3 protein, the level of one or more of the non-high-density lipoprotein (non-HDL) lipids, and/or the concentration of ApoB protein is at least 20%, at least 40%, or at least 70% three weeks, four weeks, five weeks, one month, two months, three months, four months, five months, six months, seven months, eight months, nine months, ten months, eleven months, twelve months, or longer after a single administration.

In some embodiments, eligibility and endpoints (e.g., at 6 months) for the method disclosed herein include: the subject is non-HDL-C>160 mg/dl, triglycerides>300 mg/dL, and/or ApoB>100 mg/dL before treatment, and the results of the method are determined by measuring the change in non-HDL-C(total cholesterol—HDL) from baseline, change in triglycerides from baseline, and/or change in ApoB from baseline. Non-HDL levels is 30 mg/dL above LDL Non-HDL=LDL, VLDL, IDL and Lp(a). In some embodiments, the subject has a triglyceride level of more than 300 mg/dL, a non-high-density lipoprotein (HDL) level of more than 160 mg/dL, a low-density lipoprotein cholesterol (LDL-C) level greater than 100 mg/dL, an ApoB level of more than 100 mg/dL, or a combination thereof. The method can comprise measuring the blood level of one or more of ANGPTL3, ApoB, triglyceride, very low density lipoprotein (VLDL), low-density lipoprotein (LDL), LDL-C, HDL, and non-HDL lipids in the subject prior to, during, and/or after the administration.

In some embodiments, the subject is refractory to one or more (or all) of available SOC lines of treatment, including ezetimibe and/or PCSK9 inhibitors for at least 12 weeks prior to screening. In some embodiments, HoFH subjects on Evinacumab, not reaching treatment related target lipid goals and meeting non-HDL eligibility criteria for enrolment can be treated. The subject can be on prior PCSK9 inhibitor treatment. In some embodiments, the subject has not been treated by PCSK9 inhibitor.

Pharmaceutical Compositions and Therapeutic Applications

Provided herein also includes a pharmaceutical composition for carrying out the methods disclosed herein. A composition can include one or more gRNA(s), a RNA-guided endonuclease or a nucleotide sequence encoding the RNA-guided endonuclease described herein. In some embodiments, the composition can further comprise a polynucleotide to be inserted (e.g., a donor template) in the ANGPTL3 gene to affect the desired genetic modification of the methods disclosed herein.

In some embodiments, the one or more gRNA (s) each comprises a spacer complementary to a genomic sequence within or near (for example, within any of 1, 2, 3, 4, 5, 6, 7, 8, 9, 10, 15, 20, 30, 35, 40, 45, 50, 55, 60, 65, 70, 75, 80, 85, 90, 95, 100 or more bases from) any exon of the ANGPTL3 gene. In some embodiments, the gRNA targets a sequence within exon 1 of the ANGPTL3 gene. The gRNA can comprise a spacer sequence complementary to a target sequence within exon 1 of the ANGPTL3 gene. In some embodiments, a gRNA comprises a spacer sequence of any one of SEQ ID NOs: 3-9 and SEQ ID NOs: 20-26 or a variant thereof having at least 85% homology to the spacer sequence of any one of SEQ II) NOs: 3-9 and SEQ II) NOs: 20-26. In some embodiments, a gRNA comprises a space of SEQ ID NO: 3 or SEQ ID NO: 20 or a variant thereof having at least 85% homology to the spacer having a sequence of SEQ ID NO: 3 or SEQ ID NO: 20. In some embodiments, a gRNA comprises a spacer of SEQ ID NO: 4, SEQ ID NO: 21, or a variant thereof having at least 85% homology to the spacer having a sequence of SEQ ID NO: 4 or SEQ ID NO: 21. In some embodiments, the gRNA comprises a spacer comprising or consisting of the sequence of SEQ ID NO: 12. In some embodiments, a gRNA comprises a sequence of SEQ II) NO: 10 or a variant thereof having at least 85% homology to the sequence of SEQ ID NO: 10. In some embodiments, the gRNA comprises or consists of the sequence of SEQ ID NO: 13.

In some embodiments, the RNA-guided endonuclease is a Cas1, Cas1B, Cas2, Cas3, Cas4, Cas5, Cash, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1 endonuclease, or a functional derivative thereof. In some embodiments, the DNA endonuclease is Cas9. In some embodiments, the Cas9 endonuclease is from *Streptococcus pyogenes* (SpyCas9). In some embodiments, the Cas9 endonuclease is from *Staphylococcus lugdunensis* (SluCas9). In some embodiments, a DNA sequence that is transcribed to the nucleic acid encoding the DNA endonuclease is codon optimized. In some embodiments, the nucleic acid encoding the DNA endonuclease (e.g., an mRNA) comprises a 5' CAP structure and 3' polyA tail. In some embodiments, the nucleic acid encoding the DNA endonuclease is linked to the gRNA via a covalent bond.

In some embodiments, the one or more of the nucleic acid sequences and/or polypeptides can be delivered to cells, either in vitro or in vivo, via viral based or non-viral based delivery systems, including adenovirus vectors, adeno-associated virus (AAV) vectors, retrovirus vectors, lentiviral vectors, herpes virus vectors, liposomes, lipid nanoparticles, poxviruses, naked DNA administration, plasmids, cosmids, phages, encapsulated cell technology, and the like.

In some embodiments, the compounds of the composition disclosed herein (e.g., the ANGPTL3 gRNA or the nucleic acid encoding the ANGPTL3 gRNA, and the nucleic acid encoding a RNA-guided endonuclease) can be formulated in a liposome or lipid nanoparticle. In some embodiments, the compounds of the composition are formulated in a lipid nanoparticle (LNP). LNP is a non-viral delivery system that safely and effectively deliver nucleic acids to target organs (e.g., liver). The term "lipid nanoparticle" refers to a nanoscopic particle composed of lipids having a size measured in nanometers (e.g., 1-5,000 nm). In some embodiments, the lipids comprised in the lipid nanoparticles comprise cationic lipids and/or ionizable lipids. Any suitable cationic lipids and/or ionizable lipids known in the art can be used to formulate LNPs for delivery of gRNA and Cas endonuclease to the cells. Exemplary cationic lipids include one or more amine group(s) bearing positive charge. In some embodiments, the cationic lipids are ionizable such that they can exist in a positively charged or neutral from depending on pH. In some embodiments, the cationic lipid of the lipid nanoparticle comprises a protonatable tertiary amine head group that shows positive charge at low pH. The lipid nanoparticles can further comprise one or more neutral lipids (e.g., Distearoylphosphatidylcholine (DSPC), 1,2-Dioleoyl-sn-glycero-3-phosphocholine (DOPC), 1,2-Dimyristoyl-sn-glycero-3-phosphoethanolamine (DMPE), 1,2-Dipalmitoyl-sn-glycero-3-phosphorylethanolamine (DPPE) etc. as a helper lipid), charged lipids, steroids, and polymers conjugated lipids. In some embodiments, the LNP can comprise cholesterol. In some embodiments, the LNP can comprise a polyethylene glycol (PEG) lipid.

The lipid nanoparticles can comprise varying concentration of constituent lipids. In some embodiments, the molar percent of an ionizable lipid in the total lipid of a lipid nanoparticle is about, at least, at least about, at most or at most about 30%, 35%, 40%, 45%, 50%, 55%, 60%, 65%, 70%, or a number or range between any two of these values. In some embodiments, the molar percent of an ionizable lipid in a lipid nanoparticle is in a range between about 40-70% (e.g., about 60%). In some embodiments, the lipid nanoparticle can further comprise a helper lipid (e.g., DSPC), a sterol lipid (e.g., cholesterol), and PEG lipid or a phospholipid PEG conjugate. In some embodiments, the molar percent of a helper lipid in a lipid nanoparticle is about 5%-20% (e.g., about 10.5%), the molar percent of a sterol lipid is about 10%-40% (e.g., about 21%), and the molar percent of a PEG lipid is about 0.5%-10% (e.g., about 8.5%).

The LNP uptake into hepatocytes can be mediated by the Apolipoprotein E-low density lipoprotein receptor (ApoE-LDLR) or the N-Acetyl-D-galactosamine/asialoglycoprotein receptor pathway (GalNAc-ASGPR) (Sato et al., 2020, Journal of Controlled Release, 322, 217-226.). In some embodiments, the LNP herein described for delivery of gRNA and Cas endonuclease to the cells can be formulated to follow the ApoE-LDLR uptake pathway. In some embodiments, the LNP herein described for delivery of gRNA and Cas endonuclease to the cells can be formulated to follow the GalNAc-ASGPR uptake pathway. In some embodiments, the LNP formulations herein described can be used to treat a subject with a disease or disorder that presents as heterozygous (HeFH) or homozygous (HoFH) for the loss of low density lipoprotein receptor (LDLR).

In some embodiments, the lipid nanoparticles comprise N-Acetylgalactosamine (GalNAc), an amino sugar derivative of galactose. In some embodiments, GalNAc is present in the LNP in a molar percentage of about, at least, at least about, at most, or at most about 1.0%, 1.5%, 2.0%, 2.5%, 3.0%, 3.5%, 4.0%, 4.5%, 5.0%, 5.5%, or 6.0%. In some embodiments, GalNAc is present in the LNP in a molar percentage of about 2.5%.

In some embodiments, the concentration of the nanoparticles in the compositions disclosed herein is about 58.2 mg/mL (e.g., of total lipids), and the nanoparticles are complexed with a total of about 2 mg/mL of nucleic acid of (a) the ANGPTL3 gRNA and (b) the Cas9 mRNA. In some embodiments, the concentration of the plurality of nanoparticles is about 58.2 mg/mL, and the nanoparticles are complexed with (a) the ANGPTL3 gRNA at about 1.5 mg/mL, and (b) the Cas9 mRNA at about 0.5 mg/mL.

The relative amount of the total RNA ((a) the ANGPTL3 gRNA or a nucleic acid encoding a gRNA that targets ANGPTL3 gene, and (b) a nucleic acid encoding a RNA-guided endonuclease) and the total lipid in the nanoparticles can vary in different embodiments. For example, the nanoparticles can have the total lipid and the total RNA at a weight ratio of about 15:1, 16:1, 17:1, 18:1, 19:1, 20:1, 21:1, 22:1, 23:1, 24:1, 25:1, 26:1, 27:1, 28:1, 29:1, or 30:1. In some embodiments, the nanoparticles can have the total lipid and the total RNA at a weight ratio of about 30:1. In some embodiments, the nanoparticles can have the total lipid and the total RNA at a molar ratio of about 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1 or 50:1. In some embodiments, the nanoparticles can have the total lipid and the total RNA at a molar ratio of about 40:1.

In some embodiments, the concentration of the nanoparticles in the compositions disclosed herein (e.g., of total lipids) is about, at least, at least about, at most or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg/mL, or a number or a range between any two of these values. In some embodiments, the RNA in the nanoparticles is formulated at a concentration of about, at least, at least about, at most, or at most about 50, 75, 100, 200, 400, 600, 800, 1000, 1100, 1200, 1300, 1400, 1500, 1600, 1700, 1800, 1900, 2000 µg/ml or a number or a range between any two of these values.

The amount (e.g., relative amount of (a) the ANGPTL3 gRNA or a nucleic acid encoding a gRNA that targets ANGPTL3 gene, and (b) a nucleic acid encoding a RNA-guided endonuclease (e.g., a mRNA encoding a Cas protein (e.g., a Cas9 mRNA)) in the nanoparticles can vary. For example, the nanoparticles can have the nucleic acid encoding the RNA-guided endonuclease (e.g., a SpCas9 mRNA) and the ANGPTL3 gRNA in a 1:5, 1:4, 1:3, 1:2, 1:1, 2:1, 3:1, 4:1, or 5:1 ratio (by weight). In some embodiments, the nanoparticles can have the nucleic acid encoding the RNA-guided endonuclease and the ANGPTL3 gRNA in a 3:1 ratio (by weight).

In some embodiments, the plurality of nanoparticles is administered to the subject at a dose of about 0.01-5 mg/kg (determined by the total nucleic acids (e.g., the total of ANGPTL3 gRNA and Cas9 mRNA)) per administration. For example, a single dose or each dose of the plurality of nanoparticles administrated to the subject can be nanoparticles complexed with 0.01 mg/kg, 0.05 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.5 mg/kg, 4 mg/kg, 4.5 mg/kg, or 5 mg/kg, or a number or a range between any two of these values total RNA (e.g., the total of ANGPTL3 gRNA and Cas9 mRNA). In some embodiments, the plurality of nanoparticles is administered to the subject at a dose of, or a dose about, 0.1 mg/kg, 0.3 mg/kg, 0.5 mg/kg, 0.6 mg/kg, 1 mg/kg, 1.5 mg/kg, 2.0 mg/kg, 2.5 mg/kg or 3 mg/kg (determined by the total of ANGPTL3 gRNA and SpCas9 mRNA).

Disclosed herein include compositions. In some embodiments, the composition comprises a plurality of nanoparticles complexed with (a) a guide RNA (gRNA) targeting ANGPTL3 gene (ANGPTL3 gRNA), and (b) an mRNA encoding Cas9 endonuclease, wherein the gRNA comprises a spacer sequence of SEQ ID NO: 3, SEQ ID NO: 20 or SEQ ID NO: 12. In some embodiments, the gRNA comprises the sequence of SEQ ID NO: 10 or SEQ ID NO: 13. The Cas9 endonuclease can be *S. pyogenes* Cas9 endonuclease. In some embodiments, the concentration of the plurality of nanoparticles is about 58.2 mg/mL, and is complexed with a total of about 2 mg/mL of nucleic acid of (a) the ANGPTL3 gRNA and (b) the Cas9 mRNA. In some embodiments, the concentration of the plurality of nanoparticles is about 58.2 mg/mL, and is complexed with (a) the ANGPTL3 gRNA at about 1.5 mg/mL, and (b) the Cas9 mRNA at about 0.5 mg/mL.

A non-limiting example of dose escalation of the composition disclosed herein (e.g., lipid nanoparticles complexed with the ANGPTL3 gRNA or the nucleic acid encoding the ANGPTL3 gRNA, and the nucleic acid encoding a RNA-guided endonuclease) is provided in Table 2. The dose is determined by the total of ANGPTL3 gRNA and Cas9 mRNA complexed with the nanoparticles

TABLE 2

| ANGPTL3 DOSE ESCALATION | | | |
| --- | --- | --- | --- |
| Dose (mg/kg) | Patient weight (kg) | Single dose (mg) | Number of Patients |
| 0.1 | 80 | 8 | 3 |
| 0.3 | 80 | 24 | 3 |

TABLE 2-continued

ANGPTL3 DOSE ESCALATION

| Dose (mg/kg) | Patient weight (kg) | Single dose (mg) | Number of Patients |
|---|---|---|---|
| 0.6 | 80 | 48 | 3 |
| 1 | 80 | 80 | 3 |

In some embodiments, the lipid nanoparticles can have a mean diameter of about, at least, at least about, at most or at most about 30 nm, 40 nm, 50 nm, 60 nm, 70 nm, 80 nm, 90 nm, 100 nm, 110 nm, 120 nm, 130 nm, 140 nm, 150 nm, or a number or a range between any of these values. In some embodiments, the lipid nanoparticle particle size is about 50 to about 100 nm in diameter, or about 70 to about 90 nm in diameter, or about 55 to about 95 nm in diameter.

In some embodiments, the compounds of the composition described herein are encapsulated in the lipid portion of the lipid nanoparticle or an aqueous space enveloped by some or all of the lipid portion of the lipid nanoparticle. The encapsulation can be full encapsulation, partial encapsulation, or both. In some embodiments, the nucleic acid and/or polypeptides are fully or substantially encapsulated (e.g., greater than 90% of the RNA) in the lipid nanoparticle.

In some embodiments, one or more compounds herein described are associated with a liposome or lipid nanoparticle via a covalent bond or non-covalent bond. In some embodiments, any of the compounds in the composition can be separately or together contained in a liposome or lipid nanoparticle.

A composition described above can further have one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization lifer, a reconstituting buffer, a diluting buffer, or the like. In some embodiments, a composition can also include one or more components that can be used to facilitate or enhance the on-target binding or the cleavage of DNA by the endonuclease, or improve the specificity of targeting.

In some embodiments, any components of a composition are formulated with pharmaceutically acceptable excipients such as carriers, solvents, stabilizers, adjuvants, diluents, etc., depending upon the particular mode of administration and dosage form. In some embodiments, guide RNA compositions are generally formulated to achieve a physiologically compatible pH, and range from a pH of about 3 to a pH of about 11, about pH 3 to about pH 7, depending on the formulation and route of administration. In some embodiments, the pH is adjusted to a range from about pH 5.0 to about pH 8.

Suitable excipients can include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition will depend on the nature of the disorder or condition, and can be determined by standard clinical techniques.

The terms "stable" or "stability" as used herein can refer to the ability of the compounds herein described (e.g., an RNA-guided endonuclease or a nucleic acid encoding the RNA-guided endonuclease and/or gRNA) to maintain therapeutic efficacy (e.g., all or the majority of its intended biological activity and/or physiochemical integrity) over extended periods of time. The stability of one or more of the compounds described herein (e.g., an RNA-guided endonuclease or a nucleic acid encoding the RNA-guided endonuclease and/or a gRNA, and a nanoparticle) can be 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, or more than 3 years. The temperature of storage can vary. For example, the storage temperature can be, can be about, can be at least, or can be at least about −80° C., −65° C., −20° C., 5° C., or a number or range between any two of these values. In some embodiments, the storage temperature is less than or equal to −65° C.

Stability of the compounds herein can be assessed by measuring their relative potency (e.g., to a reference). In some embodiments, the editing of target cells (e.g., Hep313 liver cell line) by, e.g., CTX310, at different target:effector ratios can be determined. The percentage of editing can be calculated relative to the negative control (i.e., no CTX310) preparation. In some embodiments, the concentration of CTX310 is plotted against the percentage of editing determined by NGS or sanger sequencing using a 4-parameter logistic fit to generate a potency curve. The relative potency of the sample is calculated against the reference standard.

In some embodiments, the compounds herein described (e.g., an RNA-guided endonuclease or a nucleic acid encoding the RNA-guided endonuclease and/or gRNA) of a composition can be delivered via transfection such as calcium phosphate transfection, DEAE-dextran mediated transfection, cationic lipid-mediated transfection, electroporation, electrical nuclear transport, chemical transduction, electrotransduction, Lipofectamine-mediated transfection, Effectene-mediated transfection, lipid nanoparticle (LNP)-mediated transfection, or any combination thereof. In some embodiments, the composition is introduced to the cells via lipid-mediated transfection using a lipid nanoparticle.

The compositions herein described can be administered to a subject in need thereof to treat an ANGPTL3-associated condition. Accordingly, the present disclosure also provides a gene therapy approach for treating an ANGPTL3-associated condition in a subject by editing the ANGPTL3 gene of the subject. In some embodiments, the gene therapy approach functionally knocks out an ANGPTL3 gene in the genome of a relevant cell type in patients (e.g., liver). The ANGPTL3 gene of relevant cells in the subject (e.g., liver) is edited using the materials and methods described herein which uses RNA-guided endonuclease, such as Cas9, to permanently delete, insert, edit, correct or replace a target sequence from a genome or insert an exogenous sequence, thereby functionally knocking out the ANGPTL3 gene. This can provide a permanent cure for the ANGPTL3-associated condition by permanently reducing the levels of ANGPTL3 protein, ApoB protein, and lipids such as triglycerides, LDL, VLDLs, total cholesterol, HDLs, non-HDLs, and/or other fat phospholipids in the blood. The term "associated" as used herein with reference to two items (e.g., ANGPTL3 and diseases/conditions) indicates a relation between the two items such that the occurrence of an item (e.g., ANGPTL3 protein level) is accompanied by the occurrence of the other item (e.g., a disease or condition), which includes but is not limited to a cause-effect relation and sign/symptom-disease relation.

As described herein, in some embodiments, the nanoparticles (e.g., LNPs comprising ionizable lipids) complexed with (a) a guide RNA (gRNA) or a nucleic acid encoding a gRNA that targets ANGPTL3 gene, and (b) a nucleic acid encoding a RNA-guided endonuclease (e.g., Cas9 mRNA) is administered to a subject in need via IV infusion. The administration can be, for example, a single dose, or two or more doses. The nanoparticles can be, for example, rapidly distributed to, e.g., liver of the subject, and the nanoparticles can enter hepatocytes of the subject (e.g., via endocytosis. In some embodiments, ionizable lipid disruption of endosome can break the nanoparticles, thereby releasing the nucleic acid encoding the RNA-guided endonuclease (e.g., Cas9 mRNA) from the nanoparticles. The RNA-guided endonuclease (e.g., Cas9) can be synthesized and form endonuclease-gRNA RNP complex to achieve gene-editing. In some embodiments, endogenous DNA repair through non-homologous end joining (NHEJ) results in introduction of indels into ANGPTL3 gene, leading to frameshift mutations that prevent production of functional ANGPTL3 protein. As demonstrated herein, using the methods, compositions, systems and kits described herein, robust on-target editing of ANGPTL3 gene can be achieved with no off-target editing.

In some embodiments, the method of treating an ANGPTL3-related disease or disorder comprises administering to a subject (e.g., a primate subject) in need thereof a plurality of nanoparticles complexed with (a) a guide RNA (gRNA) or a nucleic acid encoding a gRNA that targets ANGPTL3 gene, and (b) a nucleic acid encoding a RNA-guided endonuclease, thereby relieve the ANGPTL3-related disease or disorder in the primate subject.

ANGPTL3-related diseases and disorders includes, but are not limited to, Arteriosclerosis, Atherosclerosis, Cardiovascular Diseases, Coronary heart disease, Diabetes, Diabetes Mellitus, Non-Insulin-Dependent Diabetes Mellitus, Fatty Liver, Hyperinsulinism, Hyperlipidemia, Hypertriglyceridemia, Hypobetalipoproteinemias, Inflammation, Insulin Resistance, Metabolic Diseases, Obesity, Malignant neoplasm of mouth, Lipid Metabolism Disorders, Lip and Oral Cavity Carcinoma, Dyslipidemias, Metabolic Syndrome X, Hypotriglyceridemia, Opitz trigonocephaly syndrome, Ischemic stroke, Hypertriglyceridemia result, Hypobetalipoproteinemia Familial 2, Familial hypobetalipoproteinemia, and Ischemic Cerebrovascular Accident. Editing the ANGPTL3 gene using any of the methods described herein can be used to treat, prevent and/or mitigate the symptoms of the diseases and disorders described herein.

In some embodiments, the methods and compositions described herein are used to treat dyslipidemia, hypobetalipoproteinemia, familial hypercholesterolemia (including homozygous familial hypercholesterolemia (HoFH) and heterozygous familial hypercholesterolemia (HeFH)), hypertriglyceridemia, familial combined hyperlipidemia, familial chylomicronemia syndrome, multifactorial chylomicronemia syndrome, familial combined hyperlipidemia (FCHL), metabolic syndrome (MetS), nonalcoholic fatty liver disease (NAFLD), elevated lipoprotein (a) and total cholesterol, by permanently reducing the levels of ANGPTL3 protein and lipids such as total cholesterol, triglycerides, LDLs, HDLs, and/or other non-HDLs in the blood. In some embodiments, the method disclosed herein comprises performing genetic screening on the patient. For example, for HoFH and/or HeFH, genetic screening can be performed on one or more of LDLr, APOB and PCSK9. For FCS and/or MCS, genetic screening can be performed on one or more of LPL, Apo CII, Apo V, LMF-1, and GP1HBP1. In some embodiments, the subject receiving the ANGPTL3 gene editing treatment described herein has been genetically screened prior to receiving the treatment, for example genetically screened for one or more of LDLr, APOB and PCSK9 (e.g., for the treatment of HoFH and/or HeFH), or genetically screened for one or more of LPL, Apo CII, Apo V, LMF-1, and GP1HBP1 genotypes (e.g., for the treatment of FCS and/or MCS). In some embodiments, the subject does not carry a LPL mutation, a GP1HBP1 mutation, or a combination thereof. The subject can have monogenic, heterogenic, or polygenic background.

In some embodiments, the methods, compositions and kits described herein can be used to treat dyslipidemias. Dyslipidemias is a genetic disease characterized by elevated level of lipids in the blood that contributes to the development of clogged arteries (atherosclerosis). These lipids include plasma cholesterol, triglycerides, or high-density lipoprotein. Dyslipidemia increases the risk of heart attacks, stroke, or other circulatory concerns. Current management includes lifestyle changes such as exercise and dietary modifications as well as use of lipid-lowering drugs such as statins. Non-statin lipid-lowering drugs include bile acid sequestrants, cholesterol absorption inhibitors, drugs for homozygous familial hypercholesteremia, fibrates, nicotinic acid, omega-3 fatty acids and/or combination products. Treatment options usually depend on the specific lipid abnormality, although different lipid abnormalities often coexist. Treatment of children is more challenging as dietary changes may be difficult to implement and lipid-lowering therapies have not been proven effective.

In some embodiments, the methods, compositions and kits described herein can be used to treat hypobetalipoproteinemia. Hypobetalipoproteinemia is an inherited disease (autosomal recessive) that affects between 1 in 1000 and 1 in 3000 people worldwide. Common symptoms of hypobetalipoproteinemia includes plasma levels of LDL cholesterol or apolipoprotein B below the 5th percentile which impairs the body's ability to absorb and transport fats and can lead to retinal degeneration, neuropathy, coagulopathy, or abnormal buildup of fats in the liver called hepatic steatosis. In severely affected patients, hepatic steatosis may progress to chronic liver disease (cirrhosis). Current treatment of hypobetalipoproteinemia includes severe restriction of long-chain fatty acids to 15 grams per day to improve fat absorption. In infants with hypobetalipoproteinemia, brief supplementation with medium-chain triglycerides may be effective but amount must be closely monitored to avoid liver toxicity. Another option for treating hypobetalipoproteinemia is administration high doses of vitamin E to prevent neurologic complications. Alternatively, vitamin A (10,000-25,000 IU/d) supplementation can be effective if an elevated prothrombin time suggests vitamin K depletion.

In some embodiments, the methods, compositions and kits described herein can be used to treat familial hypercholesterolemia. Familial hypercholesterolemia ("FH") is an inherited disorder of low-density lipoprotein cholesterol which is characterized by a raised cholesterol level from birth and a high risk of premature coronary heart disease. Mutations in any of three genes (LDLR, APOB and PCSK9) are known to cause autosomal dominant FH.

In some embodiments, the methods, compositions and kits described herein can be used to treat hypertriglyceridemia. Hypertriglyceridemia is defined as an abnormal concentration of triglyceride in the blood. Hypertriglyceridemia may be primary or secondary in nature. Primary hypertriglyceridemia is the result of various genetic defects leading to disordered triglyceride metabolism. Secondary causes are acquired causes, such as high fat diet, obesity, diabetes, hypothyroidism, and certain medications.

In some embodiments, the target tissue for the compositions and methods described herein is liver tissue. In some embodiments, the target cells for the compositions and methods described herein is hepatocyte.

In some embodiments, the pharmaceutical composition thereof can be administered by aerosol delivery, nasal delivery, vaginal delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, and/or intradermal injection, or any combination thereof. The administration can be local or systemic. The systemic administration includes enteral and parenteral administration. In some embodiments, more than one administration can be employed to achieve the desired level of gene expression over a period of various intervals, e.g., daily, weekly, monthly, or yearly.

The pharmaceutical composition thereof can be administered to a subject in need thereof at a pharmaceutically effective amount. The term "pharmaceutically effective amount" as used herein means that the amount of the pharmaceutical composition that will elicit a desired therapeutic effect and/or biological or medical responses of a tissue, system, animal or human. The administration can result in a desired reduction in the expression of the ANGPTL3 gene such as a desired reduction in the levels of the ANGPTL3 protein and lipids such as triglycerides, cholesterol and/or fat phospholipids in the blood.

In some embodiments, the subject is administered an additional treatment. The additional treatment can comprise administration of a corticosteroid, an anti-H1 antihistamine, an anti-H2 antihistamine, or any combination thereof. In some embodiments, the additional treatment is administered to the subject 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, or more prior to the administration of the plurality of nanoparticles to the subject. In some embodiments, the additional treatment is administered to the subject at most 2 hours prior to administration of the plurality of nanoparticles. In some embodiments, the additional treatment and the plurality of nanoparticles are administered simultaneously.

In some embodiments, the additional treatment comprises one or more of a Hepatoprotective drug (silymarin, polyene phosphatidylcholine, bicyclol, Glycyrrhizin acid preparation, N-acetylated L-cysteine (NAC) and glutathione (GSH)); Anticholeestatic drugs (Ursodeoxycholic acid, S-adenosylmethionine, cholestyramine); immunosuppressants (glucocorticoids), and/or anti-histamines. In some embodiments, the anti-histamine comprises acrivastine, azelastine, emadastine, epinastine, brompheniramine, carbinoxamine, cetirizine, chlorpheniramine, clamastine, cyproheptadine, desloratidine, diphenhydramine, naphazoline, fexofenadine, hydroxyzine, ketotifen, levociterizine, loratadine, olopatadine, and/or pharmaceutically acceptable salts thereof. In some embodiments, the corticosteroid comprises corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradnalone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, or any combination thereof. In some embodiments, the corticosteroid is dexamethasone. In some embodiments, the anti-histamine comprises diphenhydramine, cetirizine, famotidine, or any combination thereof.

The additional treatment (e.g., corticosteroid and/or anti-histamine) can be administered orally, intramuscularly, intravenously, subcutaneously, or any combination thereof. In some embodiments, the route of administration of the corticosteroid and the anti-histamine are different. In some embodiments, the route of administration of the corticosteroid and the anti-histamine are the same. In some embodiments, the corticosteroid is administered intravenously at a dose of, of about, of at least, or of at most 10 mg. In some embodiments, the corticosteroid is administered at a dose of 10 mg or less (e.g., 10, 9, 8, 7, 6,5, 4, 3, 2, 1, or 0.5 mg or a number or a range between any two of these values). In some embodiments, the corticosteroid is administered at a dose of, of about, of at least, or of at most 5 to about 60 mg (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 mg or a number or a range between any two of these values). In some embodiments, the subject is administered dexamethasone intravenously at a dose of 10 mg.

In some embodiments, the anti-histamine is administered at a dose of about 10 mg, about 20 mg, or about 50 mg (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg or a number or a range between any two of these values). In some embodiments, the subject is administered at least one of an H1-antihistamine and an H2-antihistamine. In some embodiments, the H1-antihistamine is diphenhydramine. In some embodiments, the diphenhydramine is administered intravenously at a dose of about 50 mg. In some embodiments, the H1-antihistamine is cetirizine and the cetirizine is administered orally at a dose of about 10 mg. In some embodiments, the H2-antihistamine is famotidine. In some embodiments, the famotidine is administered orally or intravenously at a dose of about 20 mg.

In some embodiments, the subject in need of the treatment has high levels of ANGPTL3 protein (e.g., plasma ANGPTL3 protein). A subject with high levels of ANGPTL3 can include, e.g., subjects with greater ANGPTL3 levels than 90% of the human population. In some embodiments, the subject has symptoms of an ANGPTL3-associated disease or condition. In some embodiments, the subject does not have symptoms of an ANGPTL3-associated disease or condition. In some embodiments, the subject is at risk of developing an ANGPTL3-associated disease or condition. In some embodiments, the subject is suspected of having or developing an ANGPTL3-associated disease or condition.

In some embodiments, the subject has abnormal levels of ApoB protein (e.g., plasma ApoB protein). In some embodiments, the subject has plasma ApoB levels in excess of 100 mg/dL (such as in excess of about any of 100 mg/dL, 110 mg/dL, 120 mg/dL, 130 mg/dL, 140 mg/dL, 150 mg/dL, 160 mg/dL, 180 mg/dL, 200 mg/dL, 250 mg/dL, 300 mg/dL, 350 mg/dL, 400 mg/dL, 500 mg/dL, 750 mg/dL, 1000 mg/dL or greater).

In some embodiments, the subject has an abnormal level of lipids (e.g., total cholesterol, HDLs, triglycerides, LDLs, VLDLs, and other non-HDLs). Diagnostic testing such as blood and urine lab tests can be performed to measure the lipid levels. In some embodiments, the subject has total cholesterol levels in excess of 200 mg/dL (such as in excess of about any of 225 mg/dL, 250 mg/dL, 300 mg/dL, 350 mg/dL, 400 mg/dL, 500 mg/dL, 750 mg/dL, 1000 mg/dL or greater). In some embodiments, the subject has plasma triglyceride levels in excess of about 150 mg/dL (such as in excess of about any of 160 mg/dL, 180 mg/dL, 200 mg/dL, 250 mg/dL, 300 mg/dL, 350 mg/dL, 400 mg/dL, 500 mg/dL, 750 mg/dL, 1000 mg/dL or greater). In some embodiments, the subject has plasma HDL levels in excess of about 60 mg/dL (such as in excess of about 65 mg/dL, 70 mg/dL, 80 mg/dL, 90 mg/dL, 100 mg/dL, 150 mg/dL or greater). In some embodiments, the subject has plasma VLDL levels in excess of about 30 mg/dL (such as in excess of about 35 mg/dL, 40 mg/dL, 50 mg/dL, 60 mg/dL, 70 mg/dL, 80 mg/dL, 90 mg/dL, 100 mg/dL or greater). In some embodiments, the subject has plasma LDL levels in excess of about 50 mg/dL (such as in excess of about 60 mg/dL, 70 mg/dL, 75 mg/dL, 80 mg/dL, 90 mg/dL, 100 mg/dL, 130 mg/dL, 150 mg/dL, 200 mg/dL, or greater). In some embodiments, the subject has plasma LDL-C levels in excess of 100 mg/dL (such as in excess of about any of 100 mg/dL, 110 mg/dL, 120 mg/dL, 130 mg/dL, 140 mg/dL, 150 mg/dL, 160 mg/dL, 180 mg/dL, 200 mg/dL, 250 mg/dL, 300 mg/dL, 350 mg/dL, 400 mg/dL, 500 mg/dL, 750 mg/dL, 1000 mg/dL or greater). In some embodiments, the subject has plasma Lp(a) levels in excess of about 50 mg/dL (such as in excess of about 60 mg/dL, 70 mg/dL, 80 mg/dL, 90 mg/dL, 100 md/dL, 125 mg/dL, 150 mg/dL or greater). In some embodiments, the level of a lipid (e.g., triglycerides and LDL) is blood level of the lipid. In some embodiments, the level of a lipid (e.g., triglycerides and LDL) is plasma level of the lipid.

In some embodiments, the subject has one or more genetic markers (e.g., deletion, insertion, and/or mutation) in the endogenous ANGPTL3 gene or its regulatory sequences such that the activity, including the expression level or functionality of the ANGPTL3 protein is substantially increased compared to a normal, healthy subject. In some embodiments, the subject has one or more genetic mutations in genes directly or indirectly related to lipid or lipoprotein metabolism (e.g., familial hypercholesterolemia). In some embodiments, the subject is a mammal. In some embodiments, the subject is a human being.

In some embodiments, the subject in need has clinical atherosclerotic cardiovascular disease (ASCVD). Clinical ASCVD is defined as patients having a confirmed diagnosis of coronary heart disease, cardiovascular disease, stroke, or peripheral arterial disease. In some embodiments, the subject having ASCVD has elevated triglyceride and/or LDL cholesterol levels. In some embodiments, the subject having ASCVD with elevated triglyceride and/or LDL cholesterol levels also has type 2 diabetes, chronic kidney disease, and/or hepatic steatosis (e.g., non-alcoholic fatty liver disease).

In some embodiments, the subject in need has a blood sugar level (e.g., hemoglobin A1C that measures the percentage of red blood cells having sugar-coated hemoglobin) about, at least, at least about, at most, or at most about 5.0%, 5.5%, 6.0%, 6.5%, 7.0%, 7.5%, 8.0%, 8.5%, 9.0%, 9.5%, 10.0%, 10.5%, 11% or a number or a range between any of these values. In some embodiments, the subject in need has an estimated average glucose level of about, at least, at least about, at most or at most about 50, 60, 70, 80, 90, 100, 110, 120, 130, 140, 150, 160, 170, 180, 190, 200, 210, 220, 230, 240, 250, 275, 300, 325, 350 mg/dL or a number or a range between any of these values. In some embodiments, the subject in need has a normal blood sugar level. In some embodiments, the subject in need has prediabetes or diabetes. In some embodiments, the subject in need has a hemoglobin A1C in a range of about 5.7% to about 6.4%. In some embodiments, the subject in need has a hemoglobin A1C about 6.5% or greater.

In some embodiments, the subject in need has an body mass index (BMI) of about, at least, at least about, at most or at most about 10, 12, 14, 16, 18, 20, 22, 24, 26, 28, 30, 32, 34, 36, 38, 40 or a number or a range between any of these values. In some embodiments, the subject in need has a healthy weight with a BMI in a range of about 18.5 to about 24.9. In some embodiments, the subject in need is overweight with a BMI in a range of about 25 to about 29.9. In some embodiments, the subject in need has obesity with a BMI of about 30 or greater.

In some embodiments, the subject in need has an estimated glomerular filtration rate of about, at least, at least about, at most or at most about 10, 15, 20, 25, 30, 35, 40, 45, 50, 55, 60, 65, 70, 75, 80, 85, 90, 95, 100, 105, 110, 115, 120, or a number or a range between any of these values. In some embodiments, the subject in need has an estimated glomerular filtration rate in a range of 60-90 (i.e. mild loss of kidney function). In some embodiments, the subject in need has mild to moderate, moderate to severe, or severe loss of kidney function. For example, the subject in need has an estimated glomerular filtration rate below 60, such as in a range of 45-59, 30-44, 15-29, or less than 15.

In some embodiments, the subject in need has fatty liver disease or hepatic steatosis, including alcoholic liver disease and non-alcoholic fatty liver disease. In some embodiments, the subject in need has a liver fat of about, at least or at least about 5%, 6%, 7%, 8%, 9% or 10% relative to the liver's weight. A subject can be diagnosed as having a fatty liver disease by elevated levels of liver enzymes, ultrasound, magnetic resonance imaging (MRI) computed tomography (CT scan), or liver biopsy.

In some embodiments, the plasma ANGPTL3 protein level in the subject following carrying out the method is reduced by about, at least or at least about 50%, 60%, 70%, 80%, 90%, 95%, 98%, 99%, or a number or a range between any of these values. In some embodiments, the plasma ANGPTL3 protein level in the subject following carrying out the method is reduced by about, at least or at least about 75%, 80%, 90%, 95%, 98%, 99%, or greater.

In some embodiments, the plasma ApoB protein level in the subject following carrying out the method is reduced by about, at least or at least about 50%, 60%, 70%, 80%, 90%, 95%, 98%, 99%, or a number or a range between any of these values. In some embodiments, the plasma ApoB protein level in the subject following carrying out the method is reduced by about, at least or at least about 75%, 80%, 90%, 95%, 98%, 99%, or greater.

The compositions and methods herein described in some embodiments can result in reduction of cholesterol content in triglycerides and other non-HDLs which have been indicated as risk factor for cardiovascular disease.

In some embodiments, the plasma triglyceride level in the subject following carrying out the method is reduced to about 150 mg/dL or lower (e.g., about, at most, or at most about 145 mg/dL, 140 mg/dL, 130 mg/dL, 120 mg/dL, 110 mg/dL, 100 mg/dL, 90 mg/dL, 80 mg/dL, 70 mg/dL, 60 mg/dL, 50 mg/dL, 40 mg/dL, 30 mg/dL, 20 mg/dL, or lower). In some embodiments, the plasma triglyceride level in the subject following carrying out the method is reduced to about 40 mg/dL or lower. In some embodiments, the plasma triglyceride level in the subject following carrying out the method is reduced to about 30 mg/dL or lower. In some embodiments, the plasma triglyceride level in the subject following carrying out the method is reduced to about 20 mg/dL or lower.

In some embodiments, the plasma triglyceride level in the subject following carrying out the method is reduced by about, at least or at least about 30%, 35%, 40%, 50%, 60%, 70%, 80%, 90%, 95%, 98%, 99%, or a number or a range between any of these values. In some embodiments, the plasma triglyceride level in the subject following carrying out the method is reduced by about, at least or at least about 75%, 80%, 90%, 95%, 98%, 99%, or greater.

In some embodiments, the plasma LDL level in the subject following carrying out the method is reduced to about, at most, or at most about 130 mg/dL, 100 mg/dL, 70 mg/dL, 50 mg/dL, or a number between any two of these values. In some embodiments, the plasma LDL-C level in the subject following carrying out the method is reduced to about, at most, or at most about 90 mg/dL, 80 mg/dL, 70 mg/dL, 60 mg/dL, 50 mg/dL or a number between any two of these values. In some embodiments, the plasma VLDL level in the subject following carrying out the method is reduced to about, at most, or at most about, at most, or at most about 30 mg/dL, 25 mg/dL, 20 mg/dL, 10 mg/dL, or a number between any two of these values. In some embodiments, the total cholesterol level in the subject following carrying out the method is reduced to about, at most, or at most about 200 mg/dL, 175 mg/dL, 150 mg/dL, 100 mg/dL, 75 mg/dL, or a number between any two of these values.

In some embodiments, the plasma LDL level in the subject following carrying out the method is reduced by about, at least or at least about 50%, 60%, 70%, 80%, 90%, 95%, 98%, 99%, or a number or a range between any of these values. In some embodiments, the plasma LDL-C level in the subject following carrying out the method is reduced by about, at least or at least about 50%, 60%, 70%, 80%, 90%, 95%, 98%, 99%, or a number or a range between any of these values. In some embodiments, the plasma VLDL level in the subject following carrying out the method is reduced by about, at least or at least about 50%, 60%, 70%, 80%, 90%, 95%, 98%, 99%, or a number or a range between any of these values. In some embodiments, the total cholesterol level in the subject following carrying out the method is reduced by about, at least or at least about 50%, 60%, 70%, 80%, 90%, 95%, 98%, 99%, or a number or a range between any of these values.

In some embodiments, clinical studies are used to determine the safety and efficacy of the pharmaceutical formulations and compositions described herein. The inclusion/exclusion criteria for said study can vary (also, see Example 5 below). In some embodiments, the inclusion criteria can include one or more of the following:

1. Subject is a human subject between the age of 18 and 70, with a maximum body weight not to exceed 100 kg.
2. Subject is able to provide written informed consent.
3. Subject is confirmed diagnosis of clinical atherosclerotic cardiovascular disease (ASCVD) and has a high TG level greater than 200 mg/dl and/or a high LDL level greater than 100 mg/dl. The study population includes patients with history of coronary heart disease, cardiovascular disease, stroke, or peripheral arterial disease.
4. Subjects receiving statins should be on the maximum tolerated dose of statins. If deemed intolerant to statins, patients should be intolerant to all doses of two different statin formulations.

Refractory to additional current standard of care (SOC) lines of treatment, including ezetimibe, PCSK9 inhibitors etc. as per investigator's judgement.

Subjects on statins or ezetimibe should be on a stable dose >30 days before screening with no planned medication or dose increase during study participation.

5. Subjects of childbearing potential (post-menarche, has an intact uterus and at least 1 ovary, and is less than 1 year postmenopausal) and biological male subjects must agree to use acceptable method(s) of contraception from consent through at least 6 months after drug infusion (e.g., CTX310 infusion).
6. Subject is willing and able to comply with scheduled visits, treatment plan, laboratory tests, contraceptive guidelines, and other study procedures.
7. Subject is willing to participate in an additional long-term follow-up study after completion of this study.

The exclusion criteria can include one or more of the following criteria. In some embodiments, to be eligible for entry into the clinical study, a subject must not meet any of the exclusion criteria listed below.

1. Subject has a history of a significant coagulation disorder.
2. Subject has a history of any illness or any clinical condition that, in the opinion of the investigator, might confound the results of the study or pose an additional risk in administering study drug to the subject. This may include but is not limited to: history of relevant drug allergies; history of central nervous system disease; history or presence of clinically significant pathology; or history of psychiatric illness, or history of familial cancer syndrome.

3. Subject has any prior or current malignancy or myeloproliferative disorder or a significant immunodeficiency disorder.
4. Subject is a patient with confirmed diagnosis of homozygous familial hypercholesteremia.
5. Subject has the following complete blood count (CBC): normal white blood cell (WBC) less than 2,500 cells/mcL, hemoglobin (Hb) less than 11 g/dL for male and 10 g/dL for female, platelet count less than 100,000/mcL.
6. Subject has advanced liver disease, defined as: (a) Aspartate transaminase (AST), alanine transaminase (ALT) greater than 3× the upper limit of normal (ULN), or direct bilirubin value greater than 2× the ULN, or (b) Baseline prothrombin time (International Normalized Ratio [INR]) greater than 1.5× ULN, or (c) History of hepatic cirrhosis.
7. Subject has a cardiac left ventricular ejection fraction (LVEF) less than 40% by echocardiogram.
8. Subject has uncontrolled hypertension, uncontrolled arrhythmia, or New York Heart Association (NYHA) Class II, III and IV heart failure (HF).
9. Subject has an acute coronary syndrome event within 24 weeks of Day 1.
10. Subject has a central nervous system (CNS) stroke within 24 weeks of Day 1.
11. Subject has a baseline estimated glomerular filtration rate less than 60 mL/min/1.73 m$^2$.
12. Subject has a prior treatment with gene therapy/editing product.
13. Subject has positive serology for human immunodeficiency virus-1 (HIV-1) or human immunodeficiency virus-2 (HIV-2), hepatitis B virus (HBV) (Hepatitis B core antibody [HBcAb] or nuclei acid testing [NAT]), or hepatitis C virus (HCV) (NAT).
14. Subject is currently using or has used within 365 days from Day 1 of any hepatocyte targeted siRNA or antisense oligonucleotide molecule.
15. Subject is currently using or has used within 90 days from Day 1 of any monoclonal Ab treatment.
16. Subject has participated in another clinical study with an investigational drug/product within 30 days of Screening or fewer than 5 half-lives of the investigational agent, whichever is longer from Screening.
17. Subject has an assessment by the investigator that the subject would not comply with the study procedures outlined in the protocol.
18. Subject is a pregnant or breastfeeding female.
19. Subject has non-alcoholic steatohepatitis (NASH).

Methods, systems, kits and compositions disclosed herein can used to treat subjects having one or more of Clinical Atherosclerotic Cardiovascular disease (ASCVD), Homozygous Familial Hypercholesterolemia (HoFH), Heterozygous Familial Hypercholesterolemia (HeFH), Familial Chylomicronemia Syndrome (FCS), Multifactorial Chylomicronemia Syndrome (MCS), Familial Combined Hyperlipidemia (FCH or FCHL), Metabolic Syndrome (MetS), Type 2 diabetes (T2D), and nonalcoholic fatty liver disease (NAFLD). HoFH and FCS are rare diseases. In some embodiments, the method is effective in lowering LDL, and thereby treating Familial Hypercholesterolemia (FH). In some embodiments, the subject is a subject having ASCVD and increased triglyceride (TG) Levels and/or high low-density-lipoprotein cholesterol (LDL-C) levels, including such subject that are refractory to currently available treatments (e.g., non-responders for one or more of Evinacumab, Inclisiran, Ezetimibe, and statins).

Provided herein also includes kits for carrying out the methods described herein. A kit can include a genome-targeting nucleic acid (e.g., gRNA targeting the ANGPTL3 gene) and a RNA-guided endonuclease (e.g., Cas9) or a nucleic acid encoding the RNA-guided endonuclease. In any of the above kits, the kit can further comprise a polynucleotide to be inserted to effect the desired genetic modification (e.g., a donor template). Components of a kit can be in separate containers, or combined in a single container.

Any kit described above can further comprise one or more additional reagents selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. A kit can also comprise one or more components that can be used to facilitate or enhance the on-target binding or the cleavage of DNA by the endonuclease, or improve the specificity of targeting.

In some embodiments, a kit can further include instructions for using the components of the kit to practice the methods described herein. The instructions for practicing the methods are generally recorded on a suitable recording medium. For example, the instructions can be printed on a substrate, such as paper or plastic. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g., CD-ROM, diskette, flash drive, etc. In some instances, the actual instructions are not present in the kit, but means for obtaining the instructions from a remote source (e.g., via the Internet), can be provided. An example of this embodiment is a kit that includes a web address where the instructions can be viewed and/or from which the instructions can be downloaded. As with the instructions, this means for obtaining the instructions can be recorded on a suitable substrate.

EXAMPLES

Some aspects of the embodiments discussed above are disclosed in further detail in the following examples, which are not in any way intended to limit the scope of the present disclosure.

Example 1

Evaluation of ANGPTL3 Gene Editing Efficiency in Non-Human Primates (NHPs)

This example evaluates the ANGPTL3 gene editing efficiency in non-human primates (NHPs) (e.g., cynomolgus monkey) by measuring the ANGPTL3 protein levels and triglyceride levels before and after treatments.

A number of CRISPR-Cas9/gRNA combinations have been assessed, and the lead formulations that yield high efficiency of deletion in the ANGPTL3 gene with substantially low off-target effects were tested in vivo in the NHPs. Lipid nanoparticles encapsulating the gRNA molecule of SEQ ID NO: 4 (e.g., SEQ ID NO: 21) and Cas9 mRNA were injected into NHPs and plasma samples were collected hourly within the first day post-dose and according to the study design shown in FIG. 1.

As shown in Table 3, five groups of animals (2 animals/group) were treated with 1 dose or 2 doses according to the study design of FIG. 1 (see also last column of Table 3). For example, the NHPs of Group 1 (Table 3) were treated at day 1 with the first dose (e.g., 2 mg/kg) and at day 22 with the second dose (e.g., 2 mg/kg). The plasma samples were collected at day 4, day 8, day 15, day 22, day 29 and day 36. The NHPs of Group II (Table 3) were treated at day 1 with the first dose only. The plasma samples were collected at day 4, day 8, day 15 and day 22. A Sandwich Enzyme-Linked Immunosorbent Assay (ELISA) for ANGPTL3 protein was used to detect concentrations of ANGPTL3 protein in the plasma collected and EasyRA analysis was used to analyze the lipid profile of the samples.

Example 2

Evaluation of ANGPTL3 Gene Editing Efficiency in Liver and Other Organ Tissues

In this example, the ANGPTL3 gene editing efficiency (e.g., INDEL edits percentage) was measured in liver and other organ tissues including spleen, brain, heart, kidney, lung, and testis.

A biopsy of a NHP's organ was performed, cells were isolated from the biopsied material, the chromosomal DNA was extracted from these cells, and the on-target cutting

TABLE 3

NON-LIMITING EXEMPLARY NHP STUDY DESIGN

| Group No. | Animals per Group | Formulation | Animal ID | # of dose | Plasma Samples in house* |
|---|---|---|---|---|---|
| 1 | 2 | FM-1746C (T6.02/RNA097) | 6925939304 6076075382 | 2 | Baseline: Day −14, Day −10, Day 1 (pre-dose) Treatment: Day 4, Day 8, Day 15, Day 22 (pre 2$^{nd}$ dose), Day 29, Day 36 |
| 2 | 2 | FM-1796A (T39.02/RNA010) | 9113322743 8101164842 | 2 | Baseline: Day −14 (2 sets), Day −10 (2 sets), Day 1 (pre-dose) Treatment: Day 4, Day 8, Day 15, Day 22 |
| 3 | 2 | FM-1796C (T6.02/RNA010) | 7084909232 8956929929 | 2 | Baseline: Day −14, Day −10, Day 1 (pre-dose) Treatment: Day 4, Day 8, Day 15, Day 22 |
| 4 | 2 | FM-1746B (T4.01/RNA097) | 4796156004 9427798992 | 2 | Baseline: Day −14 (2 sets), Day −10 (2 sets), Day 1 (pre-dose) Treatment: Day 4, Day 8, Day 15, Day 22 |
| 5 | 2 | FM-1796B (T4.01/RNA010) | 3434257266 3539408714 | 1 | Baseline: Day −14, Day −10, Day 1 (pre-dose) Treatment: Day 4, Day 8, Day 15, Day 22 |

Figure 2:
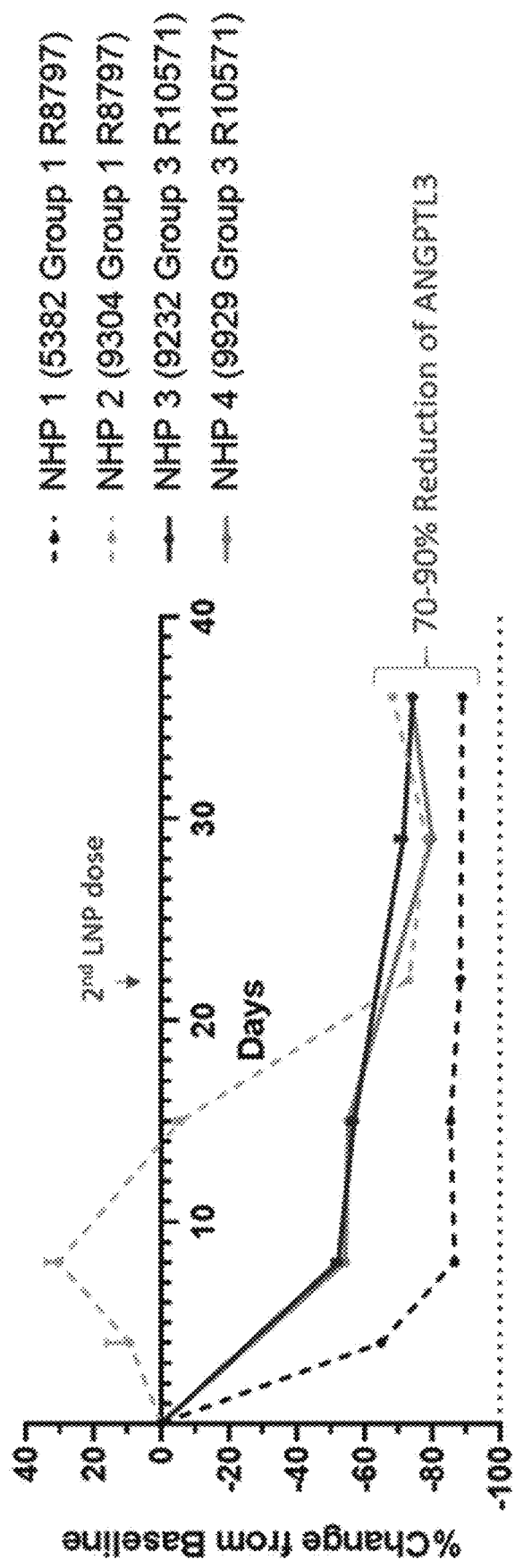
FIG. 2 is a graph showing the percentage change of plasma ANGPTL3 protein from baseline in Group 1 and Group 3 NHPs.

FIG. 2 is a graph showing the percentage change of plasma ANGPTL3 protein from baseline in Group 1 NHPs and Group 3 NHPs. The results demonstrate that the NHP plasma ANGPTL3 levels are significantly decreased using the Cas9 mRNA and the gRNA targeting at the ANGPTL3 gene. In general, about 70%-90% decrease from baseline were observed in the NHPs. For example, in Group I, 73% and 90% reduction of ANGPTL3 protein from baseline was observed.

Figure 3A:
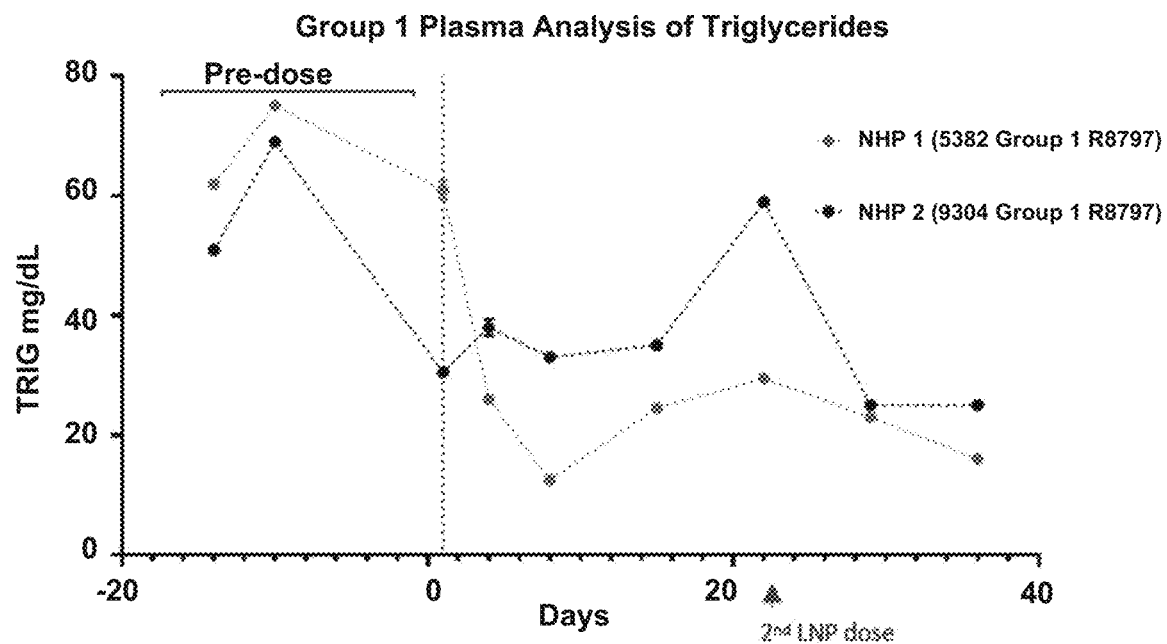
FIG. 3A-FIG. 3B depict measurements of triglyceride levels.
Figure 3B:
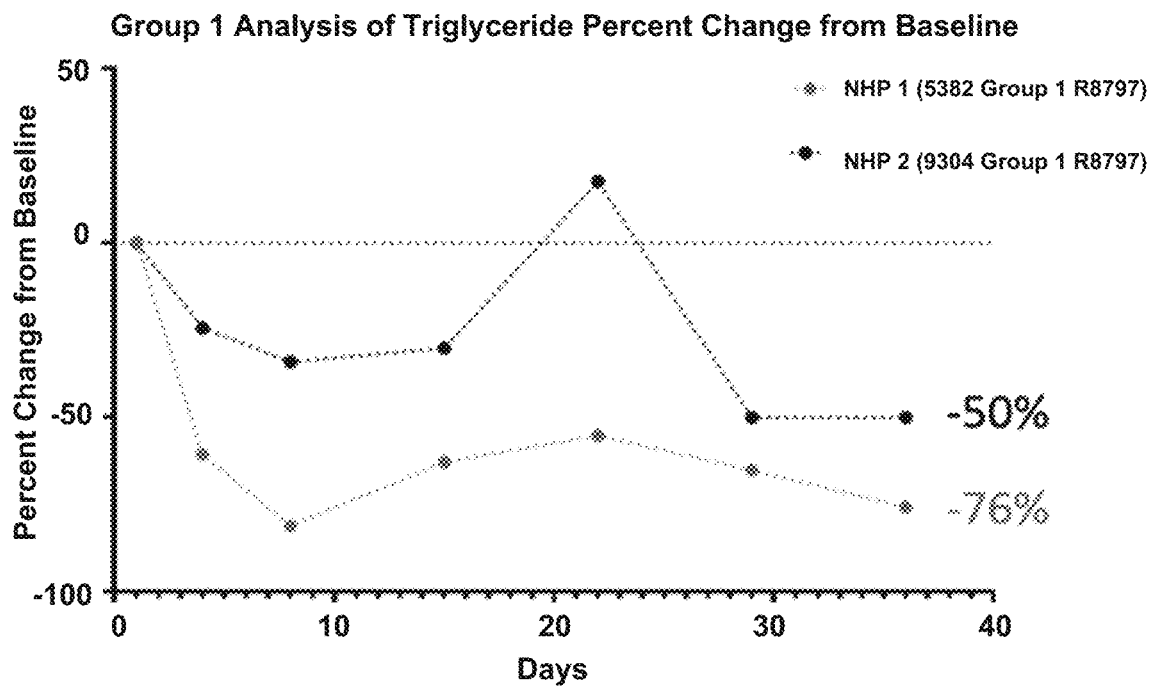
Figure 4A:
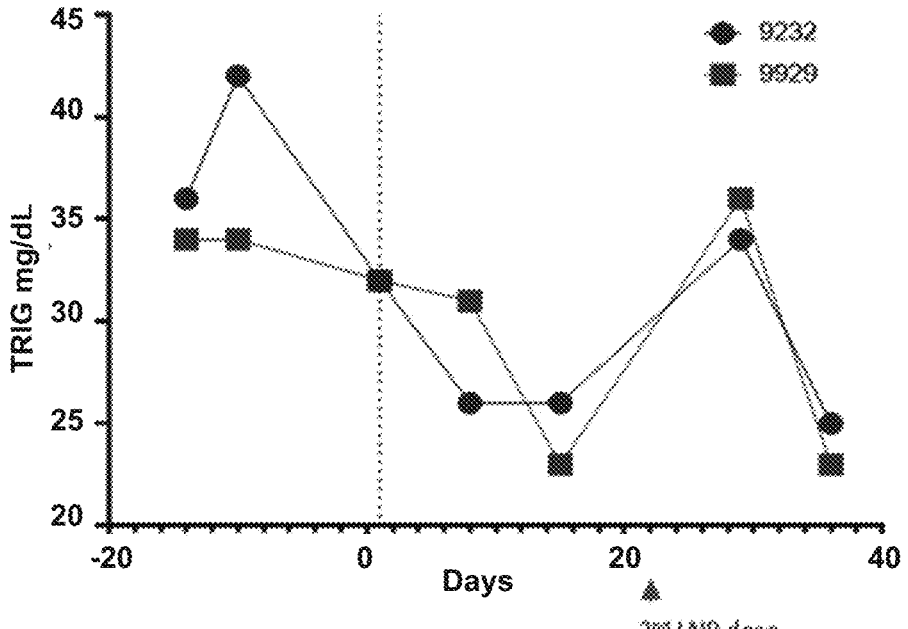
FIG. 4A-FIG. 4B depict non-limiting exemplary data related to plasma triglyceride levels.
Figure 4B:
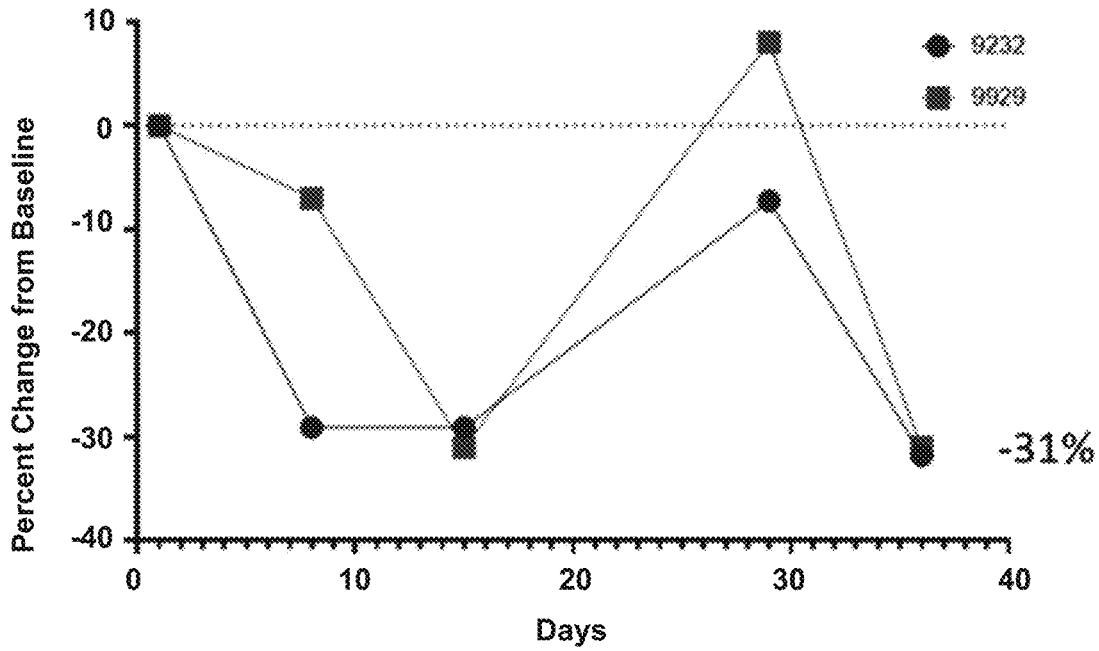
Figure 5B:
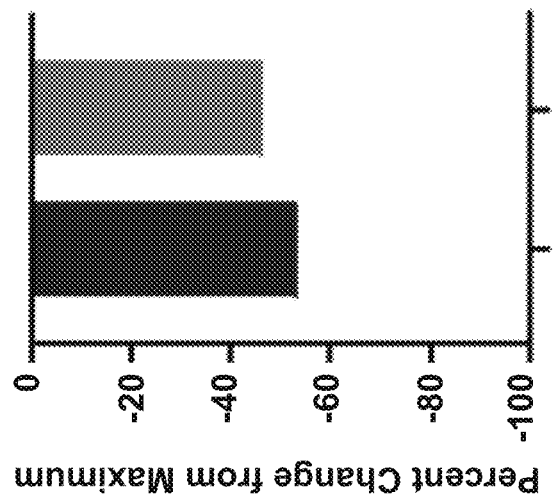
FIG. 5A-FIG. 5D depict non-limiting exemplary data related to triglyceride levels.
Figure 5A:
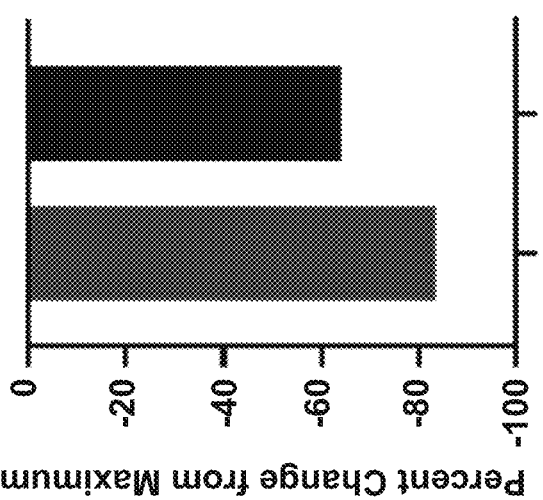
Figure 5D:
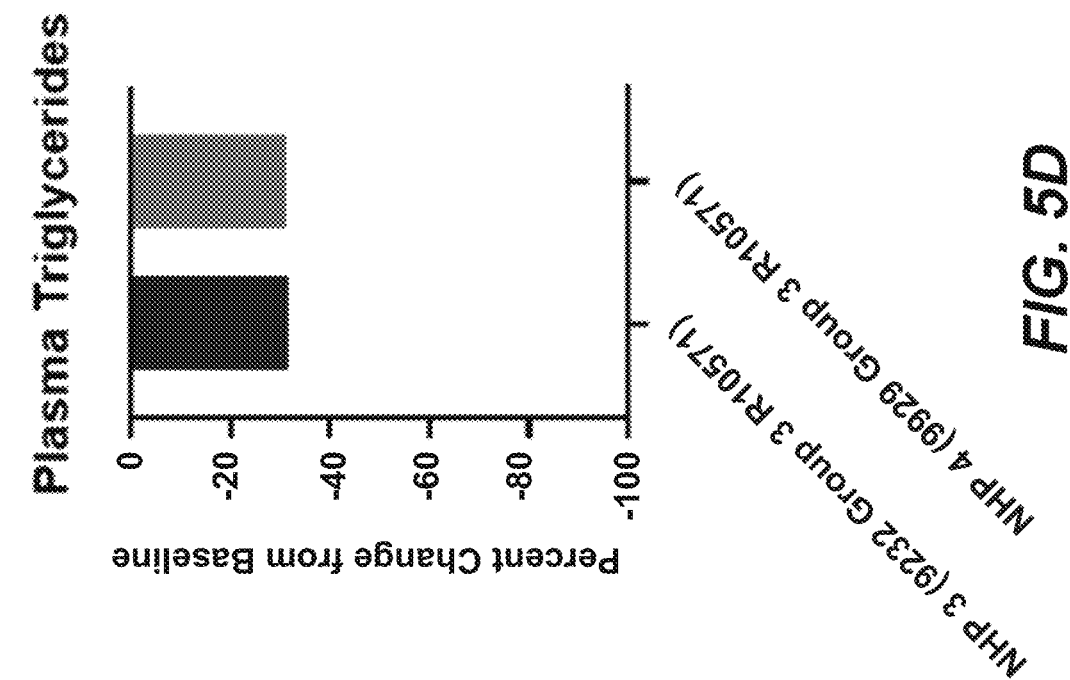
Figure 5C:
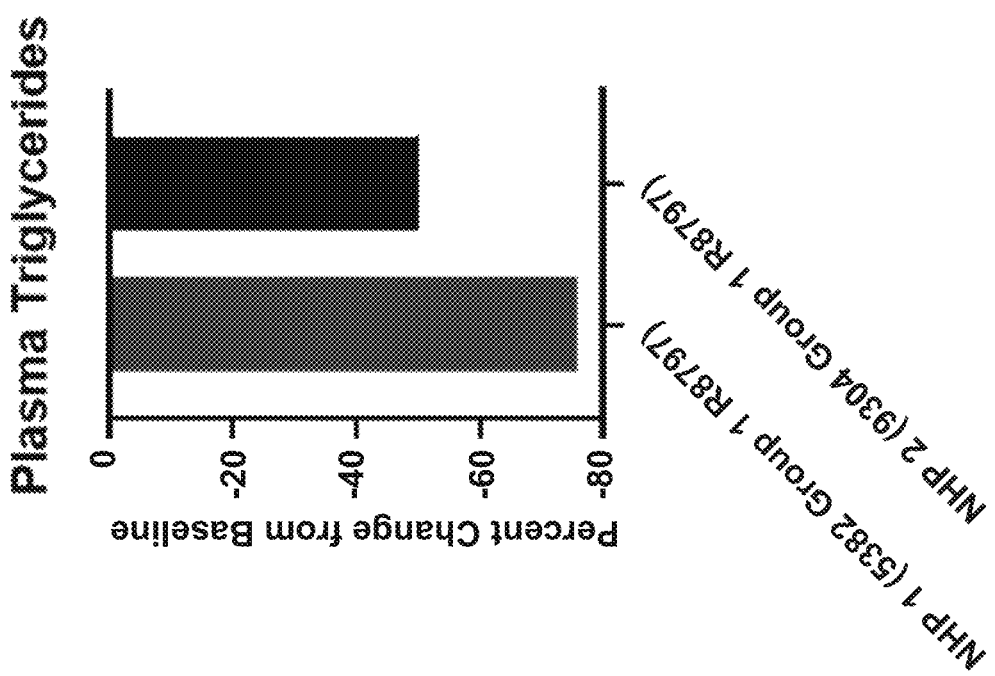
Figure 6A:
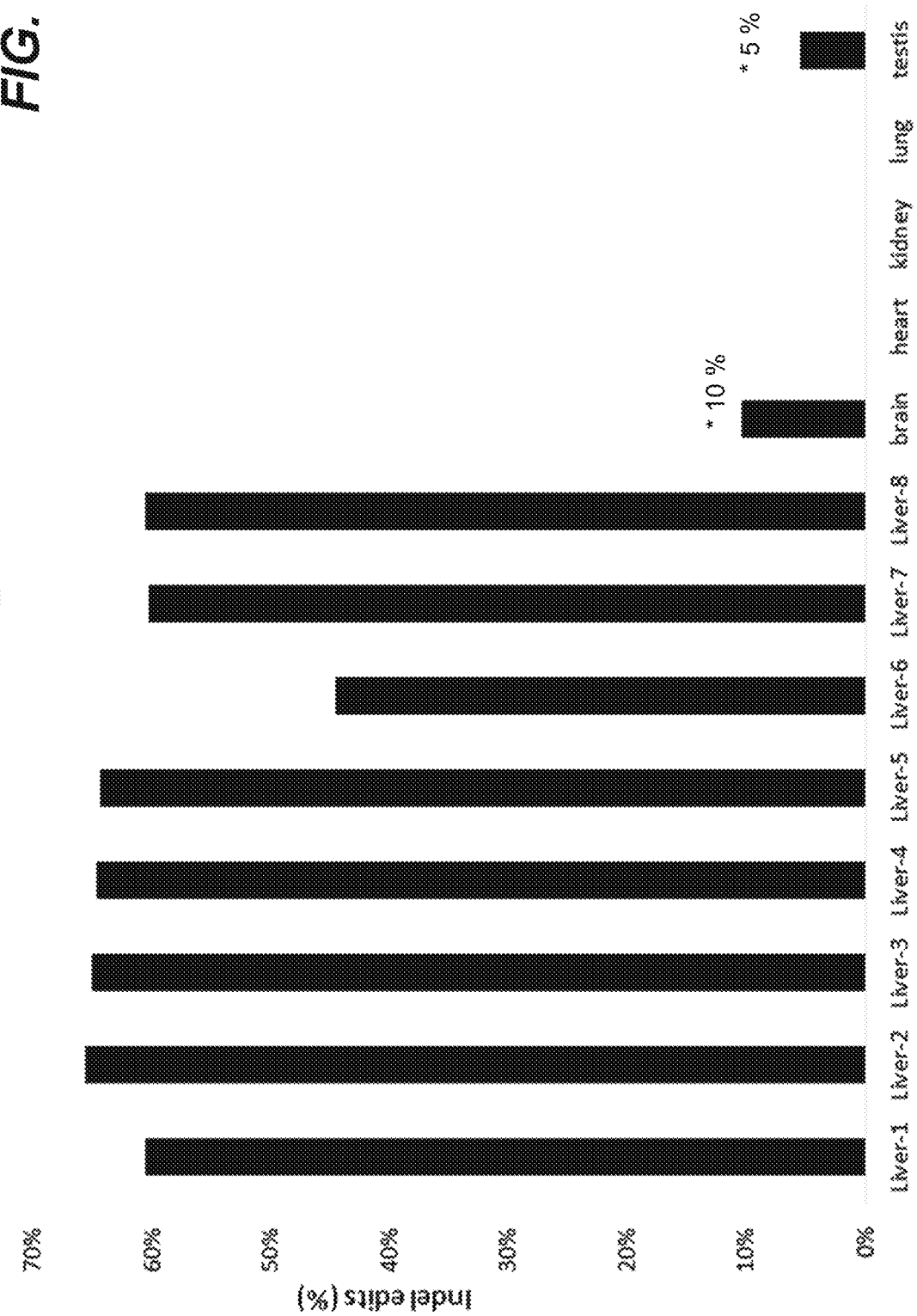
Figure 6B:
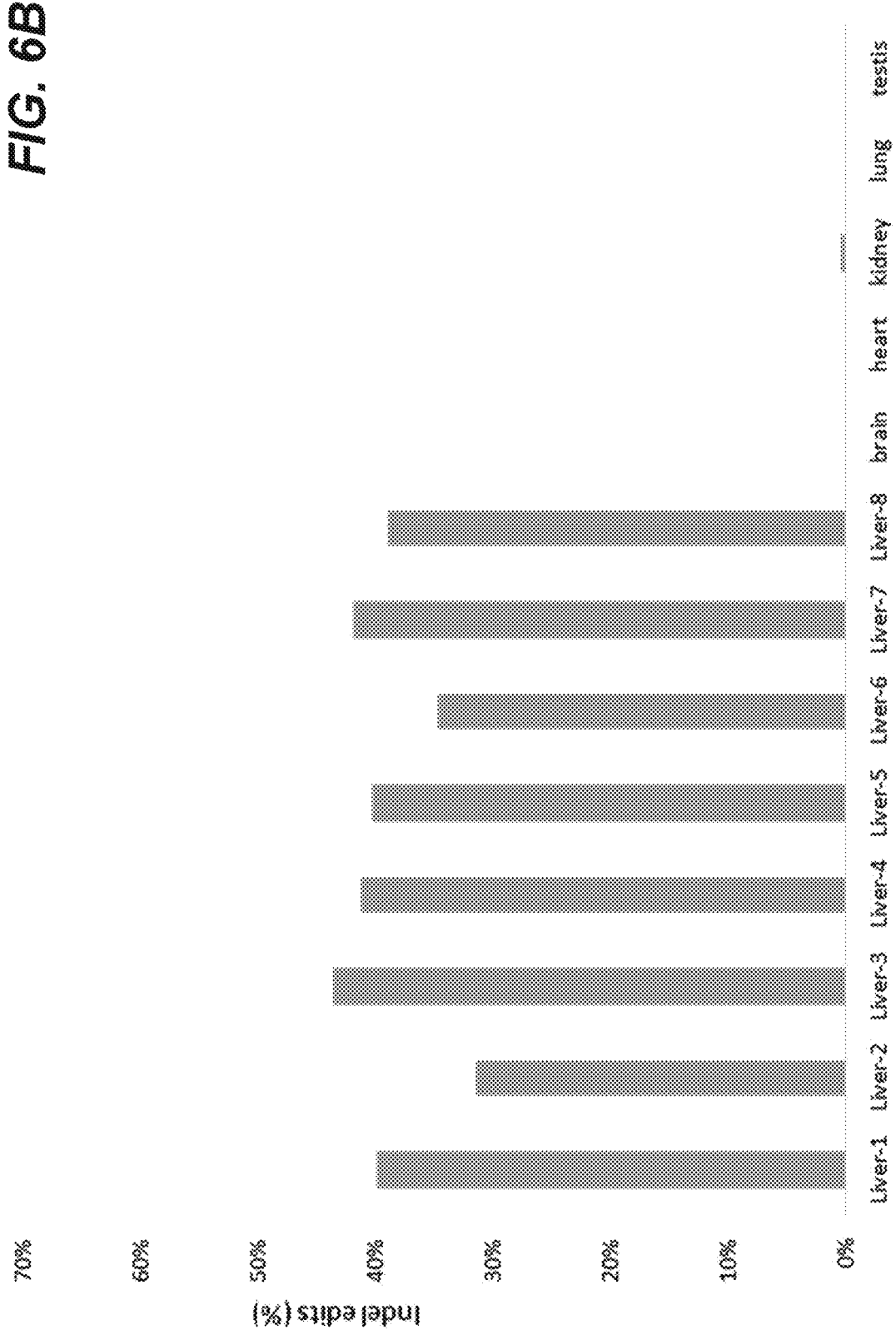
Figure 6D:
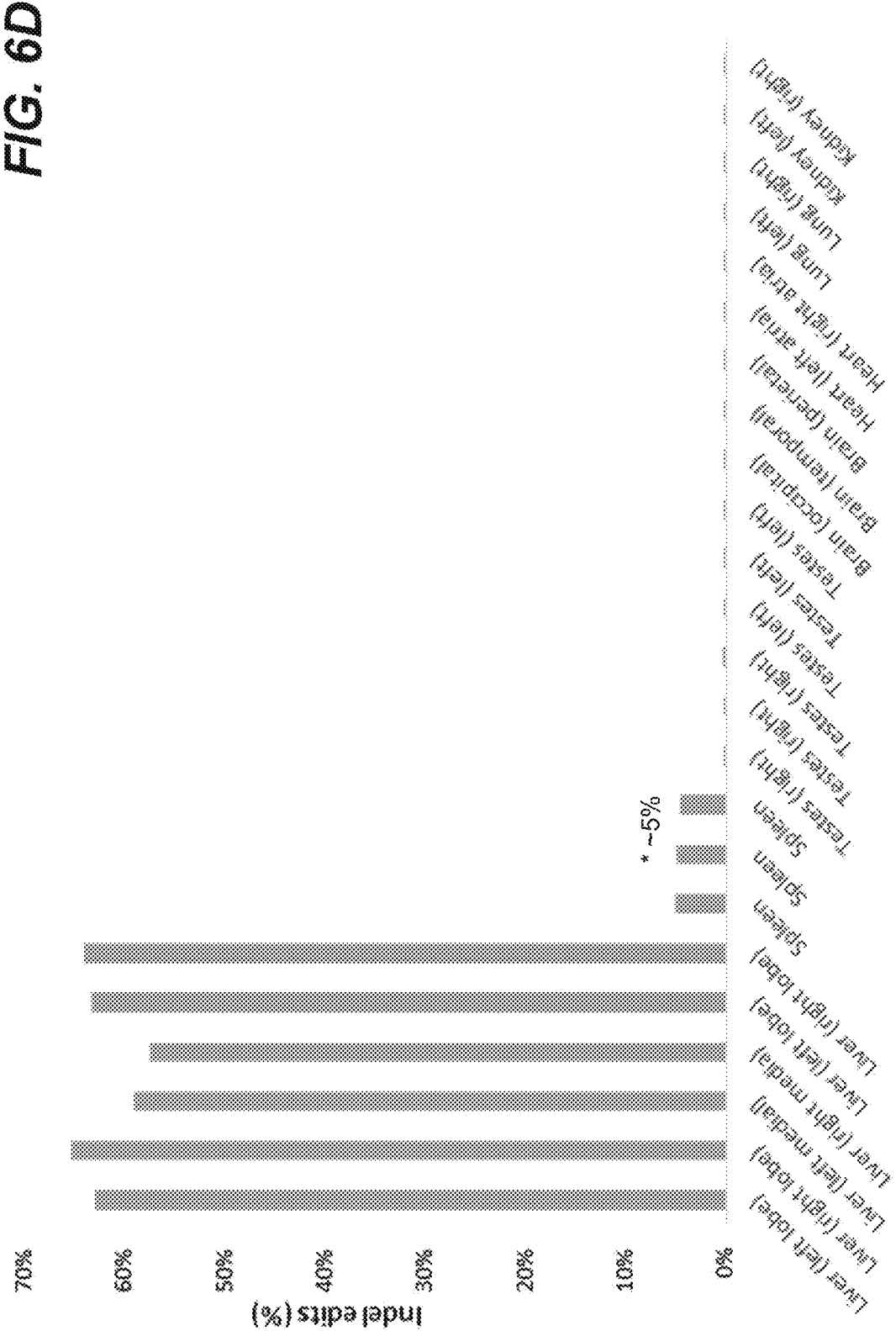

FIG. 3A is a graph showing the plasma triglyceride level of the NHPs in Group 1 before and after treatment. FIG. 3B is a graph showing the percentage change of the plasma triglyceride level from the baseline of the NHPs in Group 1. FIG. 4A is a graph showing the plasma triglyceride level of the NHPs in Group 3 before and after treatment. FIG. 4B is a graph showing the percentage change of the plasma triglyceride level from the baseline of the NHPs in Group 3. FIG. 5A-FIG. 5B are two graphs showing the maximal percentage change of the plasma triglyceride level of the NHPs in group 1 (FIG. 5A) and Group 3 (FIG. 5B). FIG. 5C-FIG. 5D are two graphs showing the percentage change of the plasma triglyceride level from baseline at day 36 in Group I (FIG. 5C) and Group 3 (FIG. 5D). At day 36, 50% and 76% reduction of the triglyceride levels from baseline were observed in Group 1 and about 31% in Group 3.

The results demonstrate that both the ANGPTL3 protein and the plasma triglyceride levels are significantly decreased using the Cas9 mRNA and gRNA targeting at the ANGPTL3 gene.

frequency was measured by determining the INDEL frequency using TIDES analysis.

Figure 7:
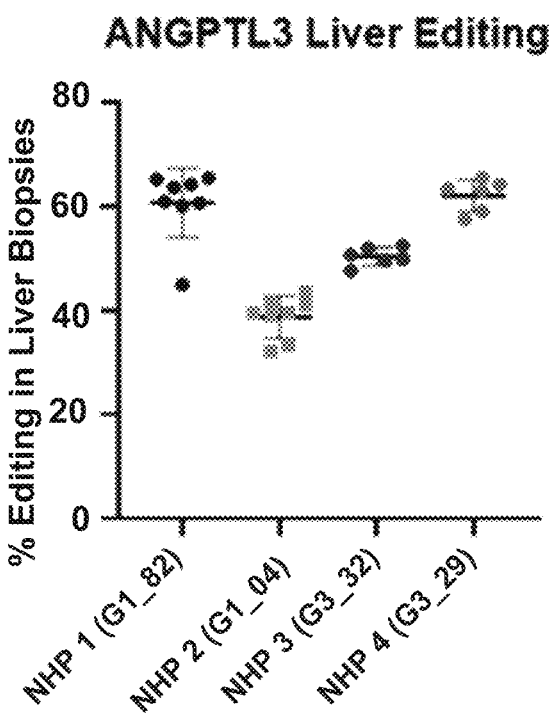
FIG. 7 is a graph showing the percentage of ANGPTL3 gene editing in liver biopsies in Group 1 and Group 3 NHPs.

FIG. 6A-FIG. 6D are graphs showing the ANGPTL3 gene editing efficiency in different organ tissues. The results demonstrate that the ANGPTL3 gene editing efficiency is significantly higher in liver than in other organ issues. The INDEL frequency ranges from 30% to 65% in liver cells of the 4 tested NHPs with substantially less INDEL frequency in other organ cells (e.g., between 0% to 10%). FIG. 7 is a graph showing the percentage of ANGPTL3 gene editing in liver cells of Group I and Group III NHPs.

Figure 8A:
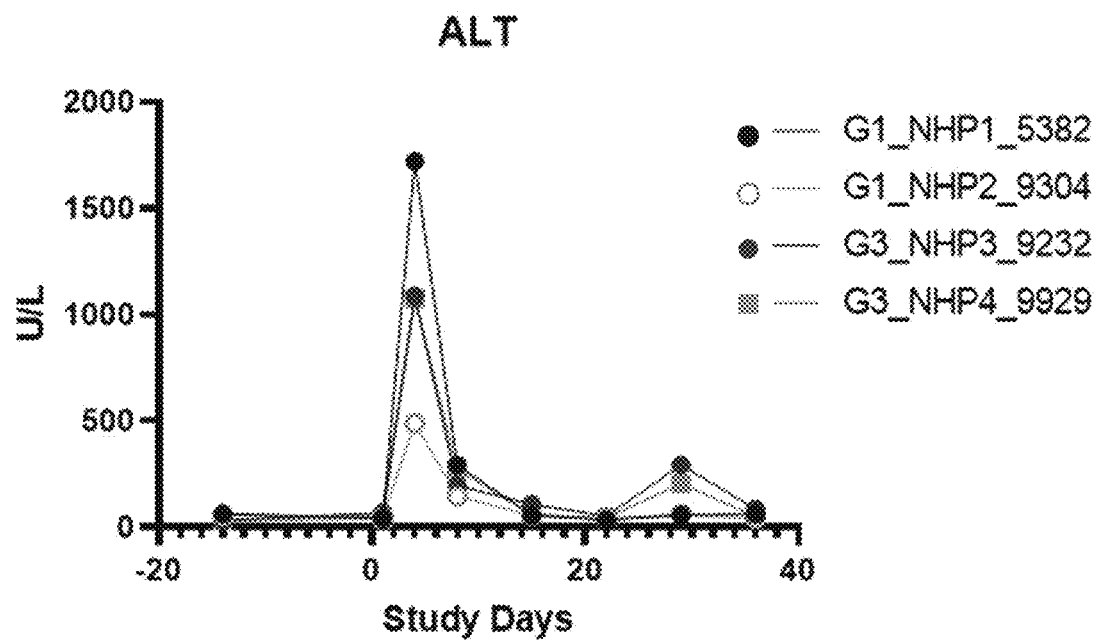
FIG. 8A-FIG. 8E are graphs showing the liver function tests of alanine aminotransferase (ALT) (FIG. 8A), alkaline phosphatase (ALP) (FIG. 8B), aspartate aminotransferase (AST) (FIG. 8C), albumin blood (ALB) (FIG. 8D), and bilirubin (TBIL) (FIG. 8E).
Figure 8B:
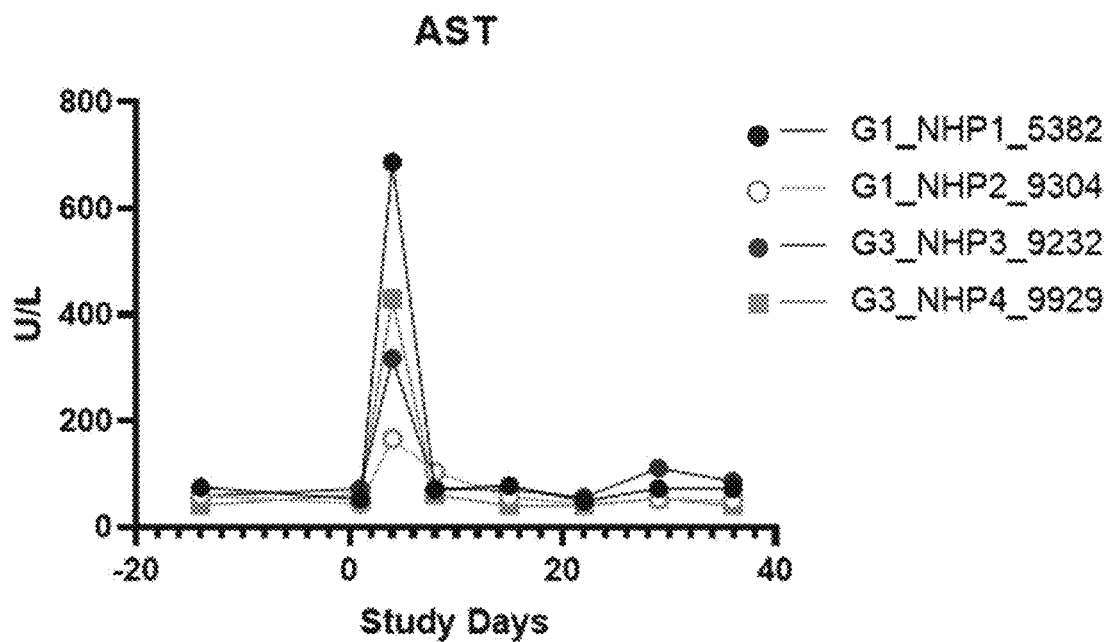
Figure 8C:
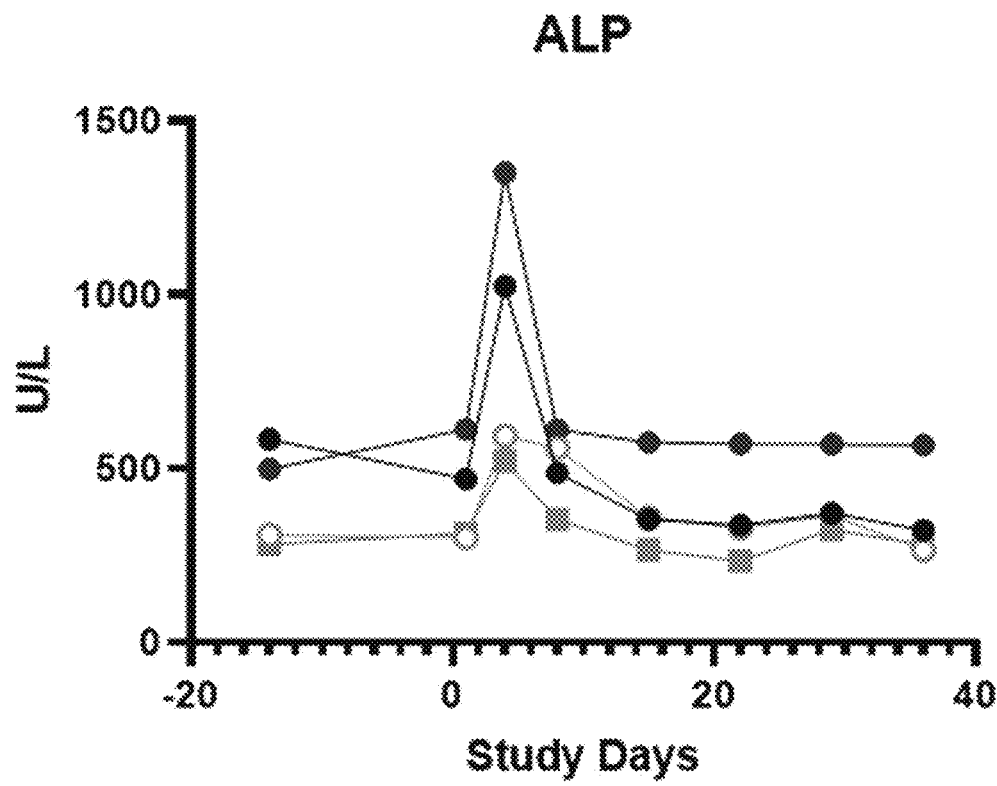
Figure 8D:
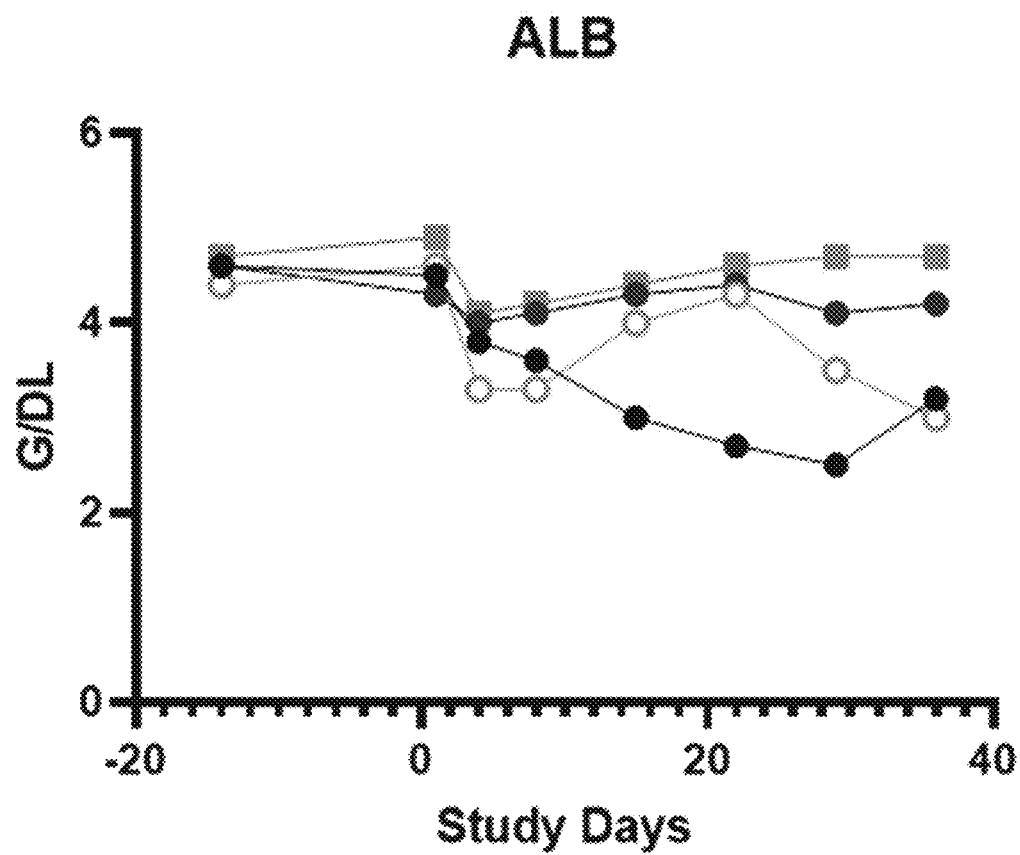
Figure 8E:
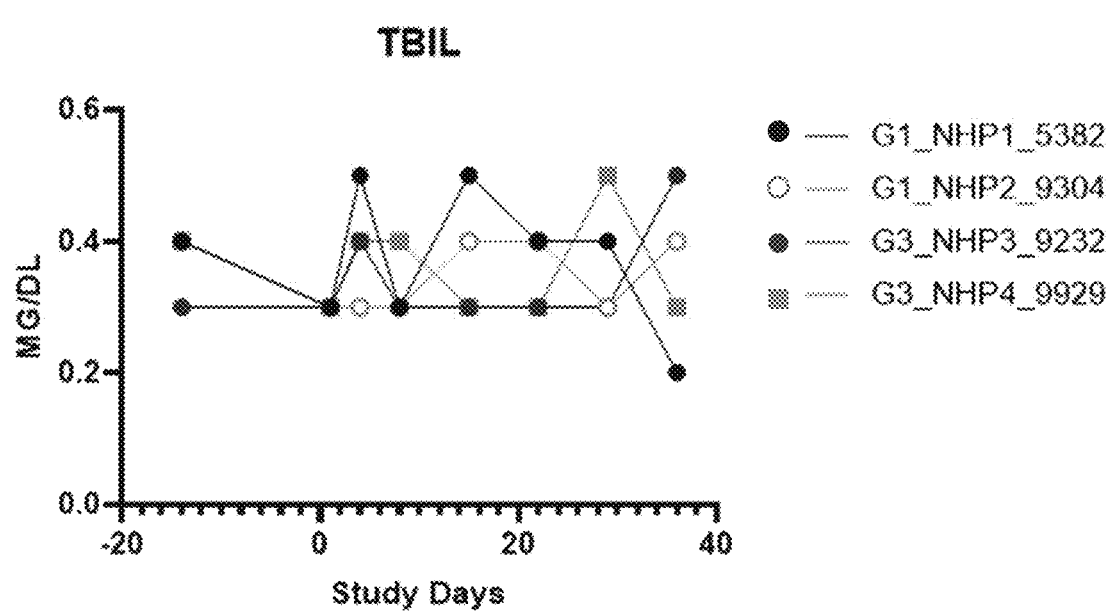

Liver function tests were also carried out before and after treatments to provide information about the state of the NHPs' liver. FIG. 8A-FIG. 8E are graphs showing the liver function tests of alanine aminotransferase (ALT) (FIG. 8A), alkaline phosphatase (ALP) (FIG. 8B), aspartate aminotransferase (AST) (FIG. 8C), albumin blood (ALB) (FIG. 8D), and bilirubin (TBIL) (FIG. 8E). No liver functional impairment or damage was detected after the ANGPTL3 gene editing.

Example 3

Toxicity Study of an ANGPTL3 gRNA Formulation

Figure 9:
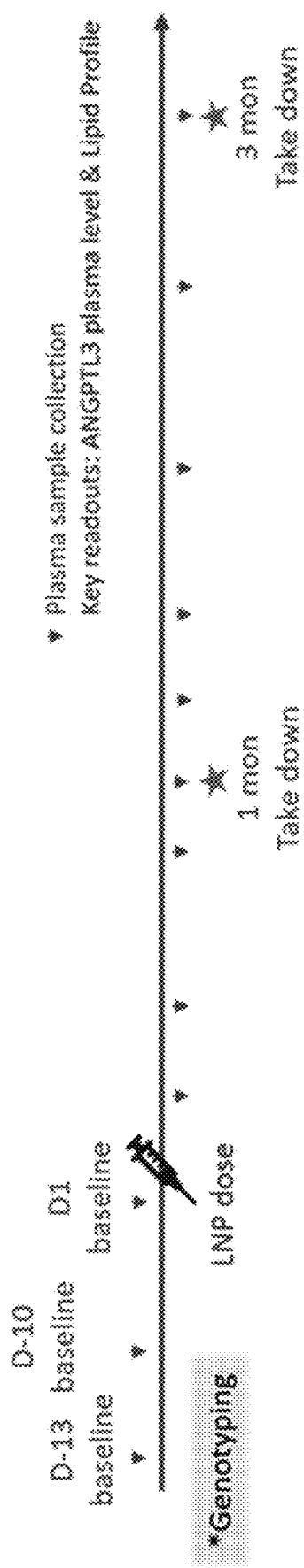
FIG. 9 depicts a non-limiting exemplary NHP study design.

In this example, a toxicity study was carried out in NHPs. Lipid nanoparticles encapsulating the gRNA molecule of SEQ ID NO: 3 (ANGPTL3_T10, e.g., SEQ ID NO: 20) and Cas9 mRNA were formulated to an ANGPTL3 gRNA formulation referred to as "CTX310." The CTX310 formulation was administered in a single dose on Day 1 via a 60-minute IV infusion into three groups of NHPs (e.g., cynomolgus monkey) at a dose level of 0.5 mg/kg, 1.5 mg/kg, and 3.0 mg/kg, respectively. Each group of NHPs includes four female and four male cynomolgus monkeys. Plasma samples were collected according to the study design shown in FIG. 9. Interim necropsy was performed on Day 37 and terminal necropsy on Day 103.

Data obtained from the CTX310 pilot toxicity study are shown with the data from the ANGPTL3 NHP study carried out in Example 1.

TABLE 4

RESULTS OF CTX310 PILOT TOXICITY STUDY

|  | ANGPTL3 Proof-of-concept | CTX310 Pilot Toxicity Study | | |
| --- | --- | --- | --- | --- |
| Time point | 5 weeks | 1 month | 1 month | 1 month |
| Dose Level | 2 mg/kg | 0.5 mg/kg | 1.5 mg/kg | 3 mg/kg |
| Number of subjects | 4 | 8 | 8 | 8 |
| % ANGPTL3 lowering | 76 ± 9% | 56 ± 16% | 84 ± 13% | 89 ± 5% |
| Liver editing (necropsy) | 53 ± 11% | 41.18 ± 15.09% | 64.76 ± 11.02% | 71.35 ± 1.80% |
| Triglyceride (% change) | 47 ± 21% | 26 ± 27% | 58 ± 11% | 52 ± 15% |
| Triglyceride absolute | 22 ± 4 mg/dL | 39 ± 11 mg/dL | 23 ± 9 mg/dL | 25 ± 7 mg/dL |
| LDL (% change) | | No data (NHP diet) | | |

Data: Average ± SD

Figure 10A:
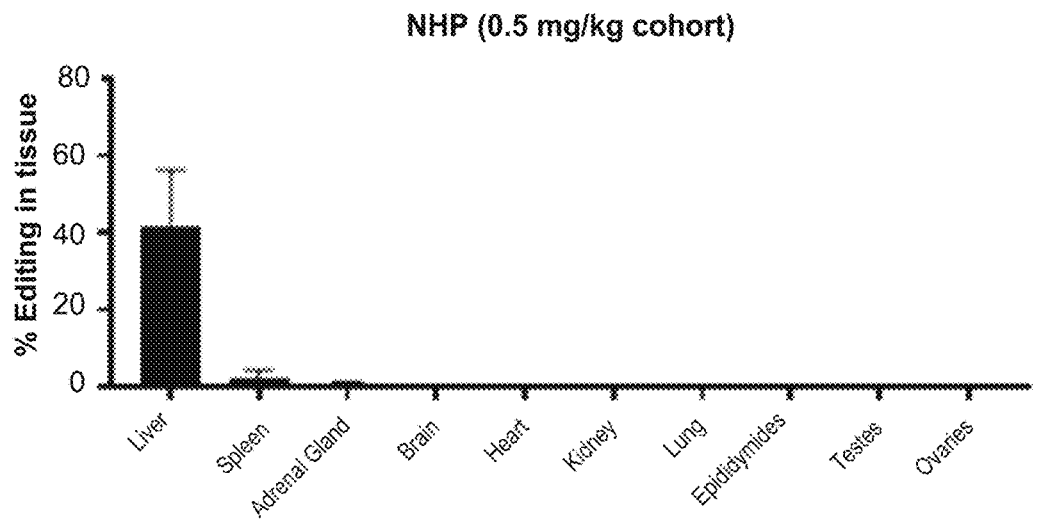
FIG. 10A-FIG. 10D are graphs showing the percentage of ANGPTL3 gene editing in different organ tissues of the NHPs treated with 0.5 mg/kg (FIG. 10A), 1.5 mg/kg (FIG. 10B) and 3.0 mg/kg CTX310 formulation (FIG. 10C).
Figure 10B:
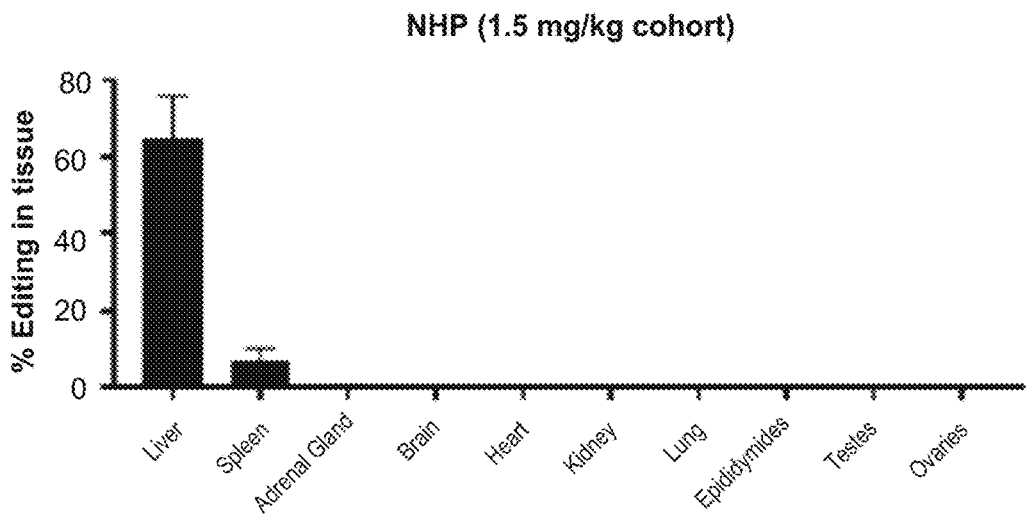
Figure 10C:
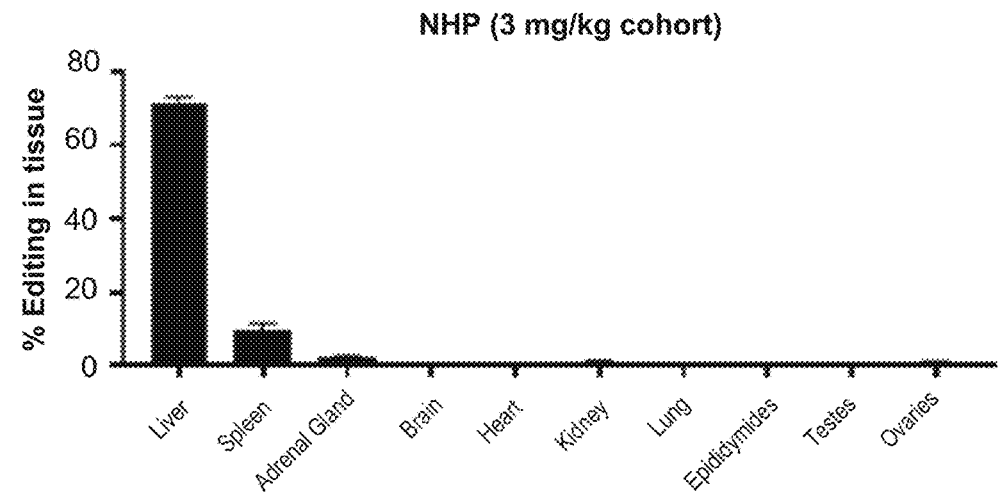
Figure 10D:
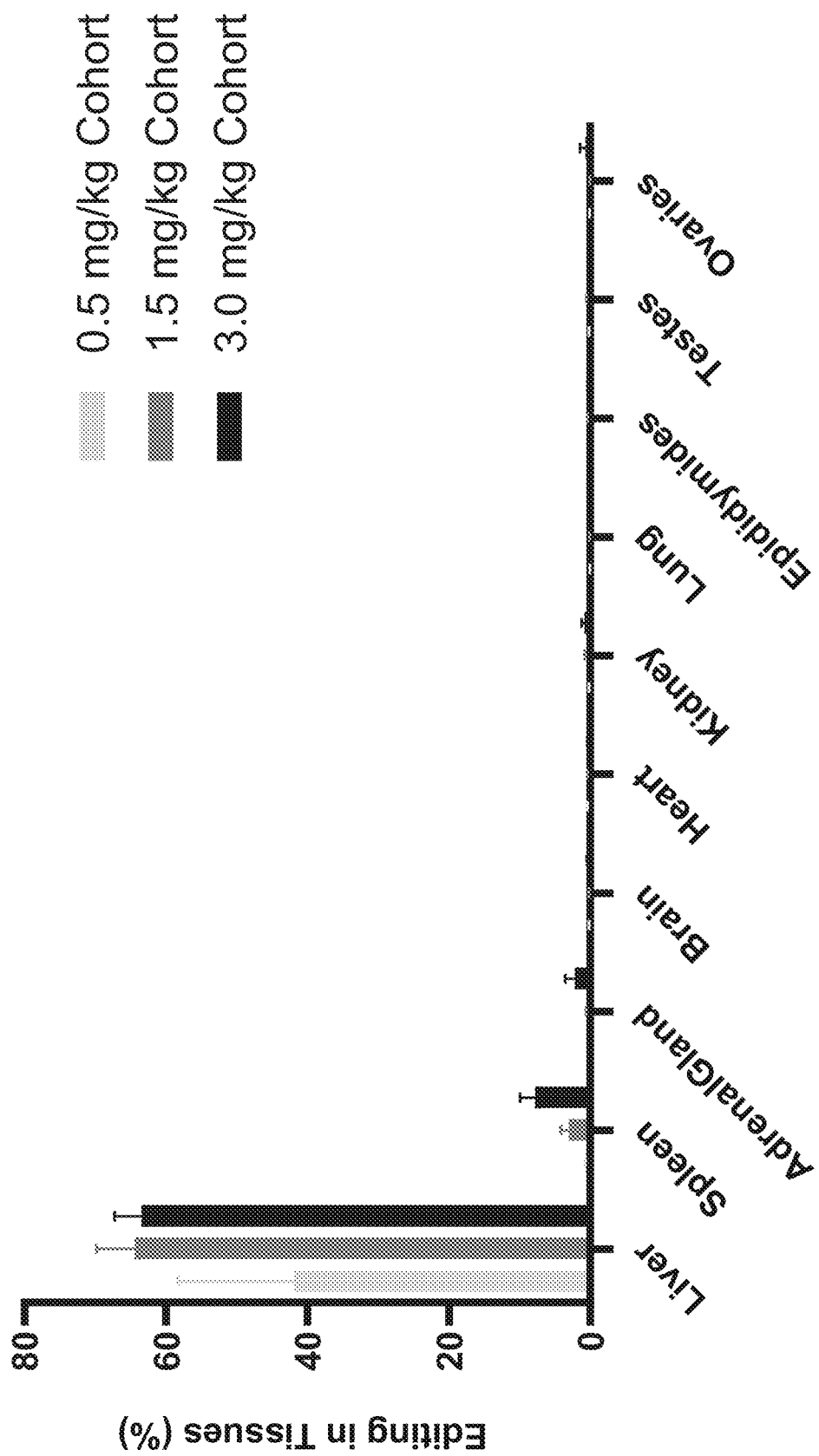

The tissue distribution of gene editing in CTX310 treated cynomolgus monkeys was also determined (see, for example, FIG. 10A-FIG. 10D). Cynomolgus monkeys were IV infused with three different doses of CTX310: 0.5 mg/kg (FIG. 10A), 1.5 mg/kg (FIG. 10B) and 3.0 mg/kg (FIG. 10C). Four monkeys from each treated group were sacrificed at Day 37 and different tissues were collected and editing frequency were measured in the necropsy samples using next-generation sequencing. Data for 0.5, 1.5 and 3 mg/kg treated cohort at Day 37 are shown in FIG. 10A, FIG. 10B, and FIG. 10C, respectively. Data were presented as mean±SD. FIG. 10D shows gene editing efficiency data out to 3 months following administration for each dosing cohort. The results demonstrate that the ANGPTL3 gene editing efficiency is significantly higher in liver than in other organ tissues. Editing efficiencies for 1-month (Table 5A) and 3-months (Table 5B) are also shown below.

TABLE 5A

TISSUES AND CELL TYPES FOR OFF-TARGET ASSESSMENT-1 MONTH COHORT

|  | Control | | CTX310 0.5 mg/kg | | CTX310 1.5 mg/kg | | CTX310 3.0 mg/kg | |
| --- | --- | --- | --- | --- | --- | --- | --- | --- |
| Tissue | Average | SD | Average | SD | Average | SD | Average | SD |
| Liver | 0.06 | 0.01 | 41.18 | 15.09 | 64.76 | 11.02 | 71.35 | 1.80 |
| Spleen | 0.04 | 0.01 | 1.87 | 2.52 | 7.19 | 2.99 | 9.42 | 2.14 |
| Adrenal gland | 0.05 | 0.02 | 0.47 | 0.70 | 0.44 | 0.18 | 2.02 | 0.79 |
| Brain | 0.09 | 0.05 | 0.09 | 0.04 | 0.10 | 0.04 | 0.18 | 0.14 |
| Heart | 0.04 | 0.01 | 0.09 | 0.03 | 0.12 | 0.03 | 0.23 | 0.03 |
| Kidney | 0.07 | 0.02 | 0.11 | 0.03 | 0.36 | 0.21 | 0.76 | 0.53 |
| Lung | 0.06 | 0.01 | 0.05 | 0.01 | 0.14 | 0.10 | 0.12 | 0.05 |
| Epididymides | 0.08 | 0.03 | 0.19 | 0.20 | 0.09 | 0.02 | 0.18 | 0.10 |
| Testes | 0.05 | 0.01 | 0.11 | 0.03 | 0.32 | 0.16 | 0.25 | NA |
| Ovaries | 0.06 | 0.02 | 0.13 | 0.08 | 0.23 | 0.12 | 0.81 | 0.20 |

TABLE 5B

TISSUES AND CELL TYPES FOR OFF-TARGET ASSESSMENT-3 MONTH COHORT

| Tissue | Average | SD | Average | SD | Average | SD | Average | SD |
|---|---|---|---|---|---|---|---|---|
| Liver | 0.07 | 0.02 | 41.89 | 16.37 | 64.43 | 5.46 | 63.46 | 3.85 |
| Spleen | 0.09 | 0.08 | 0.62 | 0.06 | 3.02 | 1.2 | 7.79 | 2.18 |
| Adrenal gland | 0.14 | 0.12 | 0.16 | 0.02 | 0.51 | 0.14 | 2.22 | 1.36 |
| Brain | 0.22 | 0.23 | 0.12 | 0.08 | 0.15 | 0.08 | 0.28 | 0.22 |
| Heart | 0.07 | 0.03 | 0.23 | 0.18 | 0.26 | 0.16 | 0.29 | 0.15 |
| Kidney | 0.06 | 0.02 | 0.15 | 0.1 | 0.51 | 0.33 | 0.83 | 0.43 |
| Lung | 0.11 | 0.03 | 0.07 | 0.03 | 0.09 | 0.04 | 0.25 | 0.1 |
| Epididymides | 0.07 | 0.02 | 0.38 | 0.01 | 0.24 | 0.13 | 0.36 | 0.03 |
| Testes | 0.04 | 0.01 | 0.16 | 0.03 | 0.36 | 0.21 | 0.3 | 0.03 |
| Ovaries | 0.29 | 0.35 | 0.09 | 0.05 | 0.08 | 0.03 | 0.68 | 0.82 |

Figure 11:
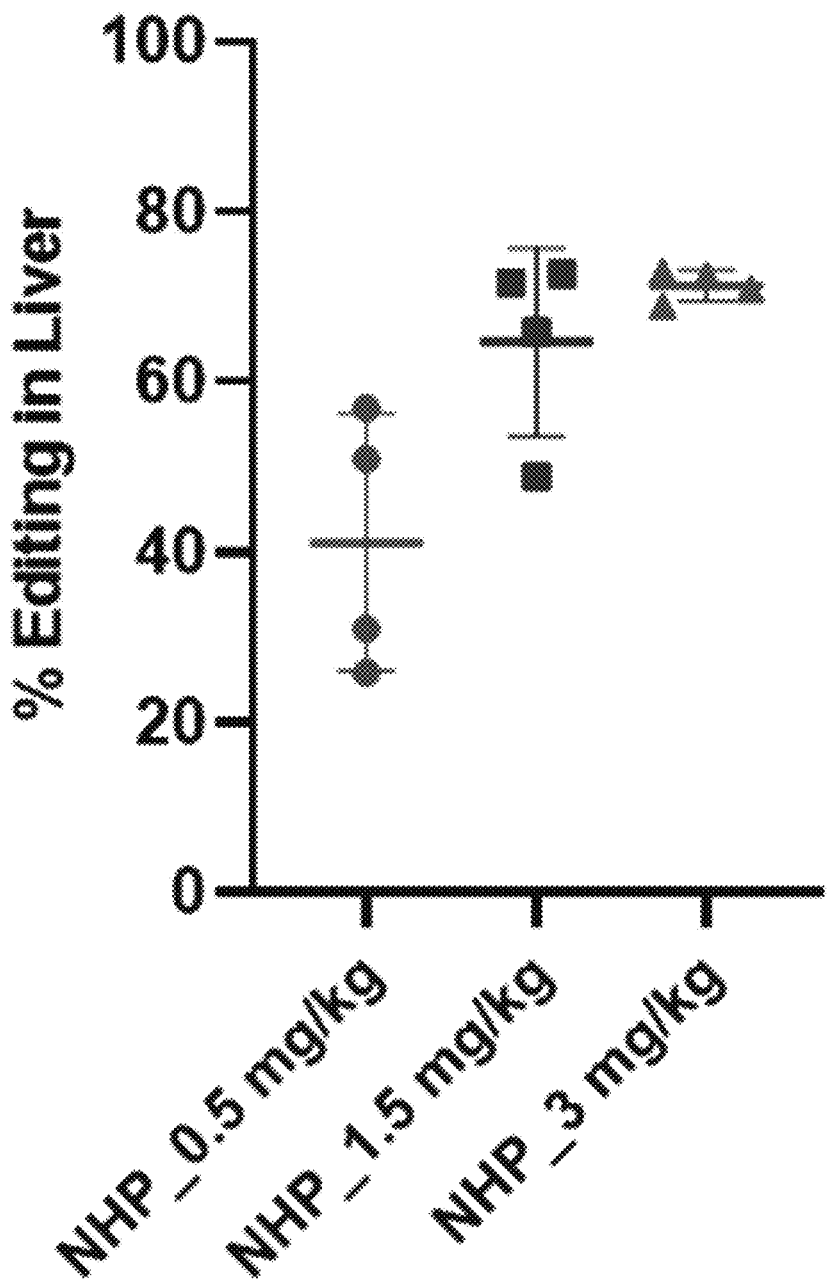
FIG. 11 is a graph showing the percentage of ANGPTL3 gene editing in liver cells of NHPs treated with 0.5 mg/kg, 1.5 mg/kg and 3.0 mg/kg CTX310 formulation.

FIG. 11 and Table 6 below show the percentage of ANGPTL3 gene editing in liver cells of cynomolgus monkeys treated with 0.5, 1.5 and 3 mg/kg CTX310. Efficient editing in liver was achieved. FIG. 11 shows dose-dependent liver editing up to 70% in NHPs.

TABLE 6

PERCENTAGE OF ANGPTL3 GENE EDITING IN LIVER

| 0.5 mg/kg | 1.5 mg/kg | 3 mg/kg |
|---|---|---|
| 31 | 66 | 73 |
| 51 | 49 | 69 |
| 26 | 72 | 71 |
| 57 | 73 | 72 |

Figure 12A:
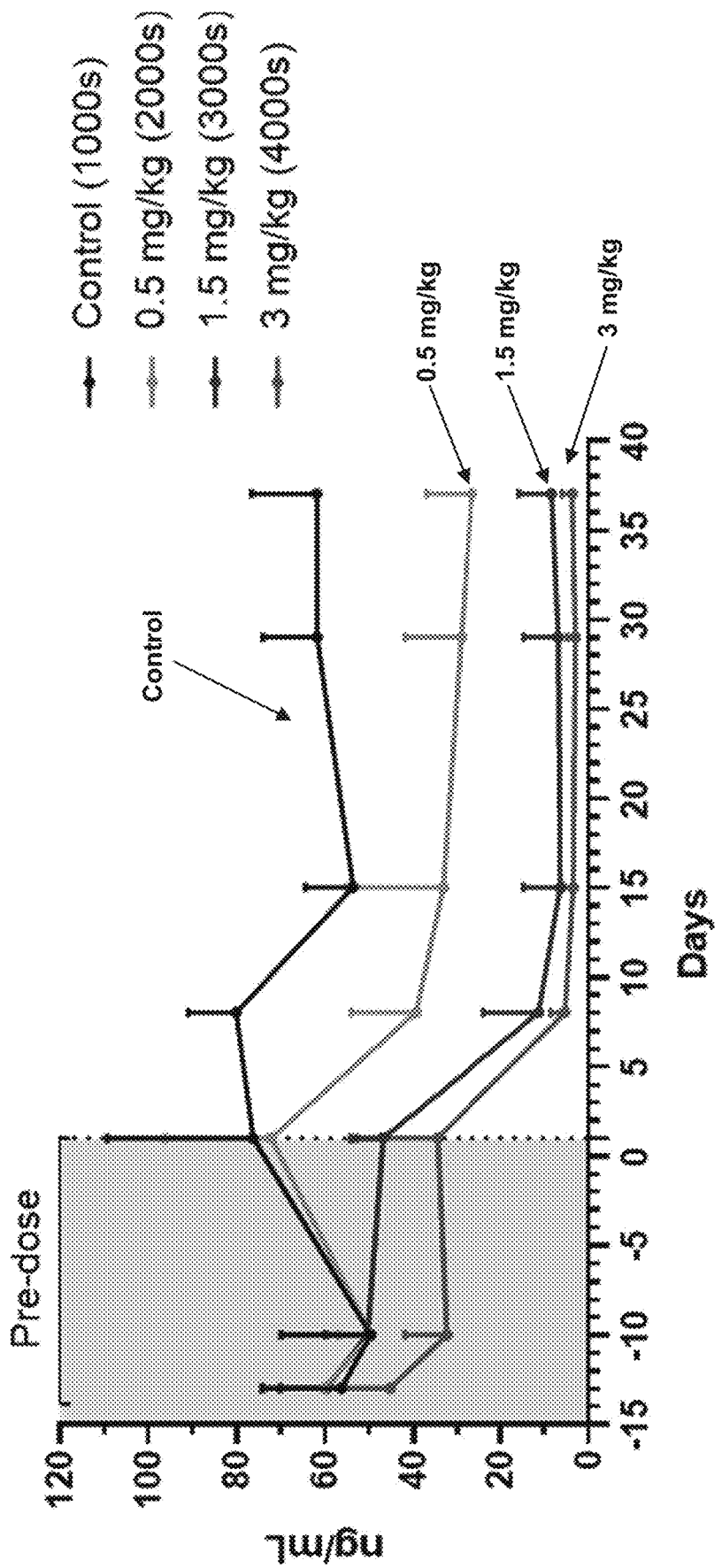
FIG. 12A-FIG. 12E depict exemplary data related to plasma ANGPTL3 levels.
Figure 12B:
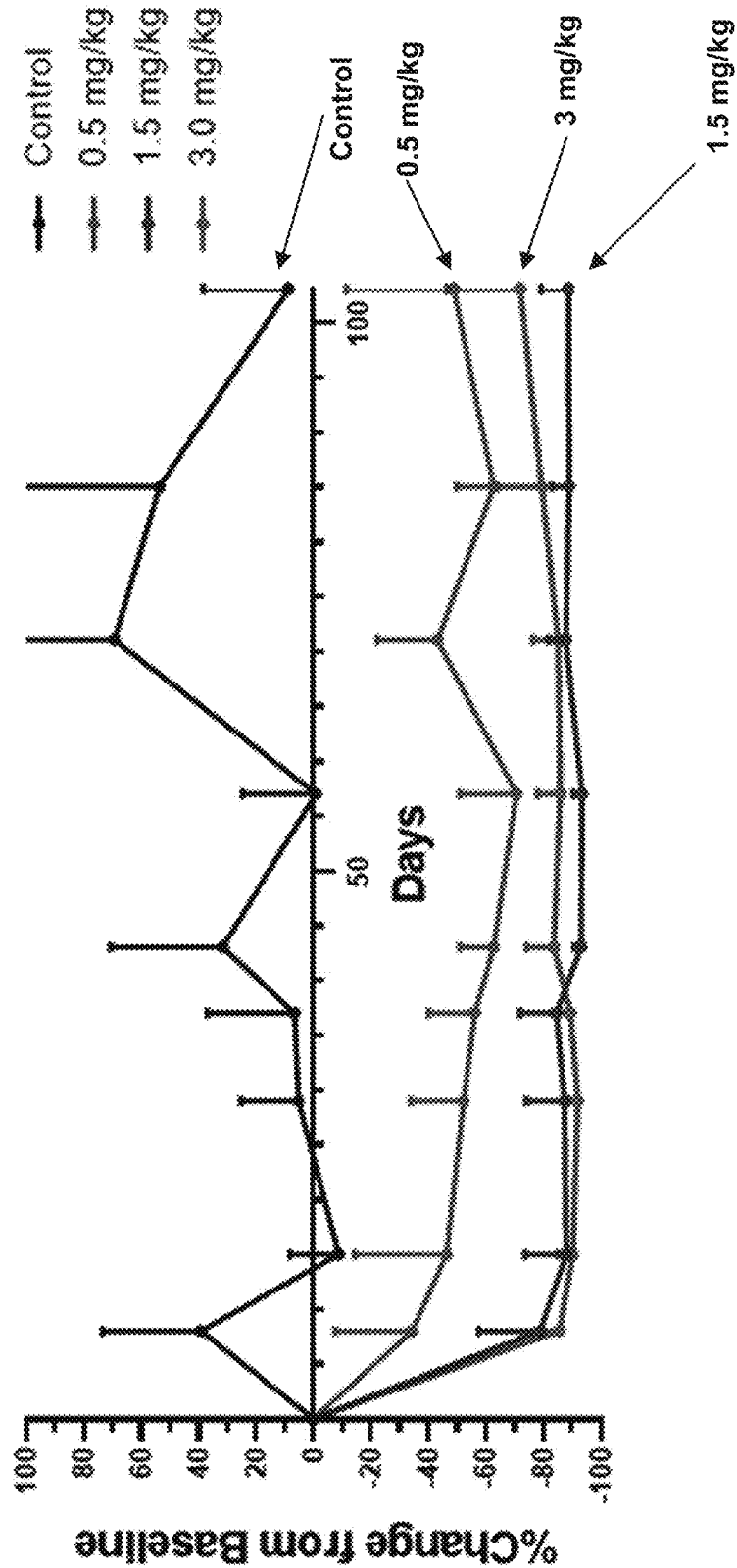

Table 7 and FIG. 12A show the plasma level of ANGPTL3 protein of the cynomolgus monkeys treated with three different doses of CTX310 (0.5, 1.5 and 3.0 mg/kg) in comparison to a control group. Table 8 and FIG. 12B show the percentage change of the plasma level of ANGPTL3 protein from a baseline of the CTX310 treated cynomolgus monkeys. The baseline is the average of the ANGPTL3 protein level thirteen days (Day −13) and ten days (Day −10) prior to the treatment and Day 1 (pre-dose).

TABLE 7

ANGPTL3 PLASMA PROTEIN LEVELS (NG/ML)

| | Pre-dose | | Treatment period | | | |
|---|---|---|---|---|---|---|
| | Day −13 | Day −10 | Day 1 | Day 8 | Day 15 | Day 29 | Day 37 |
| Control | 56 | 50 | 76 | 80 | 54 | 62 | 62 |
| 0.5 mg/kg | 60 | 50 | 72 | 39 | 33 | 29 | 27 |
| 1.5 mg/kg | 60 | 50 | 47 | 11 | 7 | 7 | 8 |
| 3 mg/kg | 45 | 32 | 35 | 5 | 4 | 3 | 4 |

TABLE 8

PERCENTAGE CHANGE OF THE ANGPTL3 PLASMA PROTEIN LEVEL FROM A BASELINE

| | Day 8 | Day 15 | Day 29 | Day 37 |
|---|---|---|---|---|
| Control | 40 | −9 | 5 | 7 |
| 0.5 mg/kg | −34 | −46 | −52 | −56 |
| 1.5 mg/kg | −79 | −88 | −87 | −84 |
| 3 mg/kg | −85 | −90 | −92 | −89 |

Figure 12C:
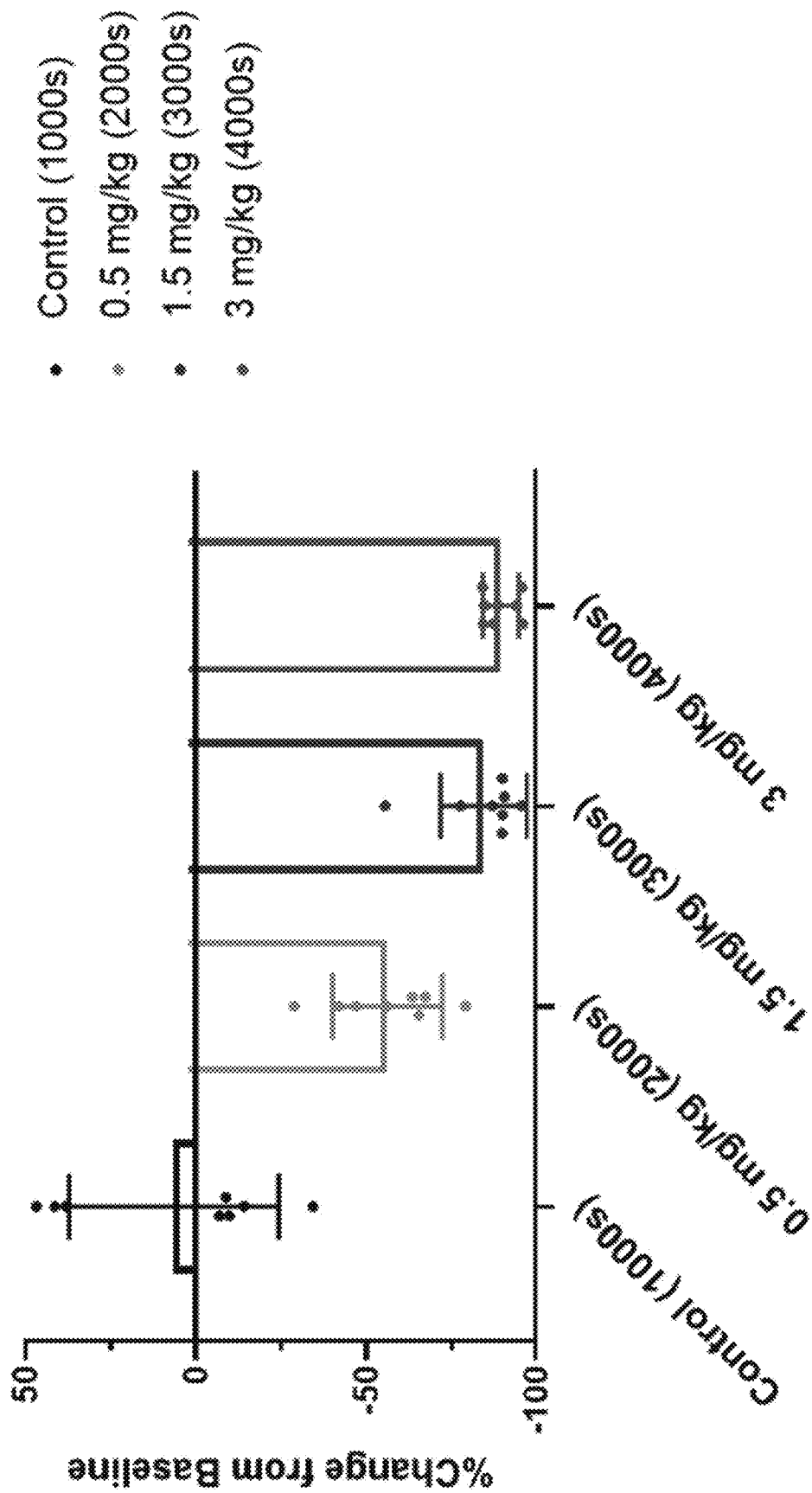
Figure 12D:
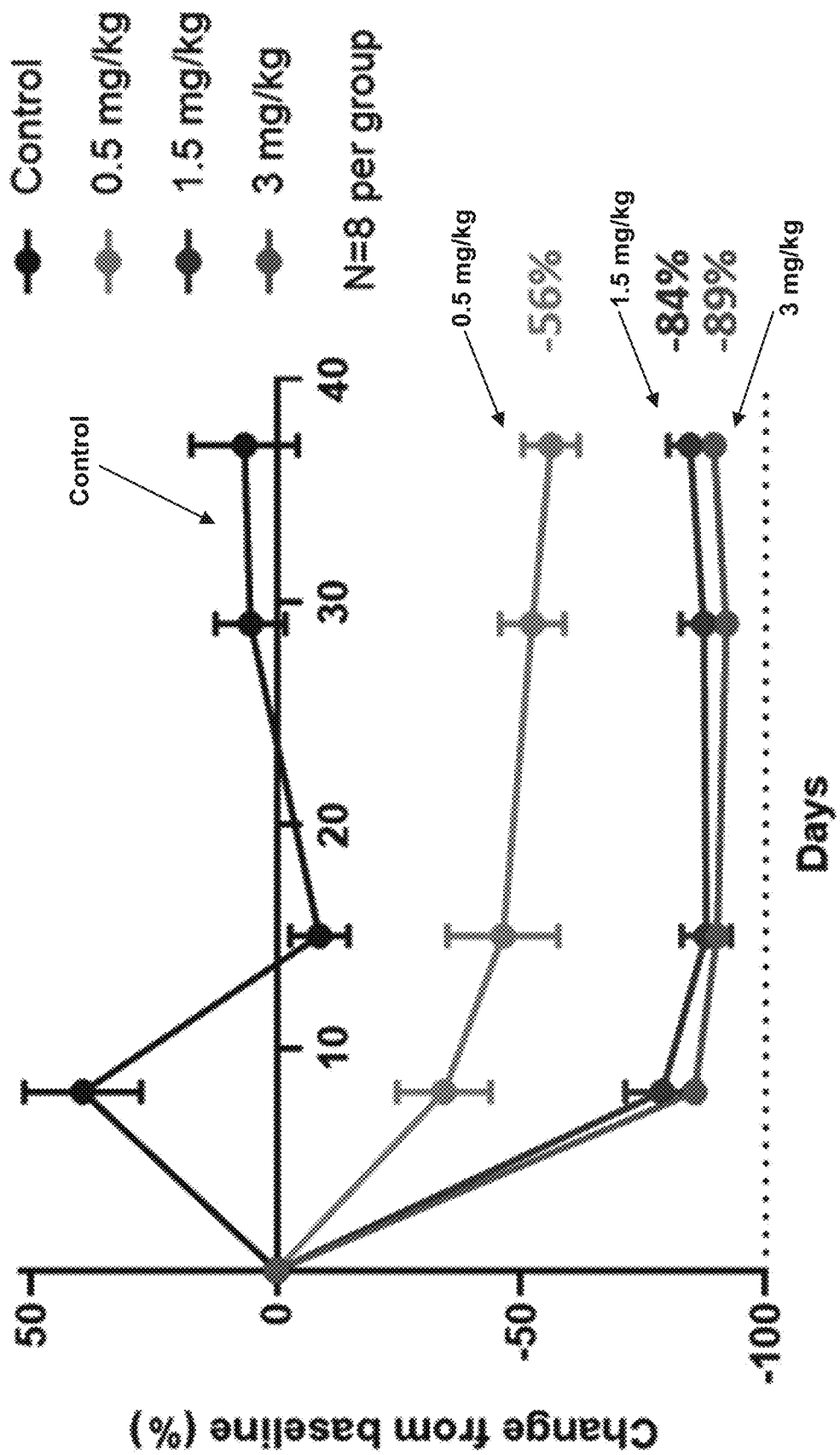
Figure 12E:
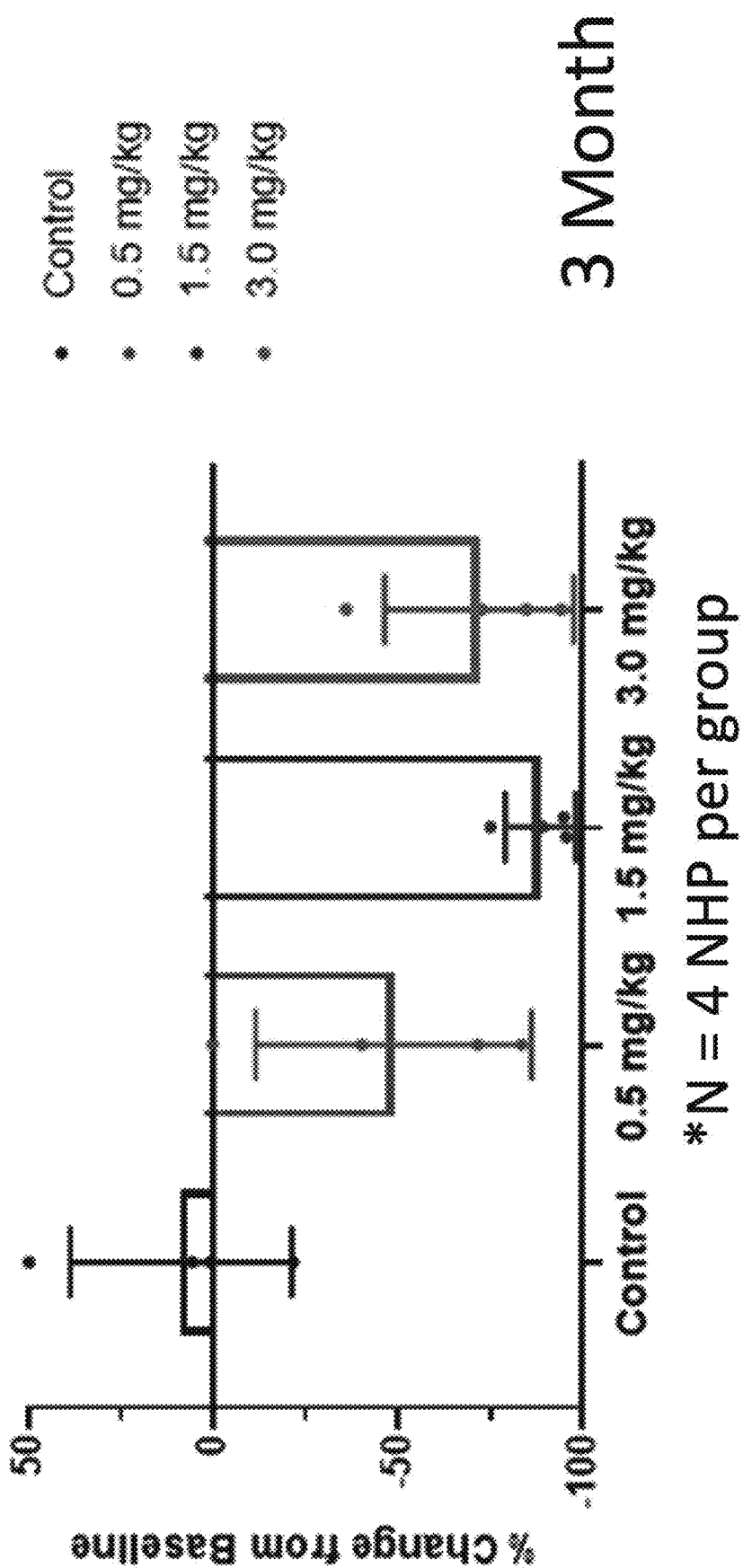

FIGS. 12A and 12B both demonstrate a dose-dependent reduction of plasma ANGPTL3 protein after CTX310 dosing. About 56% reduction of ANGPTL3 protein from baseline was observed in cynomolgus monkeys treated with 0.5 mg/kg CTX310 and about 84%-89% reduction from baseline was observed in cynomolgus monkeys treated with 1.5 mg/kg and 3 mg/kg CTX310 (see e.g., FIG. 12B). FIG. 12C is a graph showing the percentage change of the plasma ANGPTL3 protein from a baseline of the cynomolgus monkeys on Day 37 after the CTX310 treatments. FIG. 12D is a graph showing the percentage change of the serum ANGPTL3 protein, which demonstrates an about 90% reduction in serum ANGPTL3 protein. FIG. 12E is a graph showing the percentage change of the plasma ANGPTL3 protein from a baseline of the cynomolgus monkeys at about 3 months after the CTX310 treatments.

Figure 13A:
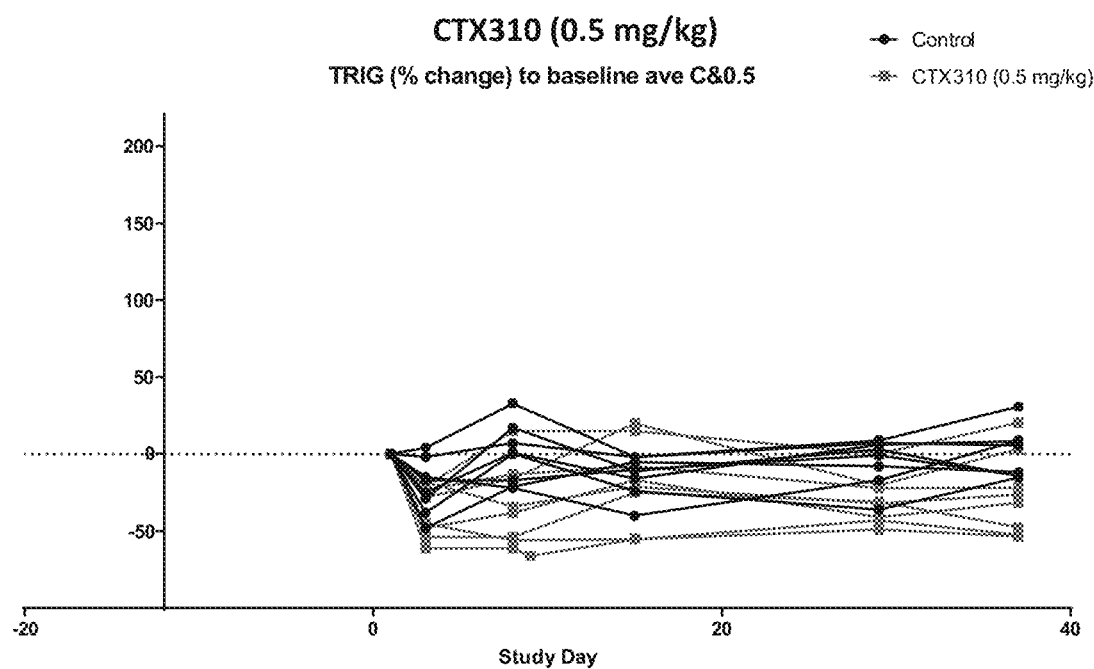
FIG. 13A-FIG. 13I depict exemplary data related to triglyceride levels.
Figure 13B:
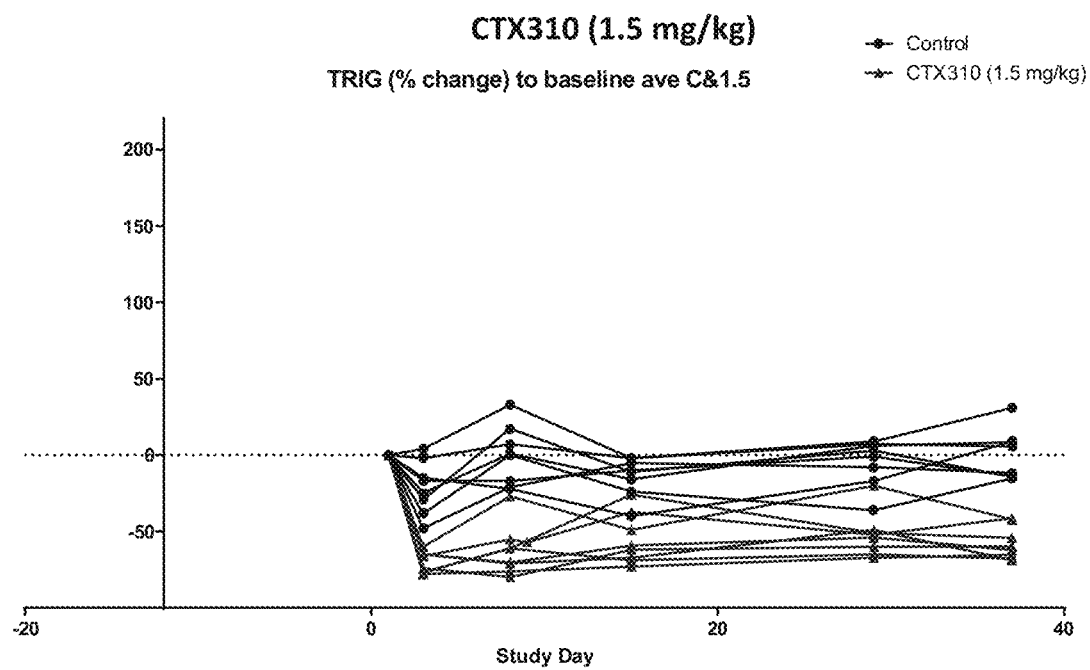
Figure 13C:
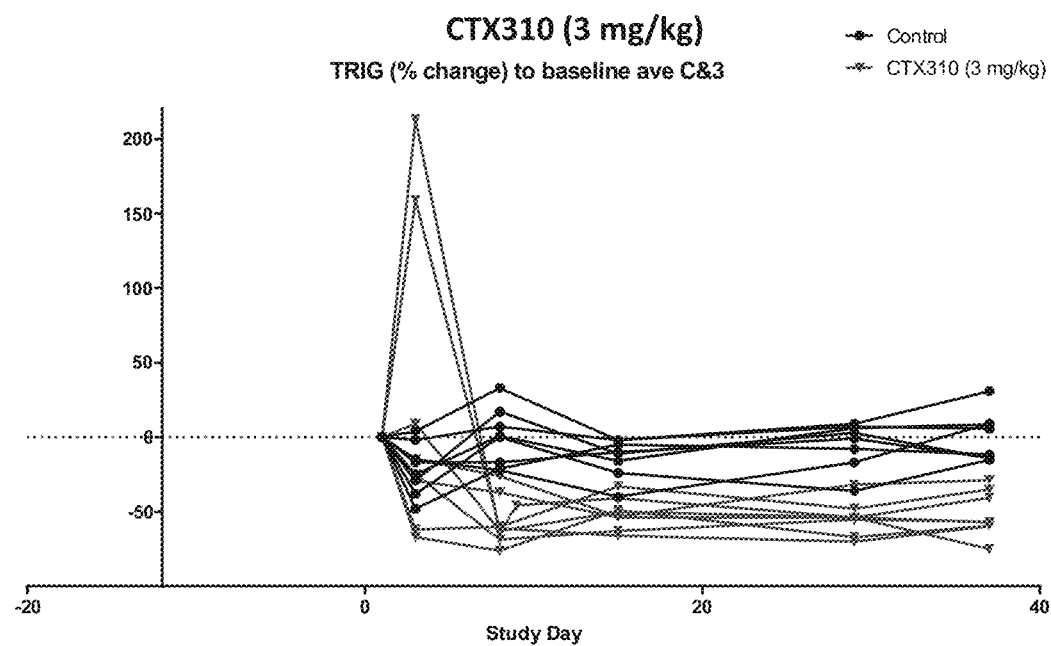
Figure 13D:
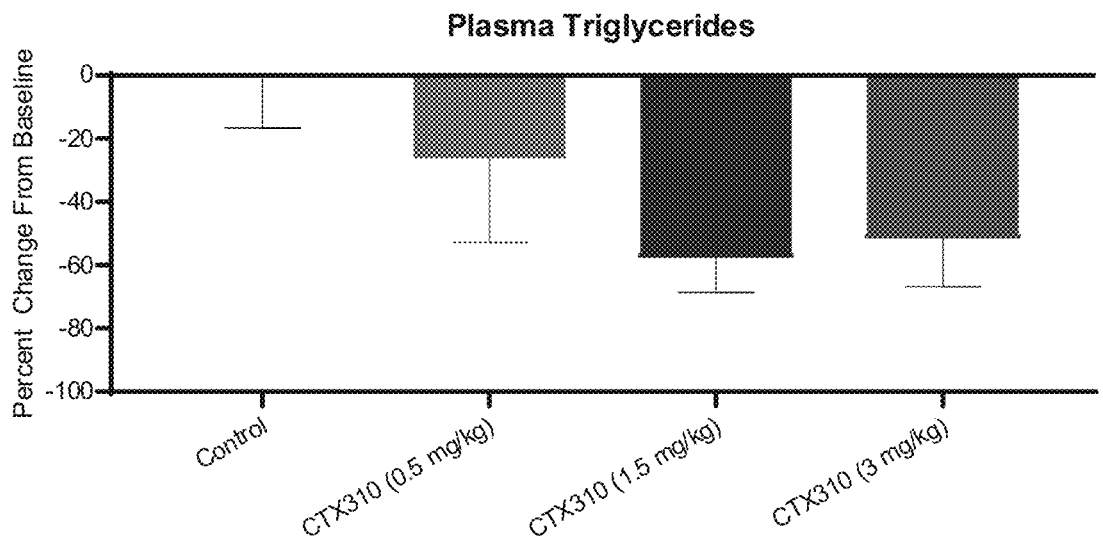
Figure 13E:
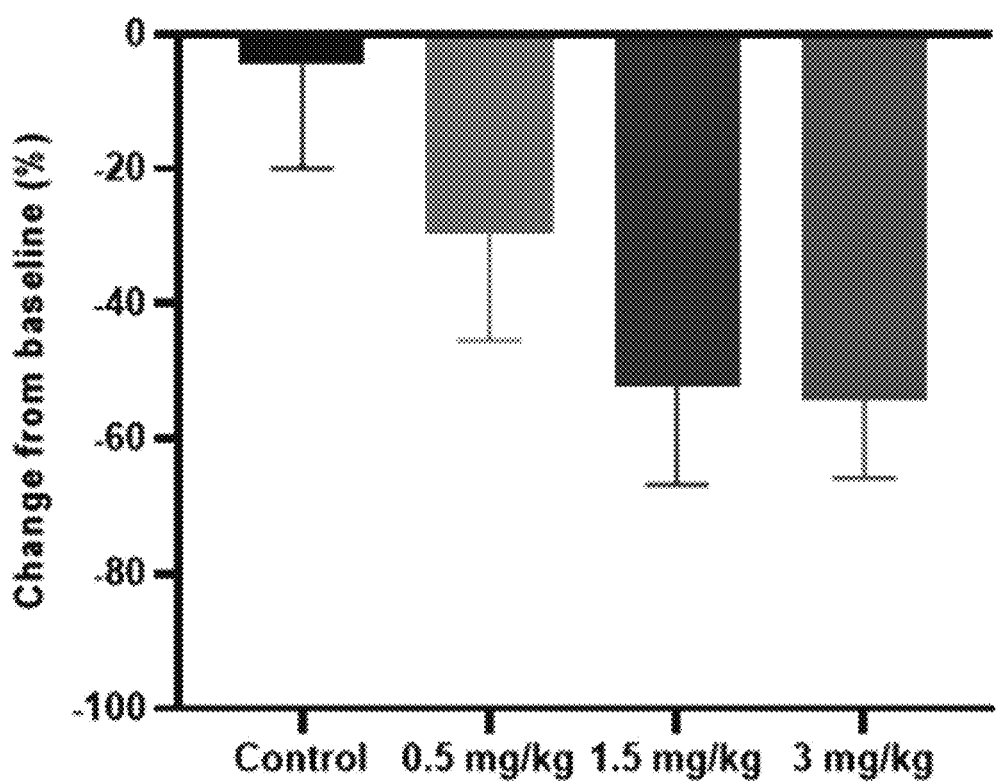
Figure 13F:
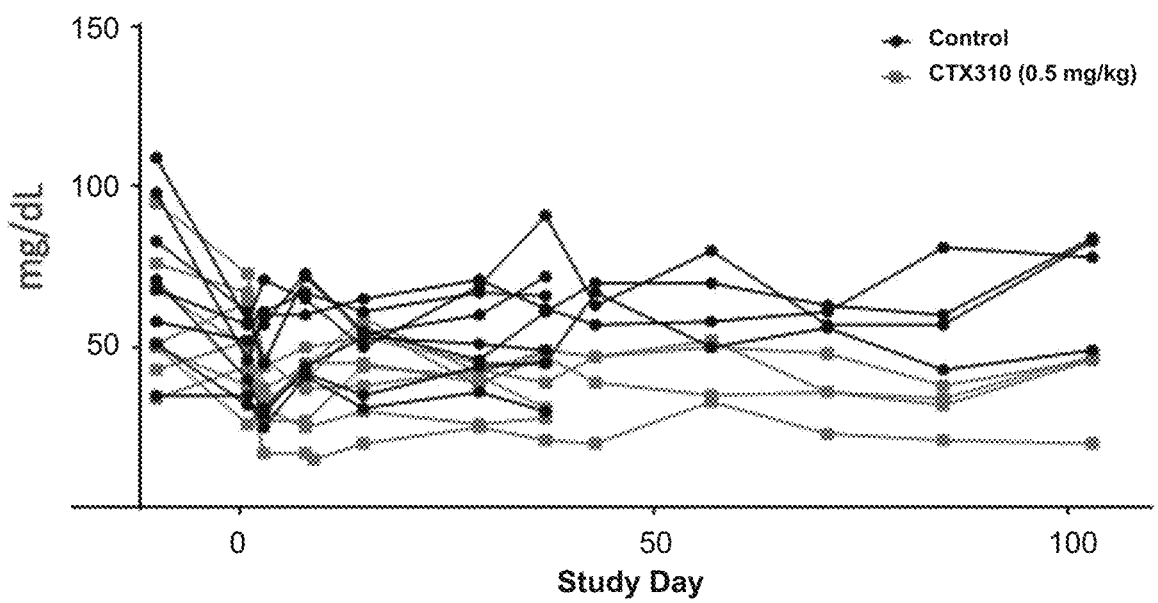
Figure 13G:
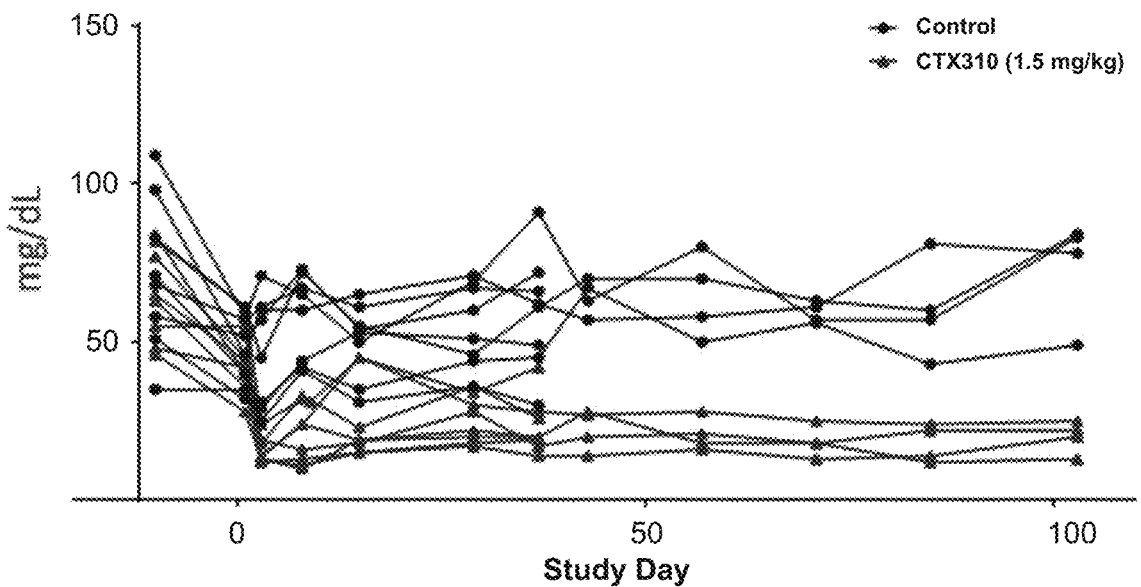
Figure 13H:
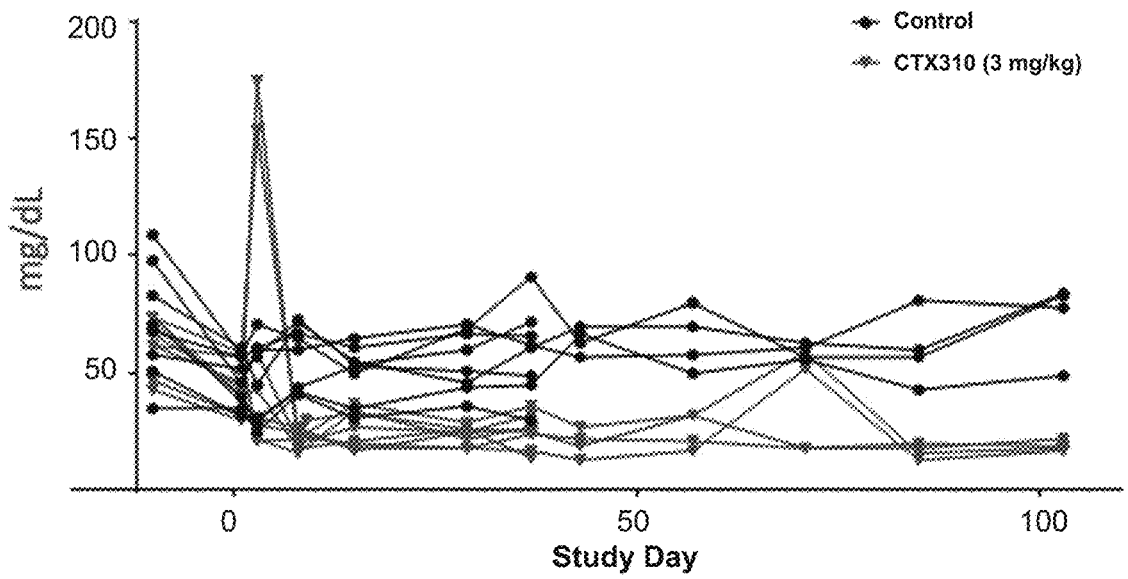
Figure 13I:
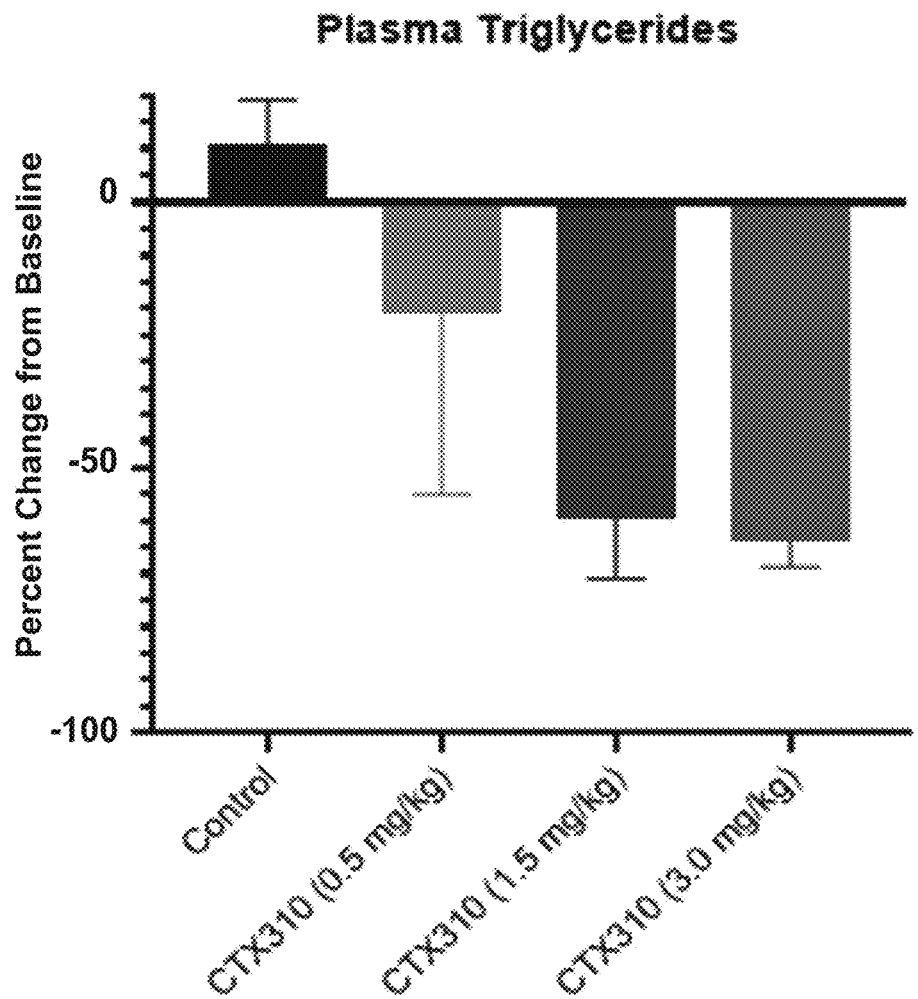

FIG. 13A-FIG. 13C are graphs showing the percentage change of the plasma triglyceride level normalized to a baseline of the cynomolgus monkeys after the CTX310 treatments with three different doses of: 0.5 mg/kg (FIG. 13A), 1.5 mg/kg (FIG. 13B) and 3.0 mg/kg (FIG. 13C). The baseline is the average of the triglyceride level ten days prior to the treatment (Day −10) and the triglyceride level of Day 1 (pre-dose). Table 9 and FIG. 13D shows the percentage change of the plasma triglyceride level from the baseline of the cynomolgus monkeys on Day 37 after the CTX310 treatments. On Day 37, over 50% reduction of the triglyceride levels from baseline were observed in NHPs treated with 1.5 mg/kg and 3 mg/kg CTX310 formulation. FIG. 13E is a graph showing the percentage change of the serum triglyceride level from baseline one month after the CTX310 treatment, which demonstrates >50% reduction in serum triglyceride at one month. FIG. 13F-FIG. 13H depict plasma triglyceride level in mg/dL of the cynomolgus monkeys after the CTX310 treatments with three different doses of: 0.5 mg/kg (FIG. 13F), 1.5 mg/kg (FIG. 13G) and 3.0 mg/kg (FIG. 13H). FIG. 13I is a graph showing the percentage change of the triglyceride level from baseline three months after the CTX310 treatment.

TABLE 9

TRIGLYCERIDE PERCENTAGE
CHANGE FROM A BASELINE

| Groups | % change |
|---|---|
| Control | −0.2 |
| 0.5 mg/kg | −26.1 |
| 1.5 mg/kg | −57.7 |
| 3 mg/kg | −51.5 |

Figure 14A:
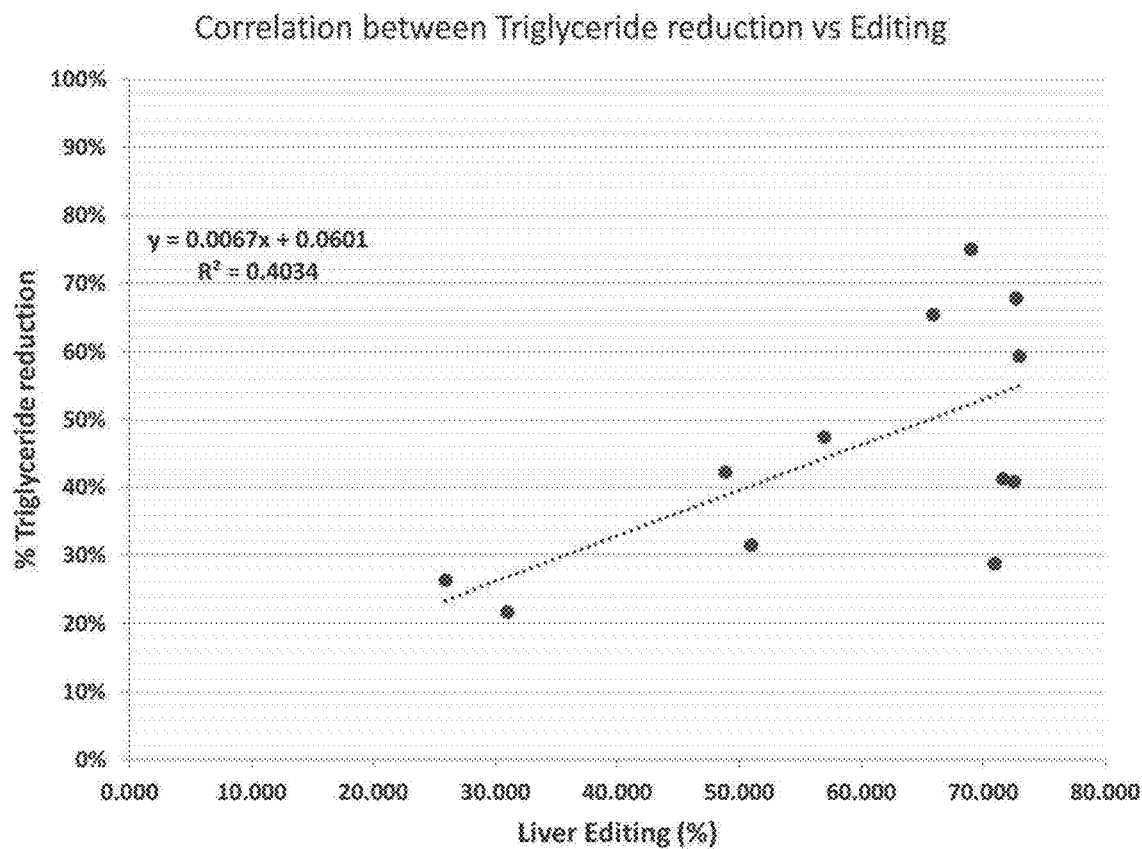
FIG. 14A-FIG. 14B depict data related to the correlation between lipid levels and gene editing.
Figure 14B:
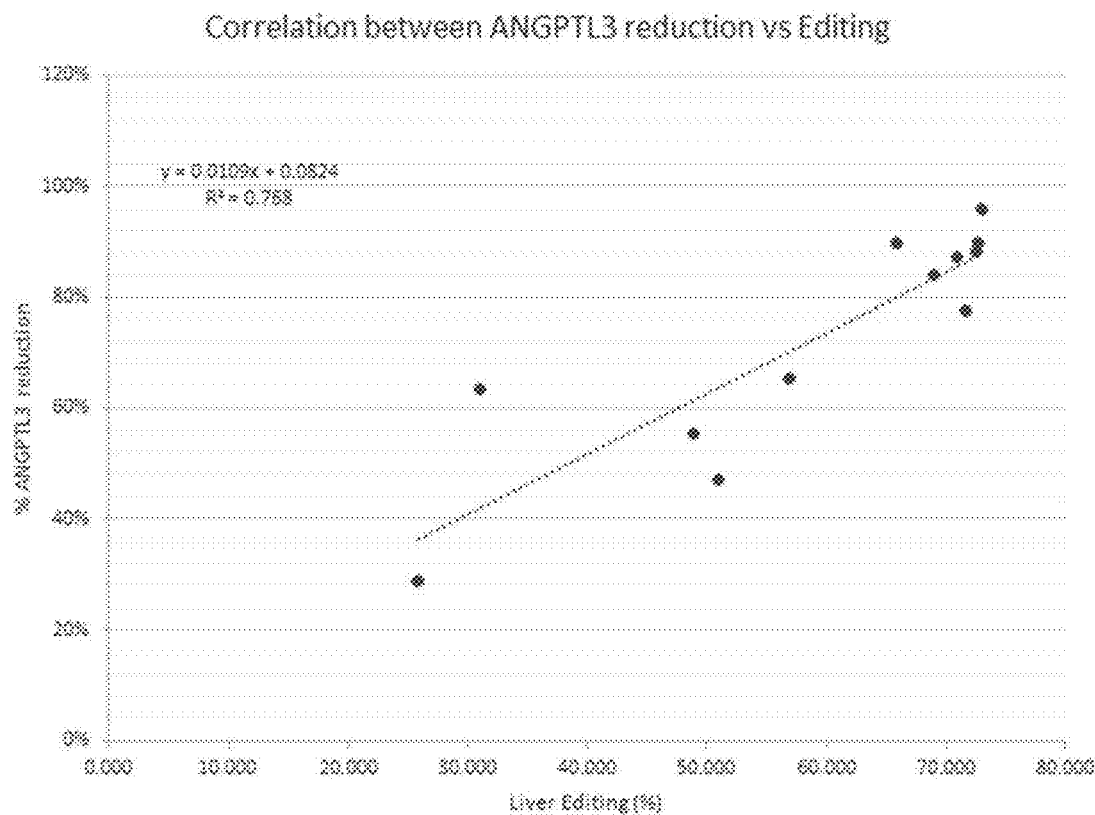

FIG. 14A is a plot showing the correlation between triglyceride reduction and ANGPTL3 gene editing percentage in liver. FIG. 14B is a plot showing the correlation between ANGPTL3 protein reduction and ANGPTL3 gene editing percentage in liver. The results demonstrate that the ANGPTL3 gene editing efficiency in liver is positively correlated to the reduction in triglyceride level and ANGPTL3 protein level.

Figure 20A:
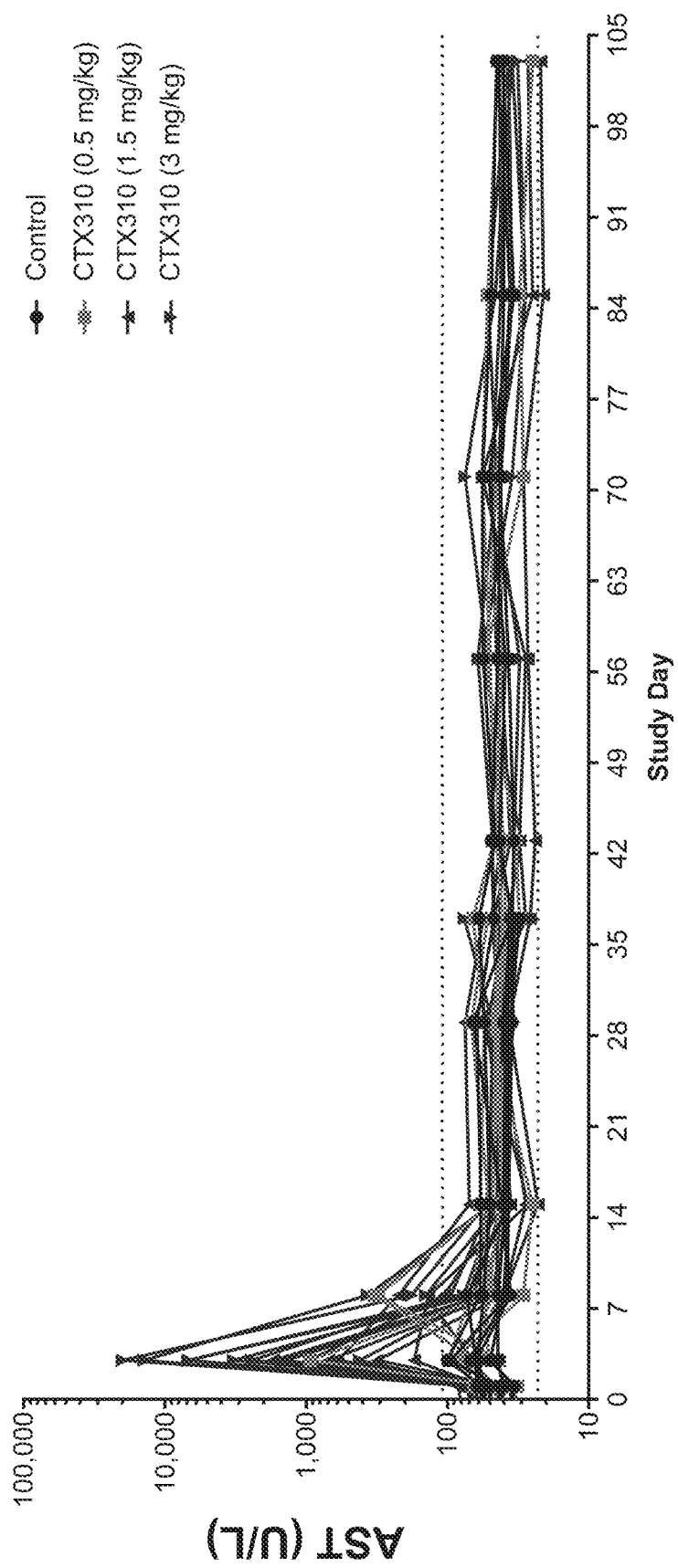
FIG. 20A-FIG. 20B depict exemplary data related to non-good-laboratory practice (GLP) toxicity studies. Shown in FIG. 20A are AST levels in animals treated with the indicated dosages out to about 3 months following administration. Shown in FIG. 20B are bilirubin levels in animals treated with the indicated dosages out to about 3 months following administration.
Figure 20B:
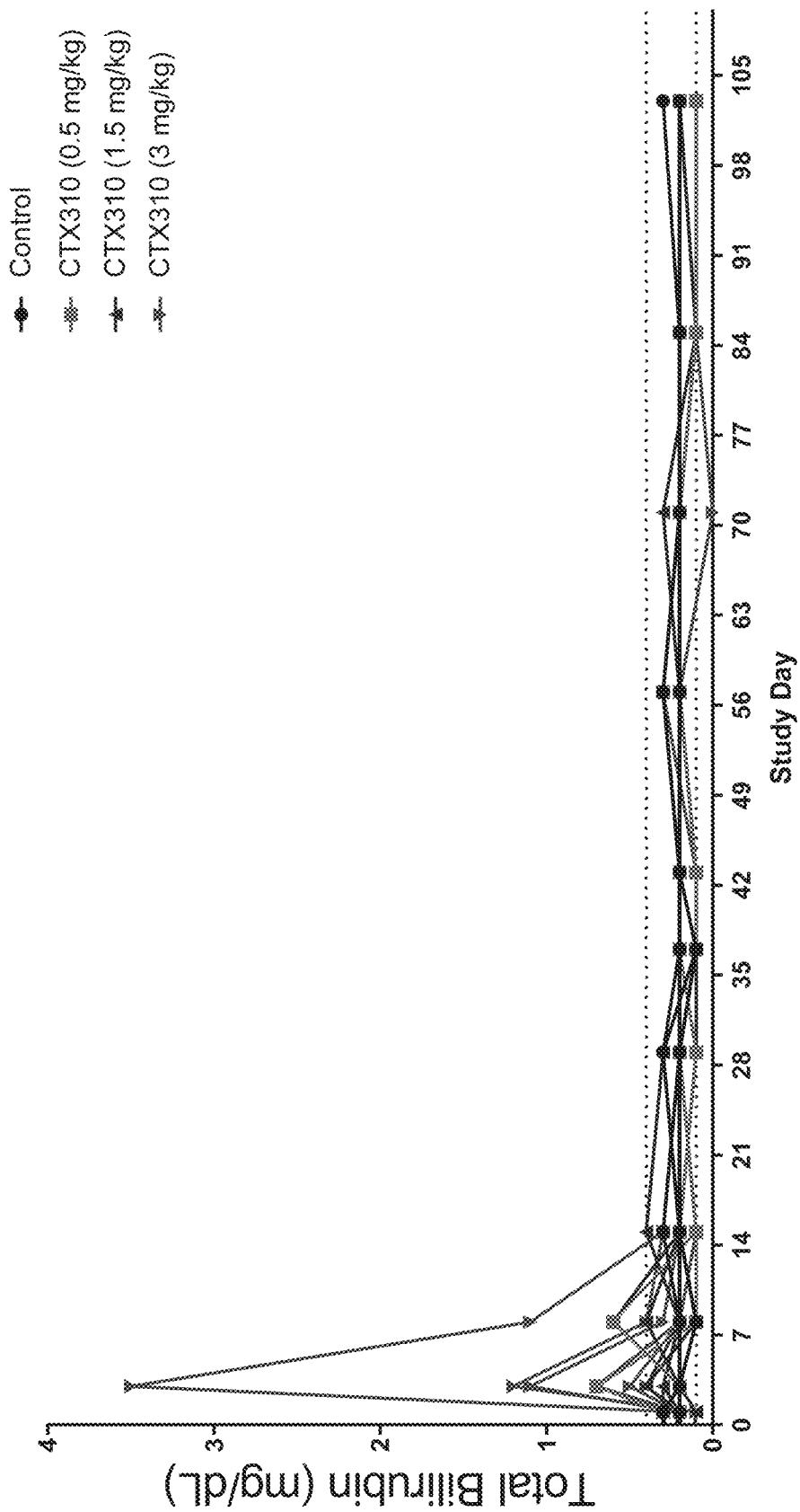
Figure 21A:
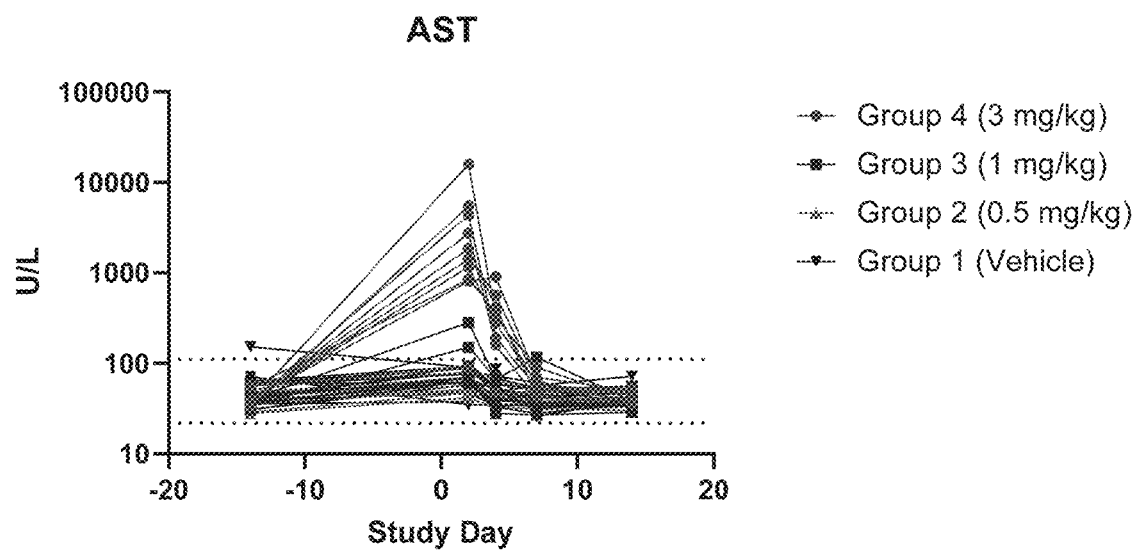
FIG. 21A-FIG. 21B depict exemplary data related to good-laboratory practice (GLP) toxicity studies showing AST (FIG. 21A) and bilirubin (FIG. 21B) levels in treated animals. Data out to about past 10 days post administration are shown.
Figure 21B:
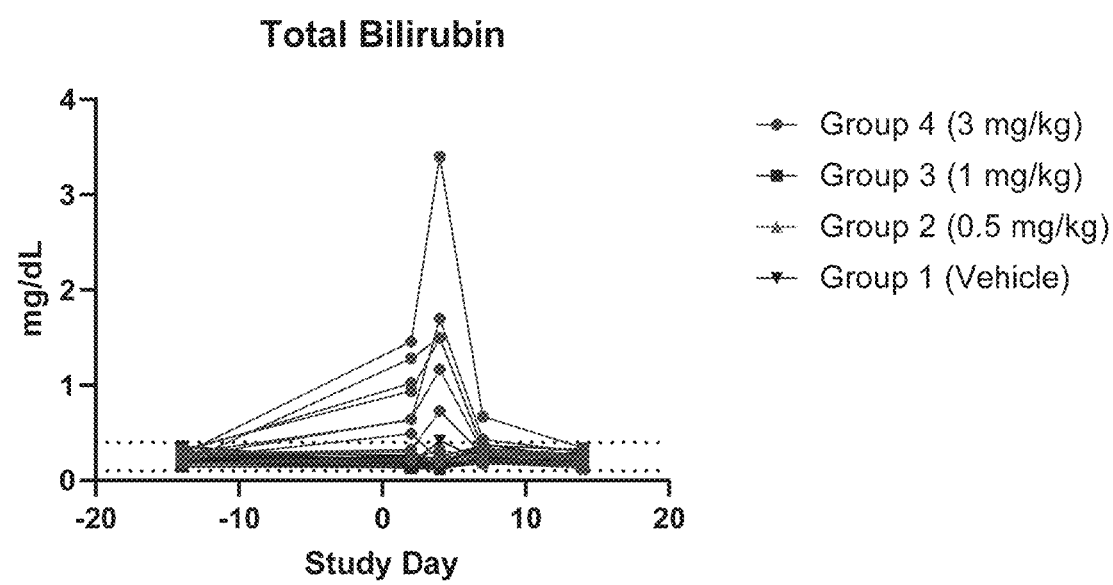

Liver function tests were also carried out before and after treatments to provide information about the status of the NHPs' liver. The data indicates that CTX310 causes dose-dependent transient elevations in ALT, AST, ALP and bilirubin. No liver functional impairment or damage was detected after the administration (e.g., 14 days after the administration) (FIG. 20A-FIG. 21B). Data shown in FIG. 20A-FIG. 20B are from a non-good laboratory practices (GLP) toxicology study (see below) and FIG. 21A-FIG. 21B are data from a GLP toxicology study.

A non-GLP dose range finding toxicity study was conducted for CTX310. This study included data on safety pharmacology. A 3-month, dose-range finding study was conducted to assess the toxicity of a single dose of CTX310 in cynomolgus monkeys (non-GLP, Table 10). Endpoints in this study included clinical observations, clinical pathology (hematology, serum chemistry, and coagulation), snapshot ECGs, and histology.

TABLE 10

DOSE RANGE FINDING STUDY DESIGN

| Test Article | Dose Level (mg/kg) | Interim Necropsy (5 weeks) Male | Interim Necropsy (5 weeks) Female | Terminal Necropsy (12 weeks) Male | Terminal Necropsy (12 weeks) Female | Endpoints |
|---|---|---|---|---|---|---|
| Vehicle | 0 | 2 | 2 | 2 | 2 | Clinical observations, body weight, hematology, serum chemistry, coagulation, histopathology, electrocardiography |
| CTX310 | 0.5 | 2 | 2 | 2 | 2 | |
|  | 1.5 | 2 | 2 | 2 | 2 | |
|  | 3.0 | 2 | 2 | 2 | 2 | |

There were no unscheduled deaths on this study. No abnormal clinical signs or changes in body weight related to CTX310 were observed. As shown in FIG. 20A-FIG. 20B, transient increases in liver enzymes (alkaline phosphatase, aspartate aminotransferase, alanine transaminase) were observed in a dose-dependent manner in animals treated with either 1.5 or 3.0 mg/kg of CTX310. These increases peaked at Day 3, partially resolved at Day 8, and returned to baseline levels by Day 15. Bilirubin levels were elevated only in the 3.0 mg/kg group and completely resolved by Day 15. TG levels were sharply increased in 2 animals in the 3.0 mg/kg group at Day 3, but quickly resolved by Day 8. Both TG levels and total cholesterol levels were decreased in a dose-dependent manner in all animals treated with CTX310. There were no CTX310-related changes to any hematology or coagulation parameters.

ECG tracings were captured once during acclimation Day −6, then once on Day 28 and once on Day 79. All the electrocardiograms evaluated in this study were qualitatively and quantitatively considered normal. No abnormalities in rhythm or waveform morphology were found at any dose level based on comparison of once during acclimation Day −6 and once on Days 28 and 79 postdose mean values and control values. No CTX310-related effects on heart rate were observed at any dose level.

At both the interim and the terminal necropsy, tissues were collected, weighed, and histopathology was assessed. No abnormal findings were observed in gross pathology or organ weights throughout the 12-week study. There was a singular abnormal histopathology finding of minimal mixed inflammatory cell infiltration that was present in both the control and treated groups, although at a higher frequency in the 3 mg/kg group (1/4 animals in the vehicle group, 4/4 animals in the 3 mg/kg group). This finding was not associated with degeneration or necrosis and was therefore considered non-adverse. The incidence and severity of this finding was similar at the 1 month and 3-month necropsies. Studies analyzing LNP persistence after administration have found that the majority of LNP is cleared from circulation within 1 week of administration.

Example 4

The Effect of LDL Receptor on Lipid Nanoparticle Uptake

Traditional LNP uptake into hepatocytes is mediated by the Apolipoprotein E-low density lipoprotein receptor (ApoE-LDLR) or the N-Acetyl-D-galactosamine/asialoglycoprotein receptor pathway (GalNAc-ASGPR). The ApoE-LDLR pathway requires the presence of LDLR on the target hepatocytes while the GalNAc-ASGPR pathway requires the presence of GalNAc on the dosed LNP. These pathways are of particular interest for an LNP-based treatment of Familial Hypercholesteremia as patients with this genetic disorder typically present as heterozygous (HeFH) or homozygous (HoFH) for the loss of LDLR. Without the presence of LDLR on hepatocytes, an LNP-based treatment may not be possible in these patients. Alternatively, GalNAc may be incorporated into the LNP to force uptake via the GalNAc-ASGPR pathway in LDLR deficient patients.

In this example, different LNPs comprising gRNA targeting mouse ANGPTL3 gene were administered to mice to determine if the delivery of LNP to liver depends on LDL receptor. Two LNPs (RIV-000005 and RIV-000006) were formulated to follow the GalNAc-ASGPR uptake pathway, one without GalNAc (RIV-000005) and the other with 2.5% GalNAc (RIV-000006). A third LNP (RIV-000004) was formulated with ALN-369/DSPC/Cholesterol/DMPE-PEG. RIV-000004 is known to follow the ApoE-LDLR uptake pathway and is not expected to be efficacious in mice with homozygous LDLR loss. All three LNPs comprise a same gRNA targeting mouse ANGPTL3 gene and SpCas9 RNA described herein. Editing efficiency in the liver, plasma ANGPTL3 protein levels, and plasma lipid levels of formulations RIV-000004, RIV-000005 and RIV-000006 were assessed in this example.

A total of 71 female mice at 4-5 weeks of age, weighing between 20-25 g, were used in these studies. 21 C57BL/6J or wildtype mice (Stock No. 000664), 25 B6.129S7-Ldlr$^{tm1}$-$_{Her}$/J or LDLR KO mice (LDLR−/−) (Stock No. 002207), and 25 LDLR Heterozygous (LDLR+/−) mice were all obtained from The Jackson Laboratory (Bar Harbor, ME). The LDLR Heterozygous mice were custom ordered from The Jackson Laboratory (Bar Harbor, ME) and created by crossing the C57BL/6J or wildtype strain with the LDLR KO mice.

The in vivo experimental design is summarized in Table 11.

TABLE 11

SUMMARY OF STUDY DETAILS.

| Study Detail | Description | | |
|---|---|---|---|
| Source Material | LNP formulations: RIV-000004, RIV-000005 and RIV-000006 | | |
| Groups & Group Size | Study 1: 2 mg/kg administered intravenously | | |
| | Test Article | Mouse Strain | Sample size (n) |
| | RIV-000005 | WT | 3 |
| | | LDLR$^{-/-}$ | 5 |
| | | LDLR$^{+/-}$ | 5 |
| | RIV-000006 | WT | 3 |
| | | LDLR$^{-/-}$ | 5 |
| | | LDLR$^{+/-}$ | 5 |
| | Control (PBS) | WT | 3 |
| | | LDLR$^{-/-}$ | 3 |
| | | LDLR$^{+/-}$ | 3 |
| | Study 1: 2 mg/kg administered intravenously | | |
| | Test Article | Mouse Strain | Sample size (n) |
| | RIV-000004 | WT | 3 |
| | | LDLR$^{-/-}$ | 3 |
| | | LDLR$^{+/-}$ | 3 |
| | RIV-000005 | WT | 3 |
| | | LDLR$^{-/-}$ | 3 |
| | | LDLR$^{+/-}$ | 3 |
| | RIV-000006 | WT | 3 |
| | | LDLR$^{-/-}$ | 3 |
| | | LDLR$^{+/-}$ | 3 |
| | Control (PBS) | WT | 3 |
| | | LDLR$^{-/-}$ | 3 |
| | | LDLR$^{+/-}$ | 3 |
| Analytical Methods | EasyRA Plasma Analysis: LDL and Triglyceride levels TIDE Analysis: Editing efficiency in liver mANGPTL3 ELISA: Circulating mANGPTL3 protein levels | | |

In Study 1 (see Table 11 for the study design), wild type and LDLR deficient mice were dosed with 2 mg/kg of RIV-000005 or RIV-000006. 96 hours post dosing, mice were sacrificed. Livers and plasma were collected immediately post sacrifice to determine editing efficiency, circulating mANGPTL3 levels and triglycerides.

Figure 15A:
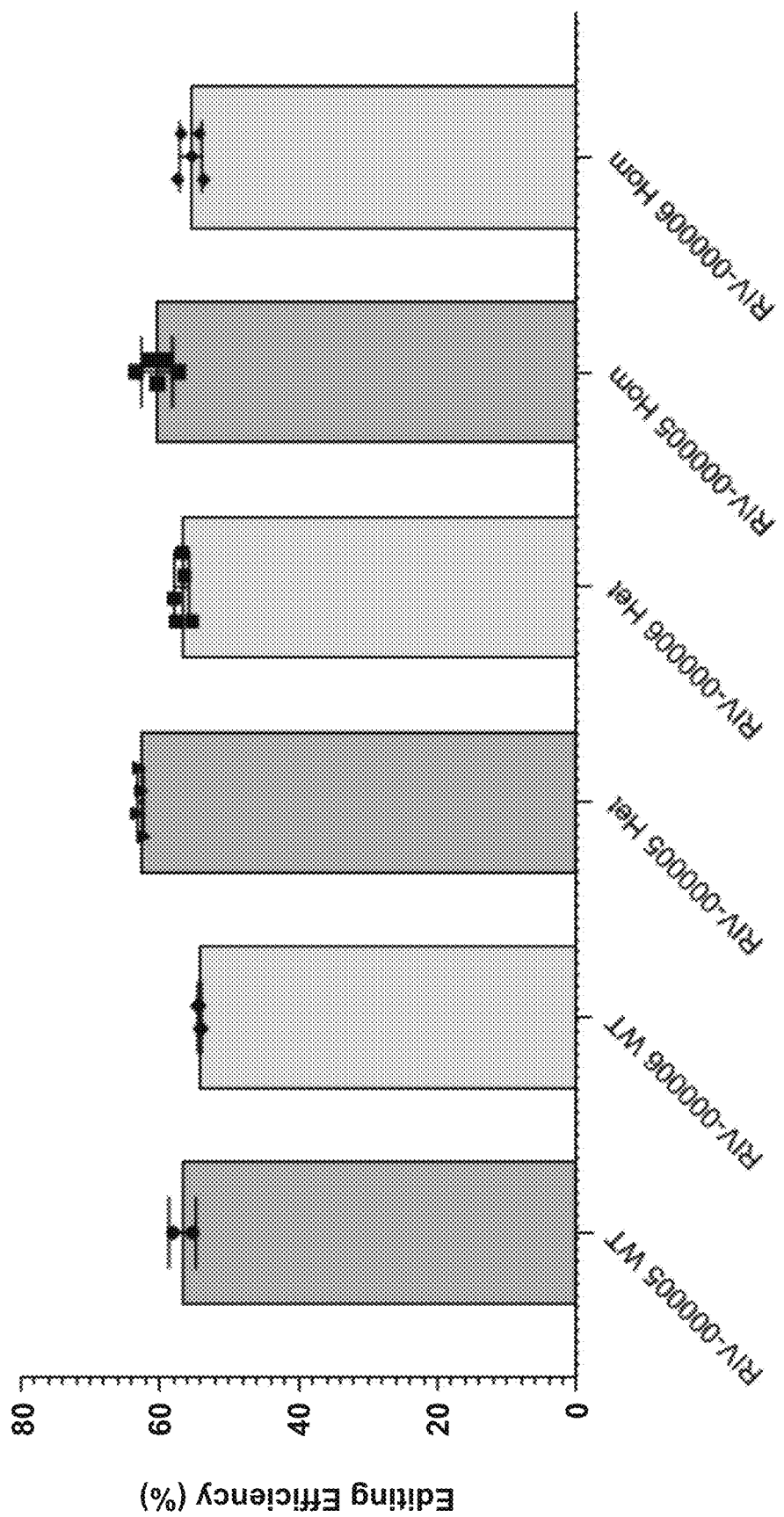
FIG. 15A-FIG. 15C are graphs showing gene editing efficiency in liver (FIG. 15A), Angptl3 protein levels (FIG. 15B), and triglyceride levels (FIG. 15C) in wild type (WT), LDLR$^{+/-}$ mice (Het) and LDLR$^{-/-}$ mice (Hom) treated with two exemplary lipid nanoparticles (RIV-000005 and RIV-000006) with gRNAs targeting mouse ANGPTL3 gene. ns: not significant.
Figure 15B:
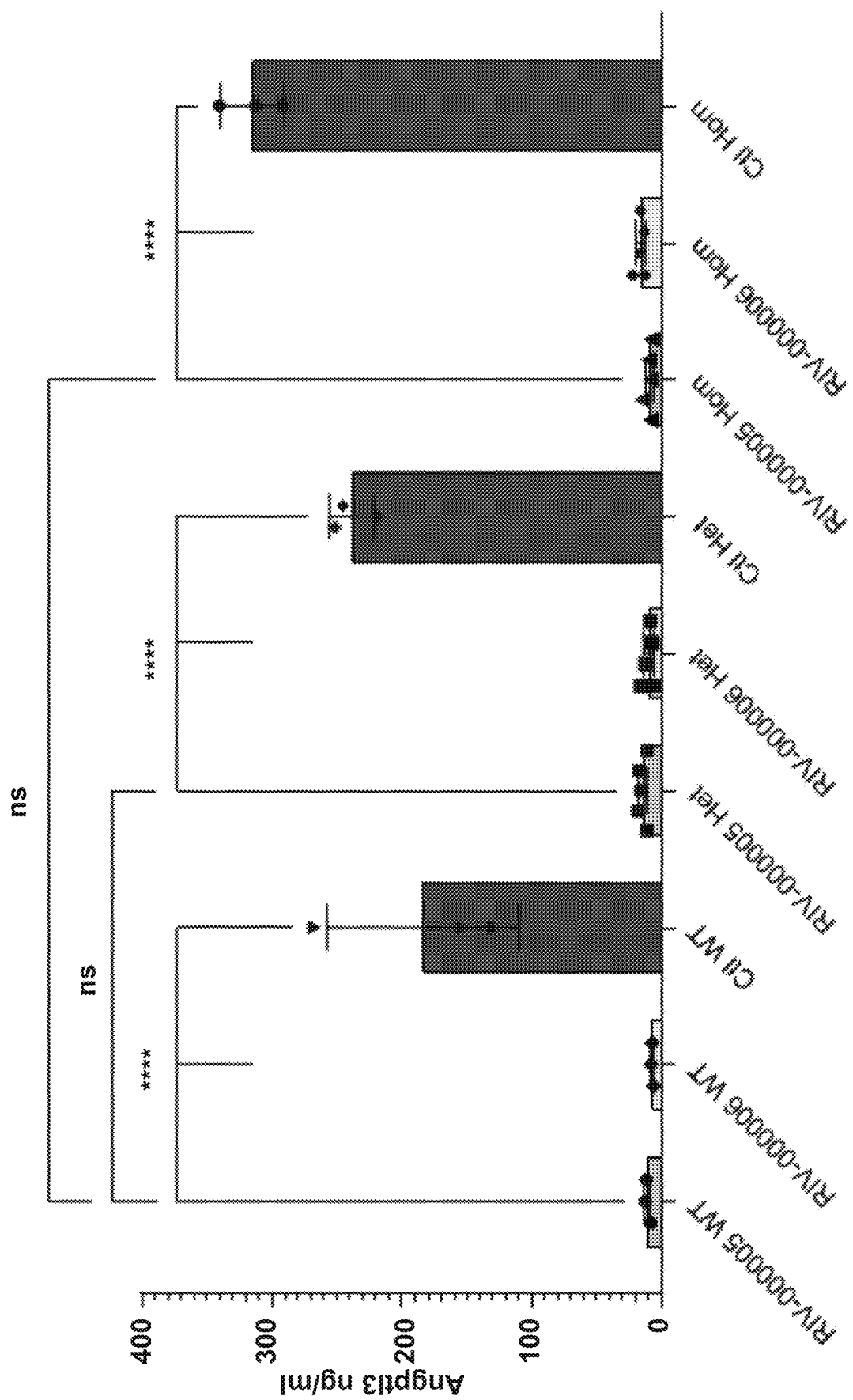
Figure 15C:
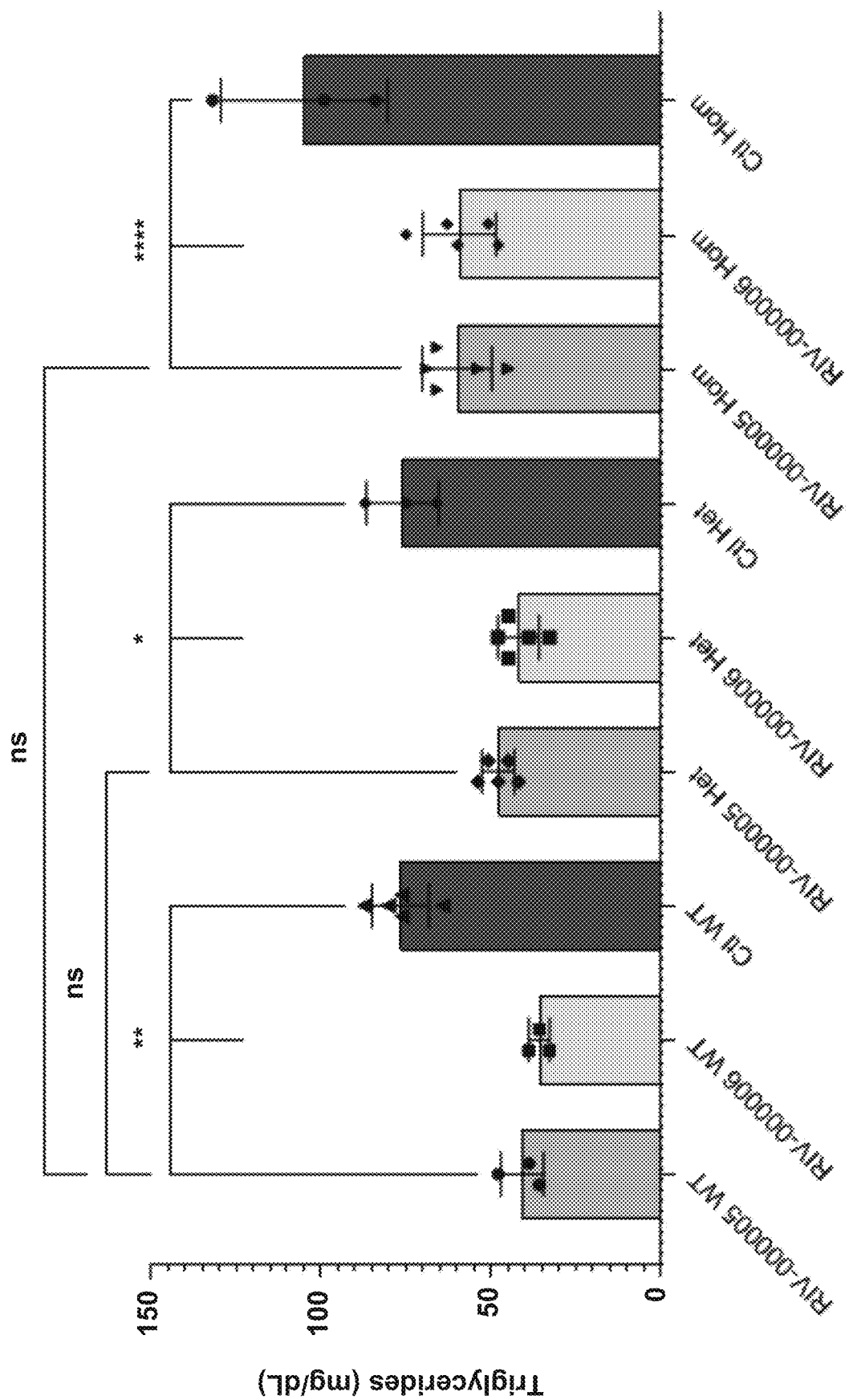

FIG. 15A-FIG. 15C are graphs showing gene editing efficiency in liver (FIG. 15A), Angptl3 protein levels (FIG. 15B), and triglyceride levels (FIG. 15C) in wild type (WT) and LDLR$^{-/-}$ mice (Hom) treated with two exemplary lipid nanoparticles (RIV-000005 and RIV-000006) with gRNAs targeting mouse ANGPTL3 gene. Editing efficiency in the livers was determined 96 hours post dosing by TIDE (FIG. 15A). Circulating mANGPTL3 protein levels were determined in collected plasma samples by ELISA (FIG. 15B). Plasma triglycerides were determined by EasyRA in collected plasma (FIG. 15C).

Comparable editing efficiency is observed between the wildtype and LDLR deficient mice dosed with RIV-000005 or RIV-000006 (FIG. 15A). In congruence with the editing efficiency, both circulating mANGPTL3 protein and plasma triglycerides are reduced in LNP-dosed mice compared to untreated controls (FIG. 15B-FIG. 15C).

Similar to Study 1, in Study 2 wild type and LDLR deficient mice were dosed with 1 mg/kg of RIV-000005 or RIV-000006. An additional study group of WT and LDLR deficient mice were dosed with the RIV-000004 LNP. 96 hours after dosing, the mice were sacrificed. Livers and plasma were collected immediately post-sacrifice to determine editing efficiency, circulating mANGPTL3 levels, triglycerides and LDL.

Figure 16A:
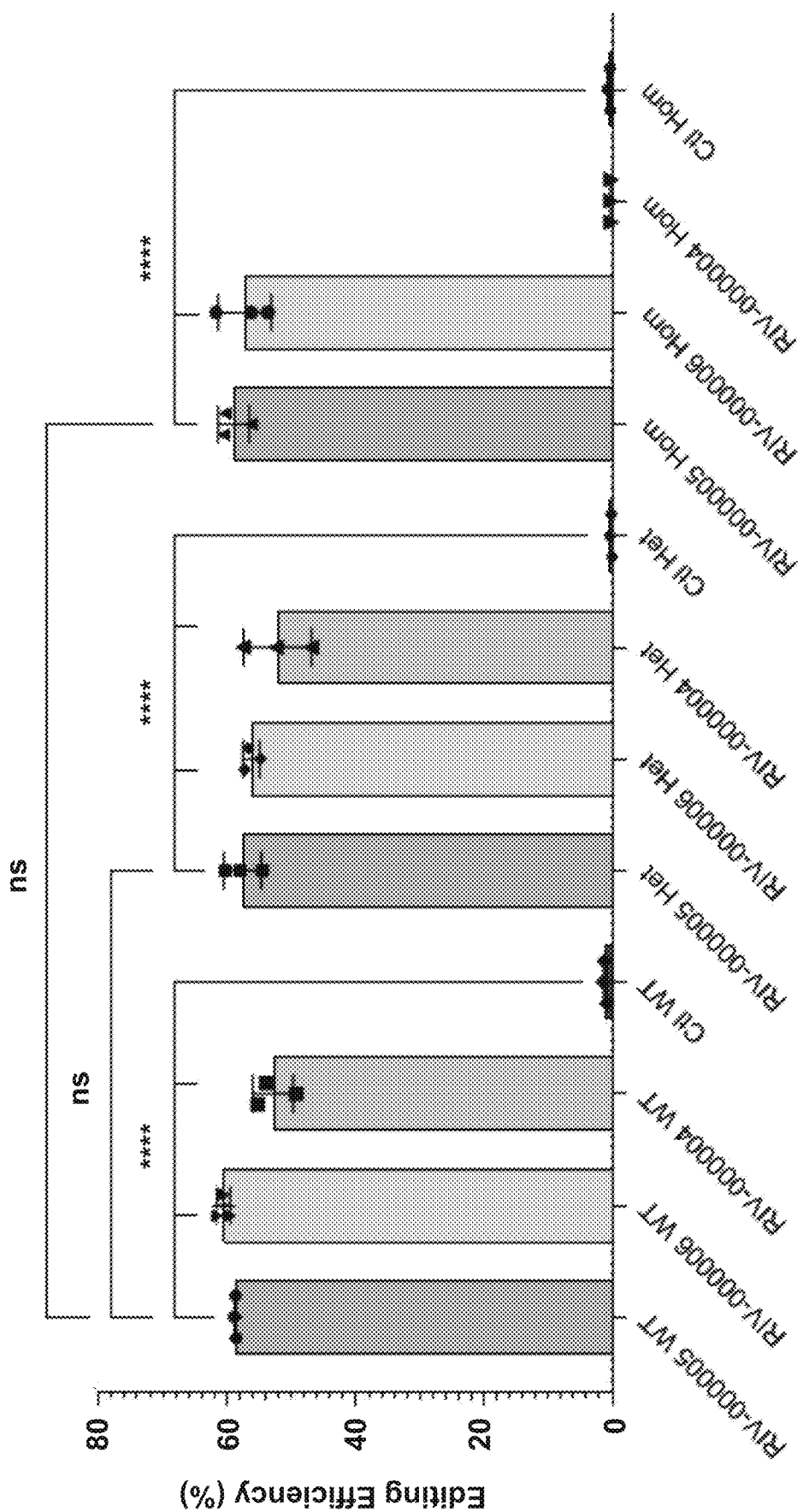
FIG. 16A-FIG. 16H depict exemplary data related to LDLR pathway. Shown in FIG. 16A-FIG. 16D are graphs depicting gene editing efficiency in liver (FIG. 16A), Angptl3 protein levels (FIG. 16B), triglyceride levels (FIG. 16C) and LDL levels (FIG. 16D) in wild type (WT), LDLR$^{+/-}$ mice (Het) and LDLR$^{-/-}$ mice (Hom) treated with three exemplary lipid nanoparticles (RIV-000004, RIV-000005 and RIV-000006) with gRNAs targeting mouse ANGPTL3 gene.
Figure 16B:
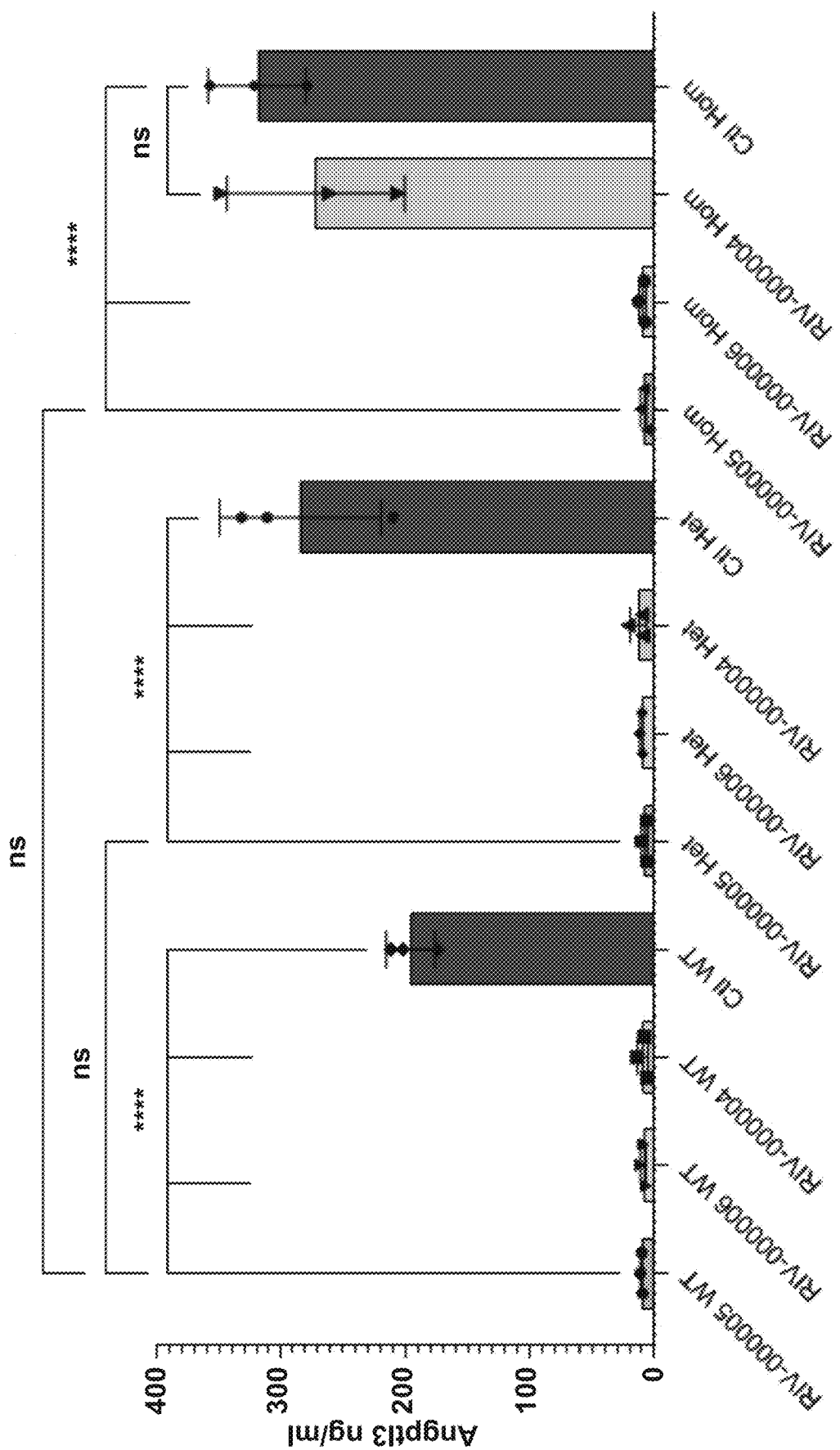
Figure 16C:
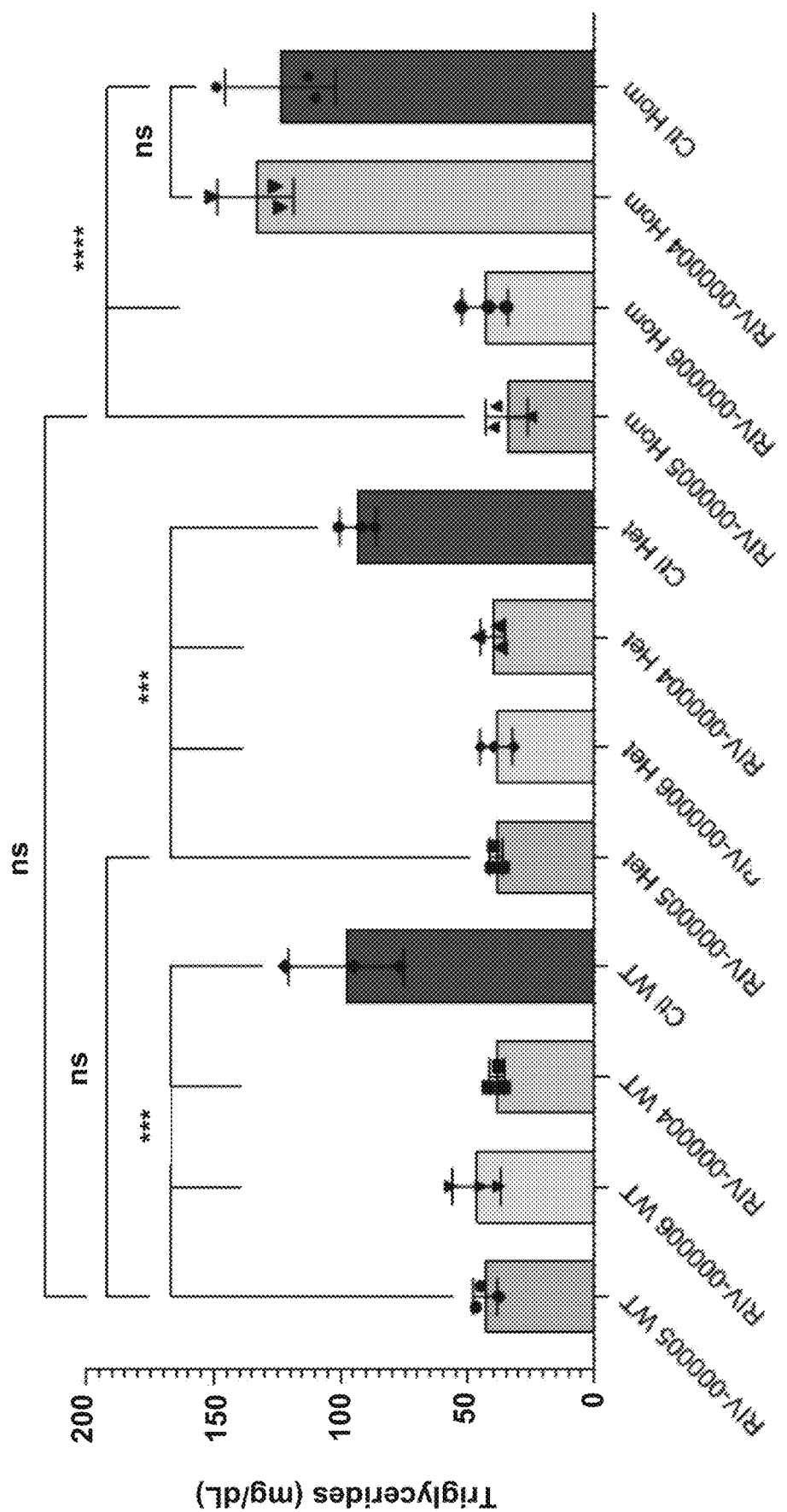

FIG. 16A-FIG. 16C are graphs showing gene editing efficiency in liver (FIG. 16A), Angptl3 protein levels (FIG. 16B), and triglyceride levels (FIG. 16C) in wild type (WT) and LDLR$^{-/-}$ mice (Hom) treated with three exemplary lipid nanoparticles (RIV-000004, RIV-000005 and RIV-000006) with gRNAs targeting mouse ANGPTL3 gene. Editing efficiency in livers was determined 96 hours post dosing by TIDE. Circulating mANGPTL3 protein levels were determined in collected plasma samples by ELISA. Plasma triglycerides were determined by EasyRA in collected plasma. No differences in editing efficiency were detected in wild type and LDLR deficient mice treated with RIV-000005 and RIV-000006 (FIG. 16A). However, no editing was observed in the LDLR homozygous mice dosed with RIV-000004 suggesting that this LNP cannot be taken up without the presence of LDLR. The reduction of circulating mANGPTL3 and plasma triglycerides is consistent with the editing data (FIG. 16B-FIG. 16C).

Figure 16D:
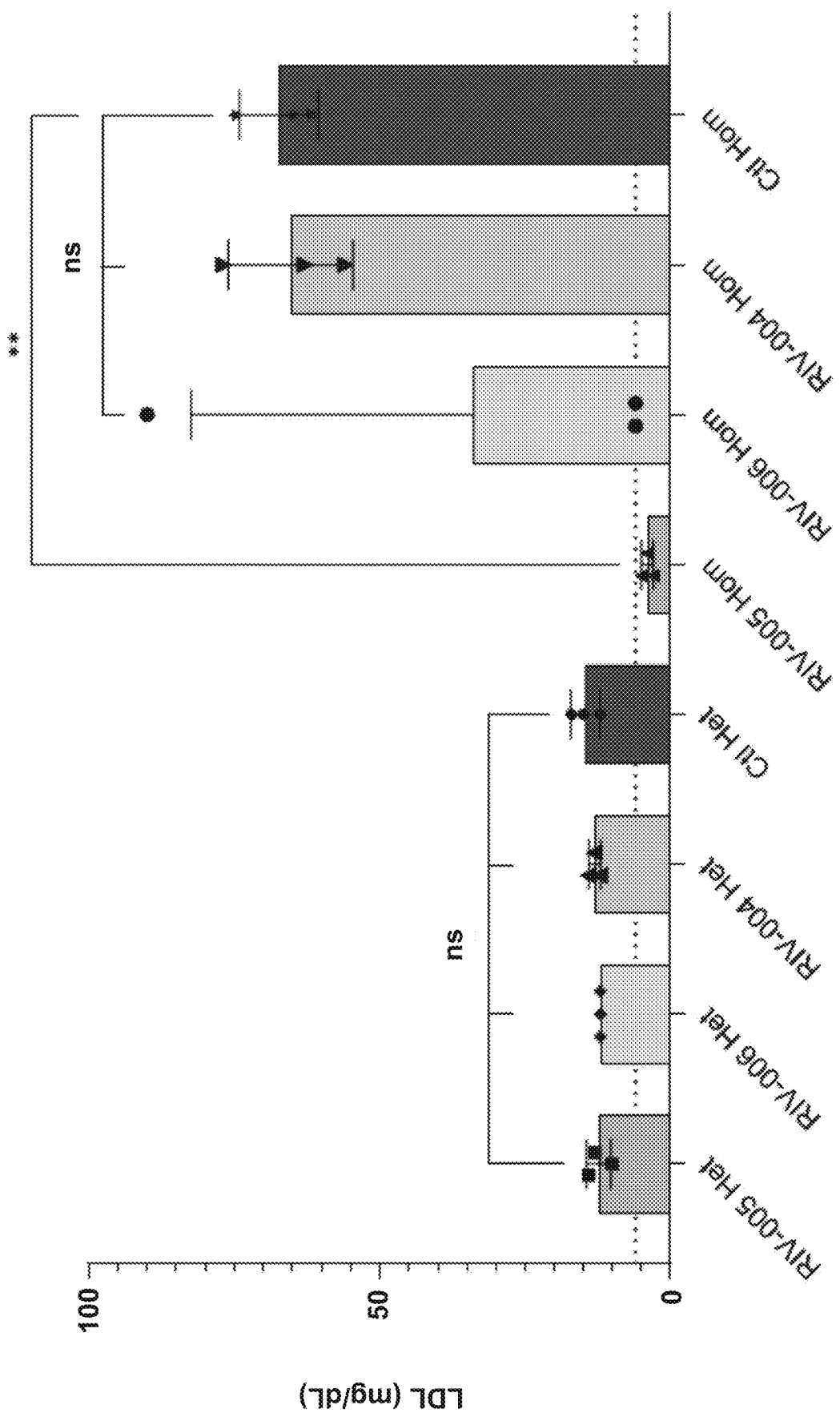
Figure 16E:
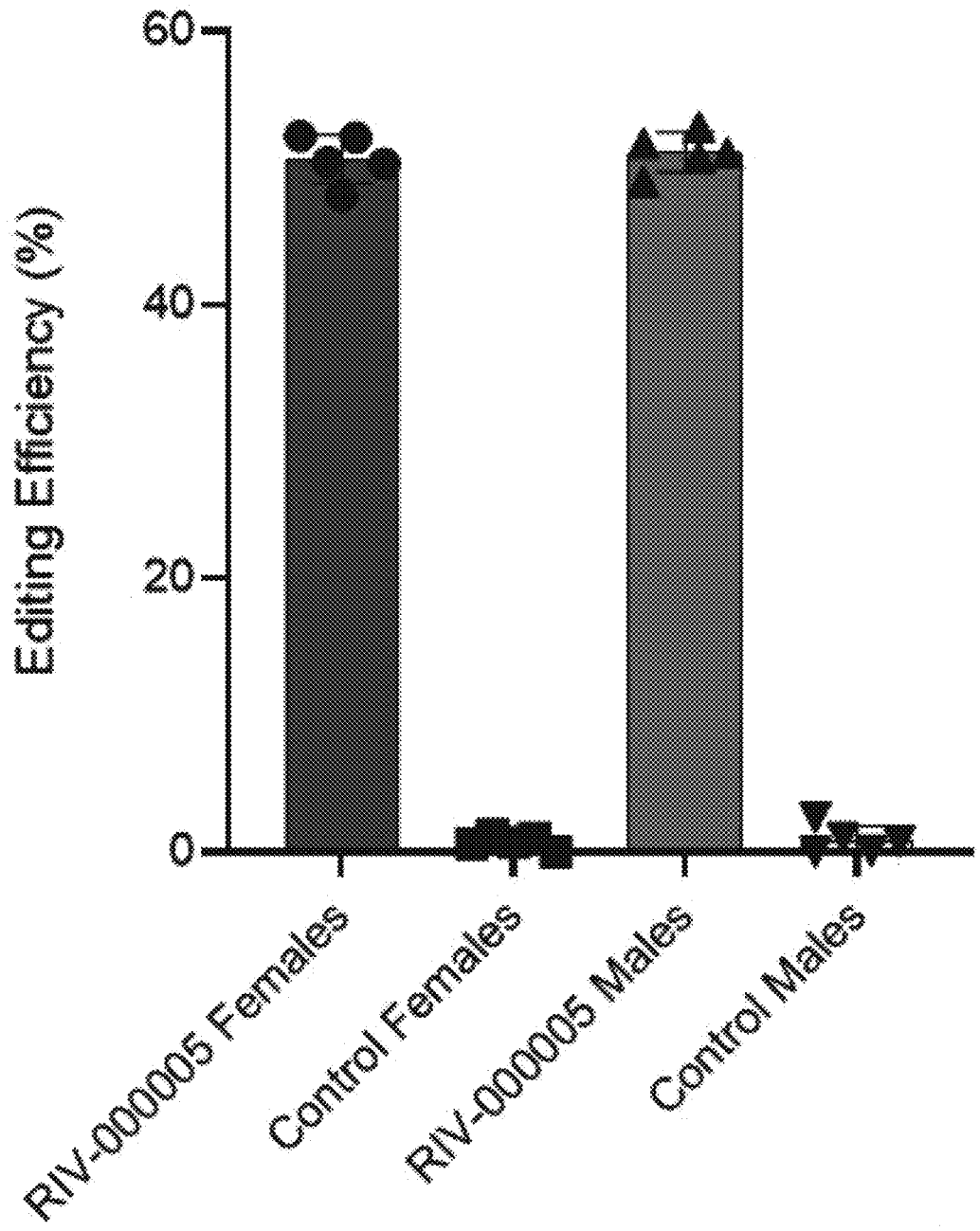
Figure 16F:
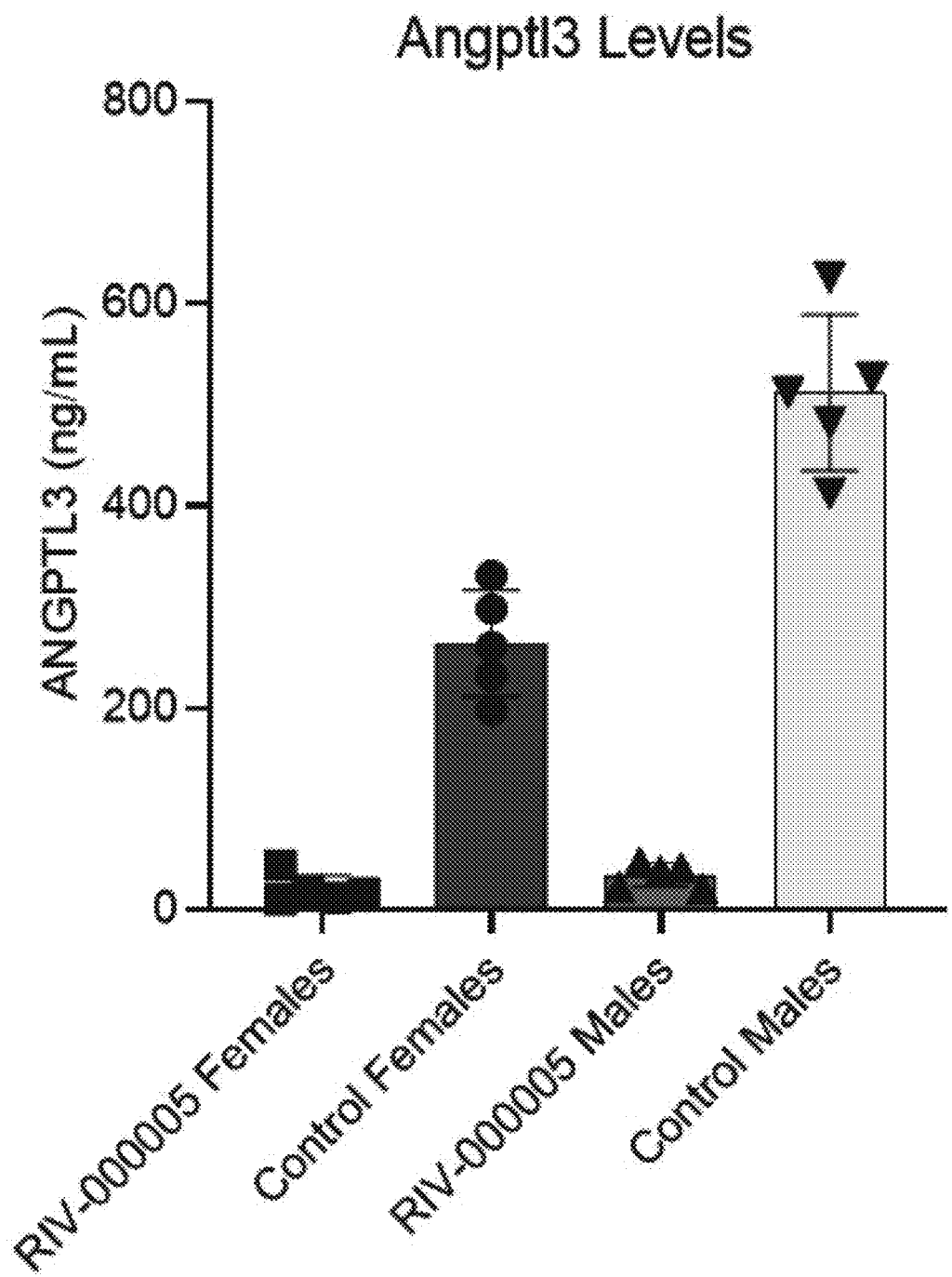
Figure 16G:
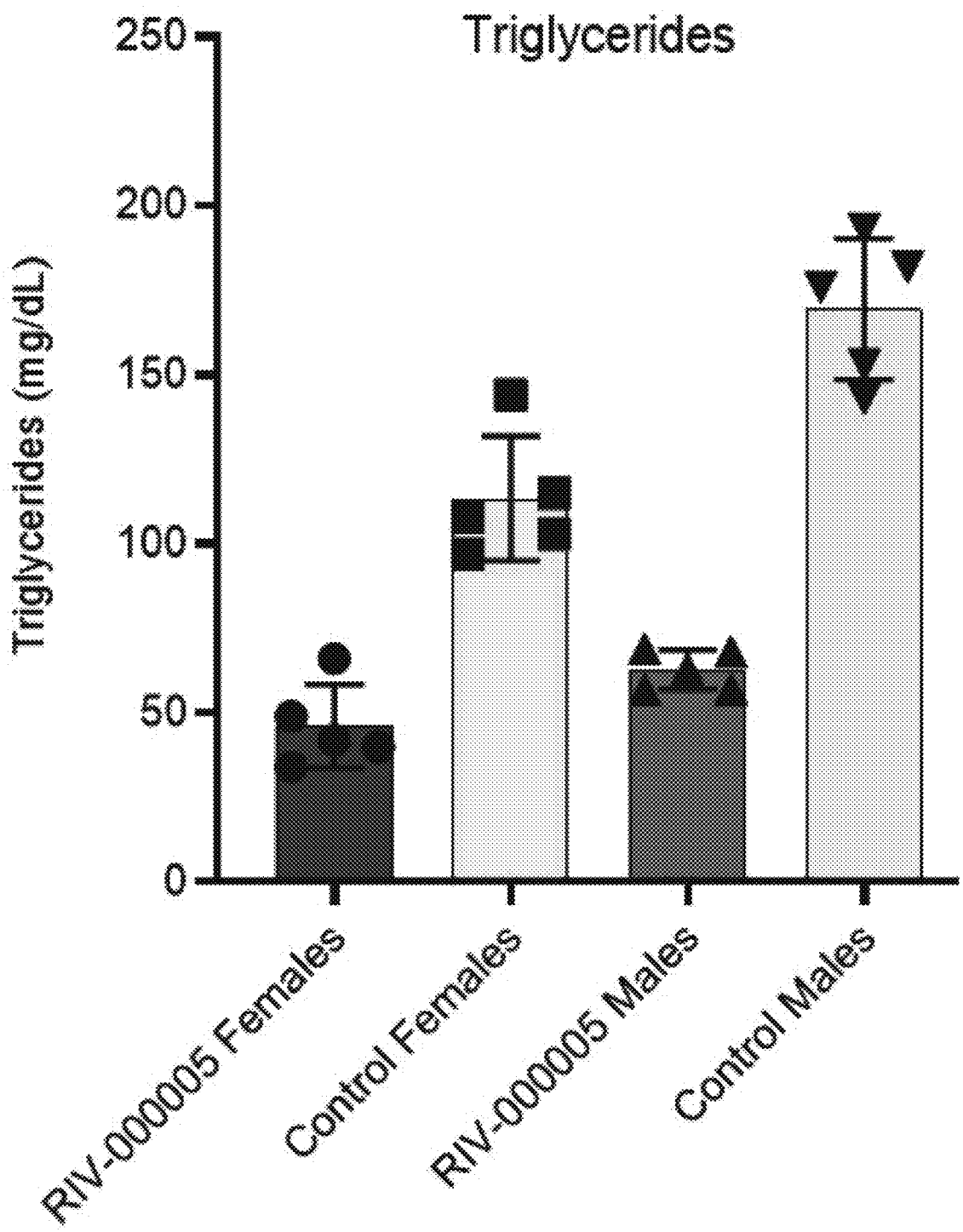
Figure 16H:
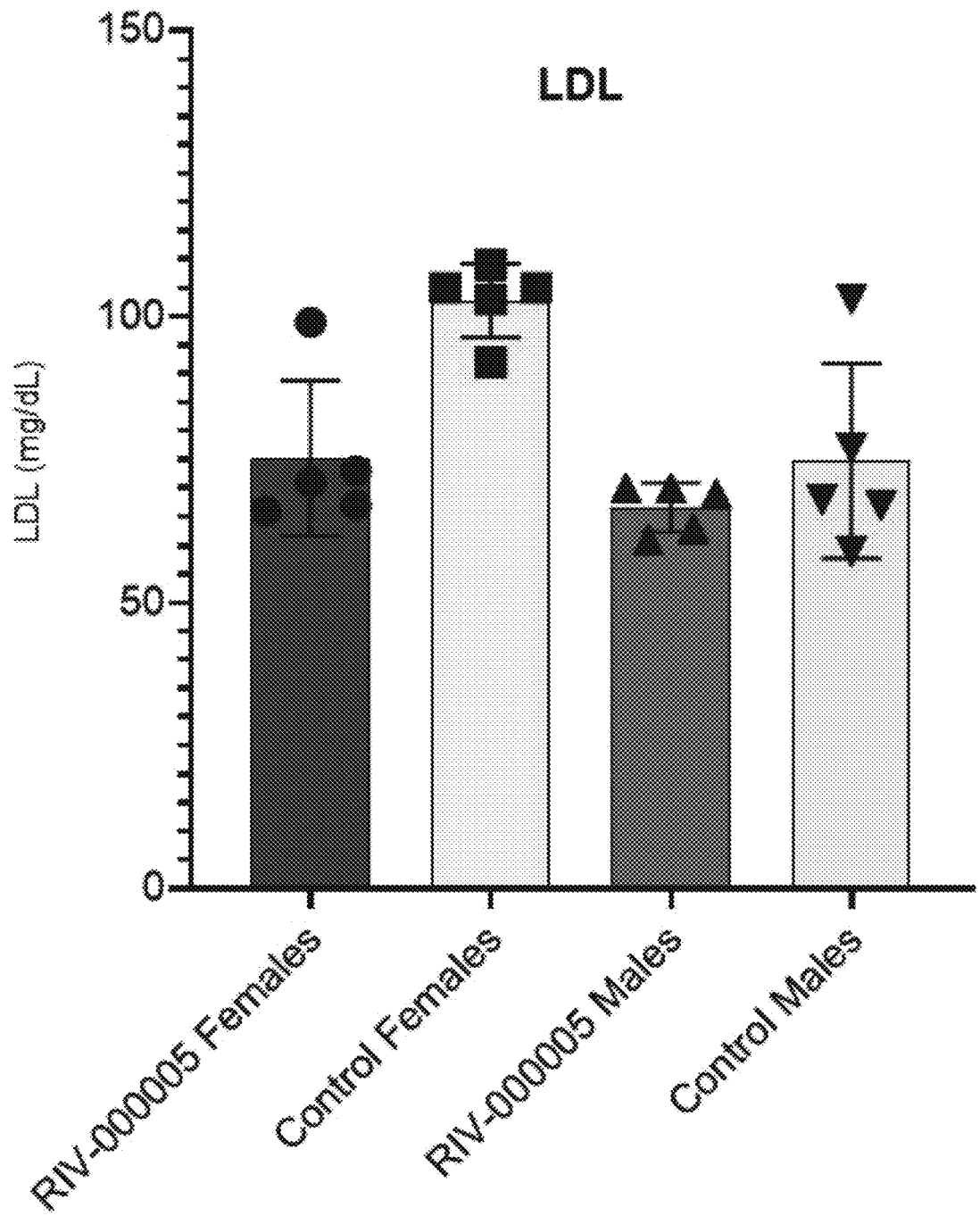

Plasma LDL levels were also determined for the Study 2 animals and shown in FIG. 16D. LDL levels were determined using the EasyRA. The red dotted line represents the 6 mg/dL limit of detection of the EasyRA for LDL.

FIG. 16E-FIG. 16H depict editing efficiency (FIG. 16E) ANGPTL3 levels (FIG. 16F), triglyceride levels (FIG. 16G), and LDL levels (FIG. 16H) data in LDLR homozygous mice treated with the indicated treatments after 1 month.

Wild type mice naturally have low levels of LDL and LDL measurements for the wildtype mice were below the limit of detection (data not shown). Heterozygous loss of LDL raises plasma LDL enough to be detected, however levels are too low to determine differences between treatment groups. Homozygous loss of LDLR results in a stark increase in plasma LDL levels. Homozygous mice treated with RIV-000005 had plasma levels reduced to below the limit of detection. Two of the three mice treated with RIV-000006 had plasma LDL levels reduced to below the limit of detection but one mouse had LDL levels consistent with untreated homozygous mice. Note that the mouse with high LDL levels presented with similar liver editing efficiency to the mice with reduced LDL levels. Consistent with the editing data, RIV-000004 treated homozygous mice showed no reduction of plasma LDL (FIG. 16D).

Taken together, in both studies, wild type mice and LDLR deficient mice treated with the LNP formulations described herein showed comparable mANGPTL3 editing in the liver and reduction in circulating mouse ANGPTL3 protein and plasma triglyceride levels regardless of the presence of GalNAc. These data indicate that LNPs formulated to follow the GalNAc-ASGPR uptake pathway is efficacious in both heterozygous and homozygous LDLR deficient settings and the addition of GalNAc is not required, while LNPs formulated to follow the ApoE-LDLR uptake pathway are not efficacious in mice with homozygous LDLR loss.

Example 5

Exemplary Inclusion and Exclusion Criteria in Clinical Studies

This example describes non-limiting exemplary criteria for the inclusion and exclusion of patients to clinical trials to determine the safety and efficacy of the pharmaceutical formulations described herein.

The inclusion criteria can include one or more of the following criteria. In some embodiments, a subject must meet all of the following criteria to be considered eligible to participate in the clinical study.

1. Age≥18 and ≤75 years of age; 2. Able to provide written informed consent; 3. Subjects diagnosed with persistent dyslipidemia as defined by a documented history of high TG levels >300 mg/dL and/or high LDL-C levels >100 mg/dL (>70 mg/dL for ASCVD) and or non-HDL levels >160 mg/dL and/or ApoB levels >100 mg/dL; 4. Subjects receiving statins must be on a stable dose for >30 days prior to screening and must be refractory to standard of care lines of treatment available through routine clinical care, including ezetimibe and/or bempedoic acid and/or PCSK9 (alirocumab or evolocumab) and/or ANGPTL3 (evinacumab) monoclonal antibodies for at least 26 weeks prior to screening; 5. Subjects with homozygous hypercholesterolemia receiving PCSK9 targeted interfering RNA therapy (inclisiran) must be refractory to at least 365 days of exposure prior to screening; 6. Subjects on available standard of care lines of treatment including statins, ezetimibe, and/or bempedoic acid and/or PCSK9 and/or ANGPTL3 inhibitors must be on a stable dose >30 days before screening with no planned medication or dose increase during study participation; 7. Subjects of childbearing potential (post-menarche, has an intact uterus and at least 1 ovary, and is less than 1 year postmenopausal) and biological male subjects must agree to use acceptable method(s) of contraception as defined in the protocol from consent through at least 1 year after CTX310 infusion; 8. Willing and able to comply with scheduled visits, treatment plan, laboratory tests, contraceptive guidelines, and other study procedures; and 9. Willing to participate in a long-term follow-up study for up to 15 years after completion of this study.

To be eligible for entry into the study, the subject must not meet any of the exclusion criteria listed below: 1. FCS patients with confirmed diagnosis of biallelic LPL or GP1HBP1 mutation; 2. Complete blood count (CBC): normal white blood cell (WBC)<2,500 cells/mcL, hemoglobin (Hb)<11 g/dL for male and <10 g/dL for female; platelet count <100,000/mcL; 3. Evidence of liver disease, defined as: Aspartate transaminase, alanine transaminase >2× upper limit of normal (ULN), or total bilirubin value >2×ULN, or: Baseline prothrombin time (international normalized ratio) >1.5× ULN, or Fibrosis score of ≥2 (NAFLD activity score); 4. Current use (except for inclisiran) or use within 365 days from Day 1 of any hepatocyte-targeted small interfering RNA or antisense oligonucleotide molecule; 5. Current use (except for evolocumab, alirocumab or evinacumab) or use within 90 days from Day 1 of any monoclonal antibody treatment; 6. Participation in another clinical study with an investigational drug/product within 30 days of screening or fewer than 5 half-lives of the investigational agent, whichever is longer from screening, 7. Cardiac left ventricular ejection fraction <50% by echocardiogram; 8. Uncontrolled hypertension or uncontrolled arrhythmial; 9. Acute coronary syndrome event within 24 weeks prior to Day 1, 8. CNS stroke within 24 weeks prior to Day 1; 10. Acute pancreatitis within 12 weeks prior to Day 1; 11. Baseline estimated glomerular filtration rate <60 mL/min/1.73 m 2; 12. Diagnosis of nephrotic syndrome or albuminuria >2+ on urine dipstick; 13. Inadequate diabetes control, with glycosylate hemoglobin (HbA1C)>10%; 14. History of alcohol or drug abuse and nonadherence to abstinence for the duration of the study; 15. History of a significant coagulation disorder; 16. Uncontrolled or untreated thyroid disease; 17. Patients on selective serotonin reuptake inhibitors medications or on chronic systemic corticosteroid therapy; 18. Prior treatment with gene therapy/editing product; 19. Current use of niacin-based supplements or nutraceuticals that may influence lipid levels at a dose/amount that has not been stable for >30 days prior to the screening visit; 20. Positive serology for human immunodeficiency virus-1 (HIV-1) or HIV-2, hepatitis B virus (hepatitis B core antibody or nucleic acid testing [NAT]), or hepatitis C virus (NAT); 21. History of any illness or any clinical condition that, in the opinion of the investigator, might confound the results of the study or pose an additional risk in administering study drug to the subject. This may include but is not limited to history of relevant drug allergies, history of central nervous system (CNS) disease, history or presence of clinically significant pathology, or history of psychiatric illness, or history of familial cancer syndrome; 22. Any prior or current malignancy or myeloproliferative disorder or a significant immunodeficiency disorder; 23. Pregnant or breastfeeding females; 24. An assessment by the investigator that the subject would not comply with the study procedures outlined in the protocol.

Example 6

Phase 1 Study Design

Figure 17:
FIG. 17 shows a non-limiting exemplary design for Phase 1 safety and tolerability clinical study for one or more of the ANGPTL3 gene-editing nanoparticles described herein (e.g., CTX310) and how determination can be made based on the results of the Phase 1 study to progress to Phase 2 clinical study.
Figure 18:
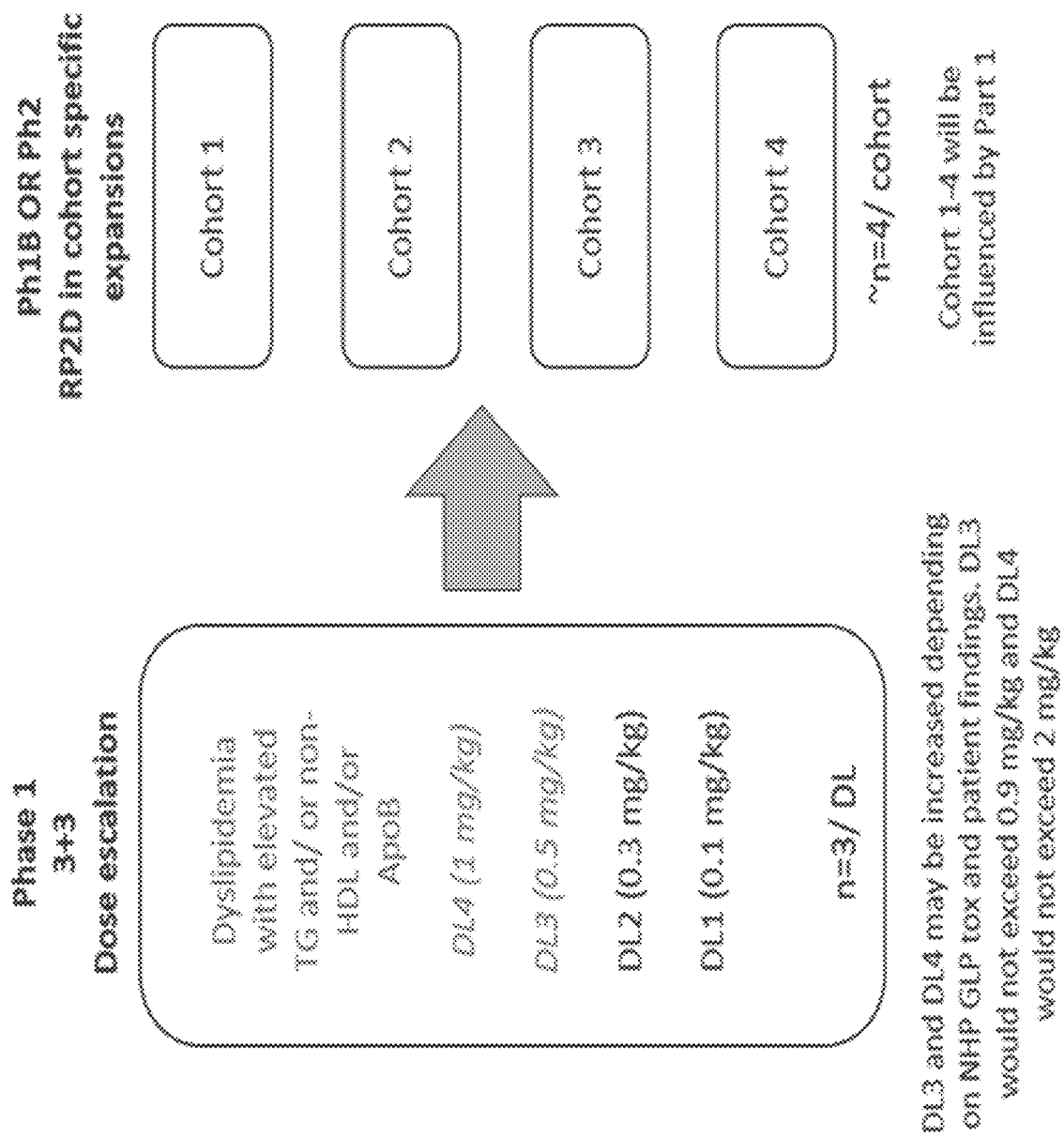
FIG. 18 shows a non-limiting exemplary design for Phase 1 safety and tolerability clinical study for one or more of the ANGPTL3 gene-editing nanoparticles described herein (e.g., CTX310) and how determination can be made based on the results of the Phase 1 study to progress to Phase 2 clinical study.

A non-limiting exemplary design for Phase 1 safety and tolerability clinical study for one or more of the ANGPTL3 gene-editing nanoparticles described herein (e.g., CTX310) and how determination can be made based on the results of the Phase 1 study to progress to Phase 2 clinical study is shown in FIG. 17 and FIG. 18. In FIG. 17 and FIG. 18, indications 1-4 and cohorts 1-4 to be pursued in Phase 2 include, but are not limited to: Clinical Atherosclerotic Cardiovascular disease (ASCVD), Homozygous Familial Hypercholesterolemia (HoFH), Heterozygous Familial Hypercholesterolemia (HeFH), Familial Chylomicronemia Syndrome (FCS), Multifactorial Chylomicronemia Syndrome (MCS), Familial Combined Hyperlipidemia (FCH or FCHL), and Metabolic Syndrome (MetS), other (Type 2 diabetes (T2D), nonalcoholic fatty liver disease (NAFLD)). HoFH and FCS are rare diseases. Subjects 18 to 75 (inclusive) years of age who have dyslipidemias with persistently high levels of TG and/or non HDL-C [including LDL, VLDL, and Lp(a)] and/or ApoB levels that are above the thresholds recommended by ACC and AHA guidelines despite maximum tolerated doses of available lipid-lowering treatments, diet, and lifestyle modifications (refractory population). Common HeFH mutants can include LDLR, ApoB, PCSK9 and LDLRAP1.

Figure 23:
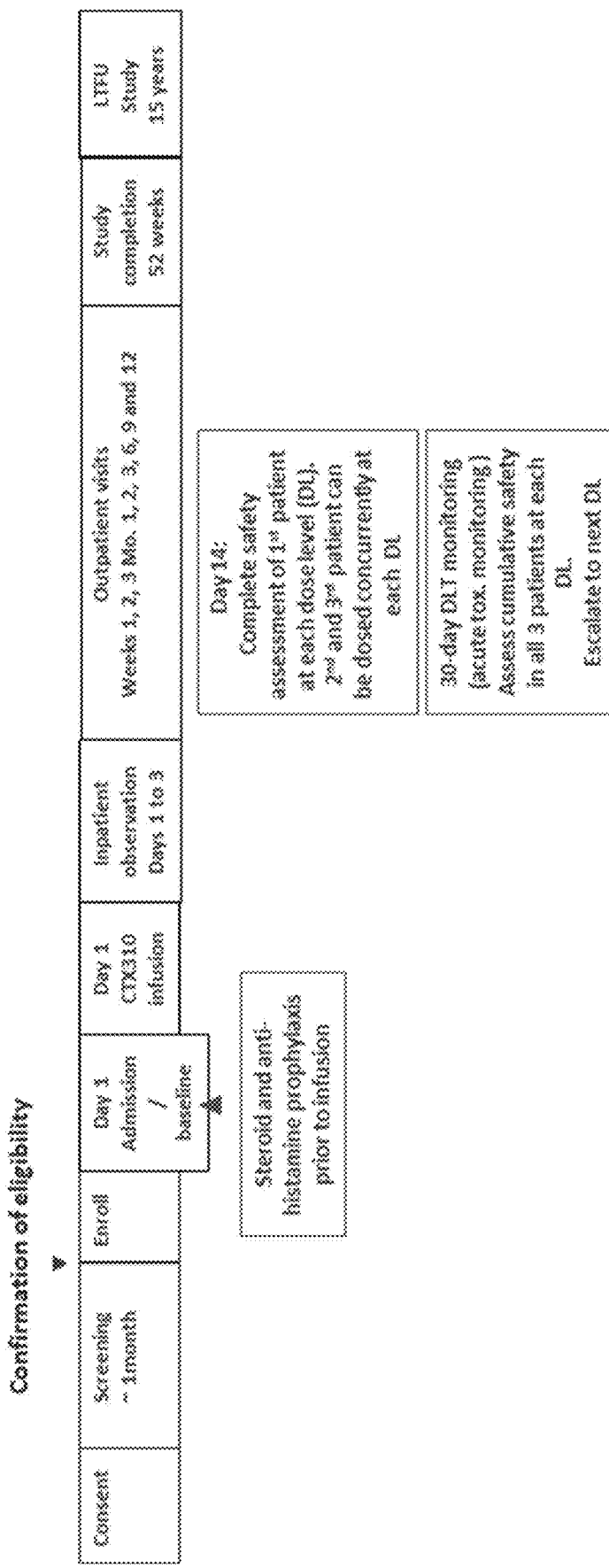
FIG. 23 depicts an exemplary clinical trial study design.
Figure 24:
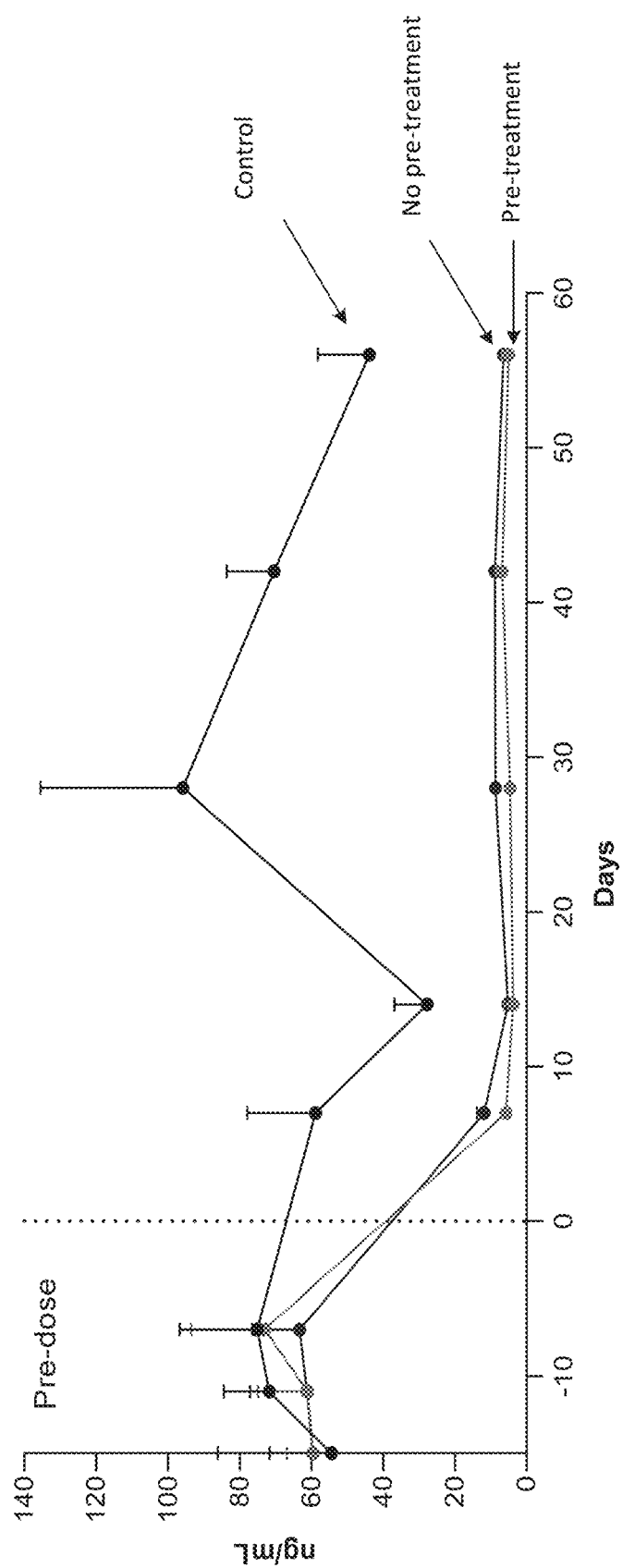
FIG. 24 depicts non-limiting exemplary data showing reduction of ANGPTL3 plasma protein (ng/mL) with and without pre-treatment. N=4 animals per group. Shown is the mean and SD.
Figure 25:
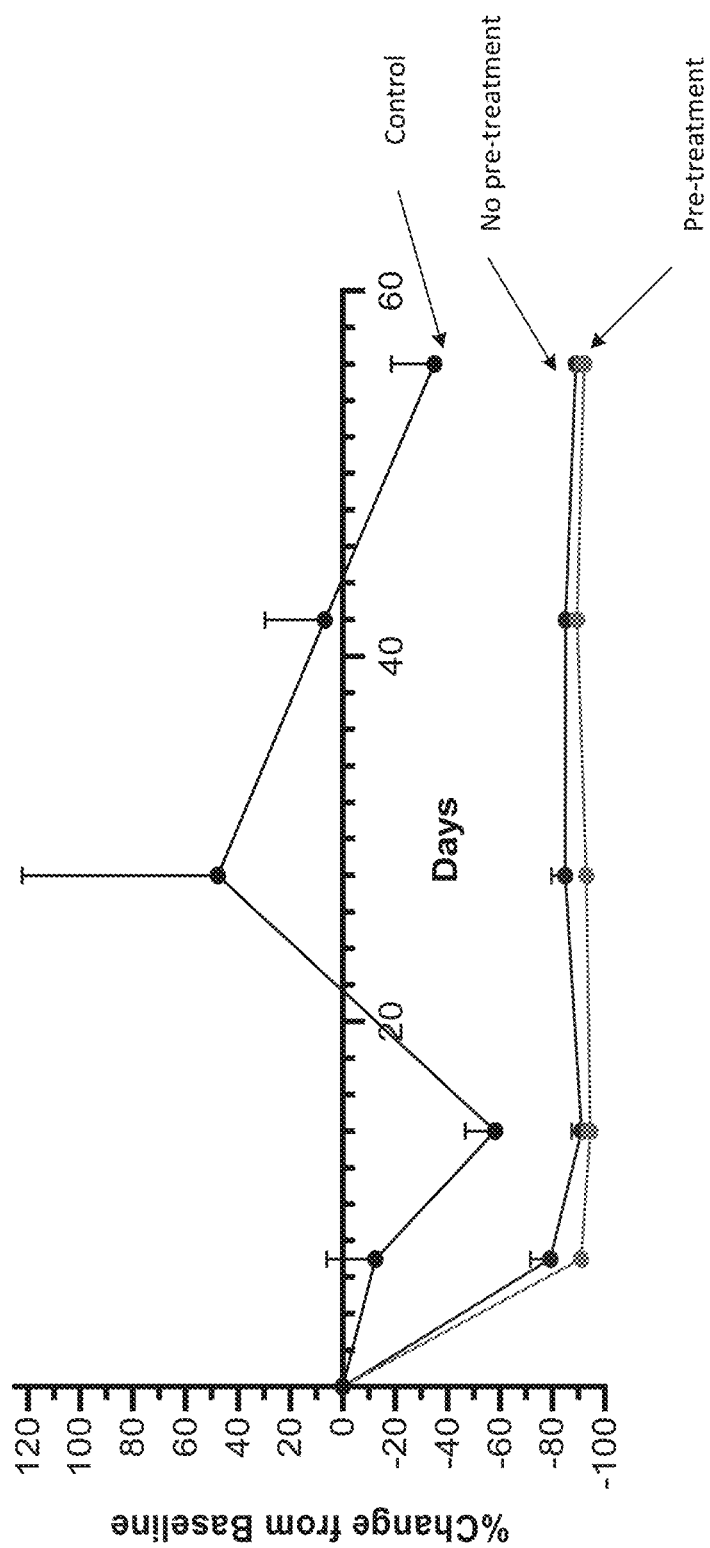
FIG. 25 depicts results from the same experiment shown in FIG. 24 as percent change reduction of ANGPTL3 plasma protein with and without pre-treatment. N=4 animals per group. Shown is the mean and SD.
Figure 26:
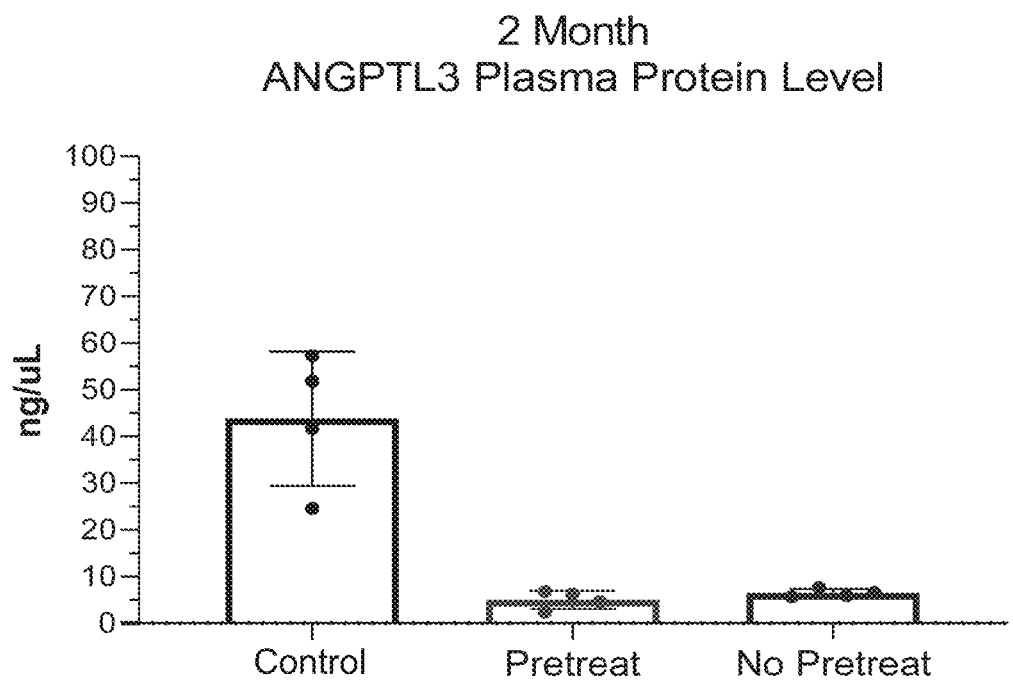
FIG. 26 depicts data from 2-months post administration. Shown is reduction of ANGPTL3 plasma protein with and without pre-treatment. N=4 animals per group. Shown is the mean and SD.
Figure 27:
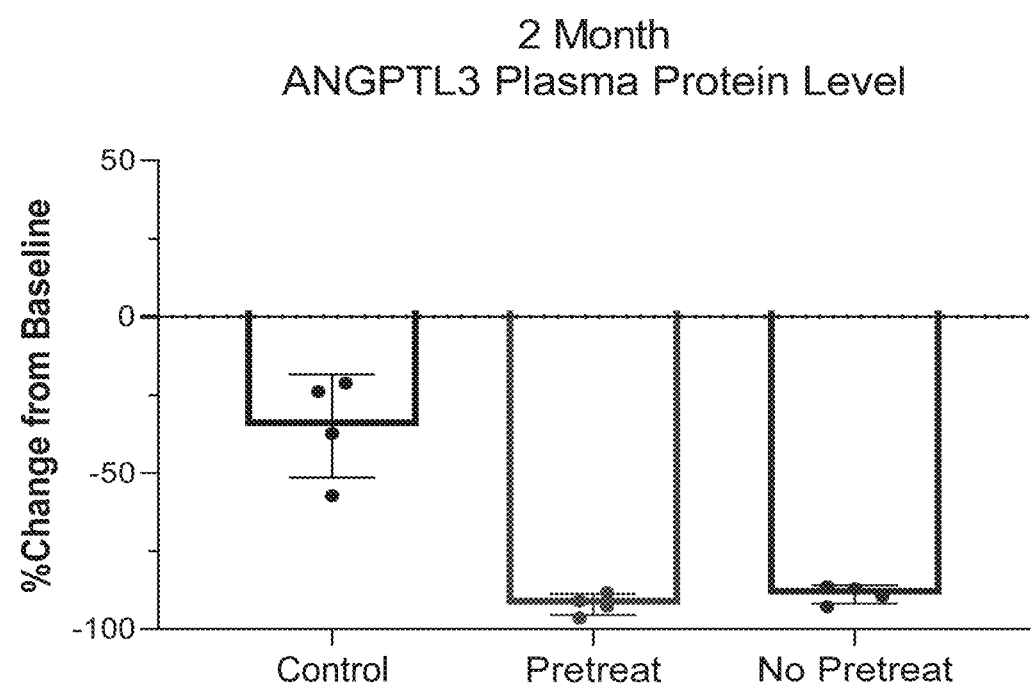
FIG. 27 depicts data from 2-months post administration. Shown is reduction of ANGPTL3 plasma protein with and without pretreatment as percent change. N=4 animals per group. Shown is the mean and SD.

In some embodiments, the objectives include the following: assess safety of LNP formulated CRISPR—Guide RNA—Cas9 Nuclease for in-vivo editing of ANGPTL3 in liver, dose finding safety study to establish optimal biological dose (OBD) or maximum tolerated dose (MTD) for the Phase 2 study, and assess activity by evaluating percent reduction in ANGPTL3 levels and percent lowering of lipids. Exemplary study objectives and endpoints are described below in Table 12. A non-limiting study schematic is shown in FIG. 23.

For example, the patient can have TG≥200 mg/dL, LDL-C≥100 mg/dL, or both. The patient can be between the age of 18 and 70. In some cases, Phase 1 safety and tolerability study of CTX310 is conducted in patients with refractory dyslipidemias with elevated triglyceride levels and/or elevated ApoB levels and/or elevated non-HDL levels (FIG. 18). For example, in some cases, the patient has, or is required to have, non-HDL-C≥160 mg/dL, TG≥300 mg/dL, ApoB≥100 mg/dL, or a combination thereof.

TABLE 12

STUDY OBJECTIVES AND ENDPOINTS

| Primary Objectives | Primary Endpoints |
|---|---|
| To evaluate the safety and tolerability of a single ascending dose of CTX310 in subjects with refractory dyslipidemias with elevated TG levels and/or elevated non-HDL-C levels and/or elevated ApoB levels and/or LDL-C | Incidence of AEs, including TEAEs, AESIs, and DLTs<br>Clinically significant safety measures |

| Secondary Objectives | Secondary Endpoints |
|---|---|
| To assess the preliminary efficacy of CTX310 | Percentage change in TGs, ApoB, non-HDL-C [including LDL, VLDL, IDL, and Lp(a)], and HDL-C concentration at 26 and 52 weeks compared to baseline |
| To assess the PK of CTX310 | Plasma levels of LNP, Plasma level of Cas9 protein |
| To assess the PD of CTX310 | Percentage change in ANGPTL3 concentration over time compared to baseline |

AE, adverse events; TEAE, treatment-emergent adverse event; AESI, adverse event of special interest; DLT, dose-limiting toxicity.

As shown in FIG. 23, oral steroid and/or anti-histamines may be provided to the subject. Oral steroids and anti-histamines are standard treatment for LNP formulated drug Tx (Onpatro, NTLA-2001 and Verve 101) to control inflammatory response (IR) and LFTs. For follow-up, each subject is monitored for adverse events (Aes), adverse events of special interest (AESIs), and effect on lipid parameters for 12 months post-infusion. For long-term follow-up, subjects can be rolled over to a separate follow-up study for up to 15 years.

Per Canadian Cardiology Society, American Heart Association, and European Society of Cardiology guidelines, ApoB and non-HDL are superior markers for calculating CVD risk compared to LDL-C. The following cut-offs shown below in Table 13 for inclusion are proposed. The cutoffs include: TG levels >300 mg/dL and/or LDL-C>100 mg/dL (or >70 mg/dL for ASCVD) and/or non-HDL levels >160 mg/dL and/or- ApoB levels >100 mg/dL.

TABLE 13

APOB AND NON-HDL-C THRESHOLD SELECTION

| LDL-C (nmol/L) | LDL-C (mg/dL) | Non-HDL-C (nmol/L) | Non-HDL-C (mg/dL) | apoB (nmol/L) | apoB (mg/dL) | apoB (g/L) |
|---|---|---|---|---|---|---|
| 1.8 | 70 | 2.4 | 93 | 1.8 | 70 | 0.7 |
| 2.6 | 100 | 4.1 | 160 | 2.6 | 100 | 1 |
| 3.5 | 135 | 4.2 | 162 | 2.7 | 105 | 1.05 |
| 5 | 193 | *5.8 | 224 | 3.7 | 145 | *1.45 |

*values selected to remain closer to the 95th percentile as defined by the 2021 CCS guidelines for FH. Values in row 1 and 3-4 represent the same percentile eq. to LDL-C.
Values in row 2 represented the inclusion cutoffs.

In some cases, Phase 1 safety and tolerability study of CTX310 is conducted in patients with clinical Atherosclerotic Cardiovascular Disease (ASCVD) and increased triglyceride (TG) Levels and/or high low-density-lipoprotein cholesterol (LDL-C) levels that are refractory to available treatments (FIG. 17). Clinical ASCVD is defined as patients having a confirmed diagnosis of coronary heart disease, cardiovascular disease, stroke, or peripheral arterial disease.

Normal TG levels are <150 mg/dL (1.7 mml/L). Borderline high levels are 150-199, High 200-500, 500 is very high. For HoFH, TG levels >300 and for HeFH the TG levels can be >130.

In some cases, the patient has failed one or more prior treatments by statins, ezetimibe and/or PCSK9 inhibitors. In some cases, the patient has been on one or more prior treatments by statins, ezetimibe and/or PCSK9 inhibitors for at least 12 weeks prior to screening. In some cases, the patient has refractory dyslipidemias. In some cases, the subject receiving statins has been on the maximum tolerated dose of statins, or if deemed intolerant to statins, the subject is intolerant to all doses of two different statin formulations. Refractory: Subjects who have not achieved recommended target lipid levels despite lifestyle changes, dietary interventions and all available and accessible medications.

Subjects receiving statins must be on a stable dose for >30 days prior to screening and must be refractory to standard of care lines of treatment available through routine clinical care, including statins, ezetimibe and/or bempedoic acid and/or PCSK9 (alirocumab or evolocumab) and/or ANGPTL3 (evinacumab) monoclonal antibodies for at least 26 weeks prior to screening.

Subjects with homozygous hypercholesterolemia receiving PCSK9 targeted interfering RNA therapy (inclisiran) must be refractory to said therapy for at least 365 days of treatment prior to screening.

In this study, a Single Dose Escalation 3+3 is performed. Proposed dose levels are shown in Table 2. Based on pre-clinical pilot toxicity, 3 mg/kg was determined as a no-observed-adverse-effect level (NOAEL) When 3 mg/kg is the anticipated NOAEL in the GLP study, ⅓rd that dose plus a ¹⁄₁₀th safety factor=0.1 mg/kg starting dose. When 1 mg/kg is determined the NOAEL in the GLP study, a ⅓rd allometric scaling is followed by an ~3× safety factor=0.1 mg/kg starting dose.

For safety monitoring and toxicity management, a 30-day dose-limiting toxicity (DLT) acute toxicity monitoring period for escalation to next dose level (DL) is used. This ensures LFTs have returned to baseline levels prior to proceeding with the next patient/DL. Eligibility criteria excludes subjects based on strict liver function criteria. ALT/AST >2× upper limit of normal (ULN), or total bilirubin value >2× ULN, or baseline prothrombin time (international normalized ratio)>1.5× ULN, or fibrosis score of >2 (NAFLD activity score) at screening. LFTs and coagulation are monitored at each assessment timepoint, e.g., Day 1, 2, 3, 4; Week 1, 2, 3; Day 30; and Month 2, 3, 6, 9, and 12. Prophylactic steroids and anti-histamines prior to infusion is used to mitigate potential infusion related reaction and elevations in LFTs.

One or more of the endpoints for the Phase 1 study can be a 6-month endpoint (or, a 3-month, a 4-month, a 5-month, a 7-month, a 8-month, a 9-month, a 10-month, a 11-month, or a 12-month endpoint), for example an end point of LDL-C level no more than 70 mg/dL. In some cases, the end point of LDL-C level is no more than 80 mg/dL, 75 mg/dL, 65 mg/dL, 60 mg/dL, 55 mg/dL, or 50 mg/dL. In some embodiments, the end point of non-HDL is about, at least, or at least about 20 mg/dL, 25 mg/dL, 30 mg/dL, 35 mg/dL, or 40 mg/dL above the LDL level. In some cases, the patient receives a liver biopsy at three months, four months, five months, six months, seven months, eight months, nine months, ten months, eleven months, twelve months, or more, post treatment.

Figure 19:
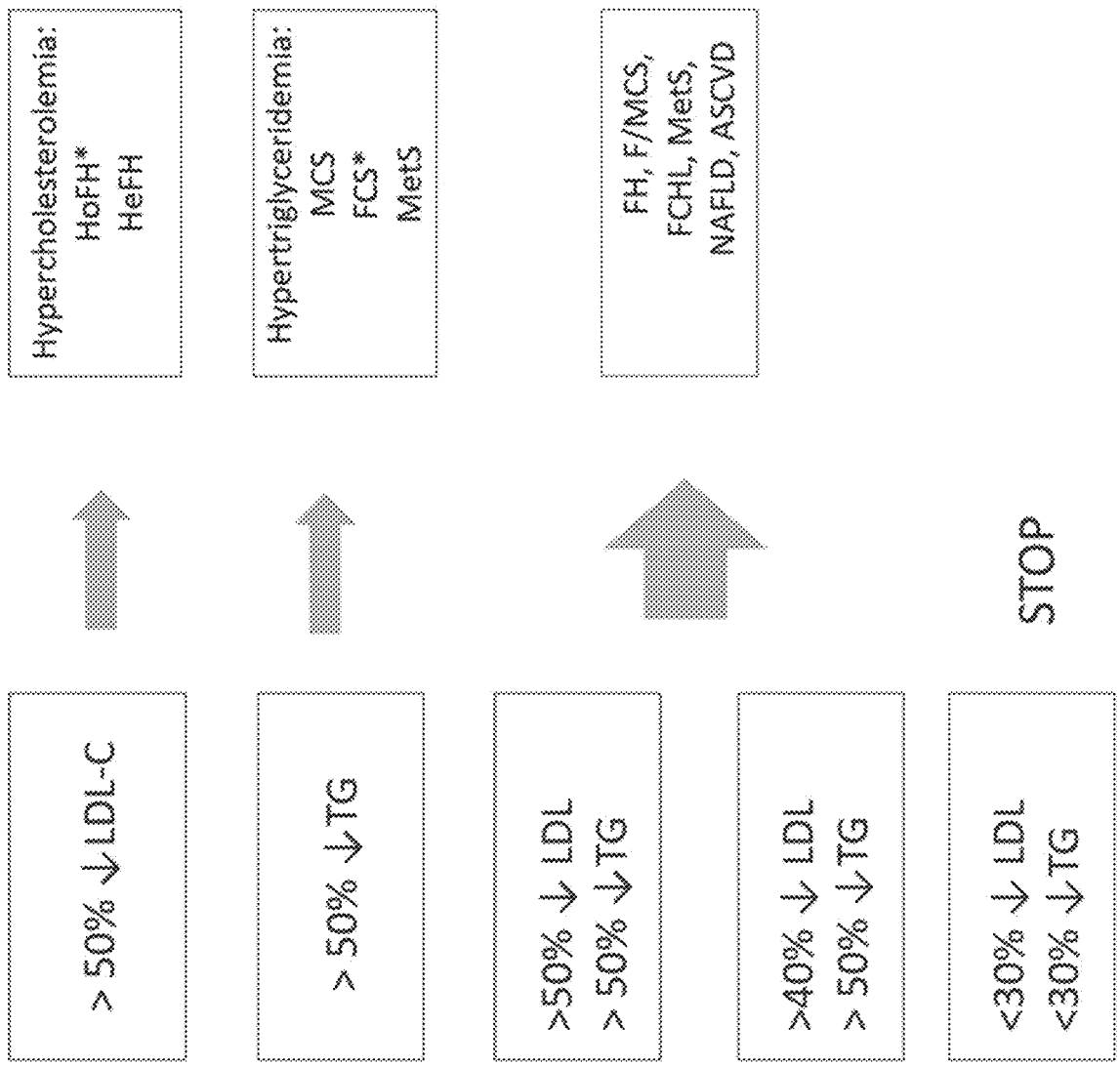
FIG. 19 shows non-limiting exemplary clinical study Phase 2 patient populations based on dose escalation outcomes (e.g., at six months post treatments).

Exemplary Phase 2 patient populations based on dose escalation out comes (e.g., at 6 months post treatments) are shown in FIG. 19.

Example 7

Genomic Editing Characterization

Computational and experimental methods are employed to assess the potential of CTX310 to introduce unintended genomic changes (Table 14). Genomic sites with potential for CTX310 sgRNA induced off-target editing are nominated using homology-dependent and genome-wide homology-independent methods. Using hybrid capture followed by deep-sequencing, indel formation at these candidate sites are assessed in PHHs, the intended cell type for editing, and cell types representative of spleen and adrenal gland tissues, tissues for which significant on-target editing observed in vivo in NHP studies indicates unintended exposure to CTX310 editing components. Importantly, the hybrid capture sequencing experiment includes measurement of on-target editing, and samples are also assessed for ANGPTL3 protein reduction. Off-target assessment uses a pharmacologically relevant in vitro editing condition. Off-target sites with statistically confirmed editing is determined and presented with discussion of potential functional disruption of proximal genomic elements and an overall assessment of safety risk.

Chromosomal rearrangements associated with CTX310 editing are characterized with 2 complementary assays: ddPCR for quantitation of homologous translocations, and long-read sequencing for characterization of large insertions and deletions. Each assay is performed on 3 donor lots of PHHs treated with a pharmacologically relevant CTX310 concentration. Shown below in Table 14 is an overview of genomic studies planned.

TABLE 14

OVERVIEW OF GENOMIC STUDIES

| Study | Cell types edited with CTX310 in pharmacologically relevant conditions |
|---|---|
| Off-target editing assessment with deep sequencing of sites nominated with homology-dependent and -independent methods | Primary human hepatocytes (PHH), primary spleen cells, primary adrenal gland cells |
| On-target editing characterization with PacBio long-read sequencing for structural variants | PHH |
| Translocation quantitation with ddPCR assays for homologous translocations | PHH |

Figure 22A:
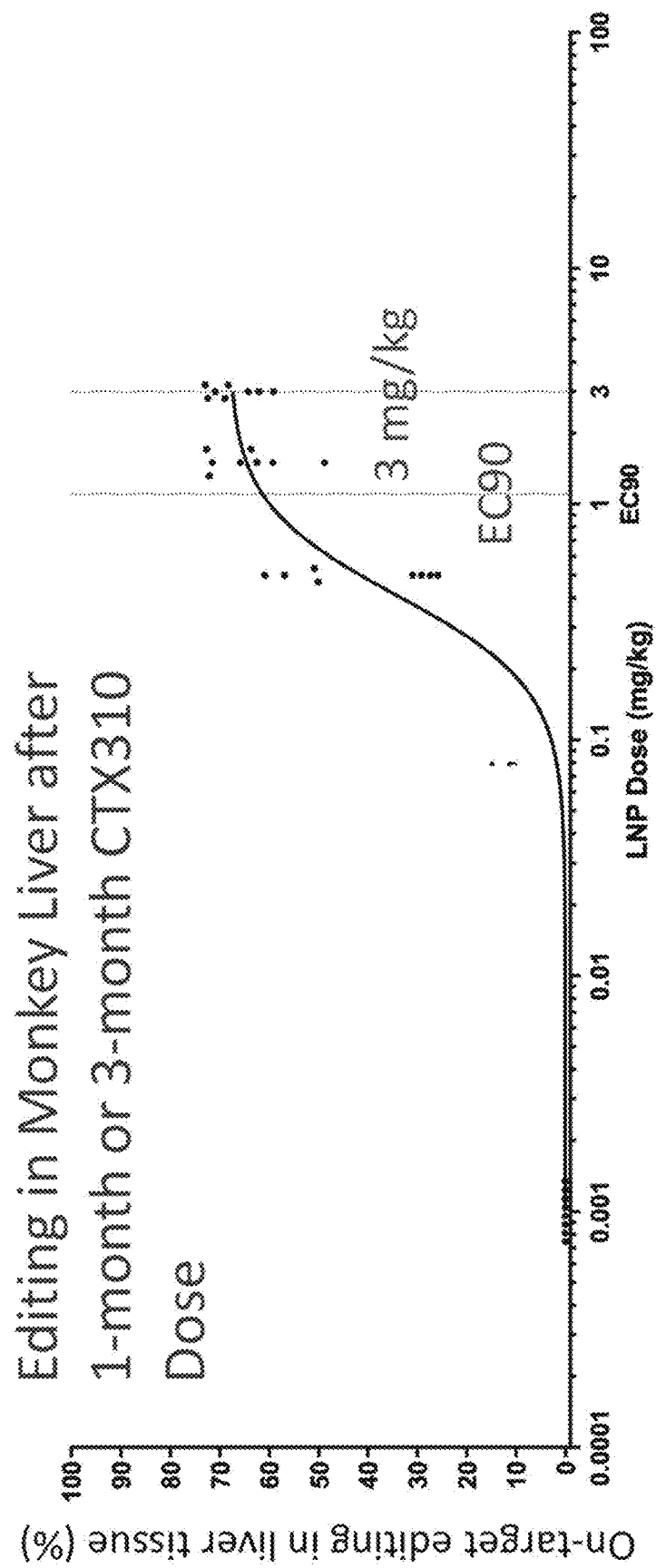
FIG. 22A-FIG. 22B depict EC90 values for editing in in vivo (FIG. 22A) and in vitro studies (FIG. 22B).
Figure 22B:
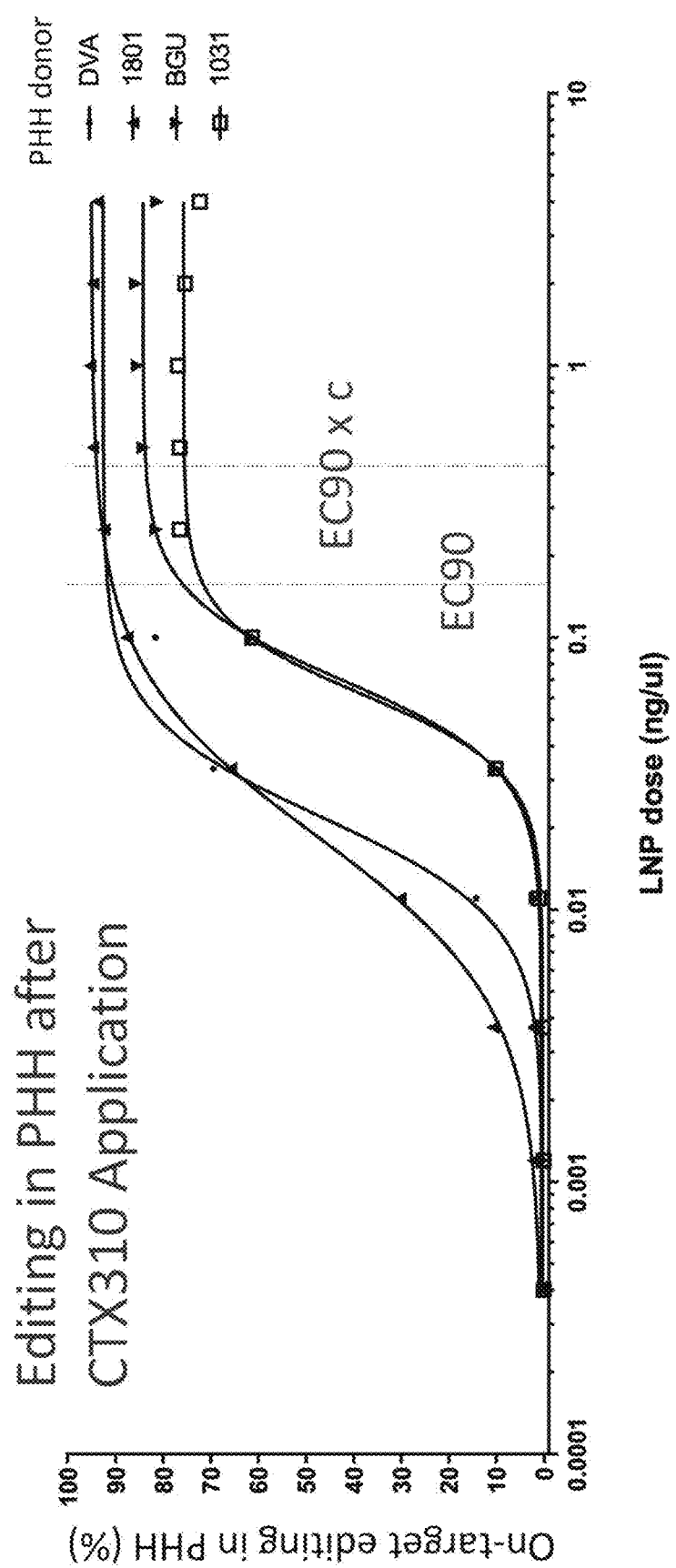

The planned in vitro editing condition can be selected to match the in vivo condition in monkey, calibrated by on-target editing (FIG. 22A-FIG. 22B). In-vivo condition to match is 3× allometric scaling of the highest proposed CTX310 dose level of 1 mg/kg in human derives a 3 mg/kg dose in monkey. Logistic curves are fit to in vivo editing rates (3 CTX310 doses in monkeys) and in vitro editing rates (CTX310 dose titrations in 4 PHH donors). EC90 is calculated from all curves, keeping the highest from the PHH donors. Scale factor c can be calculated from in vivo data to scale EC90 to the desired condition: c=(3 mg/kg)/EC90=2.7. Scale factor c can be applied to in vitro EC90 to derive the final in vitro CTX310 concentration of EC90× c (0.43 ng/μL).

Tissues with highest risk are assessed for off-target editing. Unintended tissues spleen and adrenal gland have elevated exposure to CTX310 (see FIG. 10A-FIG. 10D and Table 5A-Table 5B). Off-target editing is assessed in PHH, spleen primary cells, and adrenal gland primary cells. For spleen and adrenal gland cells, planned editing is expected to achieve on-target editing exceeding average rates observed in monkeys at 3 mg/kg dose. Tissues with low average on-target editing have a low risk for off-target editing.

To identify genomic sites of potential off-target editing, both homology dependent and independent methods with be used. For homology-dependent site nomination, human genome is searched for sites similar to the sgRNA target sequence. This includes homology distances up to 4 mismatches and NGG and 7 non-canonical PAMs. For homology-independent site nomination, a cell-free assay with Digenome-seq identifies cleaved sites with high sensitivity. Lack of chromatin means sites are not specific to any cell type. DNA from 3 unique donors is used.

For evaluation of off-target editing, in vitro editing is assessed. For in vitro editing, primary human hepatocytes (PHH) and cell types from spleen and adrenal gland tissue are used. For PHH, 4 donors and 3 technical replicates of each donor, with donor-matched untreated controls. Editing with CTX310 LNP condition that matches expected in vivo conditions are performed, specific to tissue type. For NGS assessment, hybrid capture followed by deep sequencing at nominated off-target sites is performed. Off-target editing is confirmed in any donor if editing is ≥0.2% above untreated control and t-test between treated and untreated is significant.

Structural variant and chromosomal rearrangement characterization are also assessed. Structural variants and chromosomal rearrangement may occur due to on-target editing. For in vitro editing, PHH cells are edited with CTX310 at a concentration of EC90× c, the condition derived for off-target assessment. To assess chromosomal rearrangement, the rates of homologous translocations (2 species) are quantitated with ddPCR assays. For structural variants at on-target site, PacBio sequencing of an ~10 kb amplicon at the target site is used to characterize large insertions and deletions with semi-quantitative measurement of rates.

Example 8

Durability Study

Described in this Example are studies to evaluate durability of ANGPTL3 protein knock-down in plasma (ELISA) and assess ANGPTL3 disruption in liver tissue (>1 yr). Described herein are results out to, in some embodiments, 2 months following single administration of CTX310 (e.g., LNP comprising Cas9 sequence and gRNA for targeting of ANGPTL3). In some embodiments, pre-treatment with steroids and/or anti-histamines is administered. Table 15 below displays a summary of the durability study described herein.

TABLE 15

DURABILITY STUDY OVERVIEW

| | Group size | Dose Level | ANGPTL3 ELISA | ANGPTL3 editing |
|---|---|---|---|---|
| CTX310 - no pre-treatment CTX310 - pre-treatment | 4 (2 Male + 2 Female) | 2.0 mg/kg | 7 d, 14 d, 21 d, 28 d, 6 wk, 8 wk, 10 wk, 12 wk, monthly (4 mos-24 mos) | 12 mos, 18 mos, 24 mos - liver only |

Shown in Table 16 are dosing and endpoints for the durability study. In some embodiments, pre-treatment with dexamethasone, diphenhydramine, and famotidine was administered. In some embodiments, 1 mg/kg dexamethasone, 0.5 mg/kg famotidine, and 5 mg/kg diphenhydramine was administered on the day before LNP administration and then again 30-60 min before LNP administration.

TABLE 16

DURABILITY STUDY OVERVIEW-DOSING

| | | Dose | Animals on Study | | |
|---|---|---|---|---|---|
| Group | Treatment | (mg/kg) | Males | Females | Endpoints |
| 1 | CTX310* | 2 | 2 | 2 | Necropsy: 2 years |
| 2 | CTX310 | 2 | 2 | 2 | Biopsy: 12 and 18 months Serum Chemistry PD Samples Bioanalysis/ Toxicokinetic (TK) Samples |

*Received pretreatment medications, intramuscular administration: 5 mg/kg diphenhydramine; 1 mg/kg corticosteroid; 0.5 mg/kg famotidine Study Objectives In some embodiments, the primary objective of the study described herein is to determine durability of knockdown of ANGPTL3 and efficacy in modulating lipid levels.

In some embodiments, LFTs (e.g., AST) were observed to be elevated for approximately 1 week following administration of CTX310, however, after 1 week, levels returned to baseline. In some embodiments, administration of CTX310 resulted in at least 40% decrease in total cholesterol levels, triglyceride levels, and HDL levels at 1 to 5 weeks following administration.

As shown in FIG. 24-FIG. 27, ANGPTL3 levels decreased following administration of CTX310. The effect is specific, as administration of a control targeting a different protein involved in lipidemia did not have any effect on ANGPTL3 levels. Pre-treatment with anti-histamines and steroids has no effect on the activity of CTX310. The 2 mg/kg dose results in around 90% reduction of plasma ANGPTL3 protein levels. The NHP group dosed with control targeting LNP was used as a comparison.

Example 9

Exemplary Phase I Trial Protocol

Figure 28:
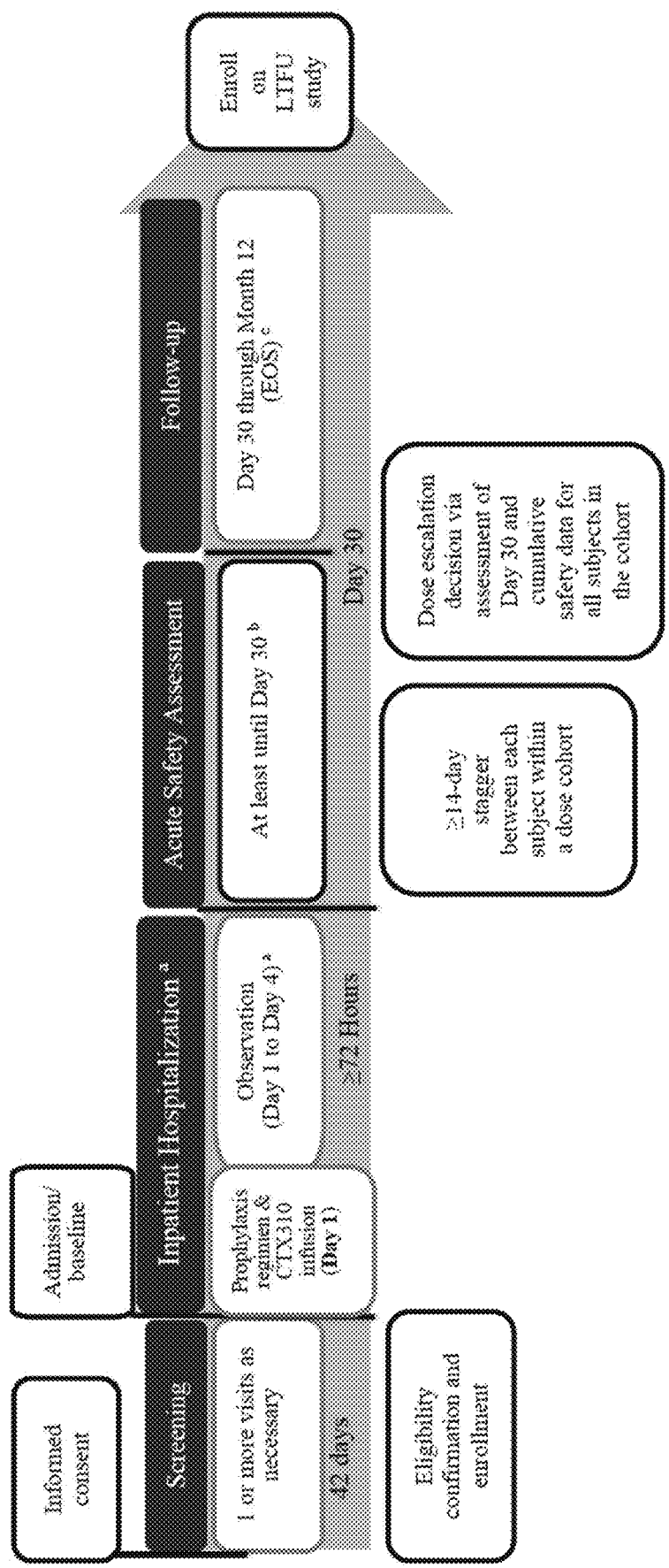
FIG. 28 depicts an exemplary schematic of phase I clinical trial design.

Provided in this prophetic example is an exemplary clinical trial protocol for testing the efficacy and safety of the compositions and methods disclosed herein for treating subjects having, e.g., refractory dyslipidemias (See, FIG. 28).

CTX310 is a LNP formulation of CRISPR-Cas9 (clustered regularly interspaced short palindromic repeats—CRISPR-associated protein 9) components for in vivo editing of the target gene ANGPTL3. In some embodiments, the investigational drug product comprises a capped and polyadenylated spacer Cas9 mRNA containing N1-methylpseudouridine and a 100 nucleotide—long single-guide RNA targeting the gene of interest. CTX310 is designed to utilize CRISPR-Cas9 to disrupt exon 1 of human ANGPTL3 in the liver, leading to a decrease of ANGPTL3 protein levels.

Rationale

Cardiovascular disease (CVD) remains the leading cause of mortality globally and the management of dyslipidemias remains the cornerstone of CVD prevention. As reported by the American Heart Association (AHA) in 2021, 38% of adults (93.9 million) in the United States had total cholesterol levels ≥200 mg/dL from 2015 to 2018, with elevated levels of low-density lipoprotein cholesterol (LDL-C; ≥130 mg/dL) reported in 29% of adults between 2013 to 2016. Dyslipidemias involving elevated levels of LDL-C(hypercholesterolemia), triglycerides (TG; hypertriglyceridemia

[HTG]), or both contribute to CVD and associated risks, including type 2 diabetes, chronic kidney disease, and nonalcoholic fatty liver disease. Additional clinical consequences are associated with rare dyslipidemias, such as severe elevations in TG increasing the risk of pancreatitis.

The latest recommendations of Canadian, Australian, European, and American cardiological associations emphasize the role of increased levels of non—high-density lipoprotein cholesterol (non—HDL-C) and apolipoprotein B (ApoB) in evaluating the risk of CVD rather than LDL-C and TG. Non-HDL cholesterol (i.e., total cholesterol—HDL-C) is the composite of LDL, intermediate-density lipoprotein (IDL), very low—density lipoprotein (VLDL), and lipoprotein(a) (Lp(a)) cholesterol. ApoB, the major structural protein in VLDL, IDL, LDL-C, and Lp(a), is a highly atherogenic lipoprotein due to its retention, resulting in plaque buildup in arterial walls over time. Although there is typically a good correlation between LDL-C and ApoB in calculating CVD risk, there is a discordance between the 2 parameters in approximately 20% of cases. Therefore, non—HDL-C(indirectly) and ApoB (directly) provide a more accurate assessment of the total concentration of atherogenic particles, especially at higher TG concentrations, in non-fasting samples and in individuals with low LDL-C concentrations. The 2021 Canadian Cardiovascular Society guidelines use either non—HDL-C or ApoB as the preferred parameter for assessment of risk. Achievement of treatment target values for ApoB and non—HDL-C have been modified from previous versions of these guidelines to accurately represent the same percentile equivalents as LDL-C for all recommended thresholds (as tabulated below in Table 17) and inform the inclusion of non—HDL-C and ApoB in this study.

TABLE 17

APOB AND NON-HDL-C THRESHOLD SELECTION

| LDL-C | | non-HDL-C | | ApoB | | |
|---|---|---|---|---|---|---|
| mmol/L | mg/dL | mmol/L | mg/dL | mmol/L | mg/dL | g/L |
| 1.8 | 70 | 2.4 | 93 | 1.8 | 70 | 0.7 |
| 2.0 | 78 | 2.6 | 101 | 2.1 | 80 | 0.8 |
| 3.5 | 135 | 4.2 | 162 | 2.7 | 105 | 1.05 |
| 5 | 193 | 5.8 | 224 | 3.7 | 145 | 1.45 |

ApoB: apolipoprotein B; CCS: Canadian Cardiovascular Society; HDL-C: high-density lipoprotein cholesterol; LDL-C: low-density lipoprotein cholesterol.
Adapted from the 2021 CCS guidelines.

Patients with dyslipidemias are typically treated with lipid-lowering therapies, which may include a statin, ezetimibe, and proprotein convertase subtilisin/kexin type 9 (PCSK9) inhibitors, monoclonal antibodies, and RNA inhibitor and ANGPTL3 monoclonal antibody where indicated and accessible. Despite all available treatments, only 45% of patients achieve the target lipid levels suggested by AHA and American College of Cardiology (ACC) guidelines, especially patients who are at very high risk of cardiovascular events.

The methods disclosed herein include a gene editing therapy that utilizes CRISPR-Cas9 to specifically target and disrupt ANGPTL3, which encodes a regulator of lipoprotein metabolism expressed in the liver and has emerged as a therapeutic target for patients with mixed dyslipidemias. ANGPTL3 has been shown to inhibit lipoprotein lipase (LPL) activity, the main enzyme involved in hydrolysis of TG-rich lipoproteins, and endothelial lipase (EL), which hydrolyzes HDL phospholipids and therefore increases levels of TG and other lipids. Decreased ANGPTL3 levels have been shown to exhibit higher LPL activity and thus, reduced levels of TG. ANGPTL3 inhibition can also lead to efficient clearance of VLDL particles via activation of EL in an LDL receptor (LDLR)-independent mechanism, leading to reduction in LDL-C, non—HDL-C, and ApoB levels.

ANGPTL3 has been identified as the gene mutated in familial combined hypolipidemia, which is characterized by low fasting plasma TG levels and low levels of LDL-C and HDL-C. Large-scale genetic studies in humans show loss-of-function variants of ANGPTL3 have low levels of TG and LDL-C and decreased risk of atherosclerotic cardiovascular disease (ASCVD). In addition, clinical studies targeting ANGPTL3 by lowering or inactivating through antisense oligonucleotide or monoclonal antibody treatments have demonstrated efficacy in subjects with various forms of dyslipidemia to markedly reduce plasma LDL-C and TG levels.

In addition to clearing and lowering VLDL and LDL (non-HDL) cholesterol and TG, ANGPTL3 inhibition substantially lowers ApoB levels, which has been shown to proportionally decrease CVD risk. Together, these studies indicate ANGPTL3 is a valid therapeutic target to lower plasma non—HDL-C, ApoB, and TG levels for patients with dyslipidemias who are unable to achieve minimum acceptable target levels of lipids with currently available treatments and remain at high risk of CVD.

In non-human primate (NHP) studies, a single dose of CTX310 resulted in significant and sustained reductions in TG levels in a dose-dependent manner, and in a mouse LDLR knockout model, a mouse surrogate of CTX310 resulted in significant lowering of LDL-C. Together, these rationale and preclinical data support the use of CTX310 as a one-time treatment to lower levels of atherogenic lipids.

Mode of Administration

In some embodiments, subjects receive a single intravenous (IV) infusion.

Study Population

The study population consists of subjects 18 to 70 years (inclusive) of age who have dyslipidemias with persistently high levels of TG and/or non—HDL-C, including LDL, VLDL, IDL, and Lp(a), and/or ApoB, above the thresholds recommended by ACC and AHA guidelines despite maximum tolerated doses of available lipid-lowering treatments, diet, and lifestyle modifications (refractory population). The Phase 1 study described herein, in some embodiments, includes subjects with the following monogenic or polygenic refractory dyslipidemias, with or without ASCVD, that encompass HTG and/or hypercholesterolemia syndromes: Familial chylomicronemia syndrome (FCS), Multifactorial chylomicronemia syndrome, Homozygous familial hypercholesterolemia, Heterozygous familial hypercholesterolemia, and other HTG/hypercholesterolemia syndromes of undetermined etiologies.

The majority of subjects enrolled are expected to be of polygenic background due to the high prevalence of polygenic hypercholesterolemia and HTG. Subjects with elevated lipids of undetermined etiology ae also eligible for enrollment based on the overall known benefit of lipid-lowering treatments in reducing CVD risk. Subjects are asked to continue to take their baseline lipid-lowering medications in the same doses through the study period until a significant beneficial effect (i.e., achievement of target lipid goals) of CTX310 is observed.

Duration of Subject Participation

All subjects are monitored for safety, tolerability, pharmacokinetics (PK), and pharmacodynamic (PD) effects for 12 months post-infusion in the trial. All subjects are asked to participate in a separate long-term follow-up study following completion or withdrawal/discontinuation.

tory cohort). Each subject undergoes the following stages: (1) Screening: 6 weeks, (2) Infusion of CTX310 (Day 1) and acute safety evaluation period (30 days post-infusion), (3)

TABLE 18

OBJECTIVES AND ENDPOINTS

| Primary Objectives | Primary Endpoints |
| --- | --- |
| To evaluate the safety and tolerability of a single ascending dose of CTX310 in subjects with refractory dyslipidemias with elevated levels of TG and/or non-HDL-C and/or ApoB and/or LDL-C, and to determine the recommended Phase 2 dose | Incidence of AEs, including TEAEs, AESIs, DLTs; clinically significant laboratory abnormalities; and clinically significant abnormal vital signs |

| Secondary Objectives | Secondary Endpoints |
| --- | --- |
| To assess the preliminary efficacy of CTX310 in human subjects | Percentage change in TG, ApoB, non-HDL-C (including LDL, VLDL, IDL, and Lp(a)), and HDL-C concentrations over time compared to baseline |
| To assess the PK of CTX310 | Plasma levels of LNP<br>Plasma level of Cas9 protein |
| To assess the PD of CTX310 | Percentage change in ANGPTL3 concentration over time compared to baseline |

| Exploratory Objectives | Exploratory Endpoints |
| --- | --- |
| To identify changes associated with CTX310 that may indicate or predict clinical response, immunogenicity, safety, or PD activity | Percentage change in FFA levels over time compared to baseline<br>Change in fatty liver disease<br>Immunogenicity of CTX310 (samples are stored and evaluated for ADA to LNP and Cas9, if required) |

ADA: anti-drug antibody; AE: adverse event; AESI: adverse event of special interest; ALC-0159: amino and PEG lipid component of CTX310; ALC-0307: amino and PEG lipid component of CTX310; ANGPTL3: angiopoietin-like 3; ApoB: apolipoprotein B; Cas9: CRISPR-associated protein 9; CRISPR: clustered regularly interspaced short palindromic repeats; DLT: dose-limiting toxicity; FFA: free fatty acids; HDL-C: high-density lipoprotein cholesterol; IDL: intermediate-density lipoprotein; LDL-C: low-density lipoprotein cholesterol; LNP: lipid nanoparticles; Lp(a): lipoprotein(a); PD: pharmacodynamic; PEG: polyethylene glycol; PK: pharmacokinetic; TEAE: treatment-emergent adverse event; TG: triglycerides; VLDL: very low-density lipoprotein.

Study Design

Described herein is a single-arm, open-label, multicenter, ascending single-dose Phase 1 study that enrolls up to 24 subjects 18 to 70 years of age with dyslipidemias and increased levels of TG (>300 mg/dL) and/or LDL-C(>100 mg/dL; >70 mg/dL for ASCVD) and/or non—HDL-C(>160 mg/dL) and/or ApoB (>100 mg/dL) that are refractory to indicated and available treatments.

Three to 6 subjects are enrolled in each of the dose levels: 0.1, 0.3, 0.6, and 1 mg/kg of total RNA in the LNP formulation. Each subject receives a single IV dose of CTX310 and is hospitalized, in some embodiments, for a minimum of 72 hours after CTX310 infusion (or longer if required by local regulation or site practice) and is closely monitored post-infusion for adverse events (AEs) defining dose-limiting toxicities (DLTs) during the 30-day acute safety evaluation period. In some embodiments, all subjects receives premedication with a corticosteroid and antihistamines (H1 and H2 blockers) prior to receiving CTX310.

After CTX310 infusion, subjects are followed for 12 months with physical exams, regular laboratory evaluations, and assessments for AEs and effects on ANGPTL3 expression and lipid profile. After completion of this study, all subjects are asked to participate in a separate long-term follow-up study for up to 15 years post-infusion. At each dose level, all AEs, including adverse events of special interest (AESIs), are reviewed by the Safety Review Committee (SRC) before proceeding to the next cohort. Once dose escalation is completed and a recommended dose has been determined, 3 to 6 more subjects are enrolled at the same dose level to confirm safety and PD effect (confirma- Follow-up: Each subject is monitored for AEs, AESIs, and effect on lipid parameters for a total of 12 months post-infusion. Subjects can be rolled over to a separate long-term follow-up study for up to 15 years post-infusion for long-term follow-up.

Study Treatment

Administration of CTX310

In some embodiments, subjects receives a single IV infusion within a 1-hour period on Day 1, administered under medical supervision during inpatient hospitalization.

Pre-Infusion Additional Treatment

Within 1 to 2 hours prior to the administration of study drug, an additional treatment infusion regimen is administered to subjects. In some embodiments, the regimen consists of: IV steroid (e.g., dexamethasone 10 mg or equivalent); IV H1 blocker (e.g., diphenhydramine 50 mg or equivalent) or oral H1 blocker (e.g., cetirizine 10 mg or equivalent); and IV or oral H2 blocker (e.g., famotidine 20 mg or equivalent).

CTX310 Post-Infusion Monitoring

Following completion of administration, subjects, in some embodiments, is observed as inpatients for 72 hours, or longer if required by local regulation or site practice. In some embodiments, safety and clinical laboratory evaluations, and collection of blood and urine samples for PK analysis are performed. In some embodiments, AEs and concomitant medications are recorded. Inpatient hospitalization for observation may be extended as needed.

Investigational Product Preparation, Handling, Storage, and Accountability

CTX310 drug product (e.g., nanoparticles comprising gRNA targeting ANGPTL3 and mRNA encoding Cas9) is provided as a frozen liquid formulation consisting of 300 mM sucrose in phosphate buffered saline at a target concentration of 2.0 (±0.4) mg/mL total RNA. In some embodiments, CTX310 must be stored frozen at <−60° C. in a glass vial until time of use and is stored onsite, thawed, and formulated immediately prior to administration.

In some embodiments, Inclisiran is not administered beginning 60 days before infusion of CTX310 and until 60 days after Day 1. In some embodiments, apheresis procedures may not be performed beginning 14 days before infusion of CTX310 and until 14 days after Day 1.

If a significant lowering of lipids (LDL-C or TG) is observed during the course of the study, i.e., lipid levels decrease to the desired levels (e.g., LDL <70 mg/dL, TG<150 mg/dL, or non-HDL-C<160 mg/dL), adjustments to relevant medications or frequency of apheresis procedures may be instituted. It is expected, in some embodiments, that the plan for tapering other lipid-lowering medications or apheresis procedures are individualized for each subject depending on the response to study treatment, underlying genotype, and assessment of risk factors for future cardiovascular events.

Study Procedures

Provided below are descriptions of study procedures. In addition to assessments described herein, subjects can be followed per institutional guidelines, and unscheduled assessments can be performed when clinically indicated. Missed evaluations can be rescheduled and performed as close to the originally scheduled date as possible except if rescheduling becomes, in the investigator's opinion, medically unnecessary or unsafe because it is too close in time to the next scheduled evaluation. In that case, the missed evaluation is recorded as a protocol deviation and should be abandoned. For the purposes of this protocol, there is no Day 0. All visit dates and windows are to be calculated using Day 1 as the date of CTX310 infusion.

Screening and Enrollment

In some embodiments, a log of all potential subjects reviewed and evaluated for study participation is kept. In some embodiments, the screening period begins on the date that the subject signs the informed consent form (ICF) and continues through confirmation of eligibility and enrollment into the study. Once informed consent has been obtained, the subjects, in some embodiments, are screened to confirm study eligibility. In some embodiments all screening assessments should be completed within 42 days after a subject signs the ICF. A medical monitor can review eligibility packets and verify information provided by the site to confirm that the subject is eligible for enrollment.

Infusion of CTX310

In some embodiments, all subjects receive a pretreatment regimen and study treatment, as described above. The acute safety evaluation period is 30 days following infusion of CTX310 for each subject. Following the 30-day acute safety evaluation period, subjects can be followed for an additional 11 months. In some embodiments, subjects are considered to have completed the study after they complete the end of study (EOS) visit at Month 12. In some embodiments, the end of the study is defined as the time at which the last subject completes the Month 12 visit, is considered lost to follow-up, withdraws consent, or dies. In some embodiments, to comply with local regulatory requirements/guidance for subjects administered a gene therapy, all subjects who receive an infusion of CTX310 and either discontinue or complete this study are asked to participate in a separate long-term follow-up study for up to 15 years post-infusion to assess long-term safety, durability, and effect on cardiovascular events.

Study Assessments and Procedures

Demographic data, including date of birth, sex, race, and ethnicity, can be collected. Medical history, including a full history of the subject's disease and response to treatment from date of diagnosis, are obtained. Cardiac and surgical history can also be obtained. Complete physical examination, including general appearance, skin, neck, head, eyes, ears, nose, throat, heart, lungs, abdomen, lymph nodes, extremities, and nervous system, can be performed at the screening, Day 30, and end of study (EOS) visits, and the results documented. Symptom-directed abbreviated physical examination may be performed at all other study visits. Changes noted from the examination performed at screening can be recorded as AEs. Weight can also be obtained. In some embodiments, height, body mass index, and waist/hip ratio are obtained at screening and end of study.

In some embodiments, vital signs are recorded at every study visit and can include blood pressure, heart rate, respiratory rate, oxygen saturation by pulse oximetry, and temperature. In some embodiments, liver imaging is performed. Standard local procedures can be used for image acquisition and analysis. In some embodiments, a 3-hour fast is recommended prior to the following imaging procedures. A liver FibroScan or MRE (depending on availability) can be performed at screening and results can be used to exclude patients with liver stiffness consistent with signs of fibrosis (See, Exclusion Criteria). A liver MRI—proton density fat fraction or ultrasound (for assessment of fatty liver/steatosis) can be performed at the screening and EOS visits. Baseline liver fat status and quantitative change in hepatic steatosis can be collected within the case report form (CRF), with clinically significant findings reported as medical history or AEs, as appropriate.

One or more transthoracic echocardiograms (for assessment of left ventricular ejection fraction) can be performed. Additional echocardiograms may be obtained. In some embodiments, twelve (12)-lead ECGs are obtained. Corrected QT interval (QTc) and QRS intervals are determined from ECGs. Additional ECGs may be obtained.

Laboratory samples can be collected and analyzed. Laboratory assessments are listed in Table 19 and Table 20.

TABLE 19

| LOCAL LABORATORY TESTING | |
| --- | --- |
| Serum chemistry | ALT (SGPT), AST (SGOT), bilirubin (total and direct), total protein, albumin, alkaline phosphatase, bicarbonate, BUN, calcium, chloride, creatinine, eGFR, glucose, magnesium, phosphorus, potassium, sodium, HbA1c, C-reactive protein |
| Urinalysis | Specific gravity, pH, glucose, protein, blood, ketones, bilirubin, urobilinogen, nitrite, leukocyte esterase, microscopic examination (if blood or protein is abnormal) |
| Coagulation | PT, PTT, fibrinogen |
| Serum or urine pregnancy test | hCG |
| CBC with differential | Hematocrit, hemoglobin, red blood cell count, white blood cell count, neutrophils, lymphocytes, monocytes, basophils, eosinophils, platelet count, absolute neutrophil count |

TABLE 19-continued

LOCAL LABORATORY TESTING

| | |
|---|---|
| Thyroid function | T3, T4, TSH |
| Viral serology | HIV-1, HIV-2, HCV antibody and RNA, HBV surface antigen, HBV surface antibody, HBV core antibody |

ALT: alanine aminotransferase; AST: aspartate aminotransferase; BUN: blood urea nitrogen; CBC: complete blood count; eGFR: estimated glomerular filtration rate; HbA1c: glycosylated hemoglobin; HBV: hepatitis B virus; hCG: human chorionic gonadotropin; HCV: hepatitis C virus; HIV: human immunodeficiency virus; PT: prothrombin time; PTT: partial thromboplastin time; SGOT: serum glutamic oxaloacetic transaminase; SGPT: serum glutamic pyruvic transaminase; T3: triiodothyronine; T4: thyroxine; TSH: thyroid-stimulating hormone.

TABLE 20

CENTRAL TESTING

| | |
|---|---|
| Genetic testing | HoFH/HeFH: LDLR, APOB, PCSK9<br>FCS/MCS: LPL, APOC2, APOA5, LMF-1, GP1HBP1 |
| Lipid panel | Total cholesterol, triglyceride, non-HDL-C, LDL-C, VLDL, ApoB, ApoC-III, lipoprotein(a) [1, 2] |

APOA5: apolipoprotein A5; ApoB or APOB: apolipoprotein B; APOC2: apolipoprotein C2, ApoC-III: apolipoprotein C-III; FCS: familial chylomicronemia syndrome; GP1HBP1: glycosylphosphatidylinositol anchored high-density lipoprotein binding protein 1; HDL: high-density lipoprotein; HoFH/HeFH: homozygous familial hypercholesterolemia/heterozygous familial hypercholesterolemia; LDL-C: low-density lipoprotein cholesterol; LDLR: low-density lipoprotein receptor; LMF-1: lipase maturation factor 1; LPL: lipoprotein lipase; MCS: multifactorial chylomicronemia syndrome; PCSK9: proprotein convertase subtilisin/kexin type 9; VLDL: very low-density lipoprotein.
[1] Subjects on apheresis should have lipid levels sampled within 5 days prior to the procedure (a pre-apheresis sample on the day of apheresis is also adequate).
[2] All lipid panel samples testing to be performed in a fasting state.

Immunogenicity

CTX310 is composed of mRNA encoding SpCas9 and sgRNA targeting the gene of interest (e.g., ANGPTL3), encapsulated in a LNP. In some embodiments, blood samples are collected and stored for potential future immunogenicity assessments (anti-drug antibody to LNP and Cas9), if required.

CTX310 Pharmacokinetic Analysis

In some embodiments, PK analysis of nanoparticle and Cas9 protein levels are performed on blood samples collected. In some embodiments, on Day 1, samples are collected prior to infusion, within 5 minutes, and at 1, 2, and 7 hours after the completion of CTX310 infusion. In some embodiments, for all other time points, a single sample are collected.

ANGPTL3

In some embodiments, plasma samples are obtained to follow the ANGPTL3 concentration.

Exploratory Biomarker Research

In some embodiments, exploratory biomarker research may be conducted to identify genomic, metabolic, and/or proteomic biomarkers that may be indicative or predictive of clinical response, resistance, safety, PD activity, and/or the mechanism of action of treatment. In addition, samples collected for protocol-specific endpoints can be used for exploratory research, pending availability of excess samples.

Whole blood samples can be obtained and stored in PAXgene® tubes (PreAnalytiX GmbH, Hombrechtikon, Switzerland) at screening. Plasma samples for storage are obtained at screening. Serum samples are obtained to follow exploratory biomarkers (e.g., cytokines).

Study Oversight

Safety Review Committee

In some embodiments, a Safety Review Committee (SRC) reviews all available safety data when the DLT observation period ends for the last subject enrolled in each cohort and are responsible for making decisions regarding dose escalation or de-escalation. Throughout dose escalation, for cases in which a dose had been cleared in a cohort and dose escalation is permitted, it can be alternatively decided, in consultation with the SRC, to enroll an additional number of subjects for a total of up to 6 subjects at the current dose level to gather additional safety data. The SRC continues to meet regularly during the dose escalation phase to discuss toxicity management algorithms and to review individual subject cases.

Following discussion with the SRC, the independent Data Safety Monitoring Board (DSMB) can be consulted regarding emergent safety data and to discuss potential revisions to DLT criteria or alternate dosing schema. Based on ongoing assessment of benefit and risk, the SRC may stop dose escalation before a maximum tolerated dose (MTD) is determined.

Data Safety Monitoring Board

An independent data monitoring safety board (DSMB) consisting of at least 3 physicians and 1 statistician with appropriate scientific and medical expertise aer formed at the start of the study, and roles and responsibilities are described in the DSMB charter. Throughout the study the DSMB reviews safety and efficacy data from dose escalation and endorse the recommended Phase 2 dose (RP2D). In some embodiments, the DSMB is alerted regarding any suspected, unexpected, serious adverse reaction related to CTX310.

Proposed Starting Dose and Dose Escalation

The following doses shown in Table 21 below are proposed for evaluation in the 4 planned dose escalation levels in the study, with a minimum of 3 and a maximum of 6 evaluable subjects per dose level (DL). The first-in-human starting dose is extrapolated from the no-observed-adverse-effect level (NOAEL) that has been determined in the NHP Good Laboratory Practice safety and toxicology study. The initial starting dose of 0.1 mg/kg of CTX310 refers to the total RNA dose that is based on an anticipated NOAEL of 1 mg/kg. A one-third allometric scaling from NHP to human, based on total body surface and application of a safety factor of 3, derives a starting dose of 0.1 mg/kg. The emerging clinical data on systemically infused LNP-associated therapeutics demonstrate a relatively safe profile. A 3-fold safety factor is proposed based on the predicted lack of liver-related AEs in humans based on nonclinical studies. With an anticipated 3- to 2-fold increment in dose levels, dose escalation is expected to proceed from 0.1 to <1 mg/kg. Dose escalation decisions are made, in some embodiments, in conjunction with the investigators and SRC based on the totality of safety, tolerability, and activity data.

TABLE 21

DOSE ESCALATION OF CTX310

| Dose Level | Planned Dose (mg/kg) [1] |
|---|---|
| 1 | 0.1 |
| 2 | 0.3 |
| 3 | 0.6 |
| 4 | 1 [2] |

DL: Dose Level
[1] Dose of CTX310 is referred to by amount of total RNA administered, which is the total amount of guide RNA+ messenger RNA per kg of body weight.
[2] Following review of the clinical data by the sponsor and Safety Review Committee for DL3, a dose in the range of 0.7 to ≤1 mg/kg may be explored at DL4.

Dosing Within a Dose Level Cohort

Dose escalation is performed using a standard 3+3 design in which 3 to 6 subjects are treated at each dose level depending on the occurrence of DLTs.

Based on NHP studies in which transient elevations in liver function tests (LFTs) after dosing with CTX310 resolved within 14 days, the dosing between each subject within a cohort is staggered to evaluate potential toxicities for a minimum of 14 days or until the laboratory values (including LFTs) have returned to <2× baseline or to normal levels, whichever is later. If the safety evaluation of a subject is acceptable, the next subject in the cohort may be dosed. Dose escalation may proceed when all subjects in the preceding dose cohort have completed dosing, the last subject has completed >30-day safety evaluation, and the cumulative safety data of all treated subjects at that dose level demonstrate an acceptable safety profile, as determined, in some embodiments, by the SRC.

Dose-limiting Toxicity Assessment

Subjects must receive CTX310 to be evaluated for DLTs. If a DLT-evaluable subject (i.e., a subject that has been administered CTX310, and has completed the 30-day DLT evaluation period) has signs or symptoms of a potential DLT, the DLT evaluation period is extended according to the protocol-defined window to allow for improvement or resolution before a DLT is declared. A minimum of 3 evaluable subjects are required per cohort. An adequate interval is applied between current lipid-lowering treatments a subject is receiving (i.e., monoclonal antibodies and/or inhibitor RNA therapy) and CTX310 infusion, to avoid overlapping toxicities. A subject who experiences a DLT is considered evaluable. Data for all subjects who receive CTX310 is part of the safety analysis set.

Dose escalation is performed according to the following rules: (1) If 0 of 3 subjects experience a DLT, escalate to the next dose level, (2) If 1 of 3 subjects experiences a DLT, expand the current dose level to 6 subjects, (3) If 1 of 6 subjects experiences a DLT, escalate to the next dose level, (4) If ≥2 of 6 subjects experience a DLT in DLs 2, 3, or 4, de-escalate to previous dose level, or declare previous dose level the MTD if 6 subjects are already tested at the previous dose level, (5) If ≥2 of 3 subjects experience a DLT in DLs 2, 3, or 4, de-escalate to previous dose level or declare previous dose level the MTD if 6 subjects are already tested at the previous dose level, (6) No dose escalation beyond highest dose planned or listed for the study (see the dose level table above).

The RP2D is declared at or below the MTD, or alternatively an optimum biological dose if an MTD is not reached, based on the analysis of secondary endpoints. At least 3 more subjects are administered with CTX310 at this dose level (confirmatory cohort) before an RP2D is selected. In some embodiments, all cumulative AEs occurring outside the DLT evaluation period that are assessed as related to CTX310 is also discussed with the DSMB.

Dose-Limiting Toxicities: Rationale and Criteria

The DLT definitions used herein are informed by nonclinical studies of CTX310, and published reporting of clinical experience with an LNP-encapsulated, CRISPR-Cas-9-based genome editing therapy. AEs that have no plausible causal relationship with CTX310 are not considered DLTs. A DLT is graded and documented according to Common Terminology Criteria for Adverse Events (CTCAE) version 5.0. The criteria for assessment of an AE occurring in the first 30 days after dosing for classification as a DLT include the following: (1) Any CTCAE grade ≥3 AE that is related to study drug, (2) Any CTCAE grade 3 laboratory abnormality that persists >7 days and is related to study drug, (3) Any CTCAE grade 4 laboratory abnormality that is related to study drug.

Study Eligibility

Inclusion Criteria

To be considered eligible to participate in this study, a subject must meet all the inclusion criteria listed below: (1) Age of >18 and <70 years at the time of signing the informed consent; (2) Able to provide written informed consent; (3) diagnosed with persistent dyslipidemia; defined by elevated fasting (and pre-apheresis, if applicable) levels of TG (>300 mg/dL) and/or LDL-C(>100 mg/dL; >70 mg/dL for subjects with ASCVD) and/or non—HDL-C(>160 mg/dL) and/or ApoB (>100 mg/dL); (4) Subjects must be refractory to the maximum tolerated doses of standard of care lines of treatment where indicated and available through routine clinical care, including statins, ezetimibe, and/or bempedoic acid, icosapent ethyl, and monoclonal antibodies to PCSK9 (alirocumab or evolocumab) or ANGPTL3 (evinacumab), for at least 26 weeks prior to screening; (5) Subjects with homozygous familial hypercholesterolemia receiving PCSK9-targeted interfering RNA therapy (inclisiran) must be refractory to at least 365 days of exposure prior to screening; (6) Subjects on available standard of care lines of treatment, including statins, ezetimibe, and/or bempedoic acid and/or PCSK9 and/or ANGPTL3 inhibitors, must be on a maximum tolerated and stable dose >30 days before screening, with no planned dose increase during the study participation; (7) Subjects on apheresis should be on a stable frequency of the procedure at least 12 weeks prior to screening, with no planned change of frequency during the study participation; (8) Female subjects must be postmenopausal (e.g., At least 12 consecutive months of amenorrhea in women with a uterus, without an alternative medical cause or Surgically sterile (i.e., documented hysterectomy, bilateral salpingectomy, and/or bilateral oophorectomy at least 1 month prior to screening)); (9) All male subjects must agree to the use of an acceptable method of effective contraception and their female partners should also agree to use an effective method of contraception, as defined in the protocol, from consent through 12 months after CTX310 infusion; (10) Willing and able to comply with scheduled visits, treatment plan, laboratory tests, contraceptive guidelines, and other study procedures; (11) Willing to participate in a long-term follow-up study for up to 15 years after completion of this study.

Exclusion Criteria

To be eligible for entry into the study, the subject must not meet any of the exclusion criteria listed below: (1) FCS subjects with confirmed genotype of biallelic LPL or GPIHBP1 mutation; (2) Evidence of liver disease (e.g., Aspartate transaminase, alanine transaminase >2× upper limit of normal (ULN), or total bilirubin value >2× ULN, or Baseline prothrombin time (international normalized ratio) >1.5× ULN, or Liver elastography measurement of >7.5 kPa on FibroScan or liver stiffness measure of >4.15 kPa on magnetic resonance elastography); (3) Complete blood count: White blood cell <2,500 cells/μL; hemoglobin <11 g/dL for males, <10 g/dL for females; or platelet count <100,000/μL; (4) Baseline estimated glomerular filtration rate <60 mL/min/1.73 m$^2$, as measured by Modification of Diet in Renal Disease equation; (5) Diagnosis of nephrotic syndrome or albuminuria >2+ on urine dipstick; (6) Inadequate diabetes control, with glycosylated hemoglobin >9%; (7) History of alcohol or drug abuse and nonadherence to abstinence for the duration of the study; (8) History of a significant coagulation disorder; (9) Uncontrolled or untreated thyroid disease (thyroid-stimulating hormone <0.1 mIU/L or >10 mIU/L); (10) Cardiac left ventricular ejection fraction <50% by echocardiogram; (11) Peripheral pulse oximetry saturation of <90%; (12) Uncontrolled hypertension, defined as average systolic >160 mmHg and diastolic of >90 mmHg; (13) 12-lead electrocardiogram (ECG) findings demonstrating, e.g., QTc of >450 ms for males and >470 ms for females at screening and/or any other ECG finding deemed clinically significant by the investigator; (14) Acute coronary syndrome event within 24 weeks prior to Day 1; (15) Central nervous system (CNS) stroke within 24 weeks prior to Day 1; (16) Acute pancreatitis within 12 weeks prior to Day 1; (17) Current use or use within 365 days from Day 1 of any hepatocyte-targeted small interfering RNA or antisense oligonucleotide molecule (except inclisiran); (18) Current use or use within 90 days from Day 1 of any monoclonal antibody treatment (except evolocumab, alirocumab, or evinacumab); (19) Participation in another clinical study with an investigational drug/product within 30 days of screening or <5 half-lives of the investigational agent, whichever is longer from screening; (20) Current use of selective serotonin reuptake inhibitors, chronic systemic corticosteroid therapy, or anabolic agents; (21) Current use of niacin-based supplements or nutraceuticals that may influence lipid levels at a dose/amount that has not been stable for >30 days prior to the screening visit; (22) Prior treatment with gene therapy/editing product; (23) Positive serology for human immunodeficiency virus type 1 (HIV-1) or HIV-2, hepatitis B virus (hepatitis B core antibody or nucleic acid testing [NAT]), or hepatitis C virus (NAT); (24) History of any illness or any clinical condition that, in the opinion of the investigator, might confound the results of the study or pose an additional risk in administering study drug to the subject. This may include but is not limited to history of relevant drug allergies, history of CNS disease, history or presence of clinically significant pathology, history of psychiatric illness, or history of familial cancer syndrome; (25) Any prior or current malignancy or myeloproliferative disorder or a significant immunodeficiency disorder; (26) Females of childbearing potential (postmenarchal, has an intact uterus and at least 1 ovary, and is less than 1 year since spontaneous amenorrhea) or breastfeeding females; (27) An assessment by the investigator that the subject would not comply with the study procedures outlined in the protocol.

Statistical Methods

The study initially enrolls approximately 24 subjects to provide a preliminary evaluation of safety and efficacy of CTX310. The safety and tolerability of CTX310 are assessed in the safety analysis set using descriptive summaries. Summaries of AEs, AESIs, clinical laboratory data, and other applicable safety measures (e.g., ECG) are provided for each dose level of CTX310 and overall. In some embodiments, summaries of AEs focus on treatment-emergent AEs (TEAEs). The incidence of TEAEs is summarized by system organ class and preferred term, protocol-specified severity grade, and relation to CTX310. The incidence of DLTs, serious adverse events, and AESIs are also summarized. Summaries of clinical laboratory data include descriptive statistics of absolute value and/or change from baseline at scheduled visits for selected laboratory parameters. The incidence of clinically significant laboratory abnormalities and other clinically significant safety measure abnormalities (e.g., ECG) is summarized.

The preliminary efficacy of CTX310 is assessed in the full analysis set using descriptive summaries. The percentage changes in lipid concentrations, including TG, ApoB, non—HDL-C [including LDL, VLDL, IDL, and Lp(a)], and HDL-C, over time compared to baseline are summarized using descriptive statistics for each dose level. Categorical summaries based on appropriate cutoff at selected time points, including 26 and 52 weeks after infusion, may be provided. PK and PD data are assessed descriptively and by exploratory modeling, as applicable.

Study Objectives and Hypotheses

In some embodiments, the primary objective is to evaluate the safety and tolerability of a single ascending dose of CTX310 in subjects with refractory dyslipidemias with elevated levels of TG and/or non—HDL-C and/or LDL-C and/or ApoB, and to determine the RP2D. In some embodiments, the secondary objectives are to assess the preliminary efficacy, PK, and PD of CTX310. No formal hypothesis testing is performed.

Study Endpoints

In some embodiments, the primary endpoints include: incidence of AEs, including treatment-emergent adverse events (TEAEs), AESIs, DLTs; clinically significant laboratory abnormalities; and clinically significant abnormal vital signs.

In some embodiments, the secondary efficacy endpoints comprise: Percentage change in TG, ApoB, non—HDL-C (including LDL, VLDL, IDL, and Lp(a)), and HDL-C concentrations over time compared to baseline. In some embodiments, the secondary pharmacokinetics/pharmacodynamics endpoints comprise: plasma levels of LNP, plasma level of Cas9 protein, and percentage change in ANGPTL3 concentration over time compared to baseline.

In some embodiments, the exploratory endpoints comprise: percentage change in FFA levels over time compared to baseline, change in fatty liver disease, and immunogenicity of CTX310 (samples are stored and evaluated for anti-drug antibody to LNP and Cas9, if required).

Analysis Sets

In some embodiments, the following analysis sets are evaluated and used for presentation of the data. The enrolled set, in some embodiments, includes all subjects who sign the informed consent and meet the inclusion/exclusion criteria. In some embodiments, the safety analysis set is a subset of the enrolled set that includes subjects who receive the CTX310 infusion. Analyses of the safety assessments are based on the safety analysis set. Subjects in the safety analysis set are classified by received CTX310 dose level. In some embodiments, the full analysis set (FAS) is a subset of the safety analysis set that includes subjects who receive CTX310 infusion and have at least 1 post-baseline lipid assessment or discontinue earlier. The efficacy analyses are performed based on the FAS. Subjects in the FAS are classified by received CTX310 dose level.

Sample Size

The sample size of the study is approximately 24 subjects.

Interim Analysis

In some embodiments, no formal efficacy interim analysis is planned. The safety and efficacy data are reviewed as needed during the study to monitor stopping rules and to provide recommendations on enrollment or protocol amendment.

Planned Method of Analyses

In some embodiments, the primary analysis occurs after all subjects have completed 26 weeks of follow-up after CTX310 infusion or discontinued earlier. A final analysis occur when all subjects complete or withdraw from the study. In some embodiments, tabulations are produced for appropriate disposition, demographic, baseline, efficacy, and safety parameters. By-subject listings are provided for all data, unless otherwise specified.

Efficacy Analysis

The full analysis set (FAS) is used as the analysis set for efficacy. The efficacy endpoints of percentage change in lipid concentrations, including TG, ApoB, non—HDL-C (including LDL, VLDL, IDL, and Lp(a)), and HDL-C, over time compared to baseline are summarized using descriptive statistics for each dose level. Categorical summaries at selected time points, including 26 and 52 weeks, based on appropriate cutoff may be provided.

Safety Analysis

Safety analysis is conducted on the safety analysis set. Summaries of AEs, AESIs, clinical laboratory data, and other applicable safety measures (e.g., ECG) are provided for each dose level of CTX310 and overall. In some embodiments, summaries of AEs focus on TEAEs, defined as AEs that start or worsen on or after CTX310 infusion. AEs are graded according to CTCAE v5.0. The incidence of TEAEs is summarized by system organ class and preferred term, grade, and relation to CTX310. Key subsets of TEAEs, including DLTs, AESIs, grade ≥3 AEs, related AEs, and SAEs, are summarized separately. In some embodiments, summaries of clinical laboratory data include descriptive statistics of absolute value and/or change from baseline at scheduled visits for selected laboratory parameters. The incidence of clinically significant laboratory abnormalities and clinically significant abnormal vital signs are summarized. The incidence of other clinically significant safety measure abnormalities (e.g., ECG) can also be summarized, if applicable.

Pharmacokinetic and Pharmacodynamic Analyses

Plasma levels of LNPs and Cas9 protein over time are summarized using descriptive statistics. Exploratory analysis based on an applicable PK model may be performed. Percentage change in ANGPTL3 concentration over time compared to baseline are summarized using descriptive statistics.

Biomarker Analyses

Additional exploratory biomarkers, including, e.g., FFA levels, fatty liver disease marker(s), and immunogenicity marker(s), if data are available, are summarized using descriptive statistics.

Example 10

ANGPTL3 GLP Toxicity Study Plasma Protein Levels

Provided in this Example is data showing declines in ANGPTL3 plasma protein levels in non-human primates treated using the methods and compositions disclosed herein (e.g., CTX310 drug product comprising an sgRNA targeting ANGPTL3 and a nucleic acid encoding Cas9).

Figure 29:
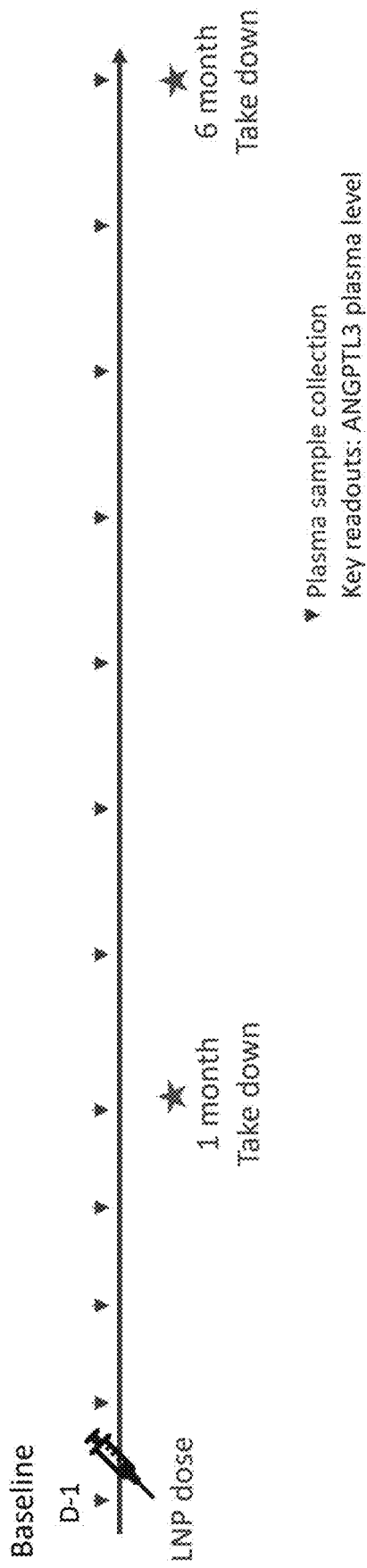
FIG. 29 depicts a non-limiting exemplary schematic of CTX310 good laboratory practices (GLP) Toxicity in non-human primate (NHP) Study Design.
Figure 30:
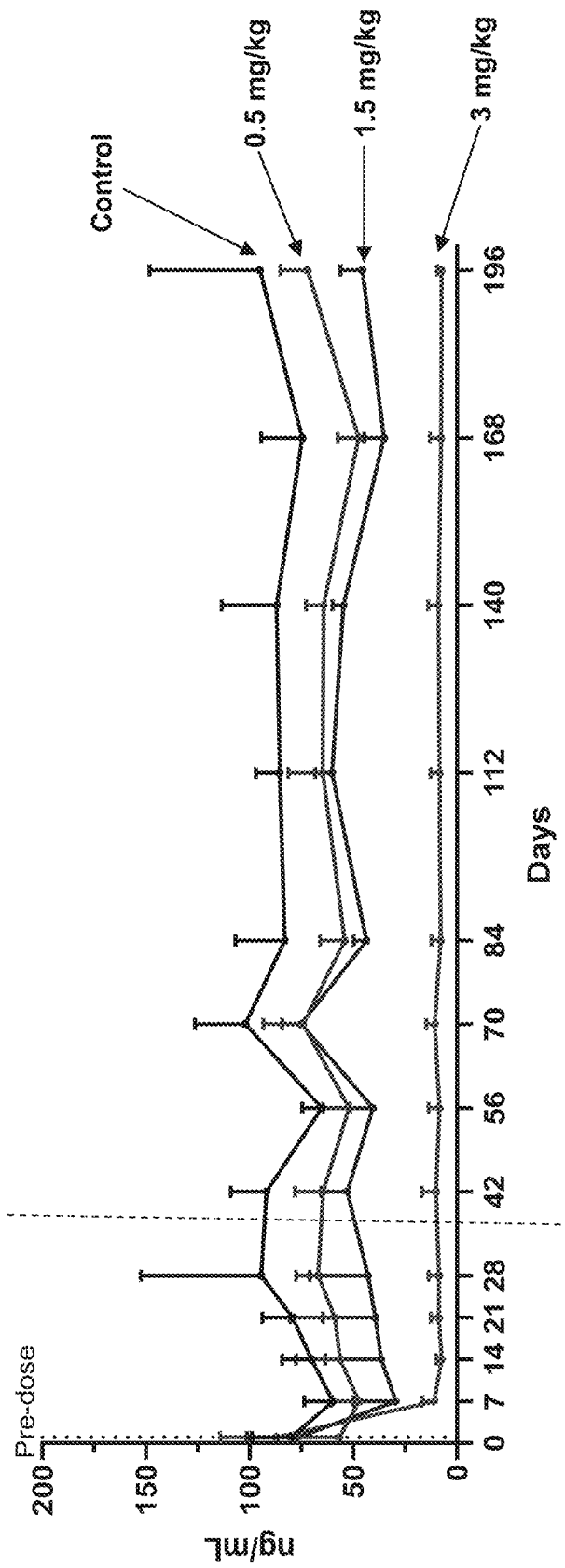
FIG. 30 shows non-limiting exemplary data for dose-dependent reduction of ANGPTL3 total plasma protein following administration of CTX310. Data is shown in ng/mL. 0 to 1 month: 8-10 NHP per group, 1 to 6 month: 5 NHP per group; Mean SD is shown.
Figure 31:
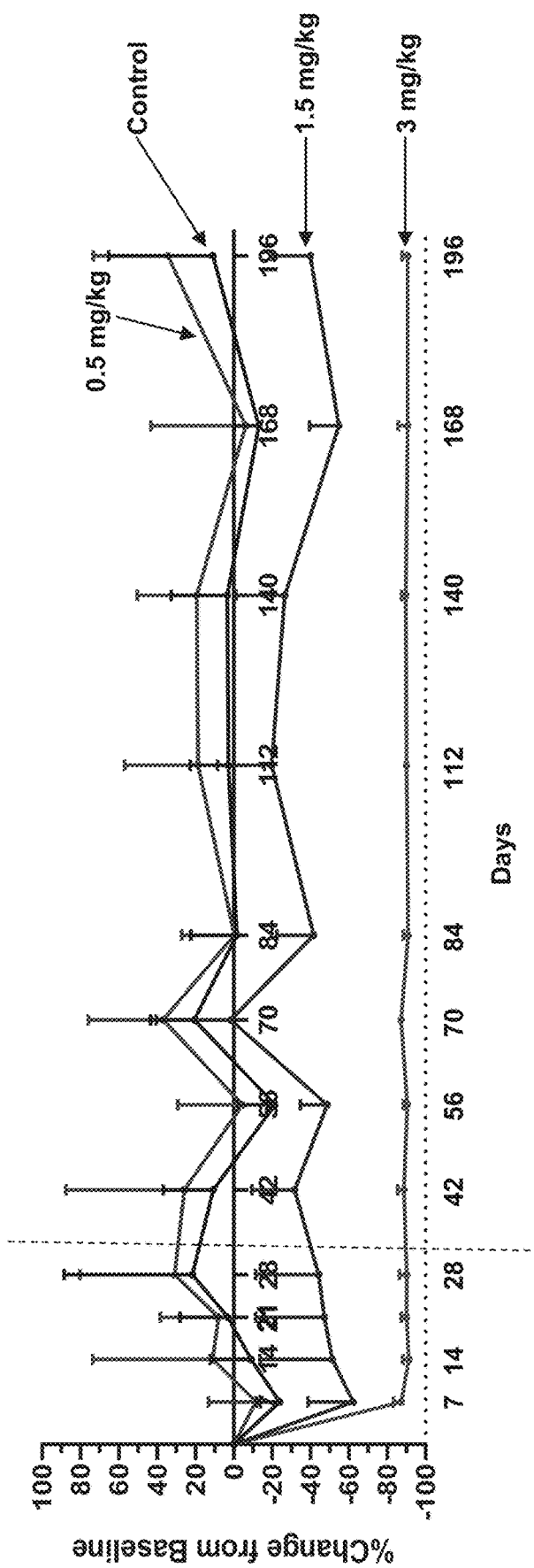
FIG. 31 shows the data from FIG. 30 as percent change. 0 to 1 month: 8-10 NHP per group, 1 to 6 month: 5 NHP per group; Mean SD is shown.
Figure 32:
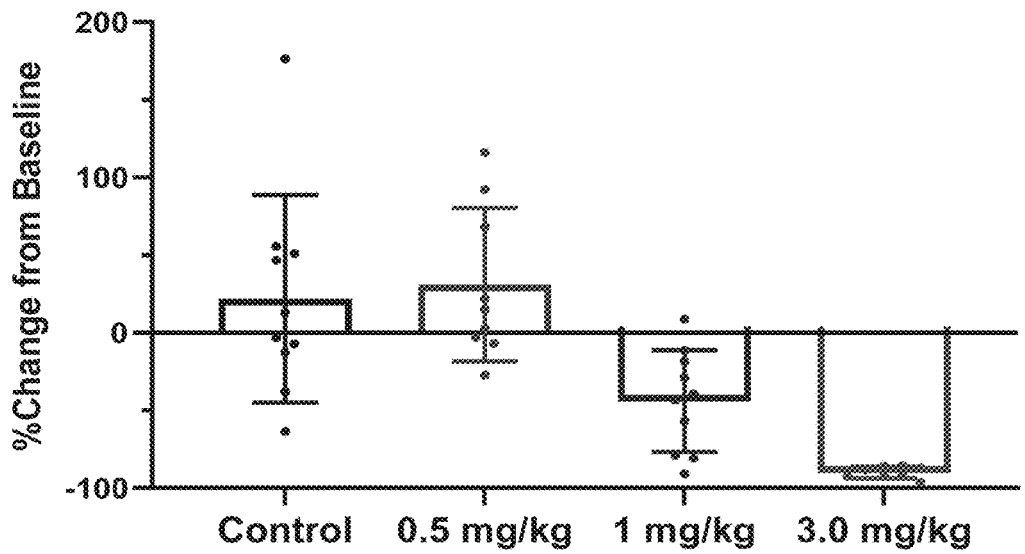
FIG. 32 displays 1-month timepoint of FIG. 31. 8-10 NHP per group; Mean SD is shown.
Figure 33:
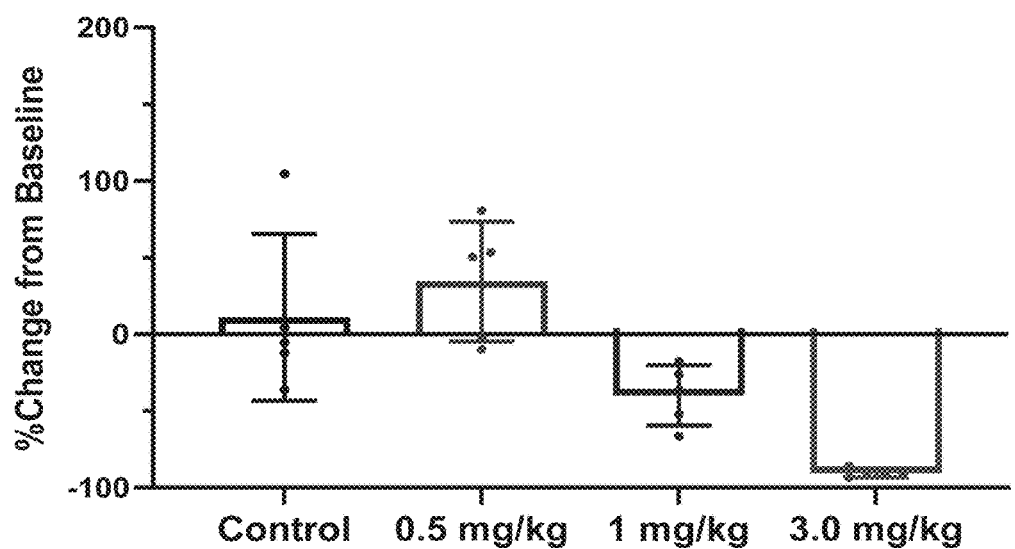
FIG. 33 displays 6-month timepoint of FIG. 31. 5 NHP per group; Mean SD is shown.

Table 22 below shows an exemplary study design (see also FIG. 29).

TABLE 22

CTX310 GLP TOX NHP STUDY DESIGN

| Dose | Number | 1 month | 6 month |
| --- | --- | --- | --- |
| 3 mg/kg | 10 (5F/5M) | 4 (2F/2M) | 5 (2F/3M) |
| 1 mg/kg | 10 (5F/5M) | 5 (3F/2M) | 5 (2F/3M) |
| 0.5 mg/kg | 10 (5F/5M) | 5 (3F/2M) | 5 (2F/3M) |
| Vehicle Control | 10 (5F/5M) | 5 (3F/2M) | 5 (2F/3M) |

M, male;
F, Female

Shown in FIG. 30-FIG. 33 are ANGPTL3 plasma protein levels as ng/mL or change from baseline following administration of CTX310 to NHPs, from 0 to 6 months.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for treating an Angiopoietin-like 3 (ANGPTL3)-related disease or disorder in a subject in need thereof, comprising administering to the subject a plurality of nanoparticles complexed with
   (a) a guide RNA (gRNA) targeting ANGPTL3 gene (ANGPTL3 gRNA) or a nucleic acid encoding the gRNA, wherein the ANGPTL3 gRNA comprises the sequence of SEQ ID NO: 13 and comprises a spacer sequence of SEQ ID NO: 20, and
   (b) a nucleic acid encoding SpCas9, wherein the gRNA induces an editing efficiency of greater than 50% in the liver of the subject; thereby treating the ANGPTL3-related disease or disorder in the subject.

2. The method of claim 1, wherein the ANGPTL3 gRNA comprises a spacer sequence of SEQ ID NO: 20 chemically modified to recite SEQ ID NO: 12.

3. The method of claim 2, wherein the ANGPTL3 gRNA is a single guide RNA (sgRNA).

4. The method of claim 1, comprising administering to the subject the plurality of nanoparticles at a single dose of about 0.1 mg/kg, 0.3 mg/kg, 0.6 mg/kg, or 1.0 mg/kg of total nucleic acids of (a) and (b).

5. The method of claim 1, wherein the expression of ANGPTL3 in the subject is reduced by at least 20% after the administration, the concentration of ANGPTL3 protein in the plasma of the subject is reduced by at least 20% after the administration, or both; and wherein the reduction is relative to (a) the ANGPTL3 expression or the concentration of ANGPTL3 protein in the plasma of the subject prior to being administered the plurality of nanoparticles; (b) the ANGPTL3 expression or the concentration of ANGPTL3 protein in one or more untreated subjects; and/or (3) a reference level of ANGPTL3 expression or the concentration of ANGPTL3 protein of healthy subjects.

6. The method of claim 5, wherein the reduction is for at least four weeks.

7. The method of claim 5, wherein the reduction in the concentration of ANGPTL3 protein in the plasma of the subject is at least 70% one month after the administration.

8. The method claim 1, wherein the plasma level of one or more of non-high-density lipoprotein (non-HDL) lipids of the subject is reduced by at least 20% after the administration, wherein the reduction of the non-HDL level is relative to (a) the non-HDL level in the plasma of the subject prior to being administered the plurality of nanoparticles; (b) the non-HDL level in one or more untreated subjects; and/or (3) a reference non-HDL level in healthy subjects.

9. The method of claim 8, wherein the one or more of non-HDL lipids is triglyceride, very low density lipoprotein (VLDL), low-density lipoprotein (LDL), or a combination thereof.

10. The method of claim 9, wherein the reduction in the plasma triglyceride level in the subject is at least 30% one month after the administration.

11. The method of claim 1, wherein the concentration of apolipoprotein B (ApoB) protein in the plasma of the subject is reduced by at least 20% after the administration, wherein the reduction is relative to (a) the concentration of ApoB protein in the plasma of the subject prior to being administered the plurality of nanoparticles; (b) the concentration of ApoB protein in one or more untreated subjects; and/or (3) a reference level of the concentration of ApoB protein of healthy subjects.

12. The method of claim 1, wherein the subject in need has a triglyceride level of more than 300 mg/dL, a non-high-density lipoprotein (HDL) level of more than 160 mg/dL, a low-density lipoprotein cholesterol (LDL-C) level greater than 100 mg/dL, an ApoB level of more than 100 mg/dL, or a combination thereof.

13. The method of claim 1, wherein the ANGPTL3-related disease or disorder is a metabolic disease, a cardiovascular disease, a lipid metabolism disease, or a combination thereof.

14. The method of claim 1, wherein the ANGPTL3-related disease or disorder is obesity, diabetes, atherosclerosis, dyslipidemia, coronary heart disease, non-alcoholic fatty liver disease (NAFLD), hyperfattyacidemia, metabolic syndrome, or a combination thereof.

15. The method of claim 1, wherein the method comprises a single administration of the plurality of nanoparticles to the subject.

16. The method of claim 15, wherein a single dose of the plurality of nanoparticles is complexed with (a) the ANGPTL3 gRNA and (b) the Cas9 mRNA at a concentration of 2.0 mg/mL total RNA.

17. The method of claim 16, wherein the total RNA comprises (a) the ANGPTL3 gRNA at about 1.5 mg/mL and (b) the Cas9 mRNA at about 0.5 mg/mL.

18. The method of claim 1, wherein the plurality of nanoparticles are lipid nanoparticles.

19. The method of claim 18, wherein the lipid nanoparticles comprise one or more neutral lipids, charged lipids, ionizable lipids, steroids, and polymers conjugated lipids.

20. The method of claim 18, wherein the lipid nanoparticles comprise cholesterol, a polyethylene glycol (PEG) lipid, or both.

* * * * *

SEQUENCE LISTING

```
Sequence total quantity: 26
SEQ ID NO: 1            moltype = RNA  length = 80
FEATURE                 Location/Qualifiers
misc_feature            1..80
                        note = Synthetic nucleotide
source                  1..80
                        mol_type = other RNA
                        organism = synthetic construct
SEQUENCE: 1
gttttagagc tagaaatagc aagttaaaat aaggctagtc cgttatcaac ttgaaaaagt   60
ggcaccgagt cggtgctttt                                              80

SEQ ID NO: 2            moltype =    length =
SEQUENCE: 2
000

SEQ ID NO: 3            moltype = DNA  length = 20
FEATURE                 Location/Qualifiers
misc_feature            1..20
                        note = Synthetic nucleotide
source                  1..20
                        mol_type = other DNA
                        organism = synthetic construct
SEQUENCE: 3
taagaccatg tcccaactga                                              20

SEQ ID NO: 4            moltype = DNA  length = 20
FEATURE                 Location/Qualifiers
misc_feature            1..20
                        note = Synthetic nucleotide
source                  1..20
                        mol_type = other DNA
                        organism = synthetic construct
SEQUENCE: 4
gccaatggcc tccttcagtt                                              20

SEQ ID NO: 5            moltype = DNA  length = 20
FEATURE                 Location/Qualifiers
misc_feature            1..20
                        note = Synthetic nucleotide
source                  1..20
                        mol_type = other DNA
                        organism = synthetic construct
SEQUENCE: 5
tatattggtc ttccacggtc                                              20

SEQ ID NO: 6            moltype = DNA  length = 20
FEATURE                 Location/Qualifiers
misc_feature            1..20
                        note = Synthetic nucleotide
source                  1..20
                        mol_type = other DNA
```

```
                            organism = synthetic construct
SEQUENCE: 6
ccagaaaagg taaggttggt                                                      20

SEQ ID NO: 7             moltype = DNA  length = 20
FEATURE                  Location/Qualifiers
misc_feature             1..20
                         note = Synthetic nucleotide
source                   1..20
                         mol_type = other DNA
                         organism = synthetic construct
SEQUENCE: 7
ggtcttccac ggtctggaga                                                      20

SEQ ID NO: 8             moltype = DNA  length = 20
FEATURE                  Location/Qualifiers
misc_feature             1..20
                         note = Synthetic nucleotide
source                   1..20
                         mol_type = other DNA
                         organism = synthetic construct
SEQUENCE: 8
ggcctccttc agttgggaca                                                      20

SEQ ID NO: 9             moltype = DNA  length = 20
FEATURE                  Location/Qualifiers
misc_feature             1..20
                         note = Synthetic polynucleotide
source                   1..20
                         mol_type = other DNA
                         organism = synthetic construct
SEQUENCE: 9
ttactaaagg aacaacaaaa                                                      20

SEQ ID NO: 10            moltype = RNA  length = 100
FEATURE                  Location/Qualifiers
misc_feature             1..100
                         note = Synthetic polynucleotide
source                   1..100
                         mol_type = other RNA
                         organism = synthetic construct
SEQUENCE: 10
taagaccatg tcccaactga gttttagagc tagaaatagc aagttaaaat aaggctagtc          60
cgttatcaac ttgaaaaagt ggcaccgagt cggtgctttt                               100

SEQ ID NO: 11            moltype = RNA  length = 100
FEATURE                  Location/Qualifiers
misc_feature             1..100
                         note = Synthetic polynucleotide
source                   1..100
                         mol_type = other RNA
                         organism = synthetic construct
SEQUENCE: 11
ttactaaagg aacaacaaaa gttttagagc tagaaatagc aagttaaaat aaggctagtc          60
cgttatcaac ttgaaaaagt ggcaccgagt cggtgctttt                               100

SEQ ID NO: 12            moltype = RNA  length = 20
FEATURE                  Location/Qualifiers
source                   1..20
                         mol_type = other RNA
                         organism = synthetic construct
modified_base            1
                         mod_base = um
modified_base            1^2
                         mod_base = OTHER
                         note = phosphorothioate linkage
modified_base            2
                         mod_base = OTHER
                         note = 2'-O-methyladenosine
modified_base            2^3
                         mod_base = OTHER
                         note = phosphorothioate linkage
modified_base            3
                         mod_base = OTHER
                         note = 2'-O-methyladenosine
modified_base            3^4
                         mod_base = OTHER
                         note = phosphorothioate linkage
SEQUENCE: 12
```

```
taagaccatg tcccaactga                                                         20

SEQ ID NO: 13           moltype = RNA   length = 100
FEATURE                 Location/Qualifiers
source                  1..100
                        mol_type = other RNA
                        organism = synthetic construct
modified_base           1
                        mod_base = um
modified_base           1^2
                        mod_base = OTHER
                        note = phosphorothioate linkage
modified_base           2
                        mod_base = OTHER
                        note = 2'-O-methyladenosine
modified_base           2^3
                        mod_base = OTHER
                        note = phosphorothioate linkage
modified_base           3
                        mod_base = OTHER
                        note = 2'-O-methyladenosine
modified_base           3^4
                        mod_base = OTHER
                        note = phosphorothioate linkage
modified_base           29
                        mod_base = gm
modified_base           30
                        mod_base = cm
modified_base           31
                        mod_base = um
modified_base           32
                        mod_base = OTHER
                        note = 2'-O-methyladenosine
modified_base           33
                        mod_base = gm
modified_base           34..36
                        mod_base = OTHER
                        note = 2'-O-methyladenosine
modified_base           37
                        mod_base = um
modified_base           38
                        mod_base = OTHER
                        note = 2'-O-methyladenosine
modified_base           39
                        mod_base = gm
modified_base           40
                        mod_base = cm
modified_base           68..69
                        mod_base = OTHER
                        note = 2'-O-methyladenosine
modified_base           70
                        mod_base = cm
modified_base           71..72
                        mod_base = um
modified_base           73
                        mod_base = gm
modified_base           74..78
                        mod_base = OTHER
                        note = 2'-O-methyladenosine
modified_base           79
                        mod_base = gm
modified_base           80
                        mod_base = um
modified_base           81..82
                        mod_base = gm
modified_base           83
                        mod_base = cm
modified_base           84
                        mod_base = OTHER
                        note = 2'-O-methyladenosine
modified_base           85..86
                        mod_base = cm
modified_base           87
                        mod_base = gm
modified_base           88
                        mod_base = OTHER
                        note = 2'-O-methyladenosine
modified_base           90
                        mod_base = um
```

| | | |
|---|---|---|
| modified_base | 91 | |
| | mod_base = cm | |
| modified_base | 92..93 | |
| | mod_base = gm | |
| modified_base | 94 | |
| | mod_base = um | |
| modified_base | 95 | |
| | mod_base = gm | |
| modified_base | 96 | |
| | mod_base = cm | |
| modified_base | 97 | |
| | mod_base = um | |
| modified_base | 97^98 | |
| | mod_base = OTHER | |
| | note = phosphorothioate linkage | |
| modified_base | 98 | |
| | mod_base = um | |
| modified_base | 98^99 | |
| | mod_base = OTHER | |
| | note = phosphorothioate linkage | |
| modified_base | 99 | |
| | mod_base = um | |
| modified_base | 99^100 | |
| | mod_base = OTHER | |
| | note = phosphorothioate linkage | |
| modified_base | 100 | |
| | mod_base = um | |
| modified_base | 89 | |
| | mod_base = OTHER | |
| | note = 2'-O-methyladenosine | |

SEQUENCE: 13

```
taagaccatg tcccaactga gttttagagc tagaaatagc aagttaaaat aaggctagtc    60
cgttatcaac ttgaaaaagt ggcaccgagt cggtgctttt                         100
```

| | | |
|---|---|---|
| SEQ ID NO: 14 | moltype = RNA  length = 20 | |
| FEATURE | Location/Qualifiers | |
| source | 1..20 | |
| | mol_type = other RNA | |
| | organism = synthetic construct | |
| modified_base | 1 | |
| | mod_base = um | |
| modified_base | 1^2 | |
| | mod_base = OTHER | |
| | note = phosphorothioate linkage | |
| modified_base | 2 | |
| | mod_base = um | |
| modified_base | 2^3 | |
| | mod_base = OTHER | |
| | note = phosphorothioate linkage | |
| modified_base | 3 | |
| | mod_base = OTHER | |
| | note = 2'-O-methyladenosine | |
| modified_base | 3^4 | |
| | mod_base = OTHER | |
| | note = phosphorothioate linkage | |

SEQUENCE: 14

```
ttactaaagg aacaacaaaa                                                20
```

| | | |
|---|---|---|
| SEQ ID NO: 15 | moltype = RNA  length = 100 | |
| FEATURE | Location/Qualifiers | |
| source | 1..100 | |
| | mol_type = other RNA | |
| | organism = synthetic construct | |
| modified_base | 1 | |
| | mod_base = um | |
| modified_base | 1^2 | |
| | mod_base = OTHER | |
| | note = phosphorothioate linkage | |
| modified_base | 2 | |
| | mod_base = um | |
| modified_base | 2^3 | |
| | mod_base = OTHER | |
| | note = phosphorothioate linkage | |
| modified_base | 3 | |
| | mod_base = OTHER | |
| | note = 2'-O-methyladenosine | |
| modified_base | 3^4 | |
| | mod_base = OTHER | |
| | note = phosphorothioate linkage | |

|  |  |
|---|---|
| modified_base | 29 |
|  | mod_base = gm |
| modified_base | 30 |
|  | mod_base = cm |
| modified_base | 31 |
|  | mod_base = um |
| modified_base | 32 |
|  | mod_base = OTHER |
|  | note = 2'-O-methyladenosine |
| modified_base | 33 |
|  | mod_base = gm |
| modified_base | 34..36 |
|  | mod_base = OTHER |
|  | note = 2'-O-methyladenosine |
| modified_base | 37 |
|  | mod_base = um |
| modified_base | 38 |
|  | mod_base = OTHER |
|  | note = 2'-O-methyladenosine |
| modified_base | 39 |
|  | mod_base = gm |
| modified_base | 40 |
|  | mod_base = cm |
| modified_base | 69 |
|  | mod_base = OTHER |
|  | note = 2'-O-methyladenosine |
| modified_base | 70 |
|  | mod_base = cm |
| modified_base | 71..72 |
|  | mod_base = um |
| modified_base | 73 |
|  | mod_base = gm |
| modified_base | 74..78 |
|  | mod_base = OTHER |
|  | note = 2'-O-methyladenosine |
| modified_base | 79 |
|  | mod_base = gm |
| modified_base | 80 |
|  | mod_base = um |
| modified_base | 81..82 |
|  | mod_base = gm |
| modified_base | 83 |
|  | mod_base = cm |
| modified_base | 84 |
|  | mod_base = OTHER |
|  | note = 2'-O-methyladenosine |
| modified_base | 85..86 |
|  | mod_base = cm |
| modified_base | 87 |
|  | mod_base = gm |
| modified_base | 88 |
|  | mod_base = OTHER |
|  | note = 2'-O-methyladenosine |
| modified_base | 89 |
|  | mod_base = gm |
| modified_base | 90 |
|  | mod_base = um |
| modified_base | 91 |
|  | mod_base = cm |
| modified_base | 92..93 |
|  | mod_base = gm |
| modified_base | 94 |
|  | mod_base = um |
| modified_base | 95 |
|  | mod_base = gm |
| modified_base | 96 |
|  | mod_base = cm |
| modified_base | 97 |
|  | mod_base = um |
| modified_base | 97^98 |
|  | mod_base = OTHER |
|  | note = phosphorothioate linkage |
| modified_base | 98 |
|  | mod_base = um |
| modified_base | 98^99 |
|  | mod_base = OTHER |
|  | note = phosphorothioate linkage |
| modified_base | 99 |
|  | mod_base = um |

| | | |
|---|---|---|
| modified_base | 99^100 | |
| | mod_base = OTHER | |
| | note = phosphorothioate linkage | |
| modified_base | 100 | |
| | mod_base = um | |

SEQUENCE: 15

```
ttactaaagg aacaacaaaa gttttagagc tagaaatagc aagttaaaat aaggctagtc   60
cgttatcaac ttgaaaaagt ggcaccgagt cggtgctttt                        100
```

| | | |
|---|---|---|
| SEQ ID NO: 16 | moltype = RNA  length = 4506 | |
| FEATURE | Location/Qualifiers | |
| misc_feature | 1..4506 | |
| | note = Synthetic | |
| source | 1..4506 | |
| | mol_type = other RNA | |
| | organism = synthetic construct | |

SEQUENCE: 16

```
agaggaaata agagagaaaa gaagagtaag aagaaatata agagccacca tggcccctaa     60
gaagaagaga aaagtcggaa ttcacggagt ccccgccgcc gacaaaaagt actccattgg   120
ccttgatatt ggaaccaact ccgtgggttg ggccgtgatc actgacgagt acaaggtgcc   180
gtccaagaag ttcaaggtgc tggggaacac tgaccggcac tcaattaaga gaacctgat   240
tgggcgctg ctgttcgact ccggagaaac gcgggagct acccgcctga agcggactgc   300
ccggcggaga tacacgcgca ggaagaaccg gatttgctac ctccaagaaa tcttcagcaa   360
cgaaatggca aaggtggacg attccttctt ccatcgcctg gaagagagct tcctggtgga   420
agaggacaag aagcacgaaa gacacccgat tttcggcaac atcgtggatg aggtcgcata   480
ccacgaaaag taccccacca tctatcatct tcggaagaag ctggtcgact ccaccgataa   540
ggccgatctg cgcctgatct acttggcgct ggctcacatg attaagttca gaggacactt   600
tctgatagag ggcgacctca atcccgataa ctccgacgtg gataagctgt tcatccaact   660
ggtgcagacg tacaaccaac tgtttgaaga gaatccaatc aacgccagcg gggtggacgc   720
caaggccatc ctgtccgccc ggctgtcaaa gtccagacgc ctggagaatc tcatcgcgca   780
actccctggc gaaaaaaaga acggactctt cgggaatctg attgctctgt ccctgggct    840
cactccgaac ttcaagtcga acttcgacct ggcggaggac gctaagctgc agctgtccaa   900
ggacacctac gatgacgatc tggataacct tctggcccag atcggggatc aatacgccga   960
tctcttcctg gccgcaaaga acttgtcgga tgctattcg ctgacgcaca ttctgcgggt  1020
caatactgaa atcaccaagg cgcccctgtc ggccagcatg atcaagcgct acgacgaaca  1080
ccaccaagac ctgactctgc tgaaggcctt cgtgcgccag cagctgcctg aaaagtacaa  1140
ggagatttc ttcgaccagt ccaagaacgg atacgccgga tacattgacg gaggggccag  1200
ccaggaggaa ttttacaaat tcatcaagcc cattctcgag aaaatggacg gaaccgaaga  1260
gttgctcgtg aagctgaaca gagaggatct cctccggaag cagcgaacct tcgacaacgg  1320
ttccatcccg caccaaatcc acctgggcga attgcacgcc atcctccggc ggcaggaaga  1380
tttctaccca ttcttgaagg acaatcgcga aaagatcgaa aagatcttga ctttccgcat  1440
cccgtactac gtgggcccttc tggcccgcgg caactcccgc ttcgcttgga tgacacgaa   1500
gtccgaggaa accattacgc cctggaactt cgaggaagtg gtggacaagg ggcgtccgc    1560
ccagagcttc atcgaacgca tgaccaattt cgacaagaac ctcccgaacg aaaaagtgct  1620
gccaaagcac tcgctcctct acgaatactt caccgtgtac aacgagctga ctaaggtcaa  1680
atacgtgact gagggaatgc ggaagccggc cttcctgtcg ggagagcaga agaaggccat  1740
agtggacttg ctttcaaga ctaaccggaa ggtcactgtg aagcaactca aggaggacta   1800
cttcaagaag atcgagtgtt tcgactcggt ggagatctcg ggtgtcgagg accgcttcaa  1860
cgcctccctg ggaacttacc acgatctgct gaagatcatc aaggacaagg acttcctcga  1920
taacgaagaa aatgaggaca tcctcgagga tatcgtgctg accctgacct tgttcgagga  1980
taggggagatg atcgaggagc ggctcaagac ctacgcccac ctgtttgacg acaaagtgat  2040
gaagcaactg aaacggcgga ggtataccgg ctggggtcgg ctgtcccgca agctgatcaa  2100
cgggatcagg gacaagcagt ccggaaagac catcctcgac ttccttaagt ccgacggatt  2160
cgcgaaccgc aacttcatgc aacttatcca cgacgactcg ctgacattca ggaagatat  2220
ccaggaaggcc caggtgtccg gacaggggga ctcgcttcat gagcacatcg ctaacctggc  2280
cggatccccc gccataaaaa agggcattct gcagaccgtc aaagtggtgg atgagctggt  2340
caaggtcatg ggccggcata agccggaaaa catcgtcatc gagatggccc gcgagaacca  2400
gactacgcag aagggccaga gaactcccg ggagcggatg aagcggattg aagagggcat   2460
caaggagctc ggcagccaga ttctgaagga acatcccgtg gaaaacaccc agctgcaaaa  2520
cgaaaagctc tatttgtact atctgcaaaa cggacgcgat atgtacgtgg atcaggagct  2580
ggacattaac agactgagcg actatgacgt ggatcacatt gtgcctcaaa gcttcctcaa  2640
ggacgactca attgacaaca aggtcctgac cagaagcgac aagaacagag aaagtcgga   2700
taatgtgccg tccgaagaag tggtcaagaa gatgaagaat tactgagac agctcctgaa  2760
tgccaagctc attacccagc ggaagttcga taacctgacc aaggccgaaa ggggtgact   2820
gtccgaactc gacaaagctg gcttcatcaa gcgccaactg gtcgaaccca gcagatcac   2880
caagcacgtc gcccagattc tggacagccg catgaacact aagtacgacg agaacgataa  2940
gctgatccgc gaagtgaagg tcatcaccct gaagtccaag ctcgtgtccg actttcggaa  3000
ggattccag ttttacaagg tccgcgagat caacaactgc catcacgccc acgacgcgta  3060
ccttaacgca gtcgtgggaa cggctcttat caagaagtac ccaaagctgg agtcggaatt  3120
tgtgtacgga gactacaaag tgtacgacgt gcgcaagatg atcgccaaat ctgagcaaga  3180
gatcgggaag gcaaccgcca atacttctt ctactcaaac attatgaatt ttttcaaaac  3240
tgagattacc ctggctaacg gagaaattcg gaagcgcccc ctgattgaaa ccaacggaga  3300
aactggagaa attgtgtggg acaagggacg ggacttcgcc accgtccgca aggtcctctc  3360
aatgccccaa gtcaacatcg tgaaaaagac cgaagtgcaa acgggcggct tctcaaagga  3420
gtccatcctg cctaagcgca acagcgacaa gctgattgcc aggaagaagg actgggaccc  3480
gaagaagtac ggaggatttg attccctac cgtggcctac tccgtgctcg tggtggcaa   3540
agtgaaaaag gggaaatcca agaagctgaa gtcggtgaag gagcttttgg gtatcaccat  3600
catgaacgc tcctcgttcg aaaagaaccc aatcgatttc ctggaagcta ggggttataa  3660
ggaagtgaaa aaggacctga ttatcaagct gcccaagtac tcactgttcg agctggaaaa  3720
```

```
cggtcggaaa aggatgctgg ccagcgccgg agaactccag aagggaaacg aactggcact    3780
gccgtccaaa tacgtcaact tcctctacct tgcatcccat tacgaaaaac tcaagggatc    3840
gccggaggac aacgagcaga agcagctttt cgtggagcaa cacaagcatt acttggacga    3900
gatcatcgag cagatttccg agttctcaaa gcgcgtgatc ctggccgacg caaatctgga    3960
caaggtcctg tccgcgtaca ataagcatcg ggacaagcct atccgcgaac aggccgagaa    4020
catcatccat ctgttcactc tgacaaacct gggcgcaccc gccgcgttca agtactttga    4080
caccaccatc gataggaagc gatacacctc aactaaggaa gtgttggacg cgacccttat    4140
ccatcagtcg atcaccgggc tgtacgaaac acggatcgac ctcagccagt tgggaggcga    4200
caagcgccct gcggctacca agaaggccgg acaggccgaa aagaagaaat gagcggccgc    4260
ttaattaagc tgccttctgc ggggcttgcc ttctggccat gcccttcttc tctcccttgc    4320
acctgtacct cttggtcttt gaataaagcc tgagtaggaa gtctagaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaa                                                                4506

SEQ ID NO: 17         moltype = RNA   length = 4444
FEATURE               Location/Qualifiers
misc_feature          1..4444
                      note = Synthetic
source                1..4444
                      mol_type = other RNA
                      organism = synthetic construct
SEQUENCE: 17
aggaaataag agagaaaaga agagtaagaa gaaatataag agccaccatg gccccaaaga     60
agaagcggaa ggtcggtatc cacggagtcc cagcagccga caagaagtac agcatcggcc    120
tggacatcgg caccaactct gtgggctggg ccgtgatcac cgacgagtac aaggtgccca    180
gcaagaaatt caaggtgctg ggcaacaccg accggcacag catcaagaag aacctgatcg    240
gagccctgct gttcgacagc ggcgaaacag ccgaggccac ccggctgaag agaaccgcca    300
gaagaagata caccagacgg aagaaccgga tctgctatct gcaagagatc ttcagcaacg    360
agatgccaa ggtggacgac agcttcttcc acagactgga agagtccttc ctggtggaag    420
aggacaagaa gcacgagaga caccccatcc tcggcaacat cgtggacgag gtggcctacc    480
acgagaagta ccccaccatc taccacctga gaaagaaact ggtggacagc accgacaagg    540
ccgacctgag actgatctac ctggcccctg cccacatgat caagttcaga ggccacttcc    600
tgatcgaggg cgacctgaac cccgacaaca gcgacgtgga caagctgttc atccagctgg    660
tgcagaccta caaccagctg ttcgaggaaa accccatcaa cgccagcggc gtggacgcca    720
aggctatcct gtctgccaga ctgagcaaga gcagaaggct ggaaaatctg atcgcccagc    780
tgcccggcga agaagaaaac ggcctgttcg gcaacctgat tgcctgagc ctgggcctga    840
cccccaactt caagagcaac ttcgacctgg ccgaggatgc caaactgcag ctgagcaagg    900
acacctacga cgacgacctg gacaacctgc tggcccagat cggcgaccag tacgccgacc    960
tgttcctggc cgccaagaac ctgtctgacg ccatcctgct gagcgacatc ctgagagtga    1020
acaccgagat caccaaggcc cccctgagcg cctctatgat caagagatac gacgagcacc    1080
accaggacct gaccctgctg aaagctctcg tgcggcagca gctgcctgag aagtacaaag    1140
aaatcttctt cgaccagagc aagaacggct acgccggtca catcgatggc gcgctagcg    1200
aggaagagtt ctacaagttc atcaagccca tcctggaaaa gatggacggc accgaggaac    1260
tgctcgtgaa gctgaacaga gaggacctgc tgagaaagca gagaaccttc gacaacggca    1320
gcatcccca ccagatccac ctgggagagc tgcacgctat cctgagaagg caggaagatt    1380
tttacccatt cctgaaggac aaccgggaaa agatcgagaa gatcctgacc ttcaggatcc    1440
cctactacgt gggccccctg gccagaggca acagcagatt cgcctggatg accagaaaga    1500
gcgaggaaac catcaccccc tggaacttcg aggaagtggt ggacaagggc gccagcgccc    1560
agagcttcat cgagagaatg acaaacttcg ataagaacct gcccaacgag aaggtgctgc    1620
ccaagcacag cctgctgtac gagtacttca cggtgtacaa cgagctgacc aaagtgaaat    1680
acgtgaccga gggaatgaga aagcccgcct tcctgagcgg cgagcagaaa aaggccatcg    1740
tggacctgct gttcaagacc aacagaaag tgaccgtgaa gcagctgaaa gaggactact    1800
tcaagaaaat cgagtgcttc gactccgtgg aaatctccgg cgtggaagat agattcaacg    1860
cctccctggg cacataccac gatctgctga aaattatcaa ggacaaggac ttcctggata    1920
acgaagagaa cgaggacatt ctggaagata tcgtgctgac cctgacactg tttgaggacc    1980
gcgagatgat cgaggaaagg ctgaaaacct acgctcacct gttcgacgac aaagtgatga    2040
agcagctgaa gagaaggcgg tacaccggct ggggcaggct gagcagaaag ctgatcaacg    2100
gcatcagaga caagcagagc ggcaagacaa tcctggattt cctgaagtcc gacggcttcg    2160
ccaaccggaa cttcatgcag ctgatccacg acgacagcct gacattcaaa gaggacatcc    2220
agaaagccca ggtgtccggc cagggcgact ctctgcacga gcatatcgct aacctggccg    2280
gcagccccgc tatcaagaag ggcatcctgc agacagtgaa ggtggtggac gagctcgtga    2340
aagtgatggg cagacacaag cccgagaaca tcgtgatcga gatggctaga gagaaccaga    2400
ccacccagaa gggacagaag aactcccgcg agaggatgaa gcggatcgaa gagggcatca    2460
aagagctggg cagccagatc ctgaaagaac accccgtgga aaacacccag ctgcagaacg    2520
agaagctgta cctgtactac ctgcagaatg gccgggatat gtacgtggac caggaactgg    2580
acatcaacag actgtccgac tacgatgtgg accatatcgt gcctcagagc tttctgaagg    2640
acgactccat cgataacaaa gtgctgactc ggagcgacaa gaacagaggc aagagcgaca    2700
acgtgccctc cgaagaggtc gtgaagaaga tgaagaacta ctggcgacag ctgctgaacg    2760
ccaagctgat tacccagagg aagttcgata acctgaccaa ggccgagaga ggcggcctga    2820
gcgagctgga taaggccggc ttcatcaaga ggcagctggt ggaaaccaga cagatcacaa    2880
agcacgtggc acagatcctg gactcccgga tgaacactaa gtacgacgaa acgatcaagc    2940
tgatccggga agtgaaagtg atcaccctga gtccaagct ggtgtccgat ttccggaagg    3000
atttccagtt ttacaaagtg cgcgagatca acaactacca ccacgcccac gacgcctacc    3060
tgaacgccgt cgtgggaacc gccctgatca aaaagtaccc taagctggaa agcgagttcg    3120
tgtacgcgga ctacaaggtg tacgacgtgc ggaagatgat cgccaagagc gagcaggaaa    3180
tcggcaaggc taccgccaag tacttcttct acagcaacat catgaacttt ttcaagaccg    3240
aaatcaccct ggccaacggc gagatcagaa agcgccctct gatcgagaca aacggcgaaa    3300
ccgggggagat cgtgtgggat aagggcagag acttcgccac agtgcgaaag gtgctgagca    3360
```

```
tgccccaagt gaatatcgtg aaaaagaccg aggtgcagac aggcggcttc agcaaagagt   3420
ctatcctgcc caagaggaac agcgacaagc tgatcgccag aaagaaggac tgggacccca   3480
agaagtacgg cggcttcgac agccctaccg tggcctactc tgtgctggtg gtggctaagg   3540
tggaaaaggg caagtccaag aaactgaaga gtgtgaaaga gctgctgggg atcaccatca   3600
tggaaagaag cagcttttgag aagaaccctta tcgactttct ggaagccaag ggctacaaag   3660
aagtgaaaaa ggacctgatc atcaagctgc ctaagtactc cctgttcgag ctggaaaacg   3720
gcagaaaaga aatgctggcc tctgccggcg aactgcagaa gggaaacgag ctggccctgc   3780
ctagcaaata tgtgaacttc ctgtacctgg cctcccacta tgagaagctg aagggcagcc   3840
ctgaggacaa cgaacagaaa cagctgtttg tggaacagca taagcactac ctggacgaga   3900
tcatcgagca gatcagcgag ttctccaaga gagtgatcct ggccgacgcc aatctggaca   3960
aggtgctgtc tgcctacaac aagcacaggg acaagcctat cagagagcag gccgagaata   4020
tcatccacct gttcaccctg acaaacctgg gcgctcctgc cgccttcaag tactttgaca   4080
ccaccatcga ccggaagagg tacaccagca ccaaagaggt gctggacgcc accctgatcc   4140
accagagcat caccggcctg tacgacaaa gaatcgacct gtctcagctg ggaggcgaca   4200
agagacctgc cgccactaag aaggccggac aggccaaaaa gaagaagtga cggccgctt   4260
aattaagctg ccttctgcgg ggcttgcctt ctggccatgc ccttcttctc tcccttgcac   4320
ctgtacctct tggtctttga ataaagcctg agtaggaagt ctagaaaaaa aaaaaaaaaa   4380
aaaaaaaaaa aaaaaaaaaa aaaaaaaaaa aaaaaaaaaa aaaaaaaaaa aaaaaaaaaa   4440
aaaa                                                                4444

SEQ ID NO: 18           moltype = RNA  length = 4506
FEATURE                 Location/Qualifiers
misc_feature            1..4506
                        note = Synthetic
source                  1..4506
                        mol_type = other RNA
                        organism = synthetic construct
misc_feature            1..4506
                        note = For every position there is a t/u, it is substituted
                        with an N1-methylpseudouridine.
SEQUENCE: 18
agaggaaata agagagaaaa gaagagtaag aagaaatata agagccacca tggcccctaa    60
gaagaagaga aaagtcggaa ttcacggagt ccccgccgcc gacaaaaagt actccattgg   120
ccttgatatt ggaaccaact ccgtgggttg ggccgtgatc tatgacgagt acaaggtgcc   180
gtccaagaag ttcaaggtgc tggggaacac tgaccgccac tcaattaaga gaacctgat   240
tggggcgctg ctgttcgact ccggagaaac cgcggaggct acccgcctga gcggactgc   300
ccggcggaga tacacgcgca ggaagaaccg gatttgctac ctccaagaaa tcttcagcaa   360
cgaaatggca aaggtggacg attccttctt ccatcgcctg gaagagagct tcctggtgga   420
agaggacaag aagcacgaaa gacaccgat tttcggcaac atcgtggatg aggtcgcata   480
ccacgaaaag taccccacca tctatcatct tcggaagaag ctggtcgact ccaccgataa   540
ggccgatctg cgcctgatct acttggcgct ggctcacatg attaagttca gaggacactt   600
tctgatagag ggcgacctca atcccgataa ctccgacgtg gataagctgt tcatccaact   660
ggtgcgacg tacaaccaac tgtttgaaga aatccaatc aacgccagcg gggtggacgc   720
caaggccatc ctgtccgccc ggctgtcaaa gtccagacgc ctggagaatc tcatcgcgca   780
actcctggc gaaaaaaaga acggactctt cgggaatctg attgctctgt ccctgggct   840
cactccgaac ttcaagtcga acttcgacct ggcggaggac gctaagctgc agctgtccaa   900
ggacacctac gatgacgatc tggataacct tctggcccaa atggggatc aatacgccga   960
tctcttcctg gccgcaaaga acttgtcgga tgctattctg ctgagcgaca ttctgcgggt  1020
caatactgaa atcaccaagg cgcccctgtc ggccagcatg atcaagcgct acgacgaaca  1080
ccaccaagac ctgactctgc tgaaggccct cgtgcgccag cagctgcctg aaaagtacaa  1140
ggagatttc ttcgaccagt ccaagaacgg atacattgac ggggccagtc ctgagatcga  1200
ccaggaggaa tttttacaaat tcatcaagcc cattctcgag aaaatggacg gaaccgaaga  1260
gttgctcgtg aagctgaaca gagaggatct cctccggaag cagcggacct tcgacaacgg  1320
ttccatcccg caccaaatcc acctgggcga attcacgcc atcctccggc ggcaggaaga  1380
tttctaccca ttcttgaagg acaatcgcga aagatcgaa aagatcttga ctttccgcat  1440
cccgtactac gtgggccctc tggcccgcgg caactcccgc ttcgcttgga tgacacggaa  1500
gtccgaggaa accattacgc cctgaacttcg cgaggaagtg gtggacaagg ggcgtccgc  1560
ccagagcttc atcgaacgca tgaccaattt cgacaagaac ctcccgaacg aaaaagtgct  1620
gccaaagcac tcgctcctct acgaatactt caccgtgtac aacgagctga ctaaggtcaa  1680
atacgtgact gagggaatgc ggaagccggc cttcctgtcg ggagagcaga agaaggccat  1740
agtggacttg cttttcaaga ctaaccggaa ggtcactgtg aagcaactca aggaggacta  1800
cttcaagaag atcgagtgtt tcgactcggt ggagatctcg ggtgtcgagg accgcttcaa  1860
cgcctcccctg ggaacttacc acgatctgct gaagatcatc aaggacaagg acttcctcga  1920
taacgaagaa aatgaggaca tcctcgagga tatcgtgctg accctgaccc tgttcgagga  1980
tagggagatg atcgaggagc ggctcaagac ctacgccac tgtttgacg acaaagtgat  2040
gaagcaactg aaacgcgga ggtataccgg ctggggtcgg ctgtcccgca agctgatcaa  2100
cgggatcagg gacaagcagt ccggaaagac catcctcgac ttccttaagt ccgacggatt  2160
cgccgaaccgc aacttcatgc aacttatcca cgacgactcg ctgacattca aggaagatat  2220
ccagaaggcc caggtcgtcc gacaggggga ctcgcttcat gagcacatcg ctaacctgga  2280
cggatccccc gccataaaaa agggcattct gcagaccgtc aaagtggtgg atgagctggt  2340
caaggtcatg ggccggcata gccggaaaa catcgtcatc gagatggccc gcgagaacca  2400
gactacgcag aagggccaga gaactcccg ggagcggat aagcggattg aagagggcat  2460
caaggagctc ggcagccaga ttctgaagga acatcccgtg gaaaacaccc agctgcaaaa  2520
cgaaaagctc tatttgtact atctgcaaaa cggacgcgat atgtacgtgg atcaggagct  2580
ggacattaac agactgagcg actatgacgt ggatcacatt gtgcctcaaa gcttcctcaa  2640
ggacgactca attgacaaca aggtcctgac cagaagcgac aagaacagag aaagtcgga  2700
taatgtgccg tccgaagaag tggtcaagaa gatgaagaat tactgagac agctcctgaa  2760
tgcgaagctc attcccagc ggaagttcga taacctgacc aaggccgaaa gggtggact  2820
gtccgaactc gacaaagctg gcttcatcaa gcgccaactg tcgaaaccc ggcagatcac  2880
```

```
caagcacgtc gcccagattc tggacagccg catgaacact aagtacgacg agaacgataa    2940
gctgatccgc gaagtgaagg tcatcaccct gaagtccaag ctcgtgtccg actttcggaa    3000
ggatttccag ttttacaagg tccgcgagat caacaactac catcacgccc acgacgcgta    3060
ccttaacgca gtcgtgggaa cggctcttat caagaagtac ccaaagctgg agtcggaatt    3120
tgtgtacgga gactacaaag tgtacgacgt gcgcaagatc atcgccaaat ctgagcaaga    3180
gatcgggaag gcaaccgcca aatacttctt ctactcaaac attatgaatt ttttcaaaac    3240
tgagattacc ctggctaacg gagaaattcg gaagcgcccc ctgattgaaa ccaacggaga    3300
aactggagaa attgtgtggg acaagggacg ggacttcgcc accgtccgca aggtcctctc    3360
aatgccccaa gtcaacatcg tgaaaaagac cgaagtgcaa accggcggct tctcaaagga    3420
gtccatcctg cctaagcgca acagcgacaa gctgattgcc aggaagaagg actgggaccc    3480
gaagaagtac ggaggatttg attccctac cgtggcctac tccgtgctcg tggtggccaa    3540
agtgaaaaag gggaaatcca agaagctgaa gtcggtgaag gagcttttgg gtatcaccat    3600
catggaacgc tcctcgttcg aaaagaaccc aatcgatttc ctggaagcta agggttataa    3660
ggaagtgaaa aaggacctga ttatcaagct gcccaagtac tcactgttcg agctggaaaa    3720
cggtcggaaa aggatgctgg ccagcgccgg agaactccag aagggaaacg aactggcact    3780
gccgtccaaa tacgtcaact tcctctacct tgcatcccat tacgaaaaac tcaagggatc    3840
gccggaggac aacgagcaga agcagctttt cgtggagcaa cacaagcatt acttggacga    3900
gatcatcgag cagatttccg agttctcaaa gcgcgtgatc ctggccgacg caaatctgga    3960
caaggtcctg tccgcgtaca ataagcatcg ggacaagcct atccgcgaac aggccgagaa    4020
catcatccat ctgttcactc tgacaaacct gggcgcaccc gccgcgttca agtactttga    4080
caccaccatc gataggaagc gatacacctc aactaaggaa gtgttggacg cgaccttat    4140
ccatcagtcg atcaccgggc tgtacgaaac acggatcgac ctcagccagt tgggaggcga    4200
caagcgccct gcggctacca agaaggccgg acaggccaag aagaagaaat gagcggccgc    4260
ttaattaagc tgccttctgc ggggcttgcc ttctggccat gcccttcttc tctcccttgc    4320
acctgtacct cttggtcttt gaataaagcc tgagtaggaa gtctagaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaa                                                                4506

SEQ ID NO: 19          moltype = RNA  length = 4506
FEATURE                Location/Qualifiers
misc_feature           1..4506
                       note = Synthetic
source                 1..4506
                       mol_type = other RNA
                       organism = synthetic construct
modified_base          9
                       mod_base = m1f
modified_base          27
                       mod_base = m1f
modified_base          37
                       mod_base = m1f
modified_base          39
                       mod_base = m1f
modified_base          51
                       mod_base = m1f
modified_base          58
                       mod_base = m1f
modified_base          75
                       mod_base = m1f
modified_base          81
                       mod_base = m1f
modified_base          82
                       mod_base = m1f
modified_base          90
                       mod_base = m1f
modified_base          110
                       mod_base = m1f
modified_base          113
                       mod_base = m1f
modified_base          117
                       mod_base = m1f
modified_base          118
                       mod_base = m1f
modified_base          123
                       mod_base = m1f
modified_base          124
                       mod_base = m1f
modified_base          127
                       mod_base = m1f
modified_base          129
                       mod_base = m1f
modified_base          130
                       mod_base = m1f
modified_base          140
                       mod_base = m1f
modified_base          144
                       mod_base = m1f
modified_base          148
```

-continued

| | |
|---|---|
| modified_base | 149  mod_base = m1f |
| modified_base | 156  mod_base = m1f |
| modified_base | 159  mod_base = m1f |
| modified_base | 163  mod_base = m1f |
| modified_base | 170  mod_base = m1f |
| modified_base | 177  mod_base = m1f |
| modified_base | 182  mod_base = m1f |
| modified_base | 191  mod_base = m1f |
| modified_base | 192  mod_base = m1f |
| modified_base | 198  mod_base = m1f |
| modified_base | 201  mod_base = m1f |
| modified_base | 211  mod_base = m1f |
| modified_base | 221  mod_base = m1f |
| modified_base | 225  mod_base = m1f |
| modified_base | 226  mod_base = m1f |
| modified_base | 237  mod_base = m1f |
| modified_base | 240  mod_base = m1f |
| modified_base | 241  mod_base = m1f |
| modified_base | 249  mod_base = m1f |
| modified_base | 252  mod_base = m1f |
| modified_base | 254  mod_base = m1f |
| modified_base | 255  mod_base = m1f |
| modified_base | 260  mod_base = m1f |
| modified_base | 280  mod_base = m1f |
| modified_base | 288  mod_base = m1f |
| modified_base | 298  mod_base = m1f |
| modified_base | 311  mod_base = m1f |
| modified_base | 333  mod_base = m1f |
| modified_base | 334  mod_base = m1f |
| modified_base | 335  mod_base = m1f |
| modified_base | 338  mod_base = m1f |
| modified_base | 342  mod_base = m1f |
| modified_base | 351  mod_base = m1f |
| modified_base | 353  mod_base = m1f |
| modified_base | 354  mod_base = m1f |
| modified_base | 366  mod_base = m1f |
| modified_base | 375  mod_base = m1f |
| modified_base | 382  mod_base = m1f |
| modified_base | 383  mod_base = m1f |

-continued

| | | |
|---|---|---|
| modified_base | 386 | |
| | mod_base = m1f | |
| modified_base | 387 | |
| | mod_base = m1f | |
| modified_base | 389 | |
| | mod_base = m1f | |
| modified_base | 390 | |
| | mod_base = m1f | |
| modified_base | 394 | |
| | mod_base = m1f | |
| modified_base | 399 | |
| | mod_base = m1f | |
| modified_base | 410 | |
| | mod_base = m1f | |
| modified_base | 411 | |
| | mod_base = m1f | |
| modified_base | 414 | |
| | mod_base = m1f | |
| modified_base | 417 | |
| | mod_base = m1f | |
| modified_base | 450 | |
| | mod_base = m1f | |
| modified_base | 451 | |
| | mod_base = m1f | |
| modified_base | 452 | |
| | mod_base = m1f | |
| modified_base | 453 | |
| | mod_base = m1f | |
| modified_base | 462 | |
| | mod_base = m1f | |
| modified_base | 465 | |
| | mod_base = m1f | |
| modified_base | 469 | |
| | mod_base = m1f | |
| modified_base | 474 | |
| | mod_base = m1f | |
| modified_base | 479 | |
| | mod_base = m1f | |
| modified_base | 491 | |
| | mod_base = m1f | |
| modified_base | 501 | |
| | mod_base = m1f | |
| modified_base | 503 | |
| | mod_base = m1f | |
| modified_base | 505 | |
| | mod_base = m1f | |
| modified_base | 508 | |
| | mod_base = m1f | |
| modified_base | 510 | |
| | mod_base = m1f | |
| modified_base | 511 | |
| | mod_base = m1f | |
| modified_base | 522 | |
| | mod_base = m1f | |
| modified_base | 525 | |
| | mod_base = m1f | |
| modified_base | 530 | |
| | mod_base = m1f | |
| modified_base | 538 | |
| | mod_base = m1f | |
| modified_base | 547 | |
| | mod_base = m1f | |
| modified_base | 549 | |
| | mod_base = m1f | |
| modified_base | 555 | |
| | mod_base = m1f | |
| modified_base | 558 | |
| | mod_base = m1f | |
| modified_base | 560 | |
| | mod_base = m1f | |
| modified_base | 563 | |
| | mod_base = m1f | |
| modified_base | 564 | |
| | mod_base = m1f | |
| modified_base | 570 | |
| | mod_base = m1f | |
| modified_base | 574 | |
| | mod_base = m1f | |
| modified_base | 579 | |

-continued

| | | |
|---|---|---|
| modified_base | 582 | mod_base = m1f |
| modified_base | 583 | mod_base = m1f |
| modified_base | 587 | mod_base = m1f |
| modified_base | 588 | mod_base = m1f |
| modified_base | 599 | mod_base = m1f |
| modified_base | 600 | mod_base = m1f |
| modified_base | 601 | mod_base = m1f |
| modified_base | 603 | mod_base = m1f |
| modified_base | 606 | mod_base = m1f |
| modified_base | 618 | mod_base = m1f |
| modified_base | 622 | mod_base = m1f |
| modified_base | 628 | mod_base = m1f |
| modified_base | 632 | mod_base = m1f |
| modified_base | 639 | mod_base = m1f |
| modified_base | 643 | mod_base = m1f |
| modified_base | 648 | mod_base = m1f |
| modified_base | 650 | mod_base = m1f |
| modified_base | 651 | mod_base = m1f |
| modified_base | 654 | mod_base = m1f |
| modified_base | 660 | mod_base = m1f |
| modified_base | 663 | mod_base = m1f |
| modified_base | 671 | mod_base = m1f |
| modified_base | 681 | mod_base = m1f |
| modified_base | 683 | mod_base = m1f |
| modified_base | 684 | mod_base = m1f |
| modified_base | 685 | mod_base = m1f |
| modified_base | 694 | mod_base = m1f |
| modified_base | 699 | mod_base = m1f |
| modified_base | 714 | mod_base = m1f |
| modified_base | 729 | mod_base = m1f |
| modified_base | 732 | mod_base = m1f |
| modified_base | 734 | mod_base = m1f |
| modified_base | 744 | mod_base = m1f |
| modified_base | 746 | mod_base = m1f |
| modified_base | 752 | mod_base = m1f |
| modified_base | 762 | mod_base = m1f |
| modified_base | 769 | mod_base = m1f |
| modified_base | 771 | mod_base = m1f |
| modified_base | 774 | mod_base = m1f |

| | | |
|---|---|---|
| modified_base | 783 | |
| | mod_base = m1f | |
| modified_base | 787 | |
| | mod_base = m1f | |
| modified_base | 807 | |
| | mod_base = m1f | |
| modified_base | 809 | |
| | mod_base = m1f | |
| modified_base | 810 | |
| | mod_base = m1f | |
| modified_base | 817 | |
| | mod_base = m1f | |
| modified_base | 819 | |
| | mod_base = m1f | |
| modified_base | 822 | |
| | mod_base = m1f | |
| modified_base | 823 | |
| | mod_base = m1f | |
| modified_base | 826 | |
| | mod_base = m1f | |
| modified_base | 828 | |
| | mod_base = m1f | |
| modified_base | 830 | |
| | mod_base = m1f | |
| modified_base | 834 | |
| | mod_base = m1f | |
| modified_base | 840 | |
| | mod_base = m1f | |
| modified_base | 844 | |
| | mod_base = m1f | |
| modified_base | 851 | |
| | mod_base = m1f | |
| modified_base | 852 | |
| | mod_base = m1f | |
| modified_base | 857 | |
| | mod_base = m1f | |
| modified_base | 863 | |
| | mod_base = m1f | |
| modified_base | 864 | |
| | mod_base = m1f | |
| modified_base | 870 | |
| | mod_base = m1f | |
| modified_base | 883 | |
| | mod_base = m1f | |
| modified_base | 888 | |
| | mod_base = m1f | |
| modified_base | 894 | |
| | mod_base = m1f | |
| modified_base | 896 | |
| | mod_base = m1f | |
| modified_base | 908 | |
| | mod_base = m1f | |
| modified_base | 913 | |
| | mod_base = m1f | |
| modified_base | 919 | |
| | mod_base = m1f | |
| modified_base | 921 | |
| | mod_base = m1f | |
| modified_base | 925 | |
| | mod_base = m1f | |
| modified_base | 930 | |
| | mod_base = m1f | |
| modified_base | 931 | |
| | mod_base = m1f | |
| modified_base | 933 | |
| | mod_base = m1f | |
| modified_base | 942 | |
| | mod_base = m1f | |
| modified_base | 949 | |
| | mod_base = m1f | |
| modified_base | 953 | |
| | mod_base = m1f | |
| modified_base | 961 | |
| | mod_base = m1f | |
| modified_base | 963 | |
| | mod_base = m1f | |
| modified_base | 965 | |
| | mod_base = m1f | |
| modified_base | 966 | |

-continued

| | |
|---|---|
| modified_base | 969 mod_base = m1f |
| modified_base | 983 mod_base = m1f |
| modified_base | 984 mod_base = m1f |
| modified_base | 986 mod_base = m1f |
| modified_base | 991 mod_base = m1f |
| modified_base | 994 mod_base = m1f |
| modified_base | 996 mod_base = m1f |
| modified_base | 997 mod_base = m1f |
| modified_base | 999 mod_base = m1f |
| modified_base | 1002 mod_base = m1f |
| modified_base | 1011 mod_base = m1f |
| modified_base | 1012 mod_base = m1f |
| modified_base | 1014 mod_base = m1f |
| modified_base | 1020 mod_base = m1f |
| modified_base | 1024 mod_base = m1f |
| modified_base | 1027 mod_base = m1f |
| modified_base | 1032 mod_base = m1f |
| modified_base | 1047 mod_base = m1f |
| modified_base | 1049 mod_base = m1f |
| modified_base | 1059 mod_base = m1f |
| modified_base | 1062 mod_base = m1f |
| modified_base | 1070 mod_base = m1f |
| modified_base | 1092 mod_base = m1f |
| modified_base | 1096 mod_base = m1f |
| modified_base | 1098 mod_base = m1f |
| modified_base | 1101 mod_base = m1f |
| modified_base | 1110 mod_base = m1f |
| modified_base | 1113 mod_base = m1f |
| modified_base | 1125 mod_base = m1f |
| modified_base | 1129 mod_base = m1f |
| modified_base | 1136 mod_base = m1f |
| modified_base | 1146 mod_base = m1f |
| modified_base | 1147 mod_base = m1f |
| modified_base | 1148 mod_base = m1f |
| modified_base | 1149 mod_base = m1f |
| modified_base | 1151 mod_base = m1f |
| modified_base | 1152 mod_base = m1f |
| modified_base | 1160 mod_base = m1f |
| modified_base | 1172 mod_base = m1f |

-continued

| | | |
|---|---|---|
| modified_base | 1181 | |
| | mod_base = m1f | |
| modified_base | 1185 | |
| | mod_base = m1f | |
| modified_base | 1186 | |
| | mod_base = m1f | |
| modified_base | 1211 | |
| | mod_base = m1f | |
| modified_base | 1212 | |
| | mod_base = m1f | |
| modified_base | 1213 | |
| | mod_base = m1f | |
| modified_base | 1214 | |
| | mod_base = m1f | |
| modified_base | 1220 | |
| | mod_base = m1f | |
| modified_base | 1221 | |
| | mod_base = m1f | |
| modified_base | 1224 | |
| | mod_base = m1f | |
| modified_base | 1233 | |
| | mod_base = m1f | |
| modified_base | 1234 | |
| | mod_base = m1f | |
| modified_base | 1236 | |
| | mod_base = m1f | |
| modified_base | 1245 | |
| | mod_base = m1f | |
| modified_base | 1262 | |
| | mod_base = m1f | |
| modified_base | 1263 | |
| | mod_base = m1f | |
| modified_base | 1266 | |
| | mod_base = m1f | |
| modified_base | 1269 | |
| | mod_base = m1f | |
| modified_base | 1275 | |
| | mod_base = m1f | |
| modified_base | 1288 | |
| | mod_base = m1f | |
| modified_base | 1290 | |
| | mod_base = m1f | |
| modified_base | 1293 | |
| | mod_base = m1f | |
| modified_base | 1310 | |
| | mod_base = m1f | |
| modified_base | 1311 | |
| | mod_base = m1f | |
| modified_base | 1321 | |
| | mod_base = m1f | |
| modified_base | 1322 | |
| | mod_base = m1f | |
| modified_base | 1326 | |
| | mod_base = m1f | |
| modified_base | 1338 | |
| | mod_base = m1f | |
| modified_base | 1344 | |
| | mod_base = m1f | |
| modified_base | 1352 | |
| | mod_base = m1f | |
| modified_base | 1353 | |
| | mod_base = m1f | |
| modified_base | 1362 | |
| | mod_base = m1f | |
| modified_base | 1365 | |
| | mod_base = m1f | |
| modified_base | 1381 | |
| | mod_base = m1f | |
| modified_base | 1382 | |
| | mod_base = m1f | |
| modified_base | 1383 | |
| | mod_base = m1f | |
| modified_base | 1385 | |
| | mod_base = m1f | |
| modified_base | 1391 | |
| | mod_base = m1f | |
| modified_base | 1392 | |
| | mod_base = m1f | |
| modified_base | 1394 | |

-continued

| | | |
|---|---|---|
| modified_base | 1395 | mod_base = m1f |
| modified_base | 1405 | mod_base = m1f |
| modified_base | 1416 | mod_base = m1f |
| modified_base | 1425 | mod_base = m1f |
| modified_base | 1427 | mod_base = m1f |
| modified_base | 1428 | mod_base = m1f |
| modified_base | 1432 | mod_base = m1f |
| modified_base | 1433 | mod_base = m1f |
| modified_base | 1434 | mod_base = m1f |
| modified_base | 1440 | mod_base = m1f |
| modified_base | 1445 | mod_base = m1f |
| modified_base | 1448 | mod_base = m1f |
| modified_base | 1452 | mod_base = m1f |
| modified_base | 1459 | mod_base = m1f |
| modified_base | 1461 | mod_base = m1f |
| modified_base | 1475 | mod_base = m1f |
| modified_base | 1481 | mod_base = m1f |
| modified_base | 1482 | mod_base = m1f |
| modified_base | 1486 | mod_base = m1f |
| modified_base | 1487 | mod_base = m1f |
| modified_base | 1491 | mod_base = m1f |
| modified_base | 1502 | mod_base = m1f |
| modified_base | 1515 | mod_base = m1f |
| modified_base | 1516 | mod_base = m1f |
| modified_base | 1523 | mod_base = m1f |
| modified_base | 1529 | mod_base = m1f |
| modified_base | 1530 | mod_base = m1f |
| modified_base | 1539 | mod_base = m1f |
| modified_base | 1542 | mod_base = m1f |
| modified_base | 1556 | mod_base = m1f |
| modified_base | 1568 | mod_base = m1f |
| modified_base | 1569 | mod_base = m1f |
| modified_base | 1572 | mod_base = m1f |
| modified_base | 1581 | mod_base = m1f |
| modified_base | 1588 | mod_base = m1f |
| modified_base | 1589 | mod_base = m1f |
| modified_base | 1590 | mod_base = m1f |
| modified_base | 1602 | mod_base = m1f |
| modified_base | 1617 | mod_base = m1f |

| | |
|---|---|
| modified_base | 1620 mod_base = m1f |
| modified_base | 1631 mod_base = m1f |
| modified_base | 1635 mod_base = m1f |
| modified_base | 1638 mod_base = m1f |
| modified_base | 1640 mod_base = m1f |
| modified_base | 1646 mod_base = m1f |
| modified_base | 1649 mod_base = m1f |
| modified_base | 1650 mod_base = m1f |
| modified_base | 1656 mod_base = m1f |
| modified_base | 1658 mod_base = m1f |
| modified_base | 1668 mod_base = m1f |
| modified_base | 1672 mod_base = m1f |
| modified_base | 1677 mod_base = m1f |
| modified_base | 1682 mod_base = m1f |
| modified_base | 1686 mod_base = m1f |
| modified_base | 1690 mod_base = m1f |
| modified_base | 1698 mod_base = m1f |
| modified_base | 1712 mod_base = m1f |
| modified_base | 1713 mod_base = m1f |
| modified_base | 1716 mod_base = m1f |
| modified_base | 1718 mod_base = m1f |
| modified_base | 1740 mod_base = m1f |
| modified_base | 1743 mod_base = m1f |
| modified_base | 1748 mod_base = m1f |
| modified_base | 1749 mod_base = m1f |
| modified_base | 1752 mod_base = m1f |
| modified_base | 1753 mod_base = m1f |
| modified_base | 1754 mod_base = m1f |
| modified_base | 1755 mod_base = m1f |
| modified_base | 1762 mod_base = m1f |
| modified_base | 1773 mod_base = m1f |
| modified_base | 1777 mod_base = m1f |
| modified_base | 1779 mod_base = m1f |
| modified_base | 1788 mod_base = m1f |
| modified_base | 1799 mod_base = m1f |
| modified_base | 1802 mod_base = m1f |
| modified_base | 1803 mod_base = m1f |
| modified_base | 1812 mod_base = m1f |
| modified_base | 1817 mod_base = m1f |
| modified_base | 1819 |

-continued

| | | |
|---|---|---|
| modified_base | 1820 | mod_base = m1f |
| modified_base | 1821 | mod_base = m1f |
| modified_base | 1826 | mod_base = m1f |
| modified_base | 1830 | mod_base = m1f |
| modified_base | 1836 | mod_base = m1f |
| modified_base | 1838 | mod_base = m1f |
| modified_base | 1843 | mod_base = m1f |
| modified_base | 1845 | mod_base = m1f |
| modified_base | 1856 | mod_base = m1f |
| modified_base | 1857 | mod_base = m1f |
| modified_base | 1865 | mod_base = m1f |
| modified_base | 1869 | mod_base = m1f |
| modified_base | 1876 | mod_base = m1f |
| modified_base | 1877 | mod_base = m1f |
| modified_base | 1885 | mod_base = m1f |
| modified_base | 1887 | mod_base = m1f |
| modified_base | 1890 | mod_base = m1f |
| modified_base | 1896 | mod_base = m1f |
| modified_base | 1899 | mod_base = m1f |
| modified_base | 1913 | mod_base = m1f |
| modified_base | 1914 | mod_base = m1f |
| modified_base | 1917 | mod_base = m1f |
| modified_base | 1921 | mod_base = m1f |
| modified_base | 1933 | mod_base = m1f |
| modified_base | 1941 | mod_base = m1f |
| modified_base | 1944 | mod_base = m1f |
| modified_base | 1951 | mod_base = m1f |
| modified_base | 1953 | mod_base = m1f |
| modified_base | 1956 | mod_base = m1f |
| modified_base | 1959 | mod_base = m1f |
| modified_base | 1965 | mod_base = m1f |
| modified_base | 1970 | mod_base = m1f |
| modified_base | 1971 | mod_base = m1f |
| modified_base | 1973 | mod_base = m1f |
| modified_base | 1974 | mod_base = m1f |
| modified_base | 1981 | mod_base = m1f |
| modified_base | 1989 | mod_base = m1f |
| modified_base | 1992 | mod_base = m1f |
| modified_base | 2004 | mod_base = m1f |

-continued

| | | |
|---|---|---|
| modified_base | 2012 | |
| | mod_base = m1f | |
| modified_base | 2022 | |
| | mod_base = m1f | |
| modified_base | 2024 | |
| | mod_base = m1f | |
| modified_base | 2025 | |
| | mod_base = m1f | |
| modified_base | 2026 | |
| | mod_base = m1f | |
| modified_base | 2037 | |
| | mod_base = m1f | |
| modified_base | 2040 | |
| | mod_base = m1f | |
| modified_base | 2049 | |
| | mod_base = m1f | |
| modified_base | 2063 | |
| | mod_base = m1f | |
| modified_base | 2065 | |
| | mod_base = m1f | |
| modified_base | 2072 | |
| | mod_base = m1f | |
| modified_base | 2077 | |
| | mod_base = m1f | |
| modified_base | 2082 | |
| | mod_base = m1f | |
| modified_base | 2084 | |
| | mod_base = m1f | |
| modified_base | 2094 | |
| | mod_base = m1f | |
| modified_base | 2097 | |
| | mod_base = m1f | |
| modified_base | 2106 | |
| | mod_base = m1f | |
| modified_base | 2120 | |
| | mod_base = m1f | |
| modified_base | 2133 | |
| | mod_base = m1f | |
| modified_base | 2136 | |
| | mod_base = m1f | |
| modified_base | 2141 | |
| | mod_base = m1f | |
| modified_base | 2142 | |
| | mod_base = m1f | |
| modified_base | 2145 | |
| | mod_base = m1f | |
| modified_base | 2146 | |
| | mod_base = m1f | |
| modified_base | 2150 | |
| | mod_base = m1f | |
| modified_base | 2159 | |
| | mod_base = m1f | |
| modified_base | 2160 | |
| | mod_base = m1f | |
| modified_base | 2174 | |
| | mod_base = m1f | |
| modified_base | 2175 | |
| | mod_base = m1f | |
| modified_base | 2178 | |
| | mod_base = m1f | |
| modified_base | 2184 | |
| | mod_base = m1f | |
| modified_base | 2185 | |
| | mod_base = m1f | |
| modified_base | 2187 | |
| | mod_base = m1f | |
| modified_base | 2198 | |
| | mod_base = m1f | |
| modified_base | 2202 | |
| | mod_base = m1f | |
| modified_base | 2207 | |
| | mod_base = m1f | |
| modified_base | 2208 | |
| | mod_base = m1f | |
| modified_base | 2218 | |
| | mod_base = m1f | |
| modified_base | 2220 | |
| | mod_base = m1f | |
| modified_base | 2235 | |

-continued

| | | |
|---|---|---|
| modified_base | 2237 | mod_base = m1f |
| modified_base | 2252 | mod_base = m1f |
| modified_base | 2256 | mod_base = m1f |
| modified_base | 2257 | mod_base = m1f |
| modified_base | 2260 | mod_base = m1f |
| modified_base | 2268 | mod_base = m1f |
| modified_base | 2272 | mod_base = m1f |
| modified_base | 2277 | mod_base = m1f |
| modified_base | 2285 | mod_base = m1f |
| modified_base | 2295 | mod_base = m1f |
| modified_base | 2307 | mod_base = m1f |
| modified_base | 2308 | mod_base = m1f |
| modified_base | 2310 | mod_base = m1f |
| modified_base | 2319 | mod_base = m1f |
| modified_base | 2325 | mod_base = m1f |
| modified_base | 2328 | mod_base = m1f |
| modified_base | 2332 | mod_base = m1f |
| modified_base | 2337 | mod_base = m1f |
| modified_base | 2340 | mod_base = m1f |
| modified_base | 2346 | mod_base = m1f |
| modified_base | 2349 | mod_base = m1f |
| modified_base | 2359 | mod_base = m1f |
| modified_base | 2373 | mod_base = m1f |
| modified_base | 2376 | mod_base = m1f |
| modified_base | 2379 | mod_base = m1f |
| modified_base | 2385 | mod_base = m1f |
| modified_base | 2404 | mod_base = m1f |
| modified_base | 2426 | mod_base = m1f |
| modified_base | 2439 | mod_base = m1f |
| modified_base | 2448 | mod_base = m1f |
| modified_base | 2449 | mod_base = m1f |
| modified_base | 2460 | mod_base = m1f |
| modified_base | 2469 | mod_base = m1f |
| modified_base | 2481 | mod_base = m1f |
| modified_base | 2482 | mod_base = m1f |
| modified_base | 2484 | mod_base = m1f |
| modified_base | 2494 | mod_base = m1f |
| modified_base | 2499 | mod_base = m1f |
| modified_base | 2514 | mod_base = m1f |

-continued

| | | |
|---|---|---|
| modified_base | 2529 | |
| | mod_base = m1f | |
| modified_base | 2531 | |
| | mod_base = m1f | |
| modified_base | 2533 | |
| | mod_base = m1f | |
| modified_base | 2534 | |
| | mod_base = m1f | |
| modified_base | 2535 | |
| | mod_base = m1f | |
| modified_base | 2537 | |
| | mod_base = m1f | |
| modified_base | 2540 | |
| | mod_base = m1f | |
| modified_base | 2542 | |
| | mod_base = m1f | |
| modified_base | 2544 | |
| | mod_base = m1f | |
| modified_base | 2560 | |
| | mod_base = m1f | |
| modified_base | 2562 | |
| | mod_base = m1f | |
| modified_base | 2564 | |
| | mod_base = m1f | |
| modified_base | 2568 | |
| | mod_base = m1f | |
| modified_base | 2572 | |
| | mod_base = m1f | |
| modified_base | 2580 | |
| | mod_base = m1f | |
| modified_base | 2586 | |
| | mod_base = m1f | |
| modified_base | 2587 | |
| | mod_base = m1f | |
| modified_base | 2595 | |
| | mod_base = m1f | |
| modified_base | 2603 | |
| | mod_base = m1f | |
| modified_base | 2605 | |
| | mod_base = m1f | |
| modified_base | 2610 | |
| | mod_base = m1f | |
| modified_base | 2614 | |
| | mod_base = m1f | |
| modified_base | 2619 | |
| | mod_base = m1f | |
| modified_base | 2620 | |
| | mod_base = m1f | |
| modified_base | 2622 | |
| | mod_base = m1f | |
| modified_base | 2626 | |
| | mod_base = m1f | |
| modified_base | 2633 | |
| | mod_base = m1f | |
| modified_base | 2634 | |
| | mod_base = m1f | |
| modified_base | 2637 | |
| | mod_base = m1f | |
| modified_base | 2648 | |
| | mod_base = m1f | |
| modified_base | 2652 | |
| | mod_base = m1f | |
| modified_base | 2653 | |
| | mod_base = m1f | |
| modified_base | 2664 | |
| | mod_base = m1f | |
| modified_base | 2667 | |
| | mod_base = m1f | |
| modified_base | 2696 | |
| | mod_base = m1f | |
| modified_base | 2701 | |
| | mod_base = m1f | |
| modified_base | 2704 | |
| | mod_base = m1f | |
| modified_base | 2706 | |
| | mod_base = m1f | |
| modified_base | 2711 | |
| | mod_base = m1f | |
| modified_base | 2721 | |

-continued

| | | |
|---|---|---|
| modified_base | 2724 | mod_base = m1f |
| modified_base | 2733 | mod_base = m1f |
| modified_base | 2740 | mod_base = m1f |
| modified_base | 2741 | mod_base = m1f |
| modified_base | 2744 | mod_base = m1f |
| modified_base | 2754 | mod_base = m1f |
| modified_base | 2757 | mod_base = m1f |
| modified_base | 2761 | mod_base = m1f |
| modified_base | 2769 | mod_base = m1f |
| modified_base | 2772 | mod_base = m1f |
| modified_base | 2773 | mod_base = m1f |
| modified_base | 2786 | mod_base = m1f |
| modified_base | 2787 | mod_base = m1f |
| modified_base | 2791 | mod_base = m1f |
| modified_base | 2796 | mod_base = m1f |
| modified_base | 2815 | mod_base = m1f |
| modified_base | 2820 | mod_base = m1f |
| modified_base | 2822 | mod_base = m1f |
| modified_base | 2829 | mod_base = m1f |
| modified_base | 2839 | mod_base = m1f |
| modified_base | 2843 | mod_base = m1f |
| modified_base | 2844 | mod_base = m1f |
| modified_base | 2847 | mod_base = m1f |
| modified_base | 2859 | mod_base = m1f |
| modified_base | 2862 | mod_base = m1f |
| modified_base | 2877 | mod_base = m1f |
| modified_base | 2889 | mod_base = m1f |
| modified_base | 2898 | mod_base = m1f |
| modified_base | 2899 | mod_base = m1f |
| modified_base | 2901 | mod_base = m1f |
| modified_base | 2913 | mod_base = m1f |
| modified_base | 2920 | mod_base = m1f |
| modified_base | 2924 | mod_base = m1f |
| modified_base | 2938 | mod_base = m1f |
| modified_base | 2943 | mod_base = m1f |
| modified_base | 2946 | mod_base = m1f |
| modified_base | 2955 | mod_base = m1f |
| modified_base | 2961 | mod_base = m1f |
| modified_base | 2964 | mod_base = m1f |

-continued

| | | |
|---|---|---|
| modified_base | 2970 | |
| | mod_base = m1f | |
| modified_base | 2975 | |
| | mod_base = m1f | |
| modified_base | 2982 | |
| | mod_base = m1f | |
| modified_base | 2985 | |
| | mod_base = m1f | |
| modified_base | 2987 | |
| | mod_base = m1f | |
| modified_base | 2993 | |
| | mod_base = m1f | |
| modified_base | 2994 | |
| | mod_base = m1f | |
| modified_base | 2995 | |
| | mod_base = m1f | |
| modified_base | 3004 | |
| | mod_base = m1f | |
| modified_base | 3005 | |
| | mod_base = m1f | |
| modified_base | 3006 | |
| | mod_base = m1f | |
| modified_base | 3011 | |
| | mod_base = m1f | |
| modified_base | 3012 | |
| | mod_base = m1f | |
| modified_base | 3013 | |
| | mod_base = m1f | |
| modified_base | 3014 | |
| | mod_base = m1f | |
| modified_base | 3021 | |
| | mod_base = m1f | |
| modified_base | 3030 | |
| | mod_base = m1f | |
| modified_base | 3038 | |
| | mod_base = m1f | |
| modified_base | 3043 | |
| | mod_base = m1f | |
| modified_base | 3059 | |
| | mod_base = m1f | |
| modified_base | 3063 | |
| | mod_base = m1f | |
| modified_base | 3064 | |
| | mod_base = m1f | |
| modified_base | 3072 | |
| | mod_base = m1f | |
| modified_base | 3075 | |
| | mod_base = m1f | |
| modified_base | 3085 | |
| | mod_base = m1f | |
| modified_base | 3087 | |
| | mod_base = m1f | |
| modified_base | 3088 | |
| | mod_base = m1f | |
| modified_base | 3090 | |
| | mod_base = m1f | |
| modified_base | 3098 | |
| | mod_base = m1f | |
| modified_base | 3108 | |
| | mod_base = m1f | |
| modified_base | 3113 | |
| | mod_base = m1f | |
| modified_base | 3119 | |
| | mod_base = m1f | |
| modified_base | 3120 | |
| | mod_base = m1f | |
| modified_base | 3121 | |
| | mod_base = m1f | |
| modified_base | 3123 | |
| | mod_base = m1f | |
| modified_base | 3125 | |
| | mod_base = m1f | |
| modified_base | 3134 | |
| | mod_base = m1f | |
| modified_base | 3141 | |
| | mod_base = m1f | |
| modified_base | 3143 | |
| | mod_base = m1f | |
| modified_base | 3150 | |

-continued

| | | |
|---|---|---|
| modified_base | 3159 | mod_base = m1f |
| modified_base | 3162 | mod_base = m1f |
| modified_base | 3170 | mod_base = m1f |
| modified_base | 3172 | mod_base = m1f |
| modified_base | 3183 | mod_base = m1f |
| modified_base | 3203 | mod_base = m1f |
| modified_base | 3206 | mod_base = m1f |
| modified_base | 3207 | mod_base = m1f |
| modified_base | 3209 | mod_base = m1f |
| modified_base | 3210 | mod_base = m1f |
| modified_base | 3212 | mod_base = m1f |
| modified_base | 3215 | mod_base = m1f |
| modified_base | 3222 | mod_base = m1f |
| modified_base | 3223 | mod_base = m1f |
| modified_base | 3225 | mod_base = m1f |
| modified_base | 3229 | mod_base = m1f |
| modified_base | 3230 | mod_base = m1f |
| modified_base | 3231 | mod_base = m1f |
| modified_base | 3232 | mod_base = m1f |
| modified_base | 3233 | mod_base = m1f |
| modified_base | 3234 | mod_base = m1f |
| modified_base | 3241 | mod_base = m1f |
| modified_base | 3246 | mod_base = m1f |
| modified_base | 3247 | mod_base = m1f |
| modified_base | 3252 | mod_base = m1f |
| modified_base | 3256 | mod_base = m1f |
| modified_base | 3267 | mod_base = m1f |
| modified_base | 3268 | mod_base = m1f |
| modified_base | 3282 | mod_base = m1f |
| modified_base | 3285 | mod_base = m1f |
| modified_base | 3286 | mod_base = m1f |
| modified_base | 3304 | mod_base = m1f |
| modified_base | 3312 | mod_base = m1f |
| modified_base | 3313 | mod_base = m1f |
| modified_base | 3315 | mod_base = m1f |
| modified_base | 3317 | mod_base = m1f |
| modified_base | 3335 | mod_base = m1f |
| modified_base | 3336 | mod_base = m1f |
| modified_base | 3345 | mod_base = m1f |

| | | |
|---|---|---|
| modified_base | 3354 mod_base = m1f | |
| modified_base | 3357 mod_base = m1f | |
| modified_base | 3359 mod_base = m1f | |
| modified_base | 3363 mod_base = m1f | |
| modified_base | 3372 mod_base = m1f | |
| modified_base | 3378 mod_base = m1f | |
| modified_base | 3381 mod_base = m1f | |
| modified_base | 3396 mod_base = m1f | |
| modified_base | 3410 mod_base = m1f | |
| modified_base | 3411 mod_base = m1f | |
| modified_base | 3413 mod_base = m1f | |
| modified_base | 3422 mod_base = m1f | |
| modified_base | 3426 mod_base = m1f | |
| modified_base | 3429 mod_base = m1f | |
| modified_base | 3433 mod_base = m1f | |
| modified_base | 3453 mod_base = m1f | |
| modified_base | 3456 mod_base = m1f | |
| modified_base | 3457 mod_base = m1f | |
| modified_base | 3473 mod_base = m1f | |
| modified_base | 3488 mod_base = m1f | |
| modified_base | 3497 mod_base = m1f | |
| modified_base | 3498 mod_base = m1f | |
| modified_base | 3499 mod_base = m1f | |
| modified_base | 3502 mod_base = m1f | |
| modified_base | 3503 mod_base = m1f | |
| modified_base | 3508 mod_base = m1f | |
| modified_base | 3513 mod_base = m1f | |
| modified_base | 3518 mod_base = m1f | |
| modified_base | 3521 mod_base = m1f | |
| modified_base | 3525 mod_base = m1f | |
| modified_base | 3528 mod_base = m1f | |
| modified_base | 3531 mod_base = m1f | |
| modified_base | 3534 mod_base = m1f | |
| modified_base | 3543 mod_base = m1f | |
| modified_base | 3557 mod_base = m1f | |
| modified_base | 3567 mod_base = m1f | |
| modified_base | 3572 mod_base = m1f | |
| modified_base | 3576 mod_base = m1f | |
| modified_base | 3585 mod_base = m1f | |
| modified_base | 3586 | |

-continued

| | | |
|---|---|---|
| modified_base | 3587 | mod_base = m1f |
| modified_base | 3588 | mod_base = m1f |
| modified_base | 3592 | mod_base = m1f |
| modified_base | 3594 | mod_base = m1f |
| modified_base | 3600 | mod_base = m1f |
| modified_base | 3603 | mod_base = m1f |
| modified_base | 3611 | mod_base = m1f |
| modified_base | 3614 | mod_base = m1f |
| modified_base | 3617 | mod_base = m1f |
| modified_base | 3618 | mod_base = m1f |
| modified_base | 3633 | mod_base = m1f |
| modified_base | 3637 | mod_base = m1f |
| modified_base | 3638 | mod_base = m1f |
| modified_base | 3639 | mod_base = m1f |
| modified_base | 3642 | mod_base = m1f |
| modified_base | 3649 | mod_base = m1f |
| modified_base | 3655 | mod_base = m1f |
| modified_base | 3656 | mod_base = m1f |
| modified_base | 3658 | mod_base = m1f |
| modified_base | 3666 | mod_base = m1f |
| modified_base | 3678 | mod_base = m1f |
| modified_base | 3681 | mod_base = m1f |
| modified_base | 3682 | mod_base = m1f |
| modified_base | 3684 | mod_base = m1f |
| modified_base | 3690 | mod_base = m1f |
| modified_base | 3698 | mod_base = m1f |
| modified_base | 3701 | mod_base = m1f |
| modified_base | 3705 | mod_base = m1f |
| modified_base | 3707 | mod_base = m1f |
| modified_base | 3708 | mod_base = m1f |
| modified_base | 3714 | mod_base = m1f |
| modified_base | 3724 | mod_base = m1f |
| modified_base | 3735 | mod_base = m1f |
| modified_base | 3738 | mod_base = m1f |
| modified_base | 3756 | mod_base = m1f |
| modified_base | 3774 | mod_base = m1f |
| modified_base | 3780 | mod_base = m1f |
| modified_base | 3785 | mod_base = m1f |
| modified_base | 3791 | mod_base = m1f |

| | | |
|---|---|---|
| modified_base | 3795 | mod_base = m1f |
| modified_base | 3800 | mod_base = m1f |
| modified_base | 3801 | mod_base = m1f |
| modified_base | 3804 | mod_base = m1f |
| modified_base | 3806 | mod_base = m1f |
| modified_base | 3810 | mod_base = m1f |
| modified_base | 3811 | mod_base = m1f |
| modified_base | 3815 | mod_base = m1f |
| modified_base | 3820 | mod_base = m1f |
| modified_base | 3821 | mod_base = m1f |
| modified_base | 3831 | mod_base = m1f |
| modified_base | 3839 | mod_base = m1f |
| modified_base | 3867 | mod_base = m1f |
| modified_base | 3868 | mod_base = m1f |
| modified_base | 3869 | mod_base = m1f |
| modified_base | 3870 | mod_base = m1f |
| modified_base | 3873 | mod_base = m1f |
| modified_base | 3889 | mod_base = m1f |
| modified_base | 3890 | mod_base = m1f |
| modified_base | 3893 | mod_base = m1f |
| modified_base | 3894 | mod_base = m1f |
| modified_base | 3903 | mod_base = m1f |
| modified_base | 3906 | mod_base = m1f |
| modified_base | 3915 | mod_base = m1f |
| modified_base | 3916 | mod_base = m1f |
| modified_base | 3917 | mod_base = m1f |
| modified_base | 3923 | mod_base = m1f |
| modified_base | 3924 | mod_base = m1f |
| modified_base | 3926 | mod_base = m1f |
| modified_base | 3936 | mod_base = m1f |
| modified_base | 3939 | mod_base = m1f |
| modified_base | 3942 | mod_base = m1f |
| modified_base | 3955 | mod_base = m1f |
| modified_base | 3957 | mod_base = m1f |
| modified_base | 3966 | mod_base = m1f |
| modified_base | 3969 | mod_base = m1f |
| modified_base | 3971 | mod_base = m1f |
| modified_base | 3977 | mod_base = m1f |
| modified_base | 3982 | mod_base = m1f |
| modified_base | 3988 | |

-continued

| | |
|---|---|
| modified_base | 4000 mod_base = m1f |
| modified_base | 4002 mod_base = m1f |
| modified_base | 4023 mod_base = m1f |
| modified_base | 4026 mod_base = m1f |
| modified_base | 4030 mod_base = m1f |
| modified_base | 4032 mod_base = m1f |
| modified_base | 4034 mod_base = m1f |
| modified_base | 4035 mod_base = m1f |
| modified_base | 4039 mod_base = m1f |
| modified_base | 4041 mod_base = m1f |
| modified_base | 4050 mod_base = m1f |
| modified_base | 4067 mod_base = m1f |
| modified_base | 4068 mod_base = m1f |
| modified_base | 4073 mod_base = m1f |
| modified_base | 4076 mod_base = m1f |
| modified_base | 4077 mod_base = m1f |
| modified_base | 4078 mod_base = m1f |
| modified_base | 4089 mod_base = m1f |
| modified_base | 4093 mod_base = m1f |
| modified_base | 4103 mod_base = m1f |
| modified_base | 4109 mod_base = m1f |
| modified_base | 4114 mod_base = m1f |
| modified_base | 4122 mod_base = m1f |
| modified_base | 4124 mod_base = m1f |
| modified_base | 4125 mod_base = m1f |
| modified_base | 4137 mod_base = m1f |
| modified_base | 4138 mod_base = m1f |
| modified_base | 4140 mod_base = m1f |
| modified_base | 4144 mod_base = m1f |
| modified_base | 4148 mod_base = m1f |
| modified_base | 4152 mod_base = m1f |
| modified_base | 4161 mod_base = m1f |
| modified_base | 4163 mod_base = m1f |
| modified_base | 4176 mod_base = m1f |
| modified_base | 4182 mod_base = m1f |
| modified_base | 4190 mod_base = m1f |
| modified_base | 4191 mod_base = m1f |
| modified_base | 4210 mod_base = m1f |
| modified_base | 4216 mod_base = m1f |

| | | |
|---|---|---|
| modified_base | 4250 | |
| | mod_base = m1f | |
| modified_base | 4261 | |
| | mod_base = m1f | |
| modified_base | 4262 | |
| | mod_base = m1f | |
| modified_base | 4265 | |
| | mod_base = m1f | |
| modified_base | 4266 | |
| | mod_base = m1f | |
| modified_base | 4271 | |
| | mod_base = m1f | |
| modified_base | 4275 | |
| | mod_base = m1f | |
| modified_base | 4276 | |
| | mod_base = m1f | |
| modified_base | 4278 | |
| | mod_base = m1f | |
| modified_base | 4286 | |
| | mod_base = m1f | |
| modified_base | 4287 | |
| | mod_base = m1f | |
| modified_base | 4291 | |
| | mod_base = m1f | |
| modified_base | 4292 | |
| | mod_base = m1f | |
| modified_base | 4294 | |
| | mod_base = m1f | |
| modified_base | 4300 | |
| | mod_base = m1f | |
| modified_base | 4305 | |
| | mod_base = m1f | |
| modified_base | 4306 | |
| | mod_base = m1f | |
| modified_base | 4308 | |
| | mod_base = m1f | |
| modified_base | 4309 | |
| | mod_base = m1f | |
| modified_base | 4311 | |
| | mod_base = m1f | |
| modified_base | 4313 | |
| | mod_base = m1f | |
| modified_base | 4317 | |
| | mod_base = m1f | |
| modified_base | 4318 | |
| | mod_base = m1f | |
| modified_base | 4324 | |
| | mod_base = m1f | |
| modified_base | 4326 | |
| | mod_base = m1f | |
| modified_base | 4330 | |
| | mod_base = m1f | |
| modified_base | 4332 | |
| | mod_base = m1f | |
| modified_base | 4333 | |
| | mod_base = m1f | |
| modified_base | 4336 | |
| | mod_base = m1f | |
| modified_base | 4338 | |
| | mod_base = m1f | |
| modified_base | 4339 | |
| | mod_base = m1f | |
| modified_base | 4340 | |
| | mod_base = m1f | |
| modified_base | 4344 | |
| | mod_base = m1f | |
| modified_base | 4351 | |
| | mod_base = m1f | |
| modified_base | 4355 | |
| | mod_base = m1f | |
| modified_base | 4362 | |
| | mod_base = m1f | |
| modified_base | 4364 | |
| | mod_base = m1f | |

SEQUENCE: 19
```
agaggaaata agagagaaaa gaagagtaag aagaaatata agagccacca tggcccctaa   60
gaagaagaga aaagtcggaa ttcacggagt ccccgccgcc gacaaaaagt actccattgg  120
ccttgatatt ggaaccaact ccgtgggttg ggccgtgatc actgacgagt acaaggtgcc  180
gtccaagaag ttcaaggtgc tggggaacac tgaccggcac tcaattaaga agaacctgat  240
```

```
tggggcgctg ctgttcgact ccggagaaac cgcggaggct acccgcctga agcggactgc   300
ccggcggaga tacacgcgca ggaagaaccg gatttgctac ctccaagaaa tcttcagcaa   360
cgaaatggca aggtggacg attccttctt ccatcgcctg gaagagagct tcctggtgga    420
agaggacaag aagcacgaaa gacacccgat tttcggcaac atcgtggatg aggtcgcata   480
ccacgaaaag tacccacca tctatcatct tcggaagaag ctggtcgact ccaccgataa    540
ggccgatctg cgcctgatct acttggcgct ggctcacatg attaagttca gaggacactt   600
tctgatagag ggcgacctca atcccgataa ctccgacgtg gataagctgt tcatccaact   660
ggtgcagacg tacaaccaac tgtttgaaga gaatccaatc aacgccagcg gggtggacgc   720
caaggccatc ctgtccgccc ggctgtcaaa gtccagacgc ctggagaatc tcatcgcgca   780
actccctggc gaaaaaaaga acggactctt cgggaatctg attgctctgt ccctggggct   840
cactccgaac ttcaagtcga acttcgacct ggcggaggac gctaagctgc agctgtccaa   900
ggacacctac gatgacgatc tggataacct tctgggcccag atcggggatc aatacgccga   960
tctcttcctg gccgcaaaga acttgtcgga tgctattctg ctgacgcaca ttctgcgggt  1020
caatactgaa atcaccaagg cgcccctgtc ggccagcatc atcaagcgct acgacgaaca  1080
ccaccaagac ctgactctgc tgaaggcccc cgtgcgccag cagctgcctg aaaagtacaa  1140
ggagattttc ttcgaccagt ccaagaacgg atacgccgga tacattgacg agggggccag  1200
ccaggaggaa ttttacaaat tcatcaagcc cattctcgag aaaatggacg gaaccgaaga  1260
gttgctcgtg aagctgaaca gagaggatct cctccggaag cagcgacct tcgacaacgg  1320
ttccatcccg caccaaatcc acctgggcga attgcacgcc atcctccggc ggcaggaaga  1380
ttttctaccca ttcttgaagg acaatcgcga aagatcgaa aagatcttga ctttccgcat  1440
cccgtactac gtgggccctc tggccgcgg caactcccgc ttcgcttgga tgacacggaa  1500
gtccgaggaa accattacgc cctggaactt cgaggaagtg gtggacaagg gggcgtccga  1560
ccagagcttc atcgaacgca tgaccaattt cgacaagaac ctcccgaacg aaaaagtgct  1620
gccaaagcac tcgctcctct acgaatactt caccgtgtac aacgagctga ctaaggtcaa  1680
atacgtgact gagggaatgc ggaagccggc cttcctgtcg ggagagcaga agaaggccat  1740
agtgggacttg ctttttcaaga ctaaccggaa ggtcactgtg aagcaactca aggaggacta  1800
cttcaagaag atcgagtgtt tcgactcggt ggagatctcg ggtgtcgagg accgcttcaa  1860
cgcctccctg ggaacttacc acgatctgct gaagatcatc aaggacaagg acttcctcga  1920
taacgaagaa aatgaggaca tcctcgagga tatcgtgctg accctgacct tgttcgagga  1980
tagggagatg atcgaggagc ggctcaagac ctacgcccac ctgtttgacg acaaagtgat  2040
gaagcaactc aaacggcgga ggtataccgg ctggggtcgg ctgtcccgca agctgatcaa  2100
cgggatcagg gacaagcagt ccggaaagac catcctcgac ttccttaagt ccgacggatt  2160
cgcgaaccgc aacttcatgc aacttatcca cgacgactcg ctgacattca aggaagatat  2220
ccagaaggcc caggtgtccg gacagggga ctcgcttcat gagcacatcg ctaacctggc  2280
cggatccccc gccataaaaa agggcattct gcagaccgtc aaagtggtgg atgagctggt  2340
caaggtcatg ggccggcata gccggaaaa catcgtcatc gagatggccc gcagaacca   2400
gactacgcag aagggccaga gaactcccg ggagcggatg aagcggattg aagagggcat  2460
caaggagctc ggcagccaga ttctgaagga acatccccgtg gaaaacaccc agctgcaaaa  2520
cgaaaagctc tatttgtact atctgcaaaa cggacgcgat atgtacgtgg atcaggagct  2580
ggacattaac agactgagcg actatgacgt ggatcacatt gtgcctcaaa gcttcctcaa  2640
ggacgactca attgacaaca aggtcctgac cagaagcgac aagaacagag aaagtcgga   2700
taatgtgccg tccgaagaag tggtcaagaa gatgaagaat tactgagac agctcctgaa   2760
tgcgagactc attacccagc ggaagttcga taacctgacc aaggccgaaa gggtggact   2820
gtccgaactc gacaaagctg gcttcatcaa gcgccaactg gtcgaaacca ggcagatcac  2880
caagcacgtc gcccagattc tggacagccg catgaacact aagtacgacg agaacgataa  2940
gctgatccgc gaagtgaagg tcatcacccct gaagtccaag ctcgtgtccg actttcggaa  3000
ggatttccag ttttacaagg tccgcgagat caacaactac catcacgccc acgacgcgta  3060
ccttaacgca gtcgtgggaa cggctcttat caagaagtac ccaaagctgg agtcggaatt  3120
tgtgtacgga gactacaaag tgtacgacgt gcgcaagatg atcgcaaat ctgagcaaga   3180
gatcgggaag gcaaccgcca aatacttctt ctactcaaac attatgaatt ttttcaaaac  3240
tgaattacc ctggctaacg gagaaattcg gaagcgcccc ctgattgaaa cgaacgaga    3300
aactggagaa attgtgtggg acaagggacg ggacttcgcc accgtccgca aggtcctctc  3360
aatgccccaa gtcaacatcg tgaaaaagac cgaagtgcaa accggcgcc tctcaaagga   3420
gtccatcctg cctaagcgca acagcgacaa gctgattgcc aggaagaagg actgggaccc  3480
gaagaagtac ggaggatttg attccccctac cgtggcctac tccgtgctcg tggtggccaa  3540
agtggaaaag gggaaatcca agaagctgaa gtcggtgaag gagcttttgg gtatcaccat  3600
catgaacgc tcctcgttcg aaaagaaccc aatcgatttc ctggaagcta agggttataa  3660
ggaagtgaaa aaggacctga ttatcaagct gcccaagtac tcactgttcg agctggaaaa  3720
cggtcggaaa aggatgctgg ccagccgg agaactccag aagggaaacg aactggcact   3780
gccgtccaaa tacgtcaact tcctctacct tgcatccat tacgaaaac tcaagggatc   3840
gccgaggac aacgagcaga agcagctttt cgtggagcaa cacaagcatt acttggacga   3900
gatcatcgag cagatttccg agttctcaaa gcgcgtgatc ctggccgacg caaatctgga  3960
caaggtcctg tccgcgtaca taagcatcg ggacaagcct atccgcgaac aggccgagaa   4020
catcatccat ctgttcactc tgacaaacct gggcgccccg gccgttca agtactttga    4080
caccaccatc gataggaagc gatacaccctc aactaaggaa gtgttggacg cgacccttat  4140
ccatcagtcg atcaccggc tgtacgaaac acggatcgac ctcagccagt tgggaggcga   4200
caagcgccct gcggctacca agaaggccgg acaggccaag aagaagaaat gagcggccgc   4260
ttaattaagc tgccttctgc ggggcttgcc ttctggccat gcccttcttc tctccccttgc  4320
acctgtaccct cttggtcttt gaataaagcc tgagtaggaa gtctagaaaa aaaaaaaaaa  4380
aaaaaaaaaa aaaaaaaaaa aaaaaaaaaa aaaaaaaaaa aaaaaaaaaa aaaaaaaaaa  4440
aaaaaaaaaa aaaaaaaaaa aaaaaaaaaa aaaaaaaaaa aaaaaaaaaa aaaaaaaaaa  4500
aaaaaa                                                             4506

SEQ ID NO: 20          moltype = RNA   length = 20
FEATURE                Location/Qualifiers
source                 1..20
                       mol_type = other RNA
                       organism = synthetic construct
SEQUENCE: 20
```

```
taagaccatg tcccaactga                                                     20

SEQ ID NO: 21          moltype = RNA  length = 20
FEATURE                Location/Qualifiers
source                 1..20
                       mol_type = other RNA
                       organism = synthetic construct
SEQUENCE: 21
gccaatggcc tccttcagtt                                                     20

SEQ ID NO: 22          moltype = RNA  length = 20
FEATURE                Location/Qualifiers
source                 1..20
                       mol_type = other RNA
                       organism = synthetic construct
SEQUENCE: 22
tatattggtc ttccacggtc                                                     20

SEQ ID NO: 23          moltype = RNA  length = 20
FEATURE                Location/Qualifiers
source                 1..20
                       mol_type = other RNA
                       organism = synthetic construct
SEQUENCE: 23
ccagaaaagg taaggttggt                                                     20

SEQ ID NO: 24          moltype = RNA  length = 20
FEATURE                Location/Qualifiers
source                 1..20
                       mol_type = other RNA
                       organism = synthetic construct
SEQUENCE: 24
ggtcttccac ggtctggaga                                                     20

SEQ ID NO: 25          moltype = RNA  length = 20
FEATURE                Location/Qualifiers
source                 1..20
                       mol_type = other RNA
                       organism = synthetic construct
SEQUENCE: 25
ggcctccttc agttgggaca                                                     20

SEQ ID NO: 26          moltype = RNA  length = 20
FEATURE                Location/Qualifiers
source                 1..20
                       mol_type = other RNA
                       organism = synthetic construct
SEQUENCE: 26
ttactaaagg aacaacaaaa                                                     20
```